United States Patent
Steiner et al.

(10) Patent No.: US 9,982,008 B2
(45) Date of Patent: *May 29, 2018

(54) PREPARATION AND USES OF OBETICHOLIC ACID

(71) Applicant: Intercept Pharmaceuticals, Inc., New York, NY (US)

(72) Inventors: André Steiner, Raubling (DE); Heidi Waenerlund Poulsen, Køge (DK); Emilie Jolibois, Cambridge (GB); Melissa Rewolinski, San Diego, CA (US); Ralf Gross, Raubling (DE); Emma Sharp, Cambridge (GB); Fiona Dubas-Fisher, Cambridge (GB); Alex Eberlin, Cambridge (GB)

(73) Assignee: Intercept Pharmaceuticals, Inc., New York, NY (US)

( * ) Notice: Subject to any disclaimer, the term of this patent is extended or adjusted under 35 U.S.C. 154(b) by 147 days.

This patent is subject to a terminal disclaimer.

(21) Appl. No.: 14/979,005

(22) Filed: Dec. 22, 2015

(65) Prior Publication Data

US 2016/0108082 A1    Apr. 21, 2016

Related U.S. Application Data

(63) Continuation-in-part of application No. 13/919,734, filed on Jun. 17, 2013, now Pat. No. 9,238,673.

(60) Provisional application No. 61/661,531, filed on Jun. 19, 2012.

(51) Int. Cl.
| | |
|---|---|
| *A61K 31/56* | (2006.01) |
| *C07J 9/00* | (2006.01) |
| *A61K 31/575* | (2006.01) |
| *C07J 51/00* | (2006.01) |
| *A61K 9/20* | (2006.01) |

(52) U.S. Cl.
CPC ............ *C07J 9/005* (2013.01); *A61K 31/575* (2013.01); *C07J 51/00* (2013.01); *A61K 9/2054* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 4,072,695 | A | 2/1978 | Saltzman |
| 4,892,868 | A | 1/1990 | Castagnola et al. |
| 4,921,848 | A | 5/1990 | Frigerio et al. |
| 5,061,701 | A | 10/1991 | Pellicciari et al. |
| 5,128,481 | A | 7/1992 | Oda et al. |
| 5,175,320 | A | 12/1992 | Pellicciari et al. |
| 6,120,969 | A | 9/2000 | Hagihara et al. |
| 6,200,998 | B1 | 3/2001 | Sahoo et al. |
| 6,559,188 | B1 | 5/2003 | Gatlin et al. |
| 6,639,078 | B1 | 10/2003 | Haffner et al. |
| 6,777,446 | B2 | 8/2004 | Houze et al. |
| 6,906,057 | B1 | 6/2005 | Forman et al. |
| 6,984,650 | B2 | 1/2006 | Haffner et al. |
| 6,987,121 | B2 | 1/2006 | Kliewer et al. |
| 7,138,390 | B2 | 11/2006 | Pellicciari |
| 7,319,109 | B2 | 1/2008 | Boggs et al. |
| 7,332,612 | B2 | 2/2008 | Dolitzky et al. |
| 7,786,102 | B2 | 8/2010 | Pellicciari |
| 7,812,011 | B2 | 10/2010 | Pellicciari |
| 7,981,876 | B2 | 7/2011 | Chellquist et al. |
| 7,994,352 | B2 | 8/2011 | Ferrari et al. |
| 8,058,267 | B2 | 11/2011 | Pellicciari |
| 8,377,916 | B2 | 2/2013 | Pellicciari |
| 2002/0094977 | A1 | 7/2002 | Robl et al. |
| 2002/0120137 | A1 | 8/2002 | Houze et al. |
| 2002/0132223 | A1 | 9/2002 | Forman et al. |
| 2003/0077329 | A1 | 4/2003 | Kipp et al. |
| 2003/0130296 | A1 | 7/2003 | Bauer et al. |

(Continued)

FOREIGN PATENT DOCUMENTS

| | | |
|---|---|---|
| CN | 102372757 A | 3/2012 |
| CN | 104558086 | 4/2015 |

(Continued)

OTHER PUBLICATIONS

Asahara, T. et al. Solvent Handbook, 1985, p. 47-51.
Shioji, Yusaku, "Kokei Seizai no Seizo Gijutsu" Manufacturing technique of solid formulation, 2003, p. 12.
Aldini et al., "Relationship between structure and intestinal absorption of bile acids with a steroid or side-chain modification", Steroids, 61(10):590-597 (1996).
Bishop-Bailey et al., "Expression and activation of the farnesoid X receptor in the vasculature", Proc. Natl. Acad. Sci. U.S.A., 101(10):3668-3673 (2004).
Bramlett et al., "Correlation of Farnesoid X Receptor Coactivator Recruitment and Cholesterol 7alpha-Hydroxylase Gene Repression by Bile Acids," Molecular Genetics and Metabolism 71:609-615 (2000).

(Continued)

*Primary Examiner* — Jared D Barsky
(74) *Attorney, Agent, or Firm* — Michelle Iwamoto-Fan

(57) ABSTRACT

The present invention relates to obeticholic acid:

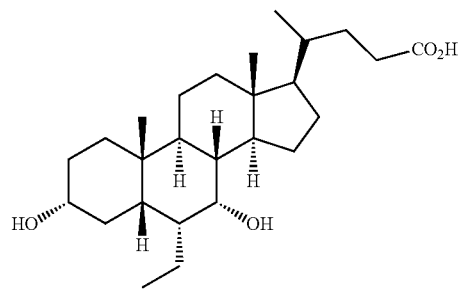

or a pharmaceutically acceptable salt, solvate or amino acid conjugate thereof. Obeticholic acid is useful for the treatment or prevention of a FXR mediated disease or condition, cardiovascular disease or cholestatic liver disease, and for reducing HDL cholesterol, for lowering triglycerides in a mammal, or for inhibition of fibrosis. The present invention also relates to processes for the synthesis of obeticholic acid.

14 Claims, 68 Drawing Sheets

(56) References Cited

U.S. PATENT DOCUMENTS

| | | | |
|---|---|---|---|
| 2006/0069070 | A1 | 3/2006 | Fiorucci et al. |
| 2007/0015796 | A1 | 1/2007 | Jones et al. |
| 2007/0087961 | A1 | 4/2007 | Eichner et al. |
| 2009/0062526 | A1 | 3/2009 | Yu et al. |
| 2013/0345188 | A1 | 12/2013 | Steiner et al. |
| 2014/0024631 | A1 | 1/2014 | Pellicciari |

FOREIGN PATENT DOCUMENTS

| | | |
|---|---|---|
| CN | 104672290 | 6/2015 |
| CN | 104876995 | 9/2015 |
| CN | 104926909 | 9/2015 |
| CN | 105085597 | 11/2015 |
| CN | 105175473 | 12/2015 |
| CN | 105294801 | 2/2016 |
| CN | 105315320 | 2/2016 |
| CN | 105481925 | 4/2016 |
| EP | 0101554 | 2/1984 |
| EP | 0124068 | 11/1984 |
| EP | 0135782 | 4/1985 |
| EP | 0186023 | 7/1986 |
| EP | 0312867 | 4/1989 |
| EP | 0382220 | 8/1990 |
| EP | 0393493 | 10/1990 |
| EP | 1137940 | 10/2001 |
| EP | 1140079 | 10/2001 |
| EP | 1165135 | 1/2002 |
| EP | 1185277 | 3/2002 |
| EP | 1378749 | 1/2004 |
| EP | 1473042 | 11/2004 |
| EP | 1536812 | 6/2005 |
| EP | 1568706 | 8/2005 |
| EP | 1568706 A1 | 8/2005 |
| EP | 1947108 | 7/2008 |
| JP | 2000-16997 | 1/2000 |
| JP | 2007-77123 | 3/2007 |
| WO | WO 9728149 | 8/1997 |
| WO | WO 9731907 | 9/1997 |
| WO | WO 9736579 | 10/1997 |
| WO | WO 9802159 | 1/1998 |
| WO | WO 9938845 | 8/1999 |
| WO | WO 0025134 | 5/2000 |
| WO | WO 0037077 | 6/2000 |
| WO | WO 0040965 | 7/2000 |
| WO | WO 0057915 | 10/2000 |
| WO | WO 0076523 | 12/2000 |
| WO | WO 0130343 | 5/2001 |
| WO | WO 0220463 | 3/2002 |
| WO | WO 02064125 | 8/2002 |
| WO | WO 2002/072598 | 9/2002 |
| WO | WO 03015771 | 2/2003 |
| WO | WO 03015777 | 2/2003 |
| WO | WO 03016280 | 2/2003 |
| WO | WO 03016288 | 2/2003 |
| WO | WO 03030612 | 4/2003 |
| WO | WO 03043581 | 5/2003 |
| WO | WO 03/080803 | 10/2003 |
| WO | WO 03086303 | 10/2003 |
| WO | WO 03090745 | 11/2003 |
| WO | WO 2004/007521 | 1/2004 |
| WO | WO 2004048349 | 6/2004 |
| WO | WO 2005032549 | 4/2005 |
| WO | WO 2005082925 | 9/2005 |
| WO | WO 2005089316 | 9/2005 |
| WO | WO-06122977 A2 | 11/2006 |
| WO | WO 2006122977 | 11/2006 |
| WO | WO 2008002573 | 1/2008 |
| WO | WO 2008091540 | 7/2008 |
| WO | WO 10014836 | 2/2010 |
| WO | WO 2010059853 | 5/2010 |
| WO | WO 11022838 A1 | 3/2011 |
| WO | WO 13192097 A1 | 12/2013 |
| WO | 2016/045480 | 3/2016 |

OTHER PUBLICATIONS

CAS Registry No. 459789-99-2, retrieved Sep. 11, 2013.
Center, S.A., "Chronic Liver Disease: Current Concepts of Disease Mechanisms", J. Small Anim. Pract., 40(3), 106-114 (1999).
Clerici et al., "Effect of Intraduodenal Administration of 23-Methyl-UDCA Diastereoisomers on Bile Flow in Hamsters", Dig. Dis. Sci., 37(5):791-798 (1992).
Cooke, J.P., "Asymmetrical Dimethylarginine: the Uber Marker?" Circulation. 109.15(2004):1813-1818.
Cui et al., "The Amino Acid Residues Asparagine 354 and Isoleucine 372 of Human Farnesoid X Receptor Confer the Receptor with High Sensitivity to Chenodeoxycholate", J. Bio. Chem., 277:25963-25969 (2002).
Dayoub et al. "Dimethylarginine Dimethylaminohydrolase Regulates Nitric Oxide Synthesis: Genetic and Physiological Evidence." Circulation. 108.24(2003):3042-3047.
Downes, M., et al., A Chemical, Genetic, and Structural Analysis of the Nuclear Bile Acid Receptor FXR, Mol. Cell., 11(4), 1079-1092 (2003).
European Search Report for European Application No. 044004408.3, dated Jul. 22, 2004.
Fiorucci et al., "The Nuclear Receptor SHP Mediates Inhibition of Hepaptic Stellate Cells by FXR and Protects Against Liver Fibrosis", Gastroenterology, 127:1497-1512 (2004).
Forman, Barry M. et al; "Identification of a Nuclear Receptor That is Activated by Farnesol Metabolites"; Cell; vol. 81; 687-693; Jun. 2, 1995.
Fukuchi et al., "5β-Cholane activators of the farnesol X receptor", J. Steroid Biochem. Mol. Biol., 94(4):311-318 (2005).
Gioiello et al. "Extending SAR of Bile Acids as FXR Ligands: Discovery of 23-N-(carbocinnamyloxy)-3a,7a-dihydroxy-6a-ethyl-24-nor-5~-cholan-23-amine." Bioorg. Med. Chem. 19.8(2011):2650-2658.
Goodwin et al., "A Regulatory Cascade of the Nuclear Receptors FXR, SHP-1, and LRH-1 Represses Bile Acid Biosynthesis", Mol. Cell., 6:517-526 (2000).
Haslewood et al., "Specificity and some characteristics of a 7.alpha.-hydroxysteroid dehydrogenase from *E. coli*", Database accession No. 1978:419015, 1998.
Honorio et al., "Hologram QSAR Studies on Farnesoid X Receptor Activators", Lett. Drug Des. Dis., 3(4):261-267 (2006).
Hooft et al. "Determination of Absolute Structure Using Bayesian Statistics on Bijvoet Differences." J. Appl. Crystallogr. 41 (2008):96-103.
International Preliminary Report on Patentability and Written Opinion for EP2006062246, dated Nov. 19, 2007.
International Search Report dated Oct. 27, 2006 for PCT/EP2006062246.
International Search Report dated Aug. 31, 2005 for PCT/EP2005/002086.
International Search Report dated Feb. 9, 2006 for PCT/US05/08575.
International Search Report dated Jun. 18, 2002 for PCT/EP02/01832.
Jones et al., "Cell-Free Ligand Binding Assays for Nuclear Receptors", Methods Enzymol., 364:53-71 (2003).
Kanda et al., "Regulation of Expression of Human Intestinal Bile Acid-Binding Protein in Caco-2 Cells", Biochem. J., 330:261-265 (1998).
Kerc et al. "Thermal Analysis of Glassy Pharmaceuticals." Thermochim. Acta. 248(1995):81-95.
Kihira et al., "Synthesis of sulfonate analogs of bile acids",Steroids, 57(4):193-198 (1992).
Kim et al., "Hypocholesterolemic Effect of Bile Acid Sulfonate Analogs in Hamsters", Biol.Pharm. Bulletin, 24(3):218-220 (2001).
Kliewer et al., "Peroxisome Proliferator-Activated Receptors: From Genes to Physiology", Recent Prog Horm Res., 56:239-263 (2001).
Lefebvre et al. "Role of Bile Acids and Bile Acid Receptors in Metabolic Regulation." Physiol. Rev. 89.1(2009):147-191.
Liu, Y. et al., "Hepatoprotection by the Farnesoid X Receptor Agonist GW4064 in Rat Models of Intra- and Extrahepatic Cholestasis", J. Clin. Invest., 112(11), 1678-1687 (2003).

(56) References Cited

OTHER PUBLICATIONS

Lu et al., "Orphan Nuclear Receptors as eliXiRs and FiXeRs of Sterol Metabolism", J. Biol. Chem. 276:37735-37738 (2001).
Makishima et al., "Identification of a Nuclear Receptor for Bile Acids", Science, 284:1362-1365 (1999).
Maloney et al., "Identification of a Chemical Tool for the Orphan Nuclear Receptor FXR", J. Med. Chem., 43(16):2971-2974 (2000).
Mangelsdorf, David J. et al; "The RXR Heterodimers and Orphan Receptors"; Cell, vol. 83; 841-850; Dec. 15, 1995.
Matsuoka et al. "Asymmetrical Dimethylarginine, an Endogenous Nitric Oxide Synthase Inhibitor, in Experimental Hypertension." Hypertension. 29(1997):242-247.
Mi et al., "Structural Basis for Bile Acid Binding and Activation of the Nuclear Receptor FXR," Mol Cell 11:1093-1100 (2003).
Mikami et al., "Effect of some sulfonate analogues of ursodeoxycholic acid on biliary lipid secretion in the rat", J. Lipid Res., 37(6)1181-1188 (1996).
Miki et al., "Sulfonate analogues of chenodeoxycholic acid: metabolism of sodium 3α, 7α-dihydroxy-25-homo-5β-cholane-25-sulfonate and sodium 3α, 7α-dihydroxy-24-nor-5β-cholane-23-sulfonate in the hamster", J. Lipid Res., 33(11):1629-1637 (1992).
Nesto et al., "Thiazolidinedione Use, Fluid Retention, and Congestive Heart Failure", Diabetes Care, 27(1):256-263 (2004).
Parks et al., "Bile Acids: Natural Ligands for an Orphan Nuclear Receptor", Science, 284:1365-1368 (1999).
Pellicciari et al. "Discovery of 6α-Ethyl-23(S)-methylcholic Acid (S-EMCA, INT-777) as a Potent and Selective Agonist for the TGR5 Receptor, a Novel Target for Diabesity." J. Med. Chem. 52(2009):7958-7961.
Pellicciari et al., "6alpha-Ethyl-Chenodeoxycholic Acid (6-ECDCA), a potent and selective FXR agonist endowed with anticholestatic activity," J.MED.CHEM. 45(17):3569-3572 (2002).
Pellicciari et al.,"Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5", J. Med. Chem., 50:4265-4268 (2007).
Pellicciari, Roberto et al.; "Bile Acid Derivatives as Ligands of the Farnesoid X Receptor. Synthesis, Evaluation and Structure-Activity Relationship of a Series of Body and Side Chain Modified Analogues of Chenodeoxycholic Acid"; Journal of Med. Chem., 47(18), 4559-4569 CODEN: JMCMAR 2004.
Raskin et al., "A Randomized Trial of Rosiglitazone Therapy in Patients With Inadequately Controlled Insulin-Treated Type 2 Diabetes", Diabetes Care, 24(7):1226-1232 (2001).
Roda et al., "23-Methyl-3α,7β-dihydroxy-5β-cholan-24-oic Acid: Dose-Response Study of Biliary Secretion in Rat", Hepatol., 8(6):1571-1576 (1988).
Roda et al., "Bile acids with a cyclopropyl-containing side chain. IV.Physicochemical and biological properties of the four diastereoisomers of 3α,7β-dihydroxy-22,23-methylene-5β-cholan-24-oic acid", J. Lipid Res., 28(12):1384-1397 (1987).
Rubin et al., "Combination Therapy With Pioglitazone and Insulin in Patients With Type 2 Diabetes", Diabetes, 48(Suppl. 1):A110 (1999) (Abstract only).
Sato et al., "Novel Potent and Selective Bile Acid Derivatives as TGR5 Agonists: Biological Screening, Structure-Activity Relationships, and Molecular Modeling Studies", J. Med. Chem., 51(6):1831-1841 (2008).
Schmider et al., "Evidence for an additional sinusoidal bile salt transport system", Database accession No. 2000:260886, Feb. 16, 2009.
Schwartz et al., "Two 7 Hydroxylase Enzymes in Bile Acid Biosynthesis", Curr. Opin. Lipidol., 9:113-118 (1998).
Sepe et al. "Conicasterol E, a Small Heterodimer Partner Sparing Farnesoid X Receptor Modulator Endowed with a Pregnane X Receptor Agonistic Activity, from the Marine Sponge Theone/la swinhoei." J. Med. Chem. 55.1 (2012):84-93.

Souillac et al., "Characterization of Delivery Systems, Differential Scanning Calorimetry", in Encyclopedia of Controlled Drug Delivery, John Wiley & Sons, pp. 212-227 (1999).
Stenner et al., "The effect of ursodeoxycholic acid on fibrosis markers in alcoholic liver disease", Flak Symposium, pp. 229-235 (2002).
Sydow et al. "Dimethylarginine Dimethylaminohydrolase Overexpression Enhances Insulin Sensitivity." Arterioscler. Thromb. Vasc. Biol. 28.4(2008):692-697.
Urizar, N.L. et al., A Natural Product that Lowers Cholesterol as an Antagonist Ligand for FXR, Science , 296(5573), 1703-1706 (2002).
Vippagunta et al., Crystalline Solid, Advanced Drug Delivery Reviews, 48:3-26 (2001).
Wang et al., "Endogenous Bile Acids are Ligands for the Nuclear Receptor FXR/BAR", Mol. Cell., 3:543-553 (1999).
Willson et al., "The PPARs: From Orphan Receptors to Drug Discovery", J. Med. Chem., 43(4):527-550 (2000).
Yu et al. "An Improved Synthesis of 6a-ethylchenodeoxycholic Acid (6ECDCA), a Potent and Selective Agonist for the Farnesoid X Receptor (FXR)." Steroids. 77.13(2012):1335-1338.
Zhang et al. "FXR Protects Lung from Lipopolysaccharide-Induced Acute Injury." Mol. Endocrinol. 26.1(2012):27-36.
Zhou et al. "The Effects of Taurochenodeoxycholic Acid in Preventing Pulmonary Fibrosis in Mice." Pak. J. Pharm. Sci. 26.4(2013):761-765.
U.S. Appl. No. 13/761,889, Pellicciari.
Gioiello et al. "Extending SAR of Bile Acids as FXR Ligands: Discovery of 23-N-(carbocinnamyloxy)-3α,7α-dihydroxy-6α-ethyl-24-nor-5β-cholan-23-amine." Bioorg. Med. Chem. 19.8(2011):2650-2658.
Hooft et al. "Determination of Absolute Structure Using Bayesian Statistics on Bijvoet Differences." J. Appl. Crystallogr. 41(2008):96-103.
Kerč et al. "Thermal Analysis of Glassy Pharmaceuticals. "Thermochim. Acta. 248(1995):81-95.
Sepe et al. "Conicasterol E, a Small Heterodimer Partner Sparing Farnesoid X Receptor Modulator Endowed with a Pregnane X Receptor Agonistic Activity, from the Marine Sponge Theonella swinhoei." J. Med. Chem. 55.1(2012):84-93.
Yu et al. "An Improved Synthesis of 6α-ethylchenodeoxycholic Acid (6ECDCA), a Potent and Selective Agonist for the Farnesoid X Receptor (FXR)." Steroids. 77.13(2012):1335-1338.
Pellicciari et al., "Nongenomic Actions of Bile Acids. Synthesis and Preliminary Characterization of 23- and 6,23-Alkyl Substituted Bile Acid Derivatives as Selective Modulator for the G-Protein Coupled Receptor TGR5," J. Med. Chem. 2007, 50, 4265-4268.
Natalini et al., "Correlation between CMC and chromatographic index: simple and effective evaluation of hydrophobic/hydrophilic balance of bile acids," Anal Bioanal Chem (2007) 388:1681-1688.
He, L, Analysis of industrial drugs, 2006, p. 113-114.
Jia, W. et al., "Progress on the development of farnesoid X receptor agonists",Chinese Journal of Medicinal Chemistry, 2010, vol. 20, No. 1, p. 64-69.
Gu C. et al. "Grouping solvents by statistical analysis of solvent property parameters: implication to polymorph screening", International Journal of Pharmaceutics, (2004), vol. 283, p. 117-125.
Hancock, B. C., et al. Journal of Pharmaceutical Sciences, 1987, vol. 86, No. 1, p. 1-12.
Jikken Kagaku Gaido Bukku, Experimental Chemistry Guidebook, 1992, 3rd print, p. 130-131.
Jikken Kagaku Koza, Experimental Chemistry Course, 1992, Fourth Edition, vol. 26, p. 159-165.
Jikken Kagaku Koza, Experimental Chemistry Course, 1992, Fourth Edition, vol. 26, p. 251-253.

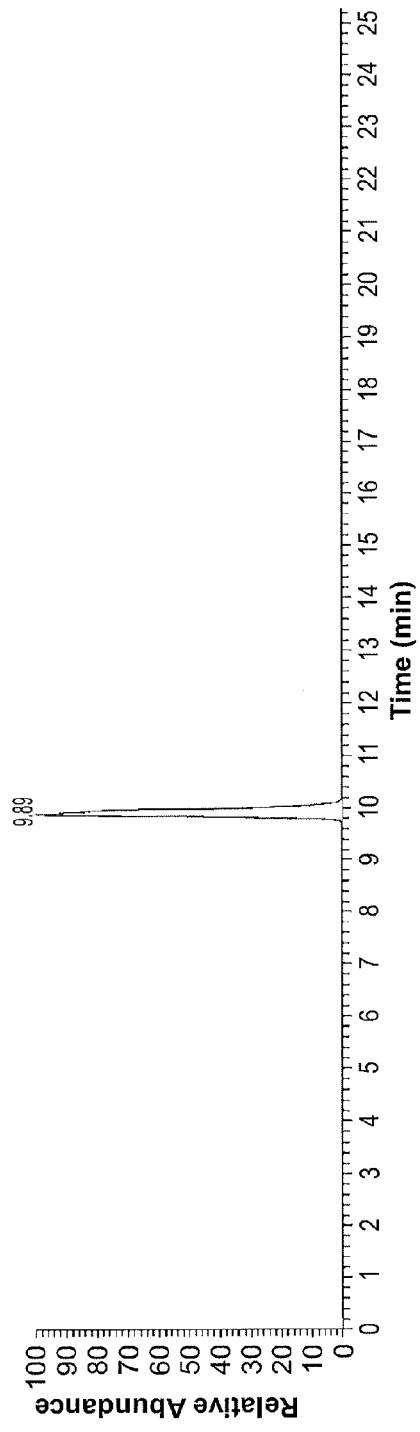
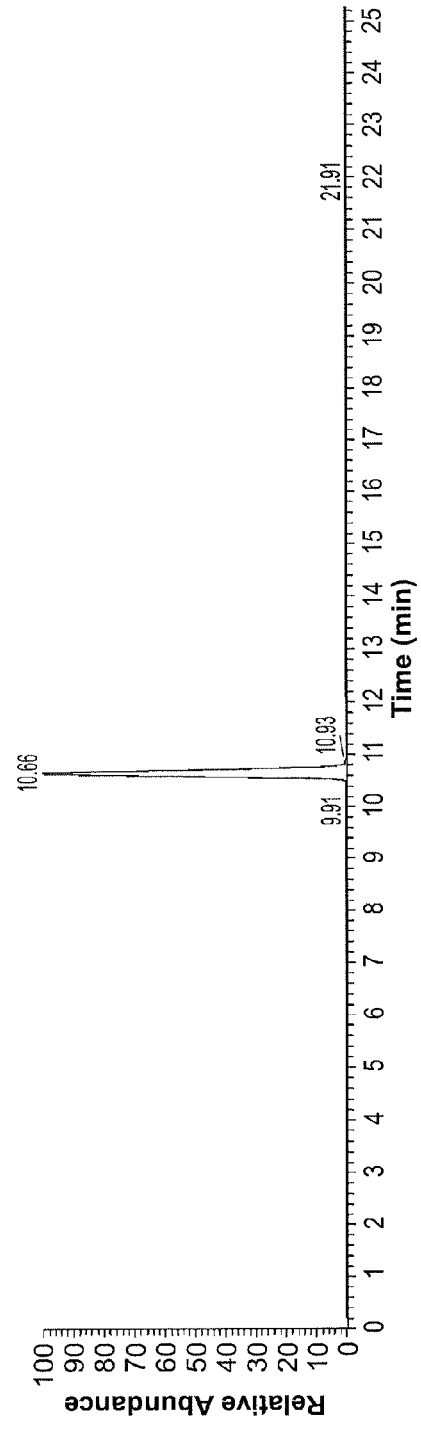
FIG. 4A
FIG. 4B

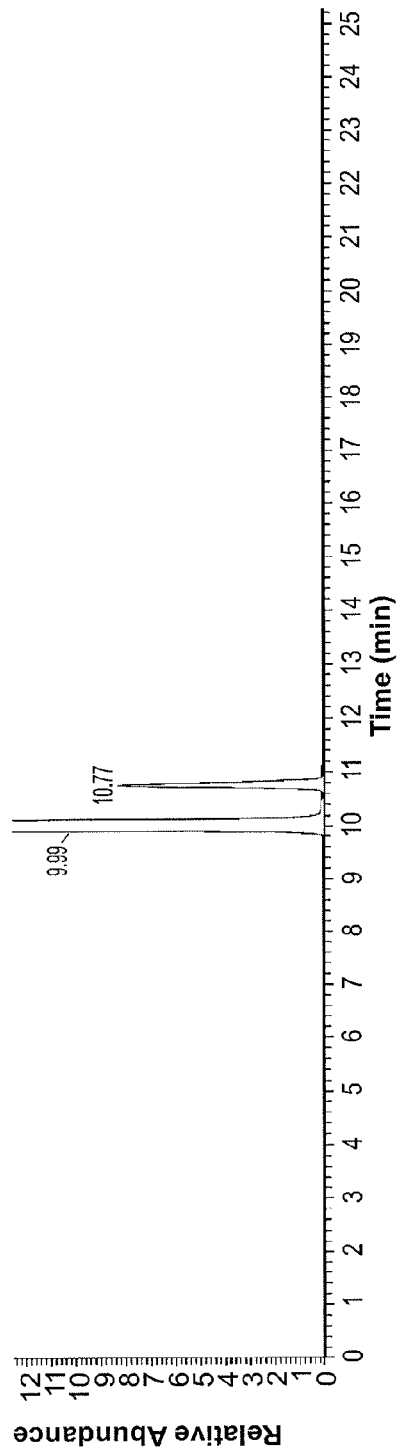
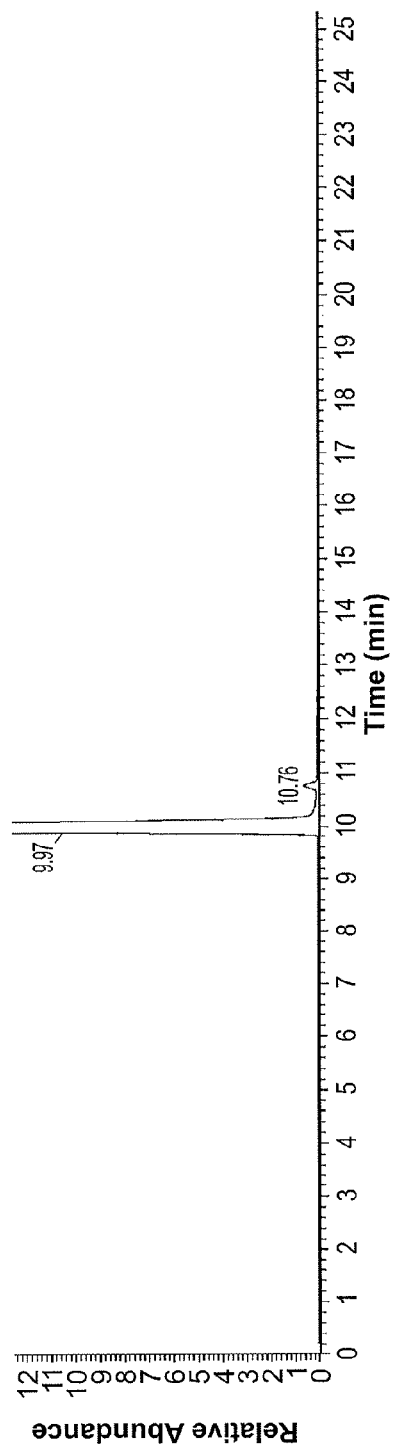

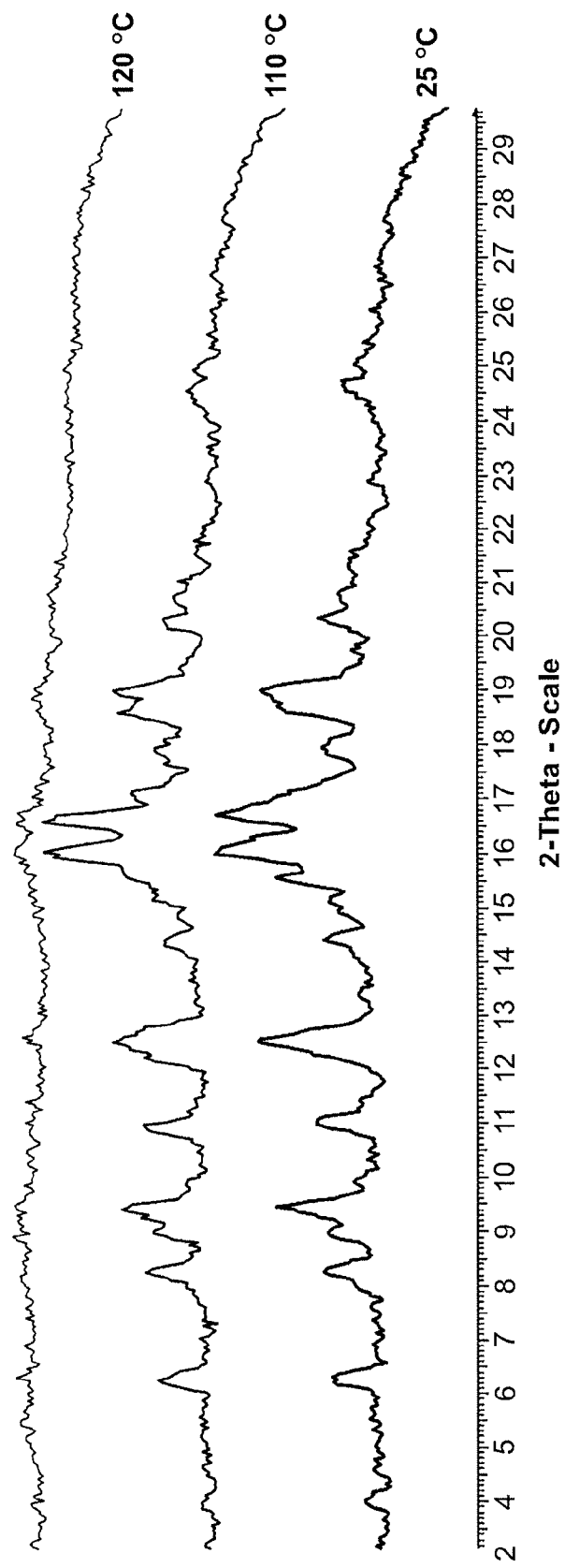

PREPARATION AND USES OF OBETICHOLIC ACID

RELATED APPLICATIONS

This application is a continuation-in-part of U.S. Ser. No. 13/919,734, filed Jun. 17, 2013, which claims priority under 35 U.S.C. § 119(e) to U.S. provisional application No. 61/661,531, filed on Jun. 19, 2012, which is incorporated herein by reference.

SUMMARY OF THE INVENTION

The present invention relates to obeticholic acid, an agonist for FXR, processes of preparation for obeticholic acid, pharmaceutical formulations comprising obeticholic acid, and the therapeutic use of the same.

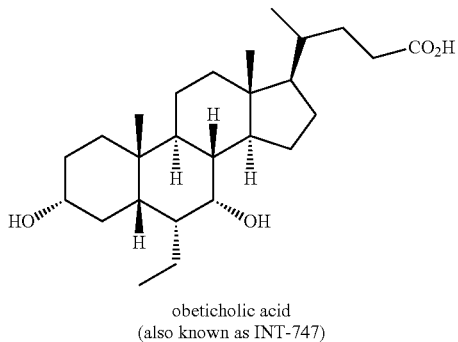

obeticholic acid
(also known as INT-747)

The present invention relates to a process for the preparation of obeticholic acid using crystalline obeticholic acid as a synthetic intermediate. The crystalline obeticholic acid is selected from the group consisting of Forms A, C, D, F, G, and I. The present invention further relates to a process for the selective preparation of crystalline obeticholic acid.

The present invention relates to a crystalline obeticholic acid Form A characterized by an X-ray diffraction pattern including characteristic peaks at about 5.0 and 5.3 degrees 2-Theta. The crystalline obeticholic acid Form A is characterized by an X-ray diffraction pattern substantially similar to that set forth in FIG. 41.

The present invention relates to a crystalline obeticholic acid Form C characterized by an X-ray diffraction pattern including characteristic peaks at about 4.2, 6.4, 9.5, 12.5, and 16.7 degrees 2-Theta. The crystalline obeticholic acid Form C is characterized by an X-ray diffraction pattern substantially similar to that set forth in FIG. 5 and further characterized by a Differential Scanning calorimetry (DSC) thermogram having an endotherm value at about 98±2° C.

The present invention relates to a crystalline obeticholic acid Form D characterized by an X-ray diffraction pattern including characteristic peaks at about 4.4, 5.2, and 7.5 degrees 2-Theta. The crystalline obeticholic acid Form D is characterized by an X-ray diffraction pattern substantially similar to that set forth in FIG. 45.

The present invention relates to a crystalline obeticholic acid Form F characterized by an X-ray diffraction pattern including characteristic peaks at about 8.0, 13.2, and 13.8 degrees 2-Theta. The crystalline obeticholic acid Form F is characterized by an X-ray diffraction pattern substantially similar to that set forth in FIG. 49.

The present invention relates to a crystalline obeticholic acid Form G characterized by an X-ray diffraction pattern including characteristic peaks at about 12.9 and 13.4 degrees 2-Theta. The crystalline obeticholic acid Form G is characterized by an X-ray diffraction pattern substantially similar to that set forth in FIG. 53.

The present invention relates to a crystalline obeticholic acid Form I characterized by an X-ray diffraction pattern including a characteristic peak at about 7.2 degrees 2-Theta. The crystalline obeticholic acid Form I is characterized by an X-ray diffraction pattern substantially similar to that set forth in FIG. 57.

The present invention relates to a process for preparing obeticholic acid Form 1, comprising the step of converting crystalline obeticholic acid to obeticholic acid Form 1.

The present invention relates to a process for preparing obeticholic acid Form 1, comprising the steps of reacting 3α-hydroxy-6α-ethyl-7-keto-5β-cholan-24-oic acid with NaBH$_4$ to form crystalline obeticholic acid and converting crystalline obeticholic acid to obeticholic acid Form 1.

The present invention relates to a process for preparing obeticholic acid Form 1, comprising the steps of reacting E- or E/Z-3α-hydroxy-6-ethylidene-7-keto-5β-cholan-24-oic acid with Pd/C and hydrogen gas to form 3α-hydroxy-6α-ethyl-7-keto-5β-cholan-24-oic acid; reacting 3α-hydroxy-6α-ethyl-7-keto-5β-cholan-24-oic acid with NaBH$_4$ to form crystalline obeticholic acid; and converting crystalline obeticholic acid to obeticholic acid Form 1.

The present invention relates to a process for preparing obeticholic acid Form 1, comprising the steps of reacting E- or E/Z-3α-hydroxy-6-ethylidene-7-keto-5β-cholan-24-oic acid methyl ester with NaOH to form E- or E/Z-3α-hydroxy-6-ethylidene-7-keto-5β-cholan-24-oic acid; reacting E- or E/Z-3α-hydroxy-6-ethylidene-7-keto-5β-cholan-24-oic acid with Pd/C and hydrogen gas to form 3α-hydroxy-6α-ethyl-7-keto-5β-cholan-24-oic acid; reacting 3α-hydroxy-6α-ethyl-7-keto-5β-cholan-24-oic acid with NaBH$_4$ to form crystalline obeticholic acid, and converting crystalline obeticholic acid to obeticholic acid Form 1.

The present invention relates to a process for preparing obeticholic acid Form 1, comprising the steps of reacting 3α,7-ditrimethylsilyloxy-5β-chol-6-en-24-oic acid methyl ester with CH$_3$CHO to form E- or E/Z-3α-hydroxy-6-ethylidene-7-keto-5β-cholan-24-oic acid methyl ester; reacting E- or E/Z-3α-hydroxy-6-ethylidene-7-keto-5β-cholan-24-oic acid methyl ester with NaOH to form E- or E/Z-3α-hydroxy-6-ethylidene-7-keto-5β-cholan-24-oic acid; reacting E- or E/Z-3α-hydroxy-6-ethylidene-7-keto-5β-cholan-24-oic acid with Pd/C and hydrogen gas to form 3α-hydroxy-6α-ethyl-7-keto-5β-cholan-24-oic acid; reacting 3α-hydroxy-6α-ethyl-7-keto-5β-cholan-24-oic acid with NaBH$_4$ to form crystalline obeticholic acid, and converting crystalline obeticholic acid to obeticholic acid Form 1.

The present invention relates to a process for preparing obeticholic acid Form 1, comprising the steps of reacting 3α-hydroxy-7-keto-5β-cholan-24-oic acid methyl ester with Li[N(CH(CH$_3$)$_2$)$_2$] and Si(CH$_3$)$_3$Cl to form 3α,7-ditrimethylsilyloxy-5β-chol-6-en-24-oic acid methyl ester; reacting 3α,7-ditrimethylsilyloxy-5β-chol-6-en-24-oic acid methyl ester with CH$_3$CHO to form E- or E/Z-3α-hydroxy-6-ethylidene-7-keto-5β-cholan-24-oic acid methyl ester; reacting E- or E/Z-3α-hydroxy-6-ethylidene-7-keto-5β-cholan-24-oic acid methyl ester with NaOH to form E- or E/Z-3α-hydroxy-6-ethylidene-7-keto-5β-cholan-24-oic acid; reacting E- or E/Z-3α-hydroxy-6-ethylidene-7-keto-5β-cholan-24-oic acid with Pd/C and hydrogen gas to form 3α-hydroxy-6α-ethyl-7-keto-5β-cholan-24-oic acid; reacting 3α-hydroxy-6α-ethyl-7-keto-5β-cholan-24-oic acid with $NaBH_4$ to form crystalline obeticholic acid, and converting crystalline obeticholic acid to obeticholic acid Form 1.

The present invention relates to a process for preparing obeticholic acid Form 1, comprising the steps of reacting 3α-hydroxy-7-keto-5β-cholan-24-oic acid with $CH_3OH$ and $H_2SO_4$ to form 3α-hydroxy-7-keto-5β-cholan-24-oic acid methyl ester; reacting 3α-hydroxy-7-keto-5β-cholan-24-oic acid methyl ester with $Li[N(CH(CH_3)_2)_2]$ and $Si(CH_3)_3Cl$ to form 3α,7-ditrimethylsilyloxy-5β-chol-6-en-24-oic acid methyl ester; reacting 3α,7-ditrimethylsilyloxy-5β-chol-6-en-24-oic acid methyl ester with $CH_3CHO$ to form E- or E/Z-3α-hydroxy-6-ethylidene-7-keto-5β-cholan-24-oic acid methyl ester; reacting E- or E/Z-3α-hydroxy-6-ethylidene-7-keto-5β-cholan-24-oic acid methyl ester with NaOH to form E- or E/Z-3α-hydroxy-6-ethylidene-7-keto-5β-cholan-24-oic acid; reacting E- or E/Z-3α-hydroxy-6-ethylidene-7-keto-5β-cholan-24-oic acid with Pd/C and hydrogen gas to form 3α-hydroxy-6α-ethyl-7-keto-5β-cholan-24-oic acid; reacting 3α-hydroxy-6α-ethyl-7-keto-5β-cholan-24-oic acid with $NaBH_4$ to form crystalline obeticholic acid, and converting crystalline obeticholic acid to obeticholic acid Form 1.

The present invention relates to a process for preparing obeticholic acid Form 1, wherein converting crystalline obeticholic acid Form A to obeticholic acid Form 1 comprises the step of dissolving crystalline obeticholic acid Form A in aqueous NaOH solution and adding HCl.

The present invention relates to a process for preparing obeticholic acid Form 1, wherein converting crystalline obeticholic acid Form C to obeticholic acid Form 1 comprises the step of dissolving crystalline obeticholic acid Form C in aqueous NaOH solution and adding HCl.

The present invention relates to a process for preparing obeticholic acid Form 1, wherein converting crystalline obeticholic acid Form D to obeticholic acid Form 1 comprises the step of dissolving crystalline obeticholic acid Form D in aqueous NaOH solution and adding HCl.

The present invention relates to a process for preparing obeticholic acid Form 1, wherein converting crystalline obeticholic acid Form F to obeticholic acid Form 1 comprises the step of dissolving crystalline obeticholic acid Form F in aqueous NaOH solution and adding HCl.

The present invention relates to a process for preparing obeticholic acid Form 1, wherein converting crystalline obeticholic acid Form G to obeticholic acid Form 1 comprises the step of dissolving crystalline obeticholic acid Form G in aqueous NaOH solution and adding HCl.

The present invention relates to a process for preparing obeticholic acid Form 1, wherein converting crystalline obeticholic acid Form I to obeticholic acid Form 1 comprises the step of dissolving crystalline obeticholic acid Form I in aqueous NaOH solution and adding HCl.

The present invention relates to a process for preparing obeticholic acid Form 1, wherein reacting 3α-hydroxy-6α-ethyl-7-keto-5β-cholan-24-oic acid with $NaBH_4$ to form crystalline obeticholic acid is carried out at a temperature at about 85° C. to about 110° C. in a basic aqueous solution.

The present invention relates to a process for preparing obeticholic acid Form 1, wherein reacting E- or E/Z-3α-hydroxy-6-ethylidene-7-keto-5β-cholan-24-oic acid with Pd/C and hydrogen gas to form 3α-hydroxy-6α-ethyl-7-keto-5β-cholan-24-oic acid is carried out at a temperature at about 20° C. to about 105° C. and at a pressure at about 0.5 to about 5 bars. In a separate embodiment, the hydrogenation is performed at a temperature range from about 20° C. to about 105° C., e.g. 30° C., 40° C., 50° C., 60° C., 70° C., 80° C., 90° C., and 100° C., as well as any increment in between. In another embodiment, the hydrogenation is performed at a pressure at about 0.5 bar to about 5.5 bar, e.g., 0.6 bar, 0.7 bar, 0.8 bar, 0.9 bar, 1.0 bar, 1.2 bar, 1.4 bar, 1.6 bar, 1.8 bar, 2.0 bar, 2.2 bar, 2.4 bar, 2.6 bar, 2.8 bar, 3.0 bar, 3.2 bar, 3.4 bar, 3.6 bar, 3.8 bar, 4.0 bar, 4.2 bar, 4.4 bar, 5.0 bar, 5.2 bar, 5.3 bar, and 5.4 bar, as well as any increment in between. The present invention relates to a process for preparing obeticholic acid Form 1, wherein reacting E- or E/Z-3α-hydroxy-6-ethylidene-7-keto-5β-cholan-24-oic acid methyl ester with NaOH to form E- or E/Z-3α-hydroxy-6-ethylidene-7-keto-5β-cholan-24-oic acid is carried out at a temperature at about 20° C. to about 60° C.

The present invention relates to a process for preparing obeticholic acid Form 1, wherein reacting 3α,7-ditrimethylsilyloxy-5β-chol-6-en-24-oic acid methyl ester with $CH_3CHO$ to form E- or E/Z-3α-hydroxy-6-ethylidene-7-keto-5β-cholan-24-oic acid methyl ester is carried out in a polar aprotic solvent at a temperature at about −50° C. to about −70° C. in the presence of $BF_3$. In one embodiment, the reaction is carried out at a temperature range of below −60° C. to about −70° C. in the presence of $BF_3$. In one embodiment, the reaction is carried out at is carried out at an upper limit temperature of about −60° C. in the presence of $BF_3$.

The present invention relates to a process for preparing obeticholic acid Form 1, wherein reacting 3α-hydroxy-7-keto-5β-cholan-24-oic acid methyl ester with $Li[N(CH(CH_3)_2)_2]$ and $Si(CH_3)_3Cl$ to form 3α,7-ditrimethylsilyloxy-5β-chol-6-en-24-oic acid methyl ester is carried out in a polar aprotic solvent at a temperature at about −10° C. to about −30° C.

The present invention relates to a process for preparing obeticholic acid Form 1, wherein reacting 3α-hydroxy-7-keto-5β-cholan-24-oic acid with $CH_3OH$ and $H_2SO_4$ to form 3α-hydroxy-7-keto-5β-cholan-24-oic acid methyl ester is heated for about 3 hours and the pH of the reaction mixture is adjusted with an aqueous basic solution to a pH-range of about 9.5 to about 10.

The present invention relates to a obeticholic acid, or a pharmaceutically acceptable salt, solvate or amino acid conjugate thereof, having a potency of greater than about 98%, greater than about 98.5%, greater than about 99.0%, or greater than about 99.5%. The present invention relates to a pharmaceutical composition comprising obeticholic acid Form 1 produced by a process of the invention and a pharmaceutically acceptable carrier.

The present invention relates to a method of treating or preventing an FXR mediated disease or condition in a subject comprise of administering an effective amount of obeticholic acid Form 1. The disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesterolemia, and hyperlipidemia. The present invention relates to a method for lowering triglycerides in a subject comprise of administering an effective amount of obeticholic acid Form 1.

BRIEF DESCRIPTION OF THE DRAWINGS

FIG. 4A is an accurate ion trace of m/z 850.61914±3 ppm from the main peak fraction (RT 29.0 min) of compound 5 of Step 4 of Example 1, purely isolated with HPLC method (see Example 2).

FIG. 4B is an accurate ion trace of m/z 850.61914±3 ppm from the minor peak fraction (RT 29.9 min) of compound 5 of Step 4 of Example 1, purely isolated with HPLC method (see Example 2).

FIG. 4C is an accurate ion trace of m/z 850.61914±3 ppm from crude compound 5 of Step 4 of Example 1 (see Example 2).

FIG. 4D is an accurate ion trace of m/z 850.61914±3 ppm from compound 5 of Step 4 of Example 1, purified reference (see Example 2).

FIG. 7 shows VT-XRPD diffractograms of crystalline obeticholic acid at 25° C., 110° C., and 120° C. (see Example 3).

DETAILED DESCRIPTION OF THE INVENTION

Figure 1:
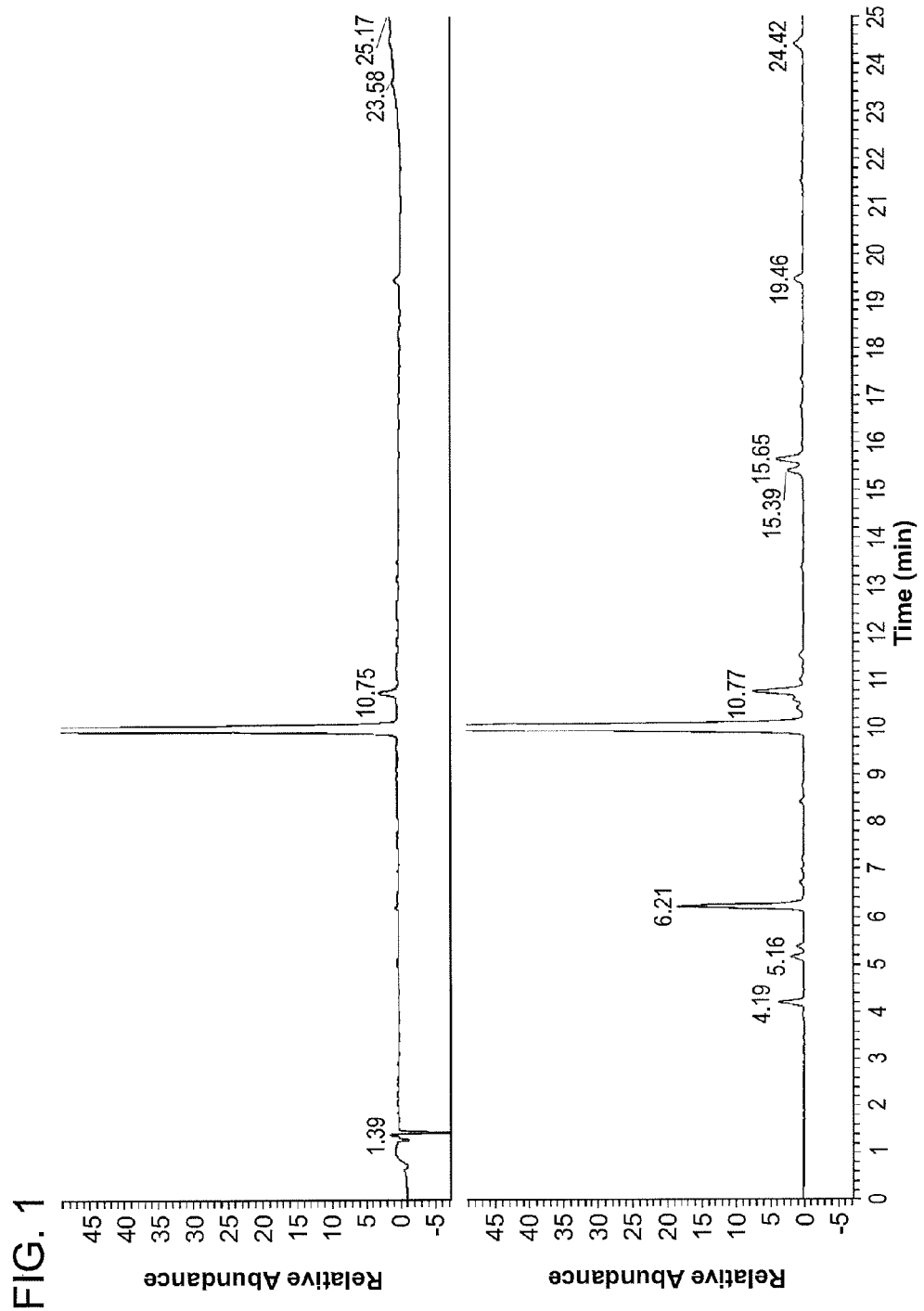
FIG. 1 is a HPLC-UV/MS chromatogram of crude compound 5 of Step 4 of Example 1 injected at 1 mg/mL, injection volume 3 µl. The chromatogram is obtained according to the method described in Example 2.

The present application is directed to obeticholic acid, a pharmaceutically active ingredient (also known as INT-747) having the chemical structure:

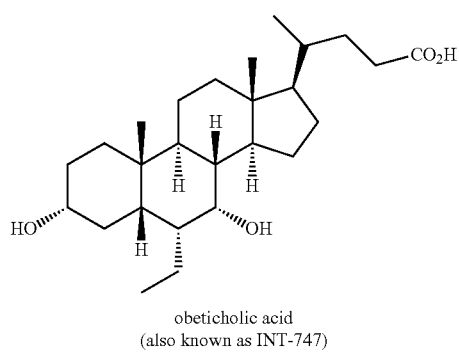

obeticholic acid
(also known as INT-747)

including, substantially pure obeticholic acid, a process for the preparation of obeticholic acid comprising crystalline obeticholic acid as a synthetic intermediate, and analytical methods for confirming the presence and purity of obeticholic acid and synthetic intermediates in the process to prepare obeticholic acid. The present application also describes pharmaceutical compositions and formulations of obeticholic acid and uses for such compositions.

Process to Prepare Obeticholic Acid

The present application is directed to a process for preparing highly pure obeticholic acid. The process of the present application is shown in Scheme 1. The process is a 6-step synthesis followed by one purification step to produce highly pure obeticholic acid.

Scheme 1

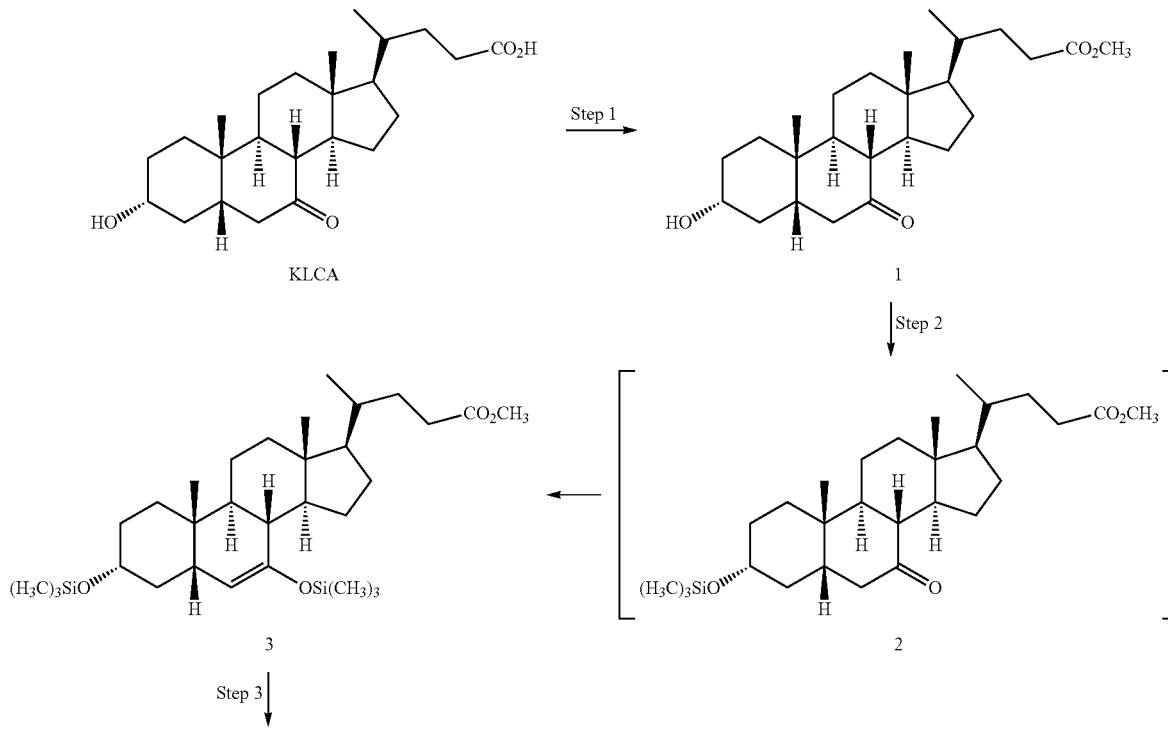

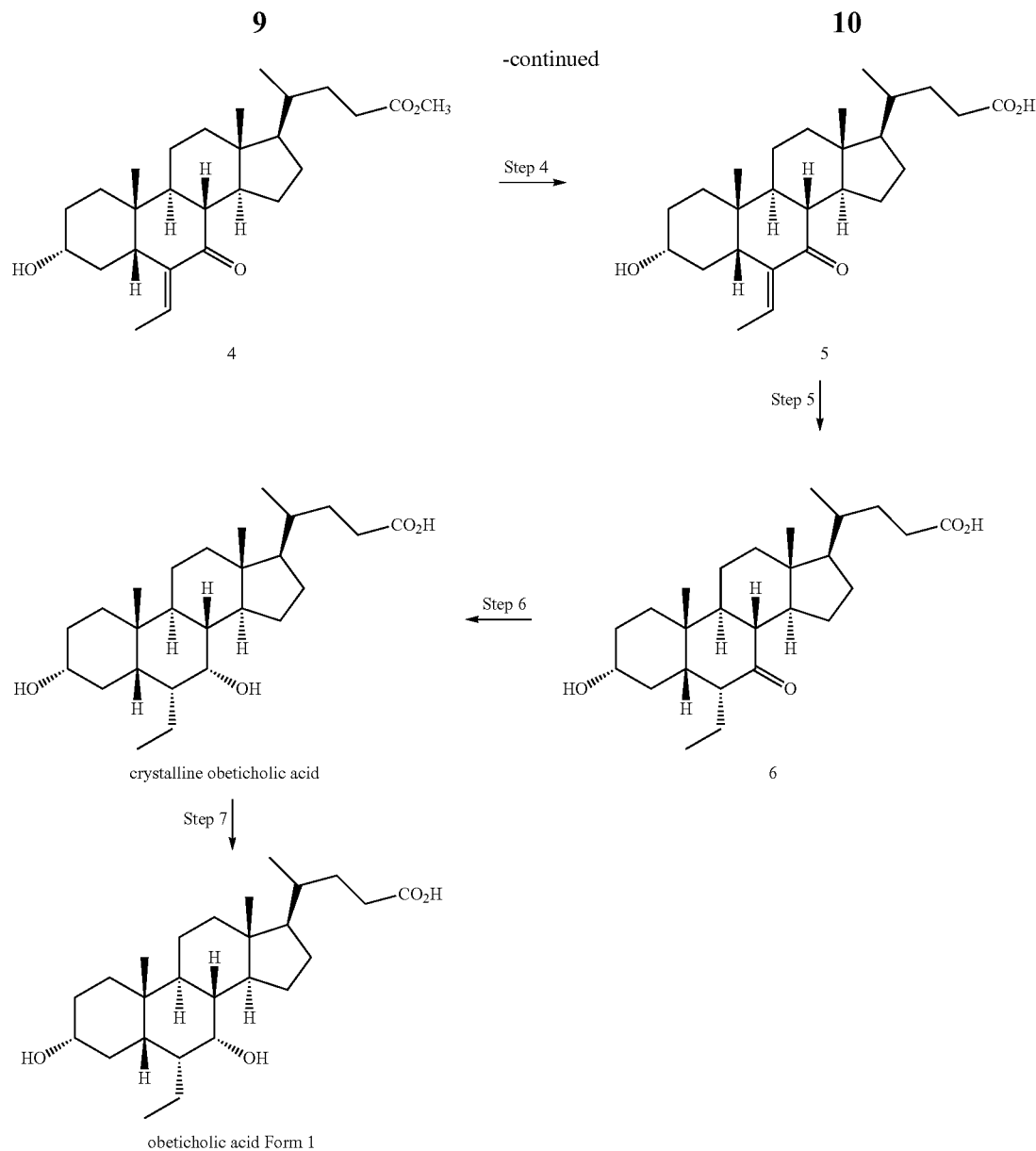

crystalline obeticholic acid obeticholic acid Form 1

The process of the present invention also includes a process according to Scheme 1 where compounds 4 and 5 are each comprised of a mixture of the E and Z isomers as illustrated by the structures of compounds 4A and 5A below:

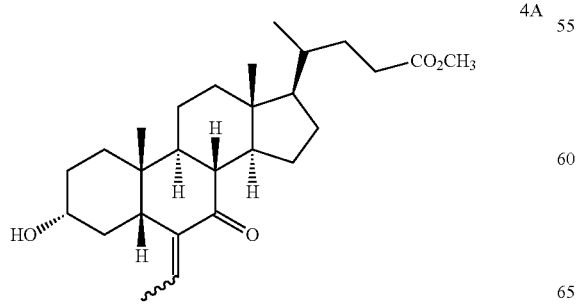

In one embodiment, the E/Z isomer ratio of E/Z-3α-hydroxy-6-ethylidene-7-keto-5β-cholan-24-oic acid methyl ester (4A) is about 50%, greater than about 60%, greater than about 70%, greater than about 80%, greater than about 83%, greater than about 85%, greater than about 90%, greater than about 93%, greater than about 95%, or greater than about 99%. In one embodiment, the E/Z ratio is determined by HPLC. In one embodiment, the ratio is greater than about 80%. In one embodiment, the ratio is greater than about 83%. In one embodiment, the ratio is greater than about 85%. In one embodiment, the ratio is greater than about 90%. In one embodiment, the ratio is greater than about 93%. In one embodiment, the ratio is greater than about 95%. In one embodiment, the ratio is greater than about 99%.

In one embodiment, the E/Z isomer ratio of E/Z-3α-hydroxy-6-ethylidene-7-keto-5β-cholan-24-oic acid (5A) is about 50%, greater than about 60%, greater than about 70%, greater than about 80%, greater than about 83%, greater than about 85%, greater than about 90%, greater than about 93%, greater than about 95%, or greater than about 99%. In one embodiment, the E/Z ratio is determined by HPLC. In one embodiment, the ratio is greater than about 80%. In one embodiment, the ratio is greater than about 83%. In one embodiment, the ratio is greater than about 85%. In one embodiment, the ratio is greater than about 90%. In one embodiment, the ratio is greater than about 93%. In one embodiment, the ratio is greater than about 95%. In one embodiment, the ratio is greater than about 99%.

The process of the present application has never been reported in the art. The process is a 6-step synthesis followed by one purification step. Step 1 is the esterification of the C-24 carboxylic acid of 7-ketolithocholic acid (KLCA) using methanol in the presence of an acid catalyst and heat to produce the methyl ester compound 1. Step 2 is silylenol ether formation from compound 1 using chlorosilane in the presence of a strong base to produce compound 3. Step 3 is an acid mediated aldol condensation reaction of the silylenol ether compound 3 and acetaldehyde in the presence of an acid to produce compound 4 (or compound 4A). Step 4 is ester hydrolysis i.e., saponification of the C-24 methyl ester of compound 4 (or compound 4A) to produce the carboxylic acid compound 5 (or compound 5A). Step 5 is the hydrogenation of the 6-ethylidene moiety of compound 5 (or compound 5A) followed by isomerization of the initially formed 6β3 ethyl group to produce compound 6. Step 6 is the selective reduction of the 7-keto group of compound 6 to a 7α-hydroxy group to produce crystalline obeticholic acid. Step 7 is the conversion of crystalline obeticholic acid to obeticholic acid Form 1.

The process of the present invention relates to a process for preparing obeticholic acid Form 1, where the process utilizes a crystalline form of obeticholic acid as a synthetic intermediate.

In one embodiment, the present invention relates to a process for preparing obeticholic acid Form 1, comprising the step of converting crystalline obeticholic acid to obeticholic acid Form 1.

In one embodiment, the present invention relates to a process for preparing obeticholic acid Form 1, comprising the steps of
reacting 3α-hydroxy-6α-ethyl-7-keto-5β-cholan-24-oic acid (6) with NaBH$_4$ to form crystalline obeticholic acid, and
converting crystalline obeticholic acid to obeticholic acid Form 1.

In one embodiment, the present invention relates to a process for preparing obeticholic acid Form 1, comprising the steps of
reacting E/Z-3α-hydroxy-6-ethylidene-7-keto-5β-cholan-24-oic acid (5A) with Pd/C and hydrogen gas to form 3α-hydroxy-6α-ethyl-7-keto-5β-cholan-24-oic acid (6),
reacting 3α-hydroxy-6α-ethyl-7-keto-5β-cholan-24-oic acid (6) with NaBH$_4$ to form crystalline obeticholic acid, and
converting crystalline obeticholic acid to obeticholic acid Form 1.

In one embodiment, the present invention relates to a process for preparing obeticholic acid Form 1, comprising the steps of
reacting E-3α-hydroxy-6-ethylidene-7-keto-5β-cholan-24-oic acid (5) with Pd/C and hydrogen gas to form 3α-hydroxy-6α-ethyl-7-keto-5β-cholan-24-oic acid (6),
reacting 3α-hydroxy-6α-ethyl-7-keto-5β-cholan-24-oic acid (6) with NaBH$_4$ to form crystalline obeticholic acid, and
converting crystalline obeticholic acid to obeticholic acid Form 1.

In one embodiment, the present invention relates to a process for preparing obeticholic acid Form 1, comprising the steps of
reacting E/Z-3α-hydroxy-6-ethylidene-7-keto-5β-cholan-24-oic acid methyl ester (4A) with NaOH to form E/Z-3α-hydroxy-6-ethylidene-7-keto-5β-cholan-24-oic acid (5A),
reacting E/Z-3α-hydroxy-6-ethylidene-7-keto-5β-cholan-24-oic acid (5A) with Pd/C and hydrogen gas to form 3α-hydroxy-6α-ethyl-7-keto-5β-cholan-24-oic acid (6),
reacting 3α-hydroxy-6α-ethyl-7-keto-5β-cholan-24-oic acid (6) with NaBH$_4$ to form crystalline obeticholic acid, and
converting crystalline obeticholic acid to obeticholic acid Form 1.

In one embodiment, the present invention relates to a process for preparing obeticholic acid Form 1, comprising the steps of
reacting E-3α-hydroxy-6-ethylidene-7-keto-5β-cholan-24-oic acid methyl ester (4) with NaOH to form E-3α-hydroxy-6-ethylidene-7-keto-5β-cholan-24-oic acid (5),
reacting E-3α-hydroxy-6-ethylidene-7-keto-5β-cholan-24-oic acid (5) with Pd/C and hydrogen gas to form 3α-hydroxy-6α-ethyl-7-keto-5β-cholan-24-oic acid (6),
reacting 3α-hydroxy-6α-ethyl-7-keto-5β-cholan-24-oic acid (6) with NaBH$_4$ to form crystalline obeticholic acid, and
converting crystalline obeticholic acid to obeticholic acid Form 1.

In one embodiment, the present invention relates to a process for preparing obeticholic acid Form 1, comprising the steps of
reacting 3α,7-ditrimethylsilyloxy-5β-chol-6-en-24-oic acid methyl ester (3) with CH$_3$CHO to form E/Z-3α-hydroxy-6-ethylidene-7-keto-5β-cholan-24-oic acid methyl ester (4A),
reacting E/Z-3α-hydroxy-6-ethylidene-7-keto-5β-cholan-24-oic acid methyl ester (4A) with NaOH to form E/Z-3α-hydroxy-6-ethylidene-7-keto-5β-cholan-24-oic acid (5A),
reacting E/Z-3α-hydroxy-6-ethylidene-7-keto-5β-cholan-24-oic acid (5A) with Pd/C and hydrogen gas to form 3α-hydroxy-6α-ethyl-7-keto-5β-cholan-24-oic acid (6),
reacting 3α-hydroxy-6α-ethyl-7-keto-5β-cholan-24-oic acid (6) with NaBH$_4$ to form crystalline obeticholic acid, and
converting crystalline obeticholic acid to obeticholic acid Form 1.

In one embodiment, the present invention relates to a process for preparing obeticholic acid Form 1, comprising the steps of reacting 3α,7-ditrimethylsilyloxy-5β-chol-6-en-24-oic acid methyl ester (3) with CH$_3$CHO to form E-3α-hydroxy-6-ethylidene-7-keto-5β-cholan-24-oic acid methyl ester (4), reacting E-3α-hydroxy-6-ethylidene-7-keto-5β-cholan-24-oic acid methyl ester (4) with NaOH to form E-3α-hydroxy-6-ethylidene-7-keto-5β-cholan-24-oic acid (5), reacting E-3α-hydroxy-6-ethylidene-7-keto-5β-cholan-24-oic acid (5) with Pd/C and hydrogen gas to form 3α-hydroxy-6α-ethyl-7-keto-5β-cholan-24-oic acid (6), reacting 3α-hydroxy-6α-ethyl-7-keto-5β-cholan-24-oic acid (6) with NaBH$_4$ to form crystalline obeticholic acid, and converting crystalline obeticholic acid to obeticholic acid Form 1.

In one embodiment, the present invention relates to a process for preparing obeticholic acid Form 1, comprising the steps of reacting 3α-hydroxy-7-keto-5β-cholan-24-oic acid methyl ester (1) with Li[N(CH(CH$_3$)$_2$)$_2$] and Si(CH$_3$)$_3$Cl to form 3α,7-ditrimethylsilyloxy-5β-chol-6-en-24-oic acid methyl ester (3), reacting 3α,7-ditrimethylsilyloxy-5β-chol-6-en-24-oic acid methyl ester (3) with CH$_3$CHO to form E/Z-3α-hydroxy-6-ethylidene-7-keto-5β-cholan-24-oic acid methyl ester (4A), reacting E/Z-3α-hydroxy-6-ethylidene-7-keto-5β-cholan-24-oic acid methyl ester (4A) with NaOH to form E/Z-3α-hydroxy-6-ethylidene-7-keto-5β-cholan-24-oic acid (5A), reacting E/Z-3α-hydroxy-6-ethylidene-7-keto-5β-cholan-24-oic acid (5A) with Pd/C and hydrogen gas to form 3α-hydroxy-6α-ethyl-7-keto-5β-cholan-24-oic acid (6), reacting 3α-hydroxy-6α-ethyl-7-keto-5β-cholan-24-oic acid (6) with NaBH$_4$ to form crystalline obeticholic acid, and converting crystalline obeticholic acid to obeticholic acid Form 1.

In one embodiment, the present invention relates to a process for preparing obeticholic acid Form 1, comprising the steps of reacting 3α-hydroxy-7-keto-5β-cholan-24-oic acid methyl ester (1) with Li[N(CH(CH$_3$)$_2$)$_2$] and Si(CH$_3$)$_3$Cl to form 3α,7-ditrimethylsilyloxy-5β-chol-6-en-24-oic acid methyl ester (3), reacting 3α,7-ditrimethylsilyloxy-5β-chol-6-en-24-oic acid methyl ester (3) with CH$_3$CHO to form E-3α-hydroxy-6-ethylidene-7-keto-5β-cholan-24-oic acid methyl ester (4), reacting E-3α-hydroxy-6-ethylidene-7-keto-5β-cholan-24-oic acid methyl ester (4) with NaOH to form E-3α-hydroxy-6-ethylidene-7-keto-5β-cholan-24-oic acid (5), reacting E-3α-hydroxy-6-ethylidene-7-keto-5β-cholan-24-oic acid (5) with Pd/C and hydrogen gas to form 3α-hydroxy-6α-ethyl-7-keto-5β-cholan-24-oic acid (6), reacting 3α-hydroxy-6α-ethyl-7-keto-5β-cholan-24-oic acid (6) with NaBH$_4$ to form crystalline obeticholic acid, and converting crystalline obeticholic acid to obeticholic acid Form 1.

In one embodiment, the present invention relates to a process for preparing obeticholic acid Form 1, comprising the steps of reacting 3α-hydroxy-7-keto-5β-cholan-24-oic acid (KLCA) with CH$_3$OH and H$_2$SO$_4$ to form 3α-hydroxy-7-keto-5β-cholan-24-oic acid methyl ester (1), reacting 3α-hydroxy-7-keto-5β-cholan-24-oic acid methyl ester (1) with Li[N(CH(CH$_3$)$_2$)$_2$] and Si(CH$_3$)$_3$Cl to form 3α,7-ditrimethylsilyloxy-5β-chol-6-en-24-oic acid methyl ester (3), reacting 3α,7-ditrimethylsilyloxy-5β-chol-6-en-24-oic acid methyl ester (3) with CH$_3$CHO to form E/Z-3α-hydroxy-6-ethylidene-7-keto-5β-cholan-24-oic acid methyl ester (4A), reacting E/Z-3α-hydroxy-6-ethylidene-7-keto-5β-cholan-24-oic acid methyl ester (4A) with NaOH to form E/Z-3α-hydroxy-6-ethylidene-7-keto-5β-cholan-24-oic acid (5A), reacting E/Z-3α-hydroxy-6-ethylidene-7-keto-5β-cholan-24-oic acid (5A) with Pd/C and hydrogen gas to form 3α-hydroxy-6α-ethyl-7-keto-5β-cholan-24-oic acid (6), reacting 3α-hydroxy-6α-ethyl-7-keto-5β-cholan-24-oic acid (6) with NaBH$_4$ to form crystalline obeticholic acid, and converting crystalline obeticholic acid to obeticholic acid Form 1.

In one embodiment, the present invention relates to a process for preparing obeticholic acid Form 1, comprising the steps of reacting 3α-hydroxy-7-keto-5β-cholan-24-oic acid (KLCA) with CH$_3$OH and H$_2$SO$_4$ to form 3α-hydroxy-7-keto-5β-cholan-24-oic acid methyl ester (1), reacting 3α-hydroxy-7-keto-5β-cholan-24-oic acid methyl ester (1) with Li[N(CH(CH$_3$)$_2$)$_2$] and Si(CH$_3$)$_3$Cl to form 3α,7-ditrimethylsilyloxy-5β-chol-6-en-24-oic acid methyl ester (3), reacting 3α,7-ditrimethylsilyloxy-5β-chol-6-en-24-oic acid methyl ester (3) with CH$_3$CHO to form E-3α-hydroxy-6-ethylidene-7-keto-5β-cholan-24-oic acid methyl ester (4), reacting E-3α-hydroxy-6-ethylidene-7-keto-5β-cholan-24-oic acid methyl ester (4) with NaOH to form E-3α-hydroxy-6-ethylidene-7-keto-5β-cholan-24-oic acid (5), reacting E-3α-hydroxy-6-ethylidene-7-keto-5β-cholan-24-oic acid (5) with Pd/C and hydrogen gas to form 3α-hydroxy-6α-ethyl-7-keto-5β-cholan-24-oic acid (6), reacting 3α-hydroxy-6α-ethyl-7-keto-5β-cholan-24-oic acid (6) with NaBH$_4$ to form crystalline obeticholic acid, and converting crystalline obeticholic acid to obeticholic acid Form 1.

The present invention relates to a process for preparing obeticholic acid Form 1 using crystalline obeticholic acid as a synthetic intermediate. In one embodiment, the crystalline obeticholic acid is Form A. In one embodiment, the crystalline obeticholic acid Form A is characterized by an X-ray diffraction pattern similar to that set forth in FIG. 41. In one embodiment, the crystalline obeticholic acid Form A is crystallized and recrystallized from n-butyl acetate.

In another embodiment, the crystalline obeticholic acid is Form C. In one embodiment, the crystalline obeticholic acid Form C is characterized by an X-ray diffraction pattern similar to that set forth in FIG. 5. In another embodiment, the crystalline obeticholic acid is Form D. In one embodiment, the crystalline obeticholic acid Form D is characterized by an X-ray diffraction pattern similar to that set forth in FIG. 45. In another embodiment, the crystalline obeticholic acid is Form F. In one embodiment, the crystalline obeticholic acid Form F is characterized by an X-ray diffraction pattern similar to that set forth in FIG. 49. In another embodiment, the crystalline obeticholic acid is Form G. In one embodiment, the crystalline obeticholic acid Form G is characterized by an X-ray diffraction pattern similar to that set forth in FIG. 53. In another embodiment, the crystalline obeticholic acid is Form I. In one embodiment, the crystalline obeticholic acid Form I is characterized by an X-ray diffraction pattern similar to that set forth in FIG. 57.

Step 1

Step 1 is the reaction of 3α-hydroxy-7-keto-5β-cholan-24-oic acid (KLCA) with $CH_3OH$ and $H_2SO_4$ to form 3α-hydroxy-7-keto-5β-cholan-24-oic acid methyl ester (1). In one embodiment of step 1, the reaction mixture is heated for about 3 hours and the pH of the reaction mixture is adjusted with an aqueous basic solution to a pH-value of about 9.5 to about 10. In one embodiment, the isolation of 3α-hydroxy-7-keto-5β-cholan-24-oic acid methyl ester (1) further comprises treatment with activated carbon. In one embodiment, the isolation of 3α-hydroxy-7-keto-5β-cholan-24-oic acid methyl ester (1) does not further comprise treatment with activated carbon. In one embodiment, isolation of 3α-hydroxy-7-keto-5β-cholan-24-oic acid methyl ester (1) without the treatment with activated carbon affords a higher yield. In one embodiment, reacting 3α-hydroxy-7-keto-5β-cholan-24-oic acid (1) with $CH_3OH$ and $H_2SO_4$ is carried out in methanol. In one embodiment, the basic solution is an aqueous NaOH solution. In one embodiment, the pH-value is about 9.5 to about 10.

In one embodiment, the methyl alcohol acts as the methylating reagent as well as the reaction solvent. In one embodiment, the solution containing the product is treated with activated carbon for about 30 minutes and filtered to remove the carbon solids. In one embodiment, the solution containing the product is not treated with activated carbon. To precipitate the product, water at about 5° C. to about 20° C. and seeding material are added. In another embodiment, the water is at about 10° C. to about 15° C. In one embodiment, the product is isolated with a centrifuge and washed with a mixture of methanol and water. In one embodiment, the water content of the wet material is quantified by Karl Fischer (KF). In one embodiment, the material is dried in a tumble dryer before use in the next step. In one embodiment, the material is not dried before use in the next step. In one embodiment, the wet material is washed with heptane to improve drying.

Step 2

Step 2 is the reaction of 3α-hydroxy-7-keto-5β-cholan-24-oic acid methyl ester (1) with $Li[N(CH(CH_3)_2)_2]$ and $Si(CH_3)_3Cl$ to form 3α,7-ditrimethylsilyloxy-5β-chol-6-en-24-oic acid methyl ester (3). In one embodiment, step 2 is carried out in a polar aprotic solvent at a temperature at about –10° C. to about –30° C. In one embodiment, the polar aprotic solvent is tetrahydrofuran. In one embodiment, the temperature is about –20° C. to about –25° C. In one embodiment, reacting 3α-hydroxy-7-keto-5β-cholan-24-oic acid methyl ester (1) with $Li[N(CH(CH_3)_2)_2]$ and $Si(CH_3)_3Cl$ is stirred for about 2 hours.

In one embodiment, compound 1 is charged into the reactor under inert conditions. In another embodiment, residual water and methanol are removed by repeated azeotropic distillation at about 65° C. and ambient pressure to avoid water hydrolysis of chlorotrimethylsilane which is added later in this step. In another embodiment, THF is added to the residue as necessary and the distillation is repeated about 4 times. In another embodiment, the distillation is repeated about 3 times, about 2 times, or about 1 time. In one embodiment, the remaining solution containing the product has a final water content of ≤0.05% (Karl Fischer Titration). In one embodiment, the solution of the product is pre-cooled to about –10° C. to about –30° C. and then chlorotrimethylsilane is added. In another embodiment, the solution is pre-cooled to about –20° C. to about –25° C.

In one embodiment, a strong base and THF are charged to a separate reactor and cooled to about –10° C. to about –30° C. In one embodiment, the strong base is lithium diisopropylamide. In another embodiment, the reactor is inert, e.g., under a nitrogen or argon atmosphere. In another embodiment, the solution of base and THF is cooled to about –20° C. to about –25° C. In one embodiment, the dry, cooled solution of 3α-hydroxy-7-keto-5β-cholan-24-oic acid methyl ester, THF, and chlorotrimethylsilane is charged into the basic solution at about –10° C. to about –30° C. In another embodiment, the temperature is about –20° C. to about –25° C. In one embodiment, the reaction mixture is stirred for about 2 hours. In one embodiment, for the workup, the reaction mixture is added to a pre-cooled acidic solution. In another embodiment, the acidic solution is an aqueous citric acid solution. In one embodiment, after the addition, the aqueous phase is separated and discarded. In one embodiment, the solvent is removed from the organic phase, by vacuum distillation at about 50° C. In one embodiment, the isolated residue is 3α,7α-ditrimethylsilyloxy-5β-chol-6-en-24-oic acid methyl ester (3) is used 'as is' in the next step. Alternatively, compound 3 can be purified before Step 3.

Step 3

Step 3 is the reaction of 3α,7-ditrimethylsilyloxy-5β-chol-6-en-24-oic acid methyl ester (3) with $CH_3CHO$ to form 3α-hydroxy-6-ethylidene-7-keto-5β-cholan-24-oic acid methyl ester (4). In one embodiment, step 3 is carried out in a polar aprotic solvent at a temperature at about –50° C. to about –70° C. in the presence of $BF_3$. In one embodiment, the polar aprotic solvent is dichloromethane. In one embodiment, the $BF_3$ is a 16% wt. solution in acetonitrile. In another embodiment, the reaction is carried out in the presence of $BF_3$ diethyl etherate. In one embodiment, the temperature is about –60° C. to about –65° C.

In one embodiment, compound 3 in a polar aprotic solvent is charged into an inert reactor. In another embodiment, the polar aprotic solvent is the residual solvent from the previous step (e.g., THF). In one embodiment, THF is added to help distill off residual water and diisopropylamine. At a maximum temperature of about 50° C., residual amounts of the polar aprotic solvent are distilled off under vacuum. The water content in the residue containing compound 3 is limited to <0.5% (Karl Fischer titration). The residue containing compound 3 is then dissolved in a polar aprotic solvent and pre-cooled to about –50° C. to about –70° C. The polar aprotic solvent is dichloromethane. In another embodiment, residue containing compound 3 in the polar aprotic solvent is pre-cooled to about –60° C. to about –65° C. Acetaldehyde ($CH_3CHO$) is added. A polar aprotic solvent and boron trifluoride ($BF_3$) solvated complex are charged into a separate reactor and then cooled to about –50° C. to about –70° C. In another embodiment, the polar aprotic solvent is dichloromethane. In another embodiment, the boron trifluoride solvated complex is a boron trifluoride acetonitrile complex. The temperature of the $BF_3$ solution is about –60° C. to about –65° C. The solution containing compound 3 and acetaldehyde is added to the BF₃ solution at about −60° C. to about −65° C. In another embodiment, the solution containing compound 3 and acetaldehyde is dry. In one embodiment, the reaction mixture is stirred for about two hours at about −60° C. to about −65° C., heated up to about 23° C. to about 28° C., stirred for another about 2 hours and cooled to about 2° C. to about 10° C. for the hydrolysis/work-up. In one embodiment, the total time for addition and stirring is about 4 hours. In one embodiment, for the workup, the cooled solution from the reactor is added to a pre-cooled aqueous basic solution. In another embodiment, the aqueous basic solution is about 50% wt. sodium hydroxide (NaOH; caustic soda). In one embodiment, the phases are separated and the (lower) organic layer is transferred to a separate reactor. In one embodiment, from the organic layer, the solvent is removed by distillation at not more than (NMT) 50° C. as far as possible. In one embodiment, the residue comprises 3α-hydroxy-6-ethylidene-7-keto-5β-cholan-24-oic acid methyl ester (4) and some remaining acetonitrile and dichloromethane. It is understood that step 4 may form E/Z-3α-hydroxy-6-ethylidene-7-keto-5β-cholan-24-oic acid methyl ester (4A). The product of Step 3 is taken on directly to Step 4.

Step 4

Step 4 is the reaction of 3α-hydroxy-6-ethylidene-7-keto-5β-cholan-24-oic acid methyl ester (4) with NaOH to form E-3α-hydroxy-6-ethylidene-7-keto-5β-cholan-24-oic acid (5). In one embodiment, prior to step 4, the residue from step 3 is heated to about 45° C. to about 60° C. to remove residual amounts of solvent. In one embodiment, the temperature is about 49° C. to about 55° C. In one embodiment, the ester hydrolysis reaction reacting 3α-hydroxy-6-ethylidene-7-keto-5β-cholan-24-oic acid methyl ester (4) with NaOH is carried out at about 20° C. to about 25° C. in methanol, water, and a NaOH solution.

In one embodiment, reacting 3α-hydroxy-6-ethylidene-7-keto-5β-cholan-24-oic acid methyl ester (4) is charged into a reactor. In another embodiment, the reactor is inert, e.g., under a nitrogen or argon atmosphere. At a temperature of NMT 50° C., residual amounts of solvent are distilled off under vacuum. In one embodiment, the residue is heated up to about 45° C. to about 60° C. In another embodiment, the residue is heated up to about 49° C. to about 55° C. In another embodiment, the residue from Step 3 (compound 4) is dissolved in methanol and water and an aqueous basic solution. In another embodiment, the aqueous basic solution is about 50% wt. sodium hydroxide (NaOH; caustic soda). The ester hydrolysis reaction of Step 4 is carried out at about 20° C. to about 60° C. and stirred until the hydrolysis reaction is complete. In one embodiment, the ester hydrolysis is carried out at about 20° C. to about 25° C. The pH of the reaction mixture is checked to verify it is >12. If the pH is <12, then additional NaOH is added. The reaction mixture is diluted with water and the temperature is adjusted to about 20° C. to about 35° C. In another aspect, the reaction mixture is diluted with water and the temperature is adjusted to about 25° C. to about 35° C. In one embodiment, for the workup, the phases are separated and the lower product-rich aqueous layer is transferred into a separate reactor and the organic layer is discarded. In one embodiment, the pH of the product-rich aqueous phase is adjusted with aqueous acid in the presence of ethyl acetate. In another embodiment, the acid is an aqueous citric acid solution. In one embodiment, the phases are separated and the upper product-rich organic layer is retained and the lower aqueous layer is discarded. In one embodiment, ethyl acetate is distilled off from the organic layer and replaced with ethyl acetate. In one embodiment, the distillation is repeated until the water content of the distillate is NMT 1% or until a constant boiling point is reached. In one embodiment, the resulting product suspension is cooled to about 10° C. to about 30° C. and isolated and washed with ethyl acetate. In one embodiment, the resulting product is isolated by filtration (e.g. filter nutche, centrifuge, etc). In another embodiment, the resulting product suspension containing compound 5 is cooled to about 20° C. to about 25° C. In one embodiment, the drying of the resulting product is done under vacuum (e.g, cone dryer, paddle dryer, tray dryer, etc.) at about 60° C.

In one embodiment, crude E-3α-hydroxy-6-ethylidene-7-keto-5β-cholan-24-oic acid (5) is crystallized using ethanol. In one embodiment, ethanol and crude compound 5 are charged into reactor. In another embodiment, the reactor is inert. In one embodiment, to dissolve the crude compound 5, the mixture is heated to reflux. In one embodiment, mixture is cooled in a controlled cooling ramp to about 15° C. to about 20° C. In one embodiment, the crystalline compound 5 is isolated using a centrifuge and then washed with ethyl acetate. In one embodiment, drying of crystalline compound 5 is done under vacuum (e.g, cone dryer, paddle dryer, tray dryer, etc.) and at about 60° C. A sample can be taken to measure assay, purity, and moisture of the purified compound 5. In one embodiment, purified compound 5 contains both E and Z isomers of 3α-hydroxy-6-ethylidene-7-keto-5β-cholan-24-oic acid. In one embodiment, the E to Z ratio is about 99:1, about 98:2, about 95:5, about 90:10, about 85:15, about 80:20, about 75:25, about 70:30, about 65:35, about 60:40, about 55:45, or about 50:50. See Example 2 for full details regarding the identification and characterization of purified compound 5.

Step 4 can also be carried out starting with a compound that is a mixture of E/Z isomer. For example, Step 4 is the reaction of E/Z-3α-hydroxy-6-ethylidene-7-keto-5β-cholan-24-oic acid methyl ester (4A) with NaOH to form E/Z-3α-hydroxy-6-ethylidene-7-keto-5β-cholan-24-oic acid (5A). In one embodiment, prior to step 4, the residue from step 3 is heated about 45° C. to about 60° C. to remove residual amounts of solvent. In one embodiment, the temperature is about 49° C. to about 55° C. In one embodiment, the ester hydrolysis reaction involving reacting E/Z-3α-hydroxy-6-ethylidene-7-keto-5β-cholan-24-oic acid methyl ester (4A) with NaOH is carried out at about 20° C. to about 25° C. in methanol, water, and a NaOH solution. In one embodiment, the NaOH solution is a 50% wt. aqueous solution.

In one embodiment, reacting E/Z-3α-hydroxy-6-ethylidene-7-keto-5β-cholan-24-oic acid methyl ester (4A) is charged into a reactor. In another embodiment, the reactor is inert, e.g., under a nitrogen or argon atmosphere. At a temperature of NMT 50° C., residual amounts of solvent are distilled off under vacuum. In one embodiment, the residue is heated up to about 45° C. to about 60° C. In one embodiment, the temperature is about 49° C. to about 55° C. In one embodiment, the residue from step 3 (compound 4A) is dissolved in methanol and water and an aqueous basic solution. In another embodiment, the aqueous basic solution is about 50% wt. sodium hydroxide (NaOH; caustic soda). The ester hydrolysis reaction of step 4 is carried out at about 20° C. to about 60° C. and stirred until the hydrolysis reaction is complete. In one embodiment, the ester hydrolysis is carried out at about 20° C. to about 25° C. The pH of the reaction mixture is checked to verify it is >12. If the pH is <12, then additional NaOH is added. The reaction mixture is diluted with water and the temperature is adjusted to about 25° C. to about 35° C. In one embodiment, for the workup, the phases are separated and the lower product-rich aqueous layer is transferred into a separate reactor and the organic layer is discarded. In one embodiment, the pH of the product-rich aqueous is adjusted with aqueous acid in the presence of ethyl acetate. In another embodiment, the acid is an aqueous citric acid solution. In one embodiment, the phases are separated and the upper product-rich organic layer is retained and the lower aqueous layer is discarded. In one embodiment, ethyl acetate is distilled off from the organic layer and replaced with ethyl acetate. In one embodiment, the distillation is repeated until the water content of the distillate is NMT 1% or until a constant boiling point is reached. In one embodiment, the resulting product suspension is cooled to about 10° C. to about 30° C. and isolated and washed with ethyl acetate. In one embodiment, the resulting product is isolated by filtration (e.g. filter nutche, centrifuge, etc.). In another embodiment, the resulting product suspension containing compound 5A is cooled to about 20° C. to about 25° C. In one embodiment, drying of the resulting product is done under vacuum (e.g, cone dryer, paddle dryer, tray dryer, etc.) at about 60° C. Compound 5A can be carried on without purification to Step 5.

In one embodiment, crude E/Z-3α-hydroxy-6-ethylidene-7-keto-5β-cholan-24-oic acid (5A) is crystallized using ethanol. In one embodiment, ethanol and crude compound 5A are charged into reactor. In another embodiment, the reactor is inert. In one embodiment, to dissolve the crude compound 5A, the mixture is heated to reflux. In one embodiment, mixture is cooled in a controlled cooling ramp to about 15° C. to about 20° C. In one embodiment, the crystalline compound 5A is isolated using a centrifuge and then washed with ethyl acetate. In one embodiment, drying of crystalline compound 5A is done under vacuum (e.g, cone dryer, paddle dryer, tray dryer, etc.) and at about 60° C. In one embodiment, the isolated crystalline product of step 4 is compound 5.

Alternative Step 4

Compound 5 can be prepared according to an alternative method. In one embodiment, compound 4 is charged into the inert reactor. At about 50° C. (maximum) residual amounts of solvent (e.g., acetonitrile, dichloromethane) may be distilled off under vacuum. The residue is dissolved in methanol and cooled. Water and caustic soda (50% weight NaOH) are added. In one embodiment, the reaction mixture is stirred for about four hours at about 20° C. to about 25° C. The solution is diluted with water and toluene is added. After stirring, the phases are separated and the lower product-rich aqueous layer is transferred into the inert reactor. The organic layer is discarded. The pH of the product rich aqueous layer is adjusted with aqueous citric acid in the presence of ethyl acetate. The phases are separated and the lower aqueous layer is discarded. The organic layer is transferred into the inert reactor. From the organic layer ethyl acetate is distilled off and replaced with ethyl acetate. In one embodiment, this operation is repeated until the water content of the distillate is not more than about 1% or until a constant boiling point is reached. The resulting product suspension is cooled to about 20° C. to about 25° C., and compound 5 is isolated and washed with ethyl acetate in the inert centrifuge. Drying is done in the tumble dryer under vacuum and approximately 60° C.

This alternative Step 4 can also be carried out starting with a compound that is a mixture of E/Z isomer. In one embodiment, compound 4A is charged into the inert reactor. At about 50° C. (maximum) residual amounts of solvent (e.g., acetonitrile, dichloromethane) may be distilled off under vacuum. The residue is dissolved in methanol and cooled. Water and caustic soda (50% wt, NaOH) are added. In one embodiment, the reaction mixture is stirred for approximately four hours at about 20° C. to about 25° C. The solution is diluted with water and toluene is added. After stirring, the phases are separated and the lower product-rich aqueous layer is transferred into the inert reactor. The organic layer is discarded. The pH of the product rich aqueous layer is adjusted with aqueous citric acid in the presence of ethyl acetate. The phases are separated and the lower aqueous layer is discarded. The product-rich organic layer is transferred into the inert reactor. From the organic layer ethyl acetate is distilled off and replaced with ethyl acetate. In one embodiment, this operation is repeated until the water content of the distillate is not more than about 1% or until a constant boiling point is reached. The resulting product suspension is cooled to 20° C. to 25° C., and compound 5A is isolated and washed with ethyl acetate in the inert centrifuge. Drying is done in the tumble dryer under vacuum and approximately 60° C.

Step 5

Step 5 is the reaction of E-3α-hydroxy-6-ethylidene-7-keto-5β-cholan-24-oic acid (5) with Pd/C and hydrogen gas to initially form 3α-hydroxy-6β-ethyl-7-keto-5β-cholan-24-oic acid, which undergoes base-mediated isomerization to form 3α-hydroxy-6α-ethyl-7-keto-5β-cholan-24-oic acid (6). Step 5 can be carried out in one phase (hydrogenation and isomerization together) or in two discrete phases (hydrogenation followed by isomerization). In one embodiment, Step 5 is carried out at a temperature at about 90° C. to about 110° C. and at a pressure at about 0.5 to about 5 bars. In one embodiment, during workup, the organic phase of the reaction mixture is treated with activated carbon. In one embodiment, the pressure is about 0.5 to about 5.5 bars. In another embodiment, the pressure is about 5 bars. In another embodiment, the hydrogenation is performed at a pressure of about 0.5 bar to about 5.5 bar, e.g 0.6 bar, 0.7 bar, 0.8 bar, 0.9 bar, 1.0 bar, 1.2 bar, 1.4 bar, 1.6 bar, 1.8 bar, 2.0 bar, 2.2 bar, 2.4 bar, 2.6 bar, 2.8 bar, 3.0 bar, 3.2 bar, 3.4 bar, 3.6 bar, 3.8 bar, 4.0 bar, 4.2 bar, 4.4 bar, 5.0 bar, 5.2 bar, as well as any increment in between. In one embodiment, the hydrogenation reaction mixture is allowed to stir for about 1 hour. In one embodiment, E-3α-hydroxy-6-ethylidene-7-keto-5β-cholan-24-oic acid (5) in the presence of Pd/C and hydrogen gas is heated to about 100° C. and stirred for about 2 hours to about 5 hours. In one embodiment, E-3α-hydroxy-6-ethylidene-7-keto-5β-cholan-24-oic acid (5) in the presence of Pd/C and hydrogen gas is heated to about 100° C. and stirred for about 3 hours.

In one embodiment, E-3α-hydroxy-6-ethylidene-7-keto-5β-cholan-24-oic acid (5) in the presence of Pd/C and hydrogen gas is carried out in the presence of a basic solution. In one embodiment, the basic solution is water containing a 50% wt. sodium hydroxide (NaOH; caustic soda) solution. After the hydrogenation reaction, the reaction mixture is heated up to about 100° C. (to carry out the isomerisation of the C-6 position from beta configuration to alpha configuration) and then cooled to about 40° C. to about 50° C. For the workup, the Pd/C is filtered off. In one embodiment, to the filtrate, n-butyl acetate and an acid are added. In another embodiment, the acid is hydrochloric acid (HCl). The aqueous phase is separated and discarded after checking the pH-value to make sure that it was acidic. The product-rich organic phase is treated with activated carbon. In one embodiment, the activated carbon is filtered off and the resulting product-rich filtrate is concentrated by distillation and the resulting product suspension is cooled to about 10° C. to about 30° C. In another embodiment, the product suspension is cooled to about 15° C. to about 20° C. The suspension containing compound 6 is isolated and washed with n-butyl acetate. Compound 6 is filtered using a pressure filter. In one embodiment, drying is done in the pressure filter under vacuum at about 80° C.

In one embodiment in Step 5, E-3α-hydroxy-6-ethylidene-7-keto-5β-cholan-24-oic acid (5), water, NaOH solution (e.g. 50% wt.), and Pd/C are mixed at about 5 bar of $H_2$ gas and at a temperature at about 100° C. to about 105° C. until $H_2$ uptake has ceased. The reaction mixture is cooled to about 40° C. to about 50° C. and Pd/C is filtered off. Then n-butyl acetate and HCl are added to the solution containing compound 6. In one embodiment, the aqueous phase is separated and discarded. The organic phase containing compound 6 is treated with activated carbon. The carbon is filtered off and the filtrate is moved to another reactor where it is concentrated by distillation, and then the suspension is cooled to about 5° C. to about 20° C. In one embodiment, compound 6 is isolated via filtration and the filtrate is dried on the pressure filter under vacuum at about 80° C.

Step 5 can also be carried out starting with a compound that is a mixture of E/Z isomer. For example, Step 5 is the reaction of E/Z-3α-hydroxy-6-ethylidene-7-keto-5β-cholan-24-oic acid (5A) with Pd/C and hydrogen gas and heat to form 3α-hydroxy-6α-ethyl-7-keto-5β-cholan-24-oic acid (6). Step 5 can be carried out in one phase (hydrogenation and isomerization together) or in two discrete phases (hydrogenation, followed by isomerization). In one aspect, step 5 is carried out at a temperature at about 90° C. to about 110° C. and at a pressure at about 4 to about 5 bars. In one embodiment, during workup, the organic phase of the reaction mixture is treated with activated carbon. In one embodiment, the pressure is about 4.5 to about 5.5 bars. In another embodiment, the pressure is about 5 bars. In one embodiment, the hydrogenation reaction mixture is allowed to stir for about 1 hour. In one embodiment, reacting E/Z-3α-hydroxy-6-ethylidene-7-keto-5β-cholan-24-oic acid (5A) with Pd/C and hydrogen gas is heated to about 100° C. and stirred for about 2 hour to about 5 hours. In one embodiment, reacting E/Z-3α-hydroxy-6-ethylidene-7-keto-5β-cholan-24-oic acid (5A) with Pd/C and hydrogen gas is heated to about 100° C. and stirred for about 3 hours.

In one embodiment, reacting E/Z-3α-hydroxy-6-ethylidene-7-keto-5β-cholan-24-oic acid (5A) with Pd/C and hydrogen gas is carried out in the presence of a basic solution. In one embodiment, the basic solution is water and a 50% wt. sodium hydroxide (NaOH; caustic soda) solution. After the hydrogenation reaction, the reaction mixture is heated up to about 100° C. (to carry out the isomerisation of the C-6 position from beta configuration to alpha configuration) and then cooled to about 40° C. to about 50° C. For the workup, the Pd/C is filtered off. In one embodiment, to the filtrate, n-butyl acetate and an acid are added. In another embodiment, the acid is hydrochloric acid (HCl). The aqueous phase is separated and discarded after checking the pH-value to make sure that it was acidic. The product-rich organic phase is treated with activated carbon. In one embodiment, the activated carbon is filtered off and the resulting product-rich filtrate is concentrated by distillation and the resulting product suspension is cooled to about 10° C. to about 30° C. In another embodiment, the product suspension is cooled to about 15° C. to about 20° C. The suspension containing compound 6 is isolated and washed with n-butyl acetate. Compound 6 is filtered using a pressure filter. In one embodiment, drying is done in the pressure filter under vacuum at about 80° C.

In one embodiment in Step 5, E/Z-3α-hydroxy-6-ethylidene-7-keto-5β-cholan-24-oic acid (5A), water, NaOH solution (e.g. 50% wt.), and Pd/C are mixed at about 5 bar of $H_2$ gas and at a temperature at about 100° C. to about 105° C. until $H_2$ uptake has ceased. The reaction mixture is cooled to about 40° C. to about 50° C. and Pd/C is filtered off. Then n-butyl acetate and HCl are added to the solution containing compound 6. In one embodiment, the aqueous phase is separated and discarded. The product rich organic phase is treated with activated carbon. The carbon is filtered off and the filtrate is moved to another reactor where it is concentrated by distillation, and then the product suspension is cooled to about 5° C. to about 20° C. In one embodiment, compound 6 is isolated via filtration and the filtrate is dried on the pressure filter under vacuum at about 80° C.

In another embodiment, the hydrogenation/isomerization reactions described above to prepare compound 6 are carried out in two phases (starting from compound 5 or compound 5A). First, the hydrogenation is carried out at about 4 to 5 bars and at about 20° C. to about 40° C. and then second, the reaction mixture is heated to about 95° C. to about 105° C. Heating the reaction mixture isomerizes the ethyl group at the 6-position from the initially formed 6-beta configuration to the desired 6-alpha configuration. The reaction mixture is heated until the isomerization is complete.

Step 6

Step 6 is the reaction of 3α-hydroxy-6α-ethyl-7-keto-5β-cholan-24-oic acid (6) with $NaBH_4$ to form crystalline obeticholic acid. In one embodiment, Step 6 is carried out at a temperature at about 85° C. to about 110° C. in a basic aqueous solution. In one embodiment, the temperature is about 90° C. to about 95° C. In one embodiment, the basic aqueous solution is an aqueous NaOH solution. In one embodiment, the basic aqueous solution is a mixture of 50% wt. NaOH solution and water. In one embodiment, the reaction mixture of compound 6 and $NaBH_4$ was stirred for about 3 hours to about 5 hours. In another embodiment, the reaction mixture was stirred for about 4 hours.

For the workup, after the reaction is complete, the mixture is cooled to about 80° C. and transferred to a cooled reactor. In one embodiment, at about 20° C. to about 60° C., n-butyl acetate and an acid are added. In one embodiment, the temperature is about 40° C. to about 45° C. In another embodiment, the acid is citric acid. The aqueous phase is separated and discarded after checking the pH-value to make sure that it was acidic. The product-rich organic phase is concentrated by distillation. In one embodiment, n-butyl acetate is added to the residue and distilled off again. In one embodiment, n-butyl acetate is added again to the residue and then is slowly cooled down. In another embodiment the residue is seeded at about 50° C. In another embodiment, after crystallization has occurred, the mixture is heated to 52° C. and then slowly cooled down to about 15° C. to about 20° C. In another embodiment, the residue is cooled to about 15° C. to about 20° C. In one embodiment, the resulting obeticholic acid is washed with n-butyl acetate. In one embodiment, the obeticholic acid is isolated and washed with n-butyl acetate (e.g, in a pressure filter). In another embodiment, the pressure filter is inert. The crystalline product is dried under vacuum at about 60° C. and is identified as Form A characterized by an X-ray diffraction pattern substantially similar to that set forth in FIG. 41 including characteristic peaks at about 5.0 and 5.3 degrees 2-Theta. In one embodiment, the resulting crystalline obeticholic acid is isolated from organic solvent (e.g., heptane) and is characterized by an X-ray diffraction pattern including characteristic peaks at about 5.0 and 5.3 degrees 2-Theta. In one embodiment, the crystalline obeticholic acid Form A is characterized by an X-ray diffraction pattern substantially similar to that set forth in FIG. 41. See example 3 for full details regarding the identification and characterization of crystalline obeticholic acid Form A.

Step 7

Step 7 is the conversion of crystalline obeticholic acid Form A to obeticholic acid Form 1. In one embodiment, Step 7 comprises the step of dissolving crystalline obeticholic acid Form A in aqueous NaOH solution and adding HCl.

In one embodiment, crystalline obeticholic acid is dissolved in water and caustic soda solution (50% wt.) at about 20° C. to about 50° C. In one embodiment, the temperature is about 30° C. to about 40° C. In one embodiment, the crystalline obeticholic acid is Form A. In one embodiment, the resulting solution of crystalline obeticholic acid Form A is added to diluted acid at about 20° C. to about 50° C. In another embodiment, the temperature is about 30° C. to about 40° C. In another embodiment, the acid is hydrochloric acid (e.g., 37%). In one embodiment, the 37% hydrochloric acid solution is diluted with water to less than about 1% by volume. In one embodiment, the 37% hydrochloric acid solution is diluted with water to about 0.7% by volume. In one embodiment, the suspension of product in the diluted acid is stirred for about 30 minutes at about 20° C. to about 50° C. In one embodiment, the temperature is about 30° C. to about 40° C. In one embodiment, obeticholic acid Form 1 is isolated and washed with water (e.g., in the pressure filter) at NMT about 20° C. In one embodiment, obeticholic acid Form 1 is isolated and washed with water (e.g., in the pressure filter) at NMT about 20° C. In another embodiment, the pressure filter is inert. The product is dried on the pressure filter under vacuum at a temperature of NMT about 50° C.

The process of the present application utilizes a crystalline intermediate in the preparation of obeticholic acid Form 1, which unexpectedly led to significant improvements in the overall preparation and purity of the final product. Specifically, Step 6 of the synthesis produces a novel crystalline form of obeticholic acid. The production of this crystalline form leads to substantially pure obeticholic acid Form 1.

The process of the present application is an improvement over the processes disclosed in the prior art. The preparation of obeticholic acid is disclosed in U.S. Publication No. 2009/0062526 A1 (herein referred to as the "'526 publication"), U.S. Pat. No. 7,138,390 (referred to herein as the "'390 patent"), and WO 2006/122977 (referred to herein as the "'977 application").

The process to prepare obeticholic acid in the '390 patent (referred to herein as the "'390 process") is depicted in Scheme 3 (R is ethyl):

Scheme 3

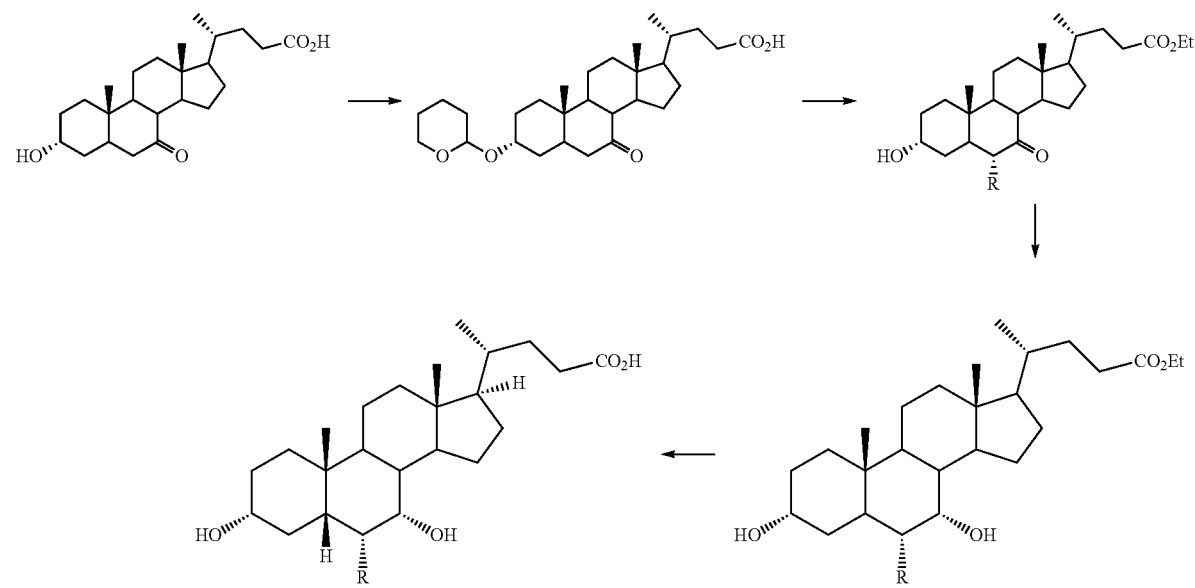

Even though this process comprises a few steps, it presents a series of drawbacks. In all of the steps, the reaction products are purified on a chromatographic column, namely a very expensive separation method that cannot be used on an industrial scale. Moreover, the reaction yield in step 2 is extremely low (12-13%) with a considerable decrease in the global yield, which is lower than 3.5%. This process also uses hexamethylenphosphonamide as reactant, which is a known carcinogenic agent.

The process to prepare obeticholic acid in the '977 application is depicted in Scheme 4.

Scheme 4
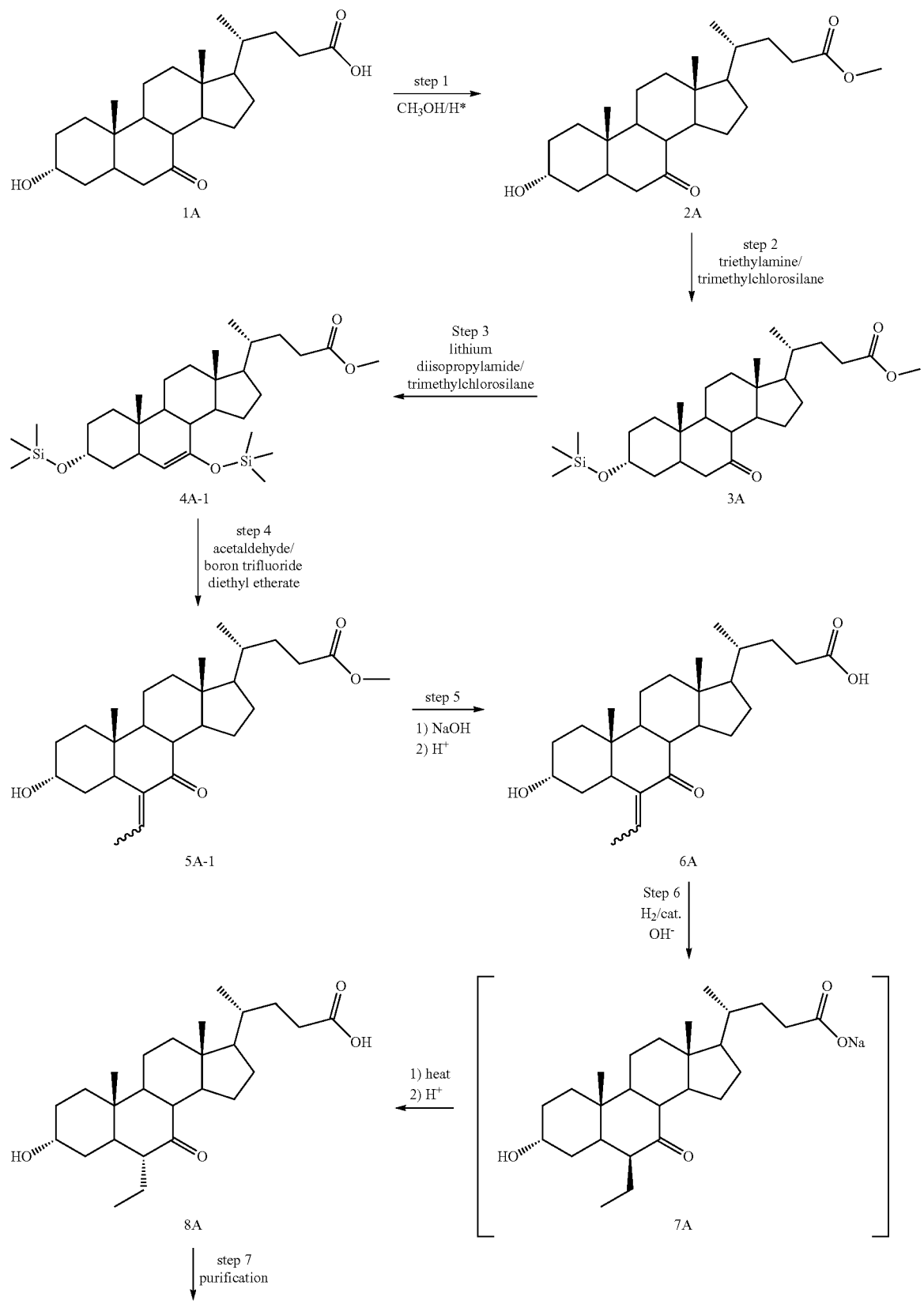

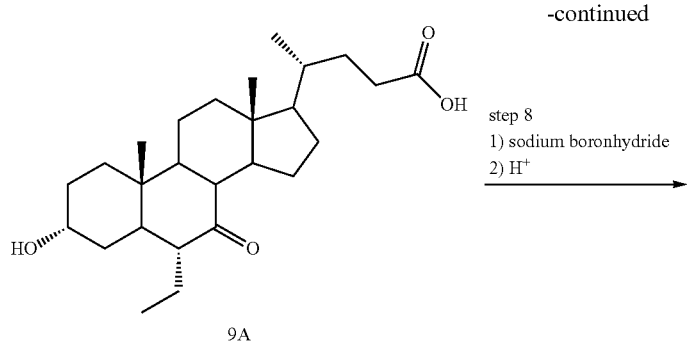

9A

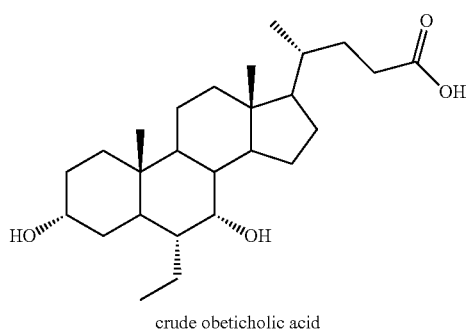

crude obeticholic acid step 8
1) sodium boronhydride
2) H$^+$ step 9
purification

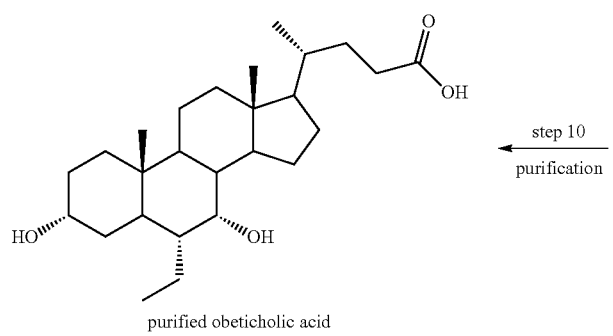

purified obeticholic acid

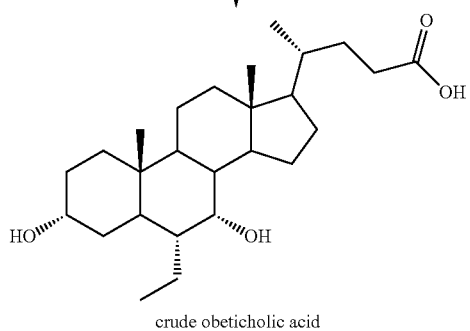

crude obeticholic acid step 10
purification

The '977 process to prepare obeticholic acid is an 8-step synthetic process which includes one purification step (step 7) followed by 2 additional purification steps. There are a significant number of differences between the '977 process and the process of the present application. Table A below describes at least some of the differences between the two processes:

TABLE A

Differences Between '977 Process and Process of the Application

| Synthetic Step | '977 Process | Process of the application | Advantages of the Change |
|---|---|---|---|
| Step 1 | Methanesulfonic acid | Sulfuric acid | Scale and safety (mesylate) |
|  | 30% ammonia (aqueous) | NaOH (aqueous) | Scale-up |
|  | No purification/treatment | Use of activated carbon treatment | Improve purity/color |
| Step 2 (Process of application step 2 combines '977 Process Steps 2 and 3) | Triethylamine | Lithium diisopropylamide (LDA) | LDA is a suitable alternative reagent for this step |
|  | Toluene | Tetrahydrofuran (THF) | THF is a suitable alternative reagent for this step |
|  | No acidic quench | Quench into citric acid solution | Scale-up |
| Step 3 (Process of application step 3 same as '977 Step 4) | Boron trifluoride diethyl etherate | Boron trifluoride acetonitrile complex | Safety concerns of handling etherate (T4 emission controls not needed) |
| Step 4 (Process of application step 4 same as '977 Step 5) | Toluene | Methanol | Safety (toluene); scale |
|  | Phosphoric acid (aqueous) quench | Citric acid (aqueous) quench | Scale-up |
|  | No purification/treatment | Crystallization step is part of workup | Improve purity |

TABLE A-continued

Differences Between '977 Process and Process of the Application

| Synthetic Step | Changes '977 Process | Process of the application | Advantages of the Change |
|---|---|---|---|
| Step 5 (Process of application step 5 combines '977 Process steps 6 and 7) | Phosphoric acid (aqueous) quench | Hydrochloric acid (aqueous) quench | Scale up |
| | No purification/treatment | Use of activated carbon treatment | Improve purity/color |
| | Purification carried out as Step 7 | Crystallization step is part of workup | Scale up |
| Step 6 (Process of application step 6 combines '977 Process steps 8 and 9) | Dichloromethane | n-Butylacetate | Safety (dichloromethane) |
| | Phosphoric acid (aqueous) quench | Citric acid (aqueous) quench | Scale-up |
| | Purification carried out as Step 9 - using dichloromethane/ethyl acetate | Crystallization step is part of workup - using n-butylacetate | Scale and safety (dichloromethane) |
| Step 7 (Process of application step 7 same as '977 step 10) | Ammonia solution | NaOH solution | Scale-up |
| | Phosphoric acid (aqueous) quench | Hydrochloric acid (aqueous) quench | Scale-up |

The differences in the process of the present application as compared to the '977 process result in significant improvements to the process, including improvements related to scale-up optimization, safety, as well as purity and improvements in the overall process. The purity of obeticholic acid produced by the processes of the present application is substantially pure. Specifically, obeticholic acid produced by the processes of the present application is substantially more pure than obeticholic acid produced by processes in the prior art, including the '390 process and the '977 process. For example, a comparison of the results presented in the Certificate of Analysis of obeticholic acid produced by a process of the present application and obeticholic acid produced by the '977 process are shown in the Table B below. The percentages of impurities were determined using HPLC methods.

TABLE B

Comparison of Impurities of Obeticholic Acid Generated from Process of the Application and '977 Process

| Parameter | Specification limit | Process of the application | '977 process |
|---|---|---|---|
| Water (KF) | NMT 4.5% | 1.0% | 2.1% |
| Impurity 1 and Impurity 4 | NMT 0.15% | <0.05% | <0.05% |
| Impurity 2 | NMT 0.15% | <0.05% | <0.1% |
| Impurity 3 | NMT 0.15% | <0.05% | <0.1% |
| Impurity 5 | NMT 3.0% | 0.2% | 1.0% |
| Impurity 6 | NMT 0.15% | <0.05% | <0.05% |

Impurity 1 is 6-ethylursodeoxycholic acid.
Impurity 2 is 3α-hydroxy-6α-ethyl-7-cheto-5β-cholan-24-oic acid.
Impurity 3 is 6β-ethylchenodeoxycholic acid.
Impurity 4 is 3α,7α-dihydroxy-6-ethyliden-5β-cholan-24-oic acid.
Impurity 5 is chenodeoxycholic acid.
Impurity 6 is 3α(3α,7α-dihydroxy-6α-ethyl-5β-cholan-24-oyloxy)-7α-hydroxy-6α-ethyl-5β-cholan-24-oic acid (6ECDCA dimer).
NMT refers to "not more than".

Crystalline Obeticholic Acid as a Synthetic Intermediate

Obeticholic acid is currently being developed as an active pharmaceutical ingredient as a non-crystalline solid. In order to facilitate the development of obeticholic acid, an initial crystallization and polymorphism study was carried out in order to determine if crystalline forms were accessible and if so, if they were suitable for development. After a preliminary solubility screen designed to give a better understanding of the behavior of the material in various solvents, it appeared that the material had a tendency to form gels and could possibly be crystallized. An extensive polymorph screen was then carried out, exposing the material to a large range of solvents and crystallization conditions in order to identify and characterize as many relevant polymorphs as possible. Five different solid forms were found during this screen.

Three forms (A, C, and D) of obeticholic acid were mixed hydrates/solvates containing 0.25 mol eq of water and varying amounts of a range of organic solvents. On heating, these solids lost crystallinity and the solvent at the same time and unfortunately, these solvated forms were not suitable for further development as a pharmaceutical ingredient due to their low melting temperatures and high solvent content. It is also noted that similar "unsuitable" forms of this type exist. For example, a low-melting solvated form was found in later experiments, as well as single crystals of another form, which was shown to be a monohydrate/anisole solvate by SCXRD (Single crystal X-ray diffraction).

The two remaining forms were higher melting and potentially more promising, but one of them (Form G) could not be reproduced on scale-up, nor repeated despite many attempts. The difficulty in producing this form alone makes it unsuitable for development. The remaining non-solvated Form F was reproducibly prepared, but it required extensive recrystallization procedures and the use of nitromethane, which is a toxic solvent and may detonate if sensitized by amines, alkalis, strong acids, or high temperatures or adiabatic compression. Concerns about the residual levels of nitromethane deemed Form F also to be unsuitable for development. Crystalline obeticholic acid Form I was also identified.

The overall results of the initial crystallization and polymorph study revealed that the material could form various forms of crystalline materials, but none of the crystalline materials or forms were considered suitable for development.

It was not until much later that it was discovered the importance of producing crystalline obeticholic acid as an intermediate in the penultimate step of the process of the present application. Crystalline obeticholic acid could readily be isolated on large scale using the process of the application. This crystalline obeticholic acid was determined to be consistent with Form A from the initial crystallization and polymorph study. The formation, ease of isolation, and highly pure crystalline obeticholic acid produced as a synthetic intermediate in step 7 in the process of the present application is indeed critical to the preparation of substantially pure obeticholic acid.

In one embodiment, the present invention relates to a crystalline obeticholic acid Form A characterized by an X-ray diffraction pattern including characteristic peaks at about 5.0 and 5.3 degrees 2-Theta. In one embodiment, the X-ray diffraction pattern includes characteristic peaks at about 5.0, 5.3 and 7.7 degrees 2-Theta. In one embodiment, the X-ray diffraction pattern includes characteristic peaks at about 5.0, 5.3, 7.7, and 10.0 degrees 2-Theta. In one embodiment, the X-ray diffraction pattern includes characteristic peaks at about 5.0, 5.3, 7.7, 10.0, and 11.0 degrees 2-Theta. In one embodiment, the X-ray diffraction pattern includes characteristic peaks at about 5.0, 5.3, 7.7, 10.0, 11.0, and 12.4 degrees 2-Theta. In one embodiment, the X-ray diffraction pattern includes characteristic peaks at about 5.0, 5.3, 7.7, 10.0, 11.0, 12.4, and 14.9 degrees 2-Theta. In one embodiment, the present invention relates to a crystalline obeticholic acid Form A characterized by an X-ray diffraction pattern substantially similar to that set forth in FIG. 41. In one embodiment, the X-ray diffraction pattern is collected on a diffractometer using Cu Kα radiation (40 kV, 40 mA).

In one embodiment, the present invention relates to a crystalline obeticholic acid, wherein said crystalline obeticholic acid is Form A and has a purity greater than about 90%. In one embodiment, the purity of said crystalline obeticholic acid Form A is determined by HPLC. In one embodiment, the present invention relates to a crystalline obeticholic acid Form A, or a pharmaceutically acceptable salt, solvate or amino acid conjugate thereof. In one embodiment, the solvate is a n-butyl solvate. In one embodiment, the purity is greater than about 92%. In one embodiment, the purity is greater than about 94%. In one embodiment, the purity is greater than about 96%. In one embodiment, the purity is greater than about 98%. In one embodiment, the purity is greater than about 99%.

In one embodiment, the present invention relates to a crystalline obeticholic acid, wherein said crystalline obeticholic acid is Form A and has a potency greater than about 90%. In one embodiment, the purity of said crystalline obeticholic acid Form A is determined by HPLC and/or other analytical procedures known in the art. In one embodiment, the present invention relates to a crystalline obeticholic acid Form A, or a pharmaceutically acceptable salt, solvate or amino acid conjugate thereof. In one embodiment, the solvate is a hydrate. In one embodiment, the potency is greater than about 92%. In one embodiment, the potency is greater than about 94%. In one embodiment, the potency is greater than about 96%. In one embodiment, the potency is greater than about 98%. In one embodiment, the potency is greater than about 99%.

In one embodiment, the present invention relates to a crystalline obeticholic acid Form A that contains a total of less than about 4% of one or more impurities selected from 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyliden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid. In one embodiment, the total impurities is less than about 3.8%. In one embodiment, the total impurities is less than about 3.6%.

In one embodiment, the present invention relates to a crystalline obeticholic acid Form C characterized by an X-ray diffraction pattern including characteristic peaks at about 4.2, 6.4, 9.5, 12.5, and 16.7 degrees 2-Theta. In one embodiment, the X-ray diffraction pattern includes characteristic peaks at about 4.2, 6.4, 9.5, 12.5, 12.6, 15.5, 15.8, 16.0, 16.7 and 19.0 degrees 2-Theta. In one embodiment, the X-ray diffraction pattern includes characteristic peaks at about 4.2, 6.4, 8.3, 9.5, 11.1, 12.2, 12.5, 12.6, 15.5, 15.8, 16.0, 16.3, 16.7, 18.6 and 19.0 degrees 2-Theta. In one embodiment, the X-ray diffraction pattern includes characteristic peaks at about 4.2, 6.4, 8.3, 9.5, 11.1, 12.2, 12.5, 12.6, 15.5, 15.8, 16.0, 16.3, 16.7, 17.0, 17.8, 18.6, 18.8, 19.0, 20.5 and 20.9 degrees 2-Theta. In one embodiment, the present invention relates to a crystalline obeticholic acid Form C characterized by an X-ray diffraction pattern substantially similar to that set forth in FIG. 5. In one embodiment, the X-ray diffraction pattern is collected on a diffractometer using Cu Kα radiation (40 kV, 40 mA). In one embodiment, the X-ray diffraction pattern includes characteristic peaks at about 12.0 to about 12.8 and about 15.4 to about 21.0.

In one embodiment, the present invention relates to a crystalline obeticholic acid Form C characterized by a Differential Scanning calorimetry (DSC) thermogram having an endotherm value at about 98±2° C., as measured by a Mettler DSC 823e instrument. In one embodiment, the Differential Scanning calorimetry (DSC) thermogram has an endotherm value at about 98±2° C., as measured by a Mettler DSC 823e instrument.

In one embodiment, the present invention relates to a crystalline obeticholic acid, wherein said crystalline obeticholic acid is Form C and has a purity greater than about 90%. In one embodiment, the purity of said crystalline obeticholic acid Form C is determined by HPLC. In one embodiment, the present invention relates to a crystalline obeticholic acid Form C, or a pharmaceutically acceptable salt, solvate or amino acid conjugate thereof. In one embodiment, the solvate is a hydrate. In one embodiment, the purity is greater than about 92%. In one embodiment, the purity is greater than about 94%. In one embodiment, the purity is greater than about 96%. In one embodiment, the purity is greater than about 98%. In one embodiment, the purity is greater than about 99%.

In one embodiment, the present invention relates to a crystalline obeticholic acid, wherein said crystalline obeticholic acid is Form C and has a potency greater than about 90%. In one embodiment, the purity of said crystalline obeticholic acid Form C is determined by HPLC and/or other analytical procedures known in the art. In one embodiment, the present invention relates to a crystalline obeticholic acid Form C, or a pharmaceutically acceptable salt, solvate or amino acid conjugate thereof. In one embodiment, the solvate is a hydrate. In one embodiment, the potency is greater than about 92%. In one embodiment, the potency is greater than about 94%. In one embodiment, the potency is greater than about 96%. In one embodiment, the potency is greater than about 98%. In one embodiment, the potency is greater than about 99%.

In one embodiment, the present invention relates to a crystalline obeticholic acid Form C that contains a total of less than about 4% of one or more impurities selected from 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyliden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid. In one embodiment, the total impurities is less than about 3.8%. In one embodiment, the total impurities is less than about 3.6%.

Example 3 of the application provides full characterization of these crystalline forms of obeticholic acid.

The single crystal X-ray structure of obeticholic acid was obtained and the absolute stereochemistry assigned. For example, the single crystal X-ray structure of crystalline obeticholic acid Form G was determined from a crystal obtained from the recrystallization of obeticholic acid from an acetonitrile solution after cooling to 5° C. at 0.1° C./min followed by maturation at RT/50° C. 8 h cycles for 1 week.

The structure is orthorhombic, space group P2$_1$2$_1$2$_1$, and contains one molecule of obeticholic acid in the asymmetric unit. Final R1 [I>2σ(I)]=3.22%. The absolute stereochemistry of the molecule was determined as shown below with a Flack parameter=−0.01 (13). The structure had no disorder.

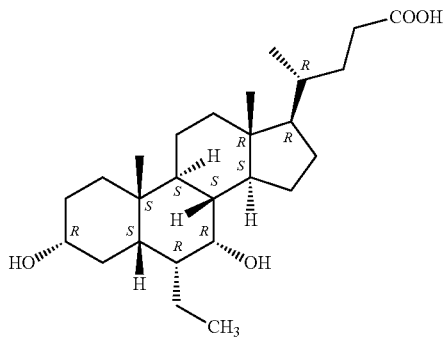

A bioavailability study of obeticholic acid Form 1 (non-crystalline) vs. crystalline obeticholic acid Form F was carried out (Example 7). The results of the study show that that physical state of a solid obeticholic acid can play a role in the bioavailability of the molecule when administered orally to a subject. The plasma kinetics after oral administration and the efficiency of the intestinal absorption and the pharmacokinetics of solid obeticholic acid Form 1 (non-crystalline) and crystalline Form F were evaluated according to methods known in the art. Example 8 of the present invention shows the profiles of obeticholic acid plasma concentration vs time, the $t_{max}$, $C_{max}$ and AUC after administration of Form 1 or Form F of obeticholic acid (see FIGS. 37-38). Crystalline Form F has a higher bioavailability than obeticholic acid Form 1 (non-crystalline). The plasma profiles show that the Form F is absorbed more efficiently (higher AUC) and even the kinetics is more regular, reflecting an optimal distribution of the drug in the intestinal content.

The water solubility of obeticholic acid Form 1 (non-crystalline) is slightly higher than that of Form F. Form F appears to be stable as the thermo gravimetric analysis (TGA) did not show any weight loss in the temperature range studied.

Substantially Pure Obeticholic Acid

The present application provides substantially pure obeticholic acid and pharmaceutically acceptable salts, solvates, or amino acid conjugates thereof:

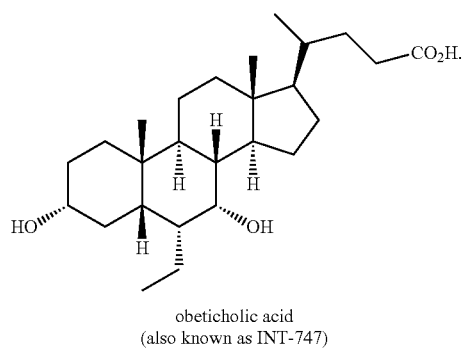

obeticholic acid
(also known as INT-747)

Other names for the pharmaceutically active ingredient obeticholic acid are INT-747, 3α,7α-dihydroxy-6α-ethyl-5β-cholan-24-oic acid, 6α-ethyl-chenodeoxycholic acid, 6-ethyl-CDCA, 6ECDCA, and cholan-24-oic acid, 6-ethyl-3,7-dihydroxy-, (3α,5β,6α,7α)-.

The present application provides compositions comprising obeticholic acid Form 1 and processes for the synthesis of highly pure obeticholic acid Form 1 which are safe and which produce obeticholic acid on a large scale. In one aspect, obeticholic acid Form 1 is produced on a commercial scale process. The term "commercial scale process" refers to a process which is run as a single batch of at least about 100 grams. In one aspect, the process of the present application produces obeticholic acid Form 1 in high yield (>80%) and with limited impurities.

The term "purity" as used herein refers to the amount of obeticholic acid based on HPLC. Purity is based on the "organic" purity of the compound. Purity does not include a measure of any amount of water, solvent, metal, inorganic salt, etc. In one aspect, the purity of obeticholic acid is compared to the purity of the reference standard by comparing the area under the peak. In another aspect, the known standard for purity is an obeticholic acid reference standard. In one aspect, obeticholic acid has a purity of greater than about 96%. In one aspect, obeticholic acid has a purity of greater than about 98%. For example, the purity of obeticholic acid Form 1 is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of obeticholic acid Form 1 is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of obeticholic acid is 98.0%, 98.5%, 99.0%, 99.5%, 99.6%, 99.7%, 99.8%, or 99.9%. For example, the purity of obeticholic acid is 98.5%, 99.0%, or 99.5%. In one embodiment, the obeticholic acid is obeticholic acid Form 1.

In one embodiment, the present invention relates to obeticholic acid having a purity greater than about 98%. In one embodiment, the purity is determined by HPLC. In another embodiment, the present invention relates to obeticholic acid, or a pharmaceutically acceptable salt, solvate or amino acid conjugate thereof. In one embodiment, the purity is greater than about 98.5%. In one embodiment, the purity is greater than about 99.0%. In one embodiment, the purity is greater than about 99.5%. In one embodiment, the obeticholic acid is obeticholic acid Form 1.

The term "potency" as used herein is a measure of the amount of obeticholic acid based on that of a known standard (e.g., acceptance criteria of about 95% to about 102%). Potency takes into account all possible impurities including water, solvents, organic, and inorganic impurities. In one aspect, the known standard is obeticholic acid. In one aspect, obeticholic acid has a potency of greater than about 96%. In one aspect, obeticholic acid has a potency of greater than about 98%. In one aspect, the known standard is obeticholic acid. In another aspect, potency is 100% minus the amounts of water, sulphated ash, residual solvents, and other impurity contents such as 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyl-iden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid. In another embodiment, potency accounts for impurities due to water, solvent, metals, inorganic salts, and other inorganic or organic impurities. For example, the potency of obeticholic acid Form 1 is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. In one aspect, the potency of obeticholic acid Form 1 is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the potency of obeticholic acid is 98.0%, 98.5%, 99.0%, 99.5%, 99.6%, 99.7%, 99.8%, or 99.9%. For example, the potency of obeticholic acid is 98.5%, 99.0%, or 99.5%. In one embodiment, the obeticholic acid is obeticholic acid Form 1.

In one embodiment, the present invention relates to obeticholic acid containing a total of less than about 2% of one or more impurities selected from 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyl-iden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid. In one embodiment, the total of impurities is less than about 1.5%. In one embodiment, the total of impurities is less than about 1.4%. In one embodiment, the obeticholic acid is obeticholic acid Form 1.

In one embodiment, obeticholic acid contains less than about 10% of water, less than about 9% of water, less than 8% of water, less than 7% of water, less than 6% of water, less than 5% of water, less than 4% of water, less than 3% of water, less than 2% of water, or less than 1% of water. In one embodiment, obeticholic acid contains less than about 1.2% of water. In one embodiment, obeticholic acid contains less than about 1.0% of water. In one embodiment, the obeticholic acid is obeticholic acid Form 1.

In another embodiment, obeticholic acid contains not more than (NMT) 0.15% of 6-ethylursodeoxycholic acid and 3α,7α-dihydroxy-6-ethyliden-5β-cholan-24-oic acid. In another embodiment, obeticholic acid contains a total of less than about 0.07% of 6-ethylursodeoxycholic acid and 3α,7α-dihydroxy-6-ethyliden-5β-cholan-24-oic acid. In one embodiment, obeticholic acid contains a total of less than about 0.06% of 6-ethylursodeoxycholic acid and 3α,7α-dihydroxy-6-ethyliden-5β-cholan-24-oic acid. In one embodiment, obeticholic acid contains a total of less than about 0.05% of 6-ethylursodeoxycholic acid and 3α,7α-dihydroxy-6-ethyliden-5β-cholan-24-oic acid. In one embodiment, the obeticholic acid is obeticholic acid Form 1.

In one embodiment, obeticholic acid contains not more than (NMT) 0.15% of 3α-hydroxy-6α-ethyl-7-cheto-5β-cholan-24-oic acid. In one embodiment, obeticholic acid contains less than about 0.07% of 3α-hydroxy-6α-ethyl-7-cheto-5β-cholan-24-oic acid. In one embodiment, obeticholic acid contains less than about 0.06% of 3α-hydroxy-6α-ethyl-7-cheto-5β-cholan-24-oic acid. In one embodiment, obeticholic acid contains less than about 0.05% of 3α-hydroxy-6α-ethyl-7-cheto-5β-cholan-24-oic acid. In one embodiment, the obeticholic acid is obeticholic acid Form 1.

In one embodiment, obeticholic acid contains not more than (NMT) 0.15% of 6β-ethylchenodeoxycholic acid. In one embodiment, obeticholic acid contains less than about 0.07% of 6β-ethylchenodeoxycholic acid. In one embodiment, obeticholic acid contains less than about 0.06% of 6β-ethylchenodeoxycholic acid. In one embodiment, obeticholic acid contains less than about 0.05% of 6β-ethylchenodeoxycholic acid. In one embodiment, the obeticholic acid is obeticholic acid Form 1.

In one embodiment, obeticholic acid contains no more than (NMT) 3% of chenodeoxycholic acid (CDCA). In one embodiment, obeticholic acid contains less than about 1% of CDCA. In one embodiment, obeticholic acid contains less than about 0.5% of CDCA. In one embodiment, obeticholic acid contains less than about 0.3% of CDCA. In one embodiment, obeticholic acid contains less than about 0.2% of CDCA. In one embodiment, the obeticholic acid is obeticholic acid Form 1.

In one embodiment, obeticholic acid contains no more than (NMT) 4% of CDCA and 6-ethylursodeoxycholic acid.

In one embodiment, obeticholic acid contains no more than (NMT) 1.5% of 3α(3α,7α-dihydroxy-6α-ethyl-5β-cholan-24-oyloxy)-7α-hydroxy-6α-ethyl-5β-cholan-24-oic acid. In one embodiment, obeticholic acid contains less than about 1% of 3α(3α,7α-dihydroxy-6α-ethyl-5β-cholan-24-oyloxy)-7α-hydroxy-6α-ethyl-5β-cholan-24-oic acid. In one embodiment, obeticholic acid contains less than about 0.07% of 3α(3α,7α-dihydroxy-6α-ethyl-5β-cholan-24-oyloxy)-7α-hydroxy-6α-ethyl-5β-cholan-24-oic acid. In one embodiment, obeticholic acid contains less than about 0.06% of 3α(3α,7α-dihydroxy-6α-ethyl-5β-cholan-24-oyloxy)-7α-hydroxy-6α-ethyl-5β-cholan-24-oic acid. In one embodiment, obeticholic acid contains less than about 0.05% of 3α(3α,7α-dihydroxy-6α-ethyl-5β-cholan-24-oyloxy)-7α-hydroxy-6α-ethyl-5β-cholan-24-oic acid. In one embodiment, the obeticholic acid is obeticholic acid Form 1.

Oral Formulation and Administration

Obeticholic acid is for oral administration. In one embodiment, the formulation is oral administration for the prevention and treatment of FXR mediated diseases and conditions. In one embodiment, the formulation comprises of obeticholic acid Form 1. In another embodiment, the formulation comprises of substantially pure obeticholic acid.

Formulations suitable for oral administration may be provided as discrete units, such as tablets, capsules, cachets (wafer capsule used by pharmacists for presenting a drug), lozenges, each containing a predetermined amount of obeticholic acid; as powders or granules; as solutions or suspensions in aqueous or non-aqueous liquids; or as oil-in-water or water-in-oil emulsions.

Formulations of the invention may be prepared by any suitable method, typically by uniformly and intimately admixing obeticholic acid with liquids or finely divided solid carriers or both, in the required proportions and then, if necessary, shaping the resulting mixture into the desired shape.

For example a tablet may be prepared by compressing an intimate mixture comprising a powder or granules of obeticholic acid and one or more optional ingredients, such as a binder, lubricant, inert diluent, or surface active dispersing agent, or by moulding an intimate mixture of powdered active ingredient and inert liquid diluent.

For example, one or more tablets may be administered to get to a target dose level based on the subject's weight, e.g., a human between about 30 kg to about 70 kg.

In one embodiment, the subject is a child and the formulation is used to treat biliary atresia. Biliary atresia, also known as "extrahepatic ductopenia" and "progressive obliterative cholangiopathy" is a congenital or acquired disease of the liver and one of the principal forms of chronic rejection of a transplanted liver allograft. In the congenital form, the common bile duct between the liver and the small intestine is blocked or absent. The acquired type most often occurs in the setting of autoimmune disease, and is one of the principal forms of chronic rejection of a transplanted liver allograft.

Infants and children with biliary atresia have progressive cholestasis with all the usual concomitant features: jaundice, pruritus, malabsorption with growth retardation, fat-soluble vitamin deficiencies, hyperlipidemia, and eventually cirrhosis with portal hypertension. If unrecognized, the condition leads to liver failure—but not kernicterus, as the liver is still able to conjugate bilirubin, and conjugated bilirubin is unable to cross the blood-brain barrier. The cause of the condition is unknown. The only effective treatments are certain surgeries such as the Kasai procedure, or liver transplantation In one embodiment, the human child has had a Kasai procedure, where the Kasai procedure effectively gives them a functional bile duct when they born either without a bile duct or one that is completely blocked at birth.

In addition to the ingredients specifically mentioned above, the oral formulations of the present invention may include other agents known to those skilled in the art of pharmacy, having regard for the type of formulation in issue. Oral formulations suitable may include flavoring agents.

In one embodiment, the present invention relates to a pharmaceutical formulation of obeticholic acid or a pharmaceutically acceptable salt, solvate, or amino acid conjugate thereof, wherein obeticholic acid is produced by a process of the invention (obeticholic acid Form 1). In another embodiment, the formulation is administered orally.

In one embodiment, the formulation is in tablet form. In another embodiment, the formulation comprises obeticholic acid and one or more components selected from microcrystalline cellulose, sodium starch glycolate, magnesium stearate, coating material, or colloidal silicon dioxide. In one embodiment, the coating material is an Opadry® coating material.

In another embodiment, the formulation comprises about 0.1 mg to about 1500 mg of obeticholic acid per tablet. In another embodiment, the formulation comprises about 1 mg to about 100 mg. In another embodiment, the formulation comprises about 1 mg to about 50 mg. In another embodiment, the formulation comprises about 1 mg to about 30 mg. In another embodiment, the formulation comprises about 4 mg to about 26 mg. In another embodiment, the formulation comprises about 5 mg to about 25 mg. In one embodiment, the formulation comprises about 1 mg to about 2 mg. In one embodiment, the formulation comprises about 1.2 mg to about 1.8 mg. In one embodiment, the formulation comprises about 1.3 mg to about 1.7 mg. In one embodiment, the formulation comprises about 1.5 mg.

In one embodiment, the formulation comprises of about 1 mg to about 25 mg of obeticholic acid per tablet. In one embodiment, the formulation comprises about 1 mg of obeticholic acid, about 180 to about 190 mg of microcrystalline cellulose, about 10 to about 15 mg of sodium starch glycolate, about 1 to about 3 mg of magnesium stearate, and about 5 mg to about 10 mg of coating material. In one embodiment, the coating material is an Opadry® coating material.

In one embodiment, the formulation comprises of about 1 mg to about 25 mg of obeticholic acid per tablet. In one embodiment, the formulation comprises about 1 mg of obeticholic acid, about 185.0 mg of microcrystalline cellulose, about 12.0 mg of sodium starch glycolate, about 2.0 mg of magnesium stearate, and about 8.0 mg of coating material. In one embodiment, the coating material is an Opadry® coating material.

In one embodiment, the formulation comprises of about 1 mg to about 25 mg of obeticholic acid per tablet. In one embodiment, the formulation comprises about 5 mg of obeticholic acid, about 175 to about 190 mg of microcrystalline cellulose, about 10 to about 15 mg of sodium starch glycolate, about 1 to about 3 mg of magnesium stearate, and about 5 mg to about 10 mg of coating material. In one embodiment, the coating material is an Opadry® coating material.

In one embodiment, the formulation comprises of about 1 mg to about 25 mg of obeticholic acid per tablet. In one embodiment, the formulation comprises about 5 mg of obeticholic acid, about 181.0 mg of microcrystalline cellulose, about 12.0 mg of sodium starch glycolate, about 2.0 mg of magnesium stearate, and about 8.0 mg of coating material. In one embodiment, the coating material is an Opadry® coating material.

In one embodiment, the formulation comprises of about 1 mg to about 25 mg of obeticholic acid per tablet. In one embodiment, the formulation comprises about 10 mg of obeticholic acid, about 170 mg to about 180 mg of microcrystalline cellulose, about 10 mg to about 15 mg of sodium starch glycolate, about 1 mg to about 3 mg of magnesium stearate, and about 5 mg to about 10 mg of coating material. In one embodiment, the coating material is an Opadry® coating material.

In one embodiment, the formulation comprises of about 1 mg to about 25 mg of obeticholic acid per tablet. In one embodiment, the formulation comprises about 10 mg of obeticholic acid, about 176.0 mg of microcrystalline cellulose, about 12.0 mg of sodium starch glycolate, about 2.0 mg of magnesium stearate, and about 8.0 mg of coating material. In one embodiment, the coating material is an Opadry® coating material.

In one embodiment, the formulation comprises of about 1 mg to about 25 mg of obeticholic acid per tablet. In one embodiment, the formulation comprises about 25 mg of obeticholic acid, about 150 mg to about 160 mg of microcrystalline cellulose, about 10 mg to about 15 mg of sodium starch glycolate, about 1 mg to about 3 mg of magnesium stearate, about 5 to about 10 mg of coating material, and about 1 to about 10 mg of colloidal silicon dioxide. In one embodiment, the coating material is an Opadry® coating material.

In one embodiment, the formulation comprises of about 1 mg to about 25 mg of obeticholic acid per tablet. In one embodiment, the formulation comprises about 25 mg of obeticholic acid, about 157.0 mg of microcrystalline cellulose, about 12.0 mg of sodium starch glycolate, about 2.0 mg of magnesium stearate, about 8.0 mg of coating material, and about 4.0 mg of colloidal silicon dioxide. In one embodiment, the coating material is an Opadry® coating material.

All percentages and ratios used herein, unless otherwise indicated, are by weight. The percent dimeric impurity is on an area percent basis, typically as quantified by analytical HPLC.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Formulation of Tablets

| Component | Quantity per Tablet | Function | Reference to Standard |
|---|---|---|---|
| *Film Coated Tablet* | | | |
| *1 mg Tablet* | | | |
| Obeticholic acid | 1.0 mg* | API | HSE |
| Microcrystalline cellulose | 185.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Opadry ® II green, white, or yellow | 8.0 mg | Coating Material | HSE |
| Total weight | 208.0 mg | | |
| *5 mg Tablet* | | | |
| Obeticholic acid | 5.0 mg* | API | HSE |
| Microcrystalline cellulose | 181.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Opadry ® II green, white, or yellow | 8.0 mg | Coating Material | HSE |
| Total weight | 208.0 mg | | |
| *10 mg Tablet* | | | |
| Obeticholic acid | 10.0 mg* | API | HSE |
| Microcrystalline cellulose | 176.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Opadry ® II green, white, or yellow | 8.0 mg | Coating Material | HSE |
| Total weight | 208.0 mg | | |
| *25 mg Tablet* | | | |
| Obeticholic acid | 25.0 mg* | API | HSE |
| Microcrystalline cellulose | 157.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Collodial silicon dioxide | 4.0 mg | Glidant | USP-NF/EP/JP |
| Opadry ® II green, white, or yellow | 8.0 mg | Coating Material | HSE |
| Total weight | 208.0 mg | | |

API: Active pharmaceutical ingredient
HSE = In house specification
USP-NF = US Pharmacopeia National Formulary
Ph Eur = European Pharmacopeia
JP = Japanese Pharmacopeia
*obeticholic acid quantity presented assumes API is anhydrous and 100% pure; actual amount is adjusted based on the potency of the drug substance Lot used, and amount of microcrystalline cellulose is correspondingly decreased.

In one embodiment, the tablet comprises yellow Opadry®. In another embodiment, the tablet comprises white Opadry®. In another embodiment, the tablet comprises green Opadry®.

Pharmaceutical Compositions

Obeticholic acid, including obeticholic acid Form 1, substantially pure forms of obeticholic acid and crystalline forms of obeticholic acid, or a pharmaceutically acceptable salt, solvate, or amino acid conjugate thereof is useful for a variety of medicinal purposes. Obeticholic acid may be used in methods for the prevention or treatment of FXR mediated diseases and conditions. In one embodiment, the disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesterolemia, and hyperlipidemia. In one embodiment, obeticholic acid Form 1 may be used in methods for lowering triglycerides. In one embodiment, crystalline obeticholic acid may be used in methods for lowering triglycerides. Obeticholic acid Form 1 or crystalline obeticholic acid may increase HDL. Other effects of obeticholic acid Form 1 or crystalline obeticholic acid include lowering of alkaline phosphatase (ALP), bilirubin, ALT, AST, and GGT.

In one embodiment, the present invention relates to a pharmaceutical composition comprising obeticholic acid and a pharmaceutically acceptable carrier, wherein the obeticholic acid is produced by a process of the invention, e.g., obeticholic acid Form 1. In one embodiment, the pharmaceutical composition comprises of substantially pure obeticholic acid and a pharmaceutically acceptable carrier. In another embodiment, the pharmaceutical composition comprises of crystalline obeticholic acid and a pharmaceutically acceptable carrier. In another embodiment, the crystalline obeticholic acid is the Form A. In another embodiment, the crystalline obeticholic acid is the Form C. In one embodiment, the crystalline obeticholic acid is Form D. In one embodiment, the crystalline obeticholic acid is Form F. In one embodiment, the crystalline obeticholic acid is Form G. In one embodiment, the crystalline obeticholic acid is Form I.

In one embodiment, the present invention relates to a method of treating or preventing an FXR mediated disease or condition in a subject comprising administering an effective amount of obeticholic acid Form 1 produced by a process of the invention or a pharmaceutical composition thereof. In one embodiment, the present invention relates to a method of treating or preventing an FXR mediated disease or condition in a subject comprising administering an effective amount of substantially pure obeticholic acid produced by a process of the invention or a pharmaceutical composition thereof. In one embodiment, the present invention relates to a method of treating or preventing an FXR mediated disease or condition in a subject comprising administering an effective amount of crystalline obeticholic acid or a pharmaceutical composition thereof. In another embodiment, the crystalline obeticholic acid is Form C. In one embodiment, the crystalline obeticholic acid is Form A. In one embodiment, the crystalline obeticholic acid is Form C. In one embodiment, the crystalline obeticholic acid is Form D. In one embodiment, the crystalline obeticholic acid is Form F. In one embodiment, the crystalline obeticholic acid is Form G. In one embodiment, the crystalline obeticholic acid is Form I.

In another embodiment, the disease or condition is cardiovascular disease or cholestatic liver disease and for lowering triglycerides. In another embodiment, the cardiovascular disease is atherosclerosis or hypercholesterolemia. In another embodiment, the subject is a mammal. In another embodiment, the mammal is human.

In another embodiment, the compound or pharmaceutical composition is administered orally, parenterally, or topically. In another embodiment, the compound or pharmaceutical composition is administered orally.

In one embodiment, the present invention relates to a method for inhibiting fibrosis in a subject who is suffering from a cholestatic condition, the method comprising the step of administering to the subject an effective amount of obeticholic acid or a pharmaceutical composition thereof, wherein obeticholic acid is produced by the process of the invention. In one embodiment, the present invention relates to a method for inhibiting fibrosis in a subject who is not suffering from a cholestatic condition, the method comprising the step of administering to the subject an effective amount of obeticholic acid or a pharmaceutical composition thereof, wherein obeticholic acid is produced by the process of the invention. In embodiment, the fibrosis to be inhibited occurs in an organ where FXR is expressed.

In one embodiment, the cholestatic condition is defined as having abnormally elevated serum levels of alkaline phosphatase, 7-glutamyl transpeptidase (GGT), and 5' nucleotidase. In another embodiment, the cholestatic condition is further defined as presenting with at least one clinical symptom. In another embodiment, the symptom is itching (pruritus). In another embodiment, the fibrosis is selected from the group consisting of liver fibrosis, kidney fibrosis, and intestinal fibrosis. In another embodiment, the cholestatic condition is selected from the group consisting of primary biliary cirrhosis, primary sclerosing cholangitis, drug-induced cholestasis, hereditary cholestasis, and intrahepatic cholestasis of pregnancy. In another embodiment, the subject is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

In another embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In another embodiment, the subject has intestinal fibrosis associated with a disease selected from the group consisting of Crohn's disease, ulcerative colitis, post-radiation colitis, and microscopic colitis.

In another embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

Definitions

For convenience, certain terms used in the specification, examples and appended claims are collected here.

As used herein the term "obeticholic acid" or "OCA" refers to a compound having the chemical structure:

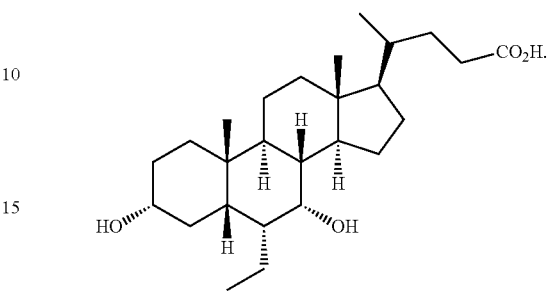

Other chemical names for obeticholic acid include: 3α,7α-dihydroxy-6α-ethyl-5β-cholan-24-oic acid, 6α-ethyl-chenodeoxycholic acid, 6-ethyl-CDCA, 6ECDCA, cholan-24-oic acid, 6-ethyl-3,7-dihydroxy-, (3α,5β,6α,7α)- and INT-747. The CAS registry number for obeticholic acid is 459789-99-2. This term refers to all forms of obeticholic acid, e.g., non-crystalline, crystalline and substantially pure.

As used herein the term "crystalline obeticholic acid" refers to any crystalline form of a compound having the chemical structure:

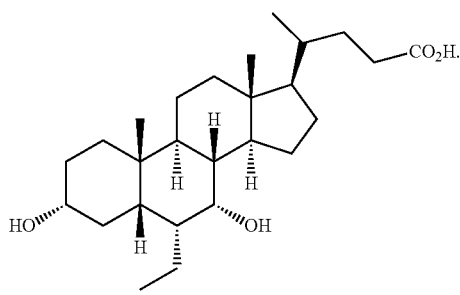

Crystalline obeticholic acid means that the compound is crystallized into a specific crystal packing arrangement in three spatial dimensions or the compound having external face planes. The crystalline form of obeticholic acid (or a pharmaceutically acceptable salt, amino acid conjugate, solvate thereof) can crystallize into different crystal packing arrangements, all of which have the same elemental composition of obeticholic acid. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystals of obeticholic acid can be prepared by crystallization under different conditions, e.g., different solvents, temperatures, etc.

Figure 41:
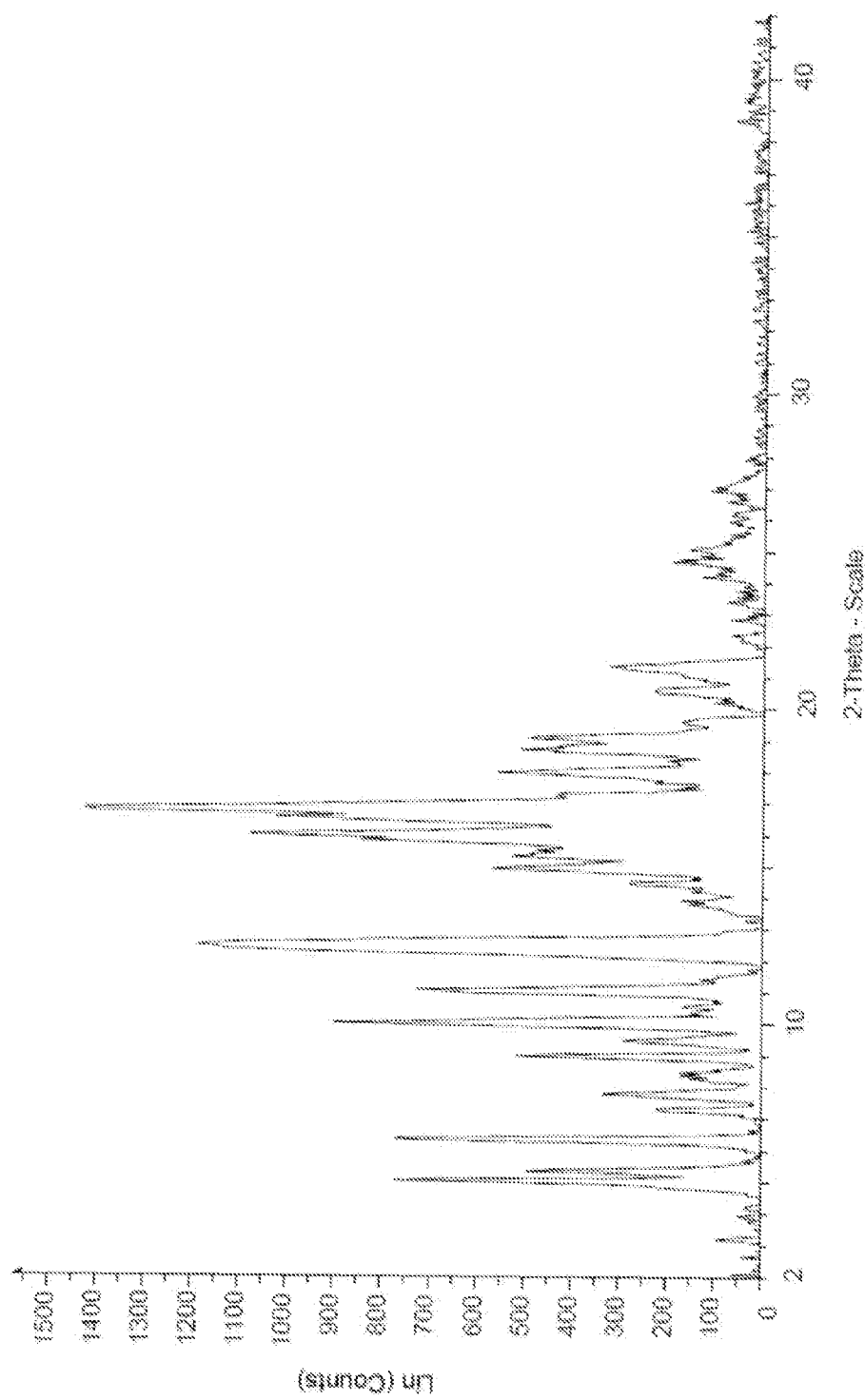
FIG. 41 is an XRPD diffractogram of crystalline obeticholic acid Form A (see example 3).

As used herein, the term "crystalline obeticholic acid Form A" refers to a crystalline form of obeticholic acid with an X-ray diffraction pattern that is substantially similar to that set forth in FIG. 41, e.g., one of the crystalline forms as characterized in Example 3.

Figure 5:
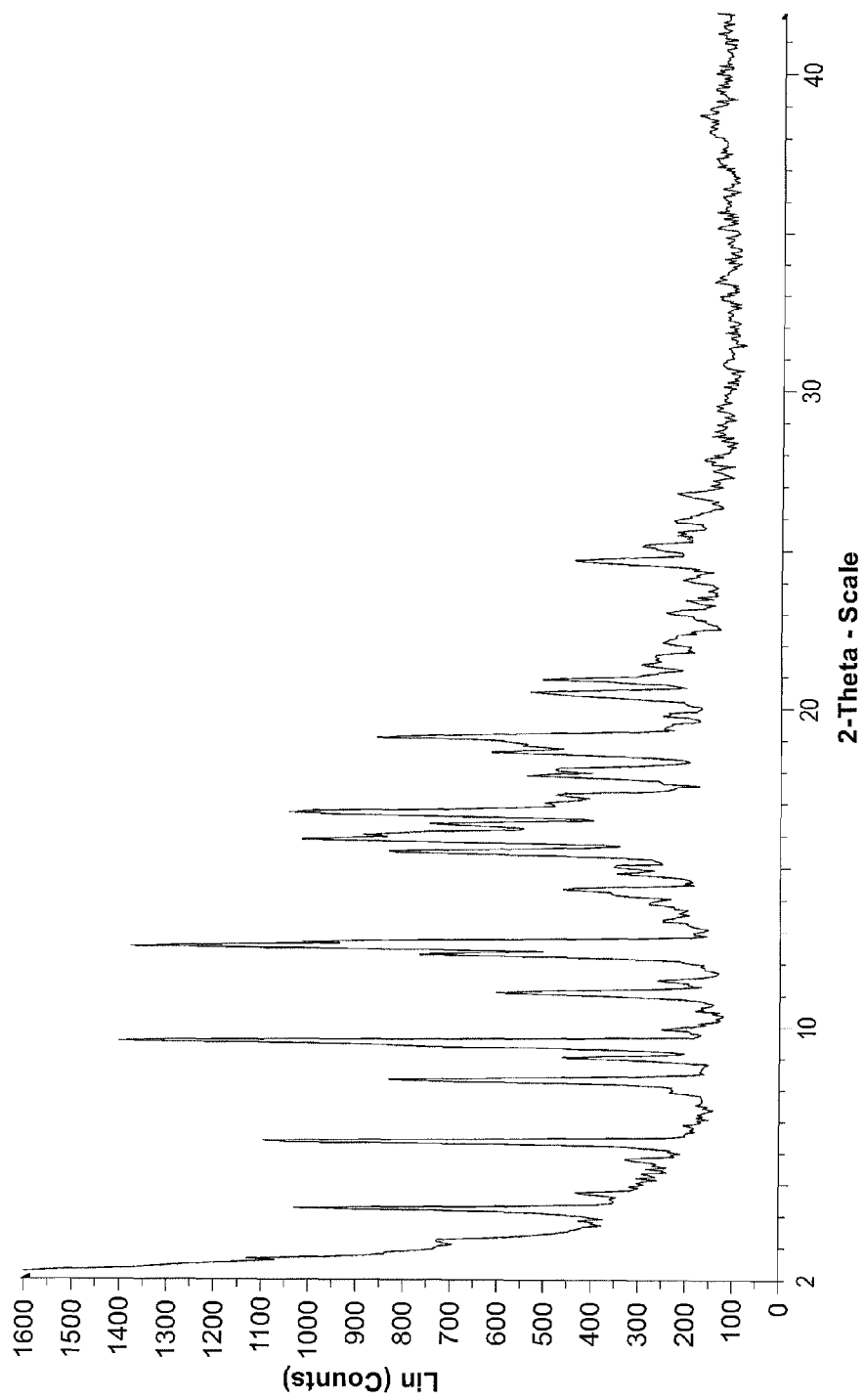
FIG. 5 is an XRPD diffractogram of crystalline obeticholic acid Form C (see Example 3).

As used herein, the term "crystalline obeticholic acid Form C" refers to a crystalline form of obeticholic acid with an X-ray diffraction pattern that is substantially similar to that set forth in FIG. 5, e.g., one of the crystalline forms as characterized in Example 3.

As used herein, the term "substantially pure obeticholic acid" refers to obeticholic acid that has a potency of greater than about 95%. The potency of the obeticholic acid takes into account impurities including e.g., water, solvents, and other organic and inorganic impurities that are in a sample of obeticholic acid. In another embodiment, the known standard for potency is 100% obeticholic acid, and the potency is determined by subtracting percentages of impurities such as solvent, water, and other organic and inorganic impurities from 100% of the known standard. In one aspect, the inorganic impurities include e.g., inorganic salts and sulphated ash. In one aspect, the organic impurities include 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyliden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid. The amounts of the impurities can be determined by procedures known in the art, e.g., HPLC, NMR, or methods from US Pharmacopeia, or European Pharmacopeia, or a combination of two or more of these methods.

As used herein, the term "purity" refers to a chemical analysis of a compound obtained from e.g., HPLC. In one embodiment, the purity of a compound is compared to the purity of the reference standard, e.g., obeticholic acid, via the area under their respective peak for comparisons. In one embodiment, purity accounts for the organic impurities in a sample.

As used herein, the term "reaction mixture" refers a mixture of one or more substances combined together. In one embodiment, the mixing or combining of the substances causes a chemical transformation or change in one or more of the original substances.

As used herein, the term "obeticholic acid Form 1" refers to non-crystalline obeticholic acid. In one embodiment, this form of obeticholic acid is produced via a crystalline obeticholic acid as a synthetic intermediate. For example, this form of obeticholic acid is produced by the process of the application via crystalline obeticholic acid Form A as the synthetic intermediate. In one embodiment, obeticholic acid Form 1 is the form that it used as the pharmaceutically active ingredient. See Example 5 for more details.

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

"Disease state" means any disease, disorder, condition, symptom, or indication.

The term "effective amount" as used herein refers to an amount of obeticholic acid (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of obeticholic acid that, when administered to a mammal for treating a disease, is sufficient to effect such treatment for the disease. The "therapeutically effective amount" will vary depending on obeticholic acid, the disease and its severity and the age, weight, etc., of the mammal to be treated.

A therapeutically effective amount of obeticholic acid can be formulated with a pharmaceutically acceptable carrier for administration to a human or an animal. Accordingly, obeticholic acid or its formulations can be administered, for example, via oral, parenteral, or topical routes, to provide an effective amount of the compound. In alternative embodiments, obeticholic acid prepared in accordance with the present invention can be used to coat or impregnate a medical device, e.g., a stent.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

The invention also comprehends isotopically-labeled obeticholic acid, or pharmaceutically acceptable salts, solvate, or amino acid conjugates thereof, which are identical to those recited in formulae of the invention and following, but for the fact that one or more atoms are replaced by an atom having an atomic mass or mass number different from the atomic mass or mass number most commonly found in nature. Examples of isotopes that can be incorporated into obeticholic acid, or pharmaceutically acceptable salts, solvate, or amino acid conjugates thereof include isotopes of hydrogen, carbon, nitrogen, fluorine, such as $^3$H, $^{11}$C, $^{14}$C and $^{18}$F.

Obeticholic acid, or pharmaceutically acceptable salts, solvates, or amino acid conjugates thereof that contain the aforementioned isotopes and/or other isotopes of other atoms are within the scope of the present invention. Isotopically-labeled obeticholic acid, or pharmaceutically acceptable salts, solvates, or amino acid conjugates thereof, for example those into which radioactive isotopes such as $^3$H, $^{14}$C are incorporated, are useful in drug and/or substrate tissue distribution assays. Tritiated, i.e., $^3$H, and carbon-14, i.e., 14C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled obeticholic acid, or pharmaceutically acceptable salts, solvates, or amino acid conjugates thereof can generally be prepared by carrying out the procedures disclosed in the Schemes and/or in the Examples of the invention, by substituting a readily available isotopically labeled reagent for a non-isotopically labeled reagent. In one embodiment, obeticholic acid, or pharmaceutically acceptable salts, solvates, or amino acid conjugates thereof are not isotopically labelled. In one embodiment, deuterated obeticholic acid is useful for bio-analytical assays. In another embodiment, obeticholic acid, or pharmaceutically acceptable salts, solvates, or amino acid conjugates thereof are radiolabelled.

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Solvates" means solvent addition forms that contain either stoichiometric or non stoichiometric amounts of solvent. Obeticholic acid may have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Tautomers" refers to compounds whose structures differ markedly in arrangement of atoms, but which exist in easy and rapid equilibrium. It is to be understood that obeticholic acid may be depicted as different tautomers. It should also be understood that when obeticholic acid and synthetic intermediates of the invention have tautomeric forms, all tautomeric forms are intended to be within the scope of the invention, and the naming of obeticholic acid does not exclude any tautomer form. Obeticholic acid and synthetic intermediates of the invention can exist in several tautomeric forms, including the keto-enol. For example, in keto-enol tautomerism a simultaneous shift of electrons and a hydrogen atom occurs. Tautomers exist as mixtures of a tautomeric set in solution. In solid form, usually one tautomer predominates. Even though one tautomer may be described, the present invention includes all tautomers of the present compounds.

It is to be understood accordingly that the isomers arising from asymmetric carbon atoms (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. Obeticholic acid and synthetic intermediates may exist in stereoisomeric form, and therefore can be produced as individual stereoisomers or as mixtures.

A "pharmaceutical composition" is a formulation containing obeticholic acid in a form suitable for administration to a subject. In one embodiment, the pharmaceutical composition is in bulk or in unit dosage form. It is can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the invention are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule, an IV bag, a tablet, a single pump on an aerosol inhaler, or a vial. The quantity obeticholic acid (e.g., a formulation of obeticholic acid, or a pharmaceutically acceptable salt, solvate, or amino acid conjugate thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, obeticholic acid is mixed under sterile conditions with a pharmaceutically acceptable carrier, and with any preservatives, buffers, or propellants that are required.

The term "flash dose" refers to obeticholic acid formulations that are rapidly dispersing dosage forms.

The term "immediate release" is defined as a release of obeticholic acid from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of obeticholic acid from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human. In one embodiment, the subject is human child (e.g., between about 30 kg to about 70 kg). In one embodiment, the human child has had a Kasai procedure, where the Kasai procedure effectively gives them a functional bile duct when they born either without a bile duct or one that is completely blocked at birth.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

While it is possible to administer obeticholic acid directly without any formulation, obeticholic acid is usually administered in the form of pharmaceutical formulations comprising a pharmaceutically acceptable excipient and obeticholic acid. These formulations can be administered by a variety of routes including oral, buccal, rectal, intranasal, transdermal, subcutaneous, intravenous, intramuscular, and intranasal. Oral formulation of obeticholic acid are described further herein under the section entitled "Oral Formulation and Administration".

In one embodiment, obeticholic acid can be administered transdermally. In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

In one embodiment of the present invention, there is provided a pharmaceutical formulation comprising at least obeticholic acid as described above in a formulation adapted for buccal and/or sublingual, or nasal administration. This embodiment provides administration of obeticholic acid in a manner that avoids gastric complications, such as first pass metabolism by the gastric system and/or through the liver. This administration route may also reduce adsorption times, providing more rapid onset of therapeutic benefit. The compounds of the present invention may provide particularly favorable solubility profiles to facilitate sublingual/buccal formulations. Such formulations typically require relatively high concentrations of active ingredients to deliver sufficient amounts of active ingredients to the limited surface area of the sublingual/buccal mucosa for the relatively short durations the formulation is in contact with the surface area, to allow the absorption of the active ingredient. Thus, the very high activity of obeticholic acid, combined with its high solubility, facilitates its suitability for sublingual/buccal formulation.

Obeticholic acid is preferably formulated in a unit dosage form, each dosage containing from about 0.1 mg to about 1500 mg. In another embodiment, the formulation comprises about 1 mg to about 100 mg. In another embodiment, the formulation comprises about 1 mg to about 50 mg. In another embodiment, the formulation comprises about 1 mg to about 30 mg. In another embodiment, the formulation comprises about 4 mg to about 26 mg. In another embodiment, the formulation comprises about 5 mg to about 25 mg. In one embodiment, the formulation comprises about 1 mg to about 2 mg. In one embodiment, the formulation comprises about 1.2 mg to about 1.8 mg. In one embodiment, the formulation comprises about 1.3 mg to about 1.7 mg. In one embodiment, the formulation comprises about 1.5 mg. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

Obeticholic acid is generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. In embodiment, the formulation comprises about 0.1 mg to about 1500 mg. In another embodiment, the formulation comprises about 1 mg to about 100 mg. In another embodiment, the formulation comprises about 1 mg to about 50 mg. In another embodiment, the formulation comprises about 1 mg to about 30 mg. In another embodiment, the formulation comprises about 4 mg to about 26 mg. In another embodiment, the formulation comprises about 5 mg to about 25 mg. In one embodiment, the formulation comprises about 1 mg to about 2 mg. In one embodiment, the formulation comprises about 1.2 mg to about 1.8 mg. In one embodiment, the formulation comprises about 1.3 mg to about 1.7 mg. In one embodiment, the formulation comprises about 1.5 mg. However, it will be understood that the amount of obeticholic acid actually administered will be determined by a physician, in the light of the relevant circumstances, including the condition to be treated, the chosen route of administration, the form of obeticholic acid administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

"Process of the invention" refers to a method for preparing obeticholic acid as described herein, wherein the method comprises of crystalline obeticholic acid.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what is an abnormally elevated blood level for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

EXAMPLES

Example 1

Synthesis of Obeticholic Acid

The compound numbers referred to in this synthetic procedure refer to those found in Scheme 1 and the reaction that correspond to each of the steps.

Step 1—Preparation of 3α-hydroxy-7-keto-5β-cholan-24-oic acid methyl ester (1)

Reaction 1: Esterification of C-24 carboxylic acid of 7-keto lithocholic acid (KLCA)

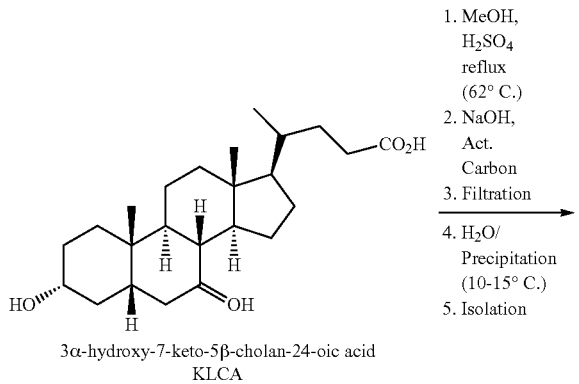

3α-hydroxy-7-keto-5β-cholan-24-oic acid
KLCA

3α-hydroxy-7-keto-5β-cholan-24-oic acid methyl ester
1

3α-hydroxy-7-keto-5β-cholan-24-oic acid (KLCA; 500.0 g, 1.28 mol) was esterified using methyl alcohol (2500 mL), in the presence of acidic catalysis (sulfuric acid, 1.0 mL) and was heated up to 62° C. to 64° C. for approximately 3 hours, to yield 3α-hydroxy-7-keto-5β-cholan-24-oic acid methyl ester (1). In this reaction, the methyl alcohol acts as the methylating reagent as well as the reaction solvent. For the work-up, the pH-value was adjusted with sodium hydroxide solution (2N) to pH 9.5 to 10. The solution was treated with activated carbon (25 g) for approximately 30 minutes and filtered to remove the carbon solids. Alternatively, the solution was not treated with activated carbon. To precipitate the product, water (625 mL) at 10° C. to 15° C. was added over 15 minutes and seeding material was added. The reaction mixture is stirred for 1 hour at 10° C. to 15° C. Another portion of water (1875 mL) was added over about 20 to 25 minutes. The product suspension was stirred for 30 minutes at 10° C. to 15° C. The product was isolated with a centrifuge and washed with a mixture of methanol and water (1:1, 350 mL). The water content of the wet material was quantified by Karl Fischer (KF). The material was dried in a tumble dryer under vacuum at NMT 70° C. The material can also be used in the next step without drying. The yield (calculated on dried product) is 501.4 g (1.24 mol, 96.8%).

Step 2—Preparation of 3α,7α-ditrimethylsilyloxy-5β-chol-6-en-24-oic acid methyl ester (3)

Reaction 2: Silylenol ether formation from 7-keto lithocholic methyl ester

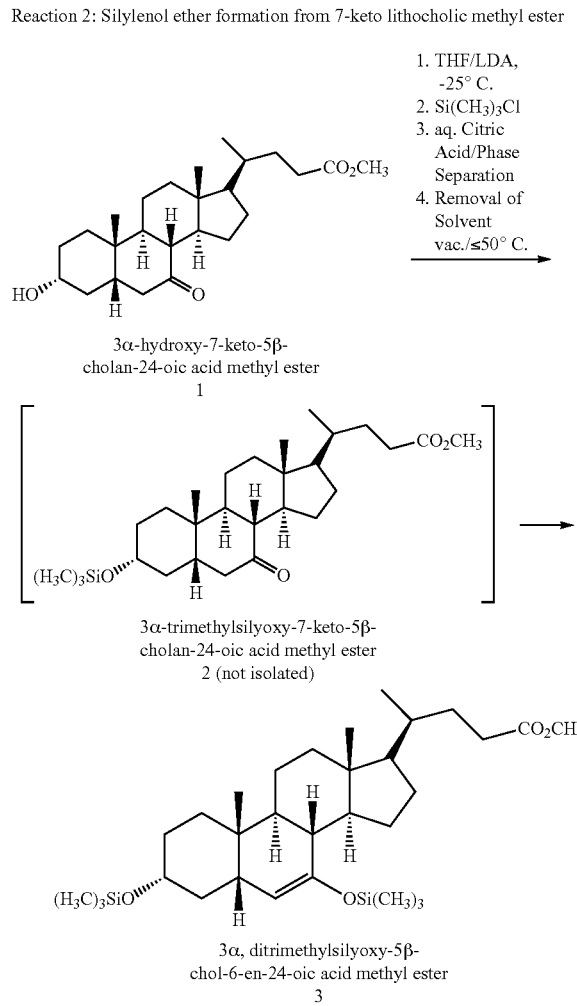

Step 3—Preparation of 3α-hydroxy-6-ethylidene-7-keto-5β-cholan-24-oic acid methyl ester (4)

Reaction 3: Aldol condensation of the silylenol ether and acetaldehyde

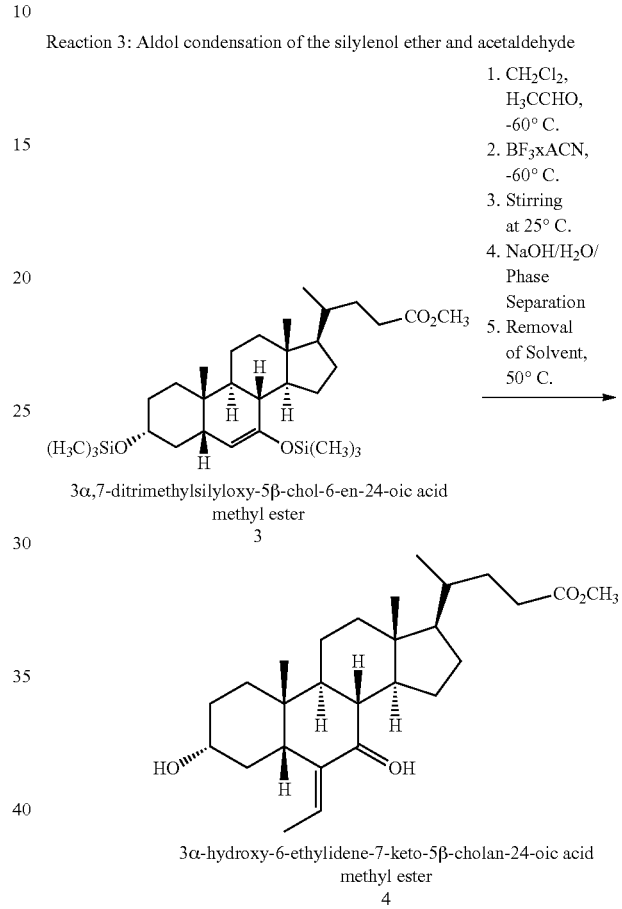

Compound 1 (60.69 g, 150 mmol, calculated as dry substance), containing residual water and methanol, was charged into the reactor under inert conditions and was dissolved in tetrahydrofuran (THF, 363 mL). Water and methanol were removed by repeated azeotropic distillation at approximately 65° C. and ambient pressure. THF was added to the residue as necessary and the distillation was repeated approximately 4 times. The remaining solution must have a final water content of ≤0.05% (Karl Fischer Titration). This solution was pre-cooled to −20° C. to −25° C. and then chlorotrimethylsilane (73.33 g, 675 mmol, 4.5 equivalents) was added in about 30 to 45 minutes. Under nitrogen atmosphere, lithium diisopropyl amide (28% LDA solution, 900 mmol) and THF (504 mL) were charged to a separate inert reactor and cooled to −20° C. to −25° C. The dry, cooled solution of compound 1, THF (84 mL), and chlorotrimethylsilane was charged into the LDA solution at −20° C. to −25° C. Then, the reaction mixture was stirred for approximately 2 hours. For the workup, the reaction mixture was added to a pre-cooled aqueous solution of citric acid (34.6 g in 300 mL) at 2° C. to 8° C. After the addition, the aqueous phase was separated and discarded. From the organic phase, the liquid was removed by vacuum distillation at maximum 50° C. The isolated residue contained compound 3 and some residual solvents and was used 'as is' in the next step.

Compound 3 (164.68 g, 300 mmol, calculated as dried substance) solution in THF was charged into an inert reactor. At a maximum temperature of 50° C., residual amounts of THF were distilled off under vacuum. The water content in the residue was limited to <0.5% (Karl Fischer titration) in order to proceed. The residue was then dissolved in dichloromethane (200 mL) and pre-cooled to −60° C. to −65° C. Acetaldehyde (33.8 mL, 600 mmol) was then added. Under nitrogen atmosphere, dichloromethane (700 mL) and boron trifluoride (16 wt % solution in acetonitrile, 318 g, 750 mmol) acetonitrile complex were charged into a separate reactor and then cooled to −60° C. to −65° C. At −60° C. to −65° C., the dry compound 3 solution was added. The reaction mixture was stirred for approximately two hours at −60° C. to −65° C., heated up to 23° C. to 28° C., stirred for another approximately 3 hours and cooled to approximately 2° C. to 10° C. for the hydrolysis/work-up. For the workup, the cooled solution from the reactor was added to a pre-cooled aqueous solution of 50% wt. caustic soda (40 mL) and 660 mL of water. After about 10 minutes of intensive stirring, the phases were separated and the (lower) organic layer was transferred to a separate reactor. From the organic layer, the solvent was removed by distillation at NMT 50° C. as far as possible. The residue, consisting of compound 4 and some remaining acetonitrile and dichloromethane, was discharged into drums. Compound 4A, a mixture of E/Z-isomers can also be prepared by the procedure described above for Step 3.

Step 4—Preparation of 3α-hydroxy-6-ethylidene-7-keto-5β-cholan-24-oic acid (5)

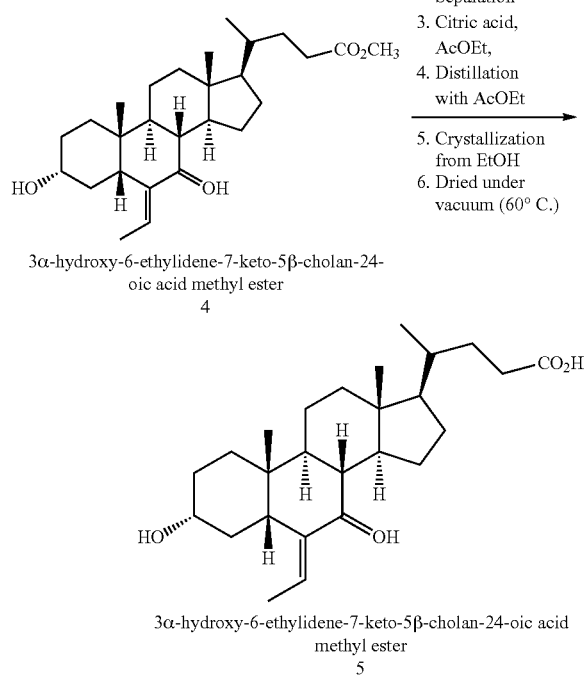

Compound 4 (258.37 g, 600 mmol, calculated as dried substance) was charged into an inert reactor. At a temperature of NMT 50° C., residual amounts of solvent were distilled off under vacuum. The residue was dissolved in methanol (360 mL) and water (54 mL) and caustic soda 50% wt. (54 mL) were added. The reaction mixture was heated up to 49° C. to 53° C. and stirred at this temperature for at least 2 hours. The pH of the reaction mixture is checked and verified to be >12. If the pH is <12, additional NaOH is added and the 2 hour reaction time is repeated. The solution was diluted with water (1000 mL) and the temperature was adjusted to 25° C. to 35° C. For the workup, reaction mixture was allowed to rest for at least 30 minutes. The phases were separated and the lower aqueous layer was transferred into a separate reactor and the organic layer was discarded. Ethyl acetate (1400 mL) and aqueous citric acid (244 g in 480 mL) were added with intensive stirring to the aqueous layer. The reaction mixture was stirred at 25° C. to 35° C. for 10 minutes. The phases were separated and the lower aqueous layer was discarded. Ethyl acetate was distilled off from the organic layer and replaced with ethyl acetate (800 mL). This operation was repeated until the water content of the distillate was NMT 1% or until a constant boiling point was reached. The suspension was cooled to 20° C. to 25° C., stirred for 30 minutes, and then the product was isolated and washed with ethyl acetate (100 mL, 3 to 4 times). Drying was done in a tumble dryer under vacuum at approximately 60° C. The yield is 118.71 g (47.5% from KLCA) of crude compound 5. Compound 4A, a mixture of E/Z isomers also can be used as starting material to produce compound 5A, a mixture of E/Z isomers.

Crude compound 5 was then crystallized using ethanol. The crude compound for crystallization can also be a mixture of E/Z isomers, compound 5A. Ethanol (390 to 520 mL) and crude compound 5 (130 g) were charged into an inert reactor. To dissolve the crude compound 5, the reaction mixture was heated to reflux. Then, the reaction mixture was cooled in a controlled cooling ramp to 15° C. to 20° C. within 3 to 5 hours by a linear profile. The crystalline compound 5A was isolated using a centrifuge and then washed with ethyl acetate (50-100 mL, 2 times). Drying was done in the tumble dryer under vacuum and at approximately 60° C. This leads to 85.8 g (66%) yield. A sample was taken to measure assay, purity, and moisture of the purified compound 5. Purified compound 5 is the E isomer of 3α-hydroxy-6-ethylidene-7-keto-5β-cholan-24-oic acid. See example 2 for full details regarding the identification and characterization of purified compound 5. Isolation of the purified compound 5, the E isomer, can be optional. The E isomer and Z isomers have different solubilities. The E isomer is less soluable and crystallizes such that the Z isomer can be washed away.

An alternative method to prepare compound 5 is as follows. Compound 4 (111.96 g) was charged into the inert reactor. At maximum 50° C. residual amounts of solvent (e.g., acetonitrile, dichloromethane) were distilled off under vacuum. The residue was dissolved in methanol (156 mL) and cooled to about 10° C. Tap-water (23.4 mL) and caustic soda 50% (23.4 mL) were added. The reaction mixture was stirred for about four hours at about 20° C. to about 25° C. The solution was diluted with tap-water (433 mL) and toluene (144 mL) was added. After stirring, the phases were separated and the lower, aqueous layer was transferred into the inert reactor. The organic layer was discarded. Ethyl acetate (607 mL) and a solution of citric acid (105.7 g in 208 mL of water) were added during intensive stirring to the aqueous layer. The phases were separated and the lower, aqueous layer was discarded. The organic layer was transferred into the inert reactor. From the organic layer ethyl acetate was distilled off and replaced with ethyl acetate (347 mL). In one embodiment, this operation was repeated with ethyl acetate (173 mL) until the water content of the distillate was not more than about 1% or until a constant boiling point was reached. The present suspension was cooled to 20° C. to 25° C. Compound 5 was isolated and washed with ethyl acetate (3 to 4 times each 43 mL) with inert centrifuge. Drying was done in the tumble dryer under vacuum and approximately 60° C. (64.8% yield based on compound 1). Compound 4A (a mixture of E/Z isomers) can also be used as starting material for Step 4 to produce Compound 5A (a mixture of E/Z isomers).

Step 5—Preparation of 3α-hydroxy-6α-ethyl-7-keto-5β-cholan-24-oic acid (6)

Reaction 5: Hydrogenation of the 6-ethylidene moiety

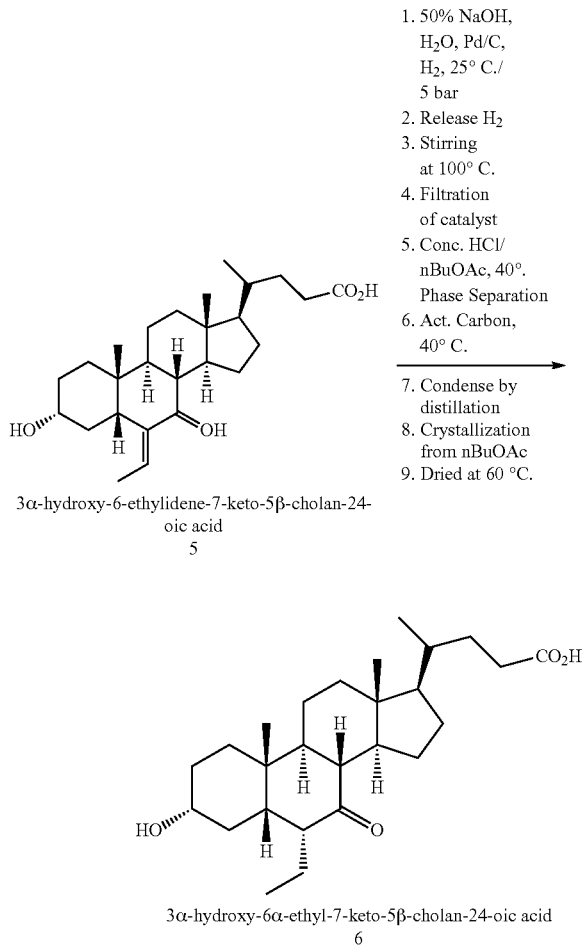

3α-hydroxy-6-ethylidene-7-keto-5β-cholan-24-oic acid
5

1. 50% NaOH, H₂O, Pd/C, H₂, 25° C./5 bar
2. Release H₂
3. Stirring at 100° C.
4. Filtration of catalyst
5. Conc. HCl/nBuOAc, 40°. Phase Separation
6. Act. Carbon, 40° C.
7. Condense by distillation
8. Crystallization from nBuOAc
9. Dried at 60 °C.

3α-hydroxy-6α-ethyl-7-keto-5β-cholan-24-oic acid
6

A mixture of purified compound 5 (110 g, 264 mmol), water (1100 mL), caustic soda solution (35.8 mL, 682 mmol) at 50% and palladium catalyst (Pd/C, 11 g) were charged to a hydrogenation reactor. The temperature was adjusted to 25° C. to 35° C. and the reactor was flushed three times with nitrogen (2 bar) and three times with hydrogen (1 bar). These pressure values were given relative to ambient pressure (=0 bar). A hydrogen pressure of 5 bar was applied and the reaction mixture was heated up to 100° C. (for isomerisation to the alpha position) over a period of 1.5 hours and then stirred for 3 hours while maintaining the hydrogen pressure at 4.5 to 5 bar. The reaction mixture is then cooled to 40° C. to 50° C. For the workup, the Pd/C is filtered off. To the filtrate, n-butyl acetate (1320 mL) and hydrochloric acid (67.8 mL, 815 mmol, 37%) were added. The aqueous phase was separated and discarded. The organic phase was treated with activated carbon (5.5 g) for about 10 minutes at 40 to 50° C. The activated carbon was filtered off and the filtrate was condensed by distillation and the resulting suspension was cooled to 15° C. to 20° C. within 2 to 3 hours. The precipitated compound 6 was isolated and washed with n-butyl acetate (160 mL). The product was filtered using a pressure filter. Drying was done in the pressure filter under vacuum at approximately 60° C. This leads to 89.8 g (81.2%) of Compound 6. Compound 5A, a mixture of E/Z isomers, can be used in step 5 to prepare Compound 6.

Step 6—Preparation of 3α,7α-dihydroxy-6α-ethyl-5β-cholan-24-oic acid (obeticholic acid)

Reaction 7: Selective reduction of 7-keto group to 7α-hydroxy group

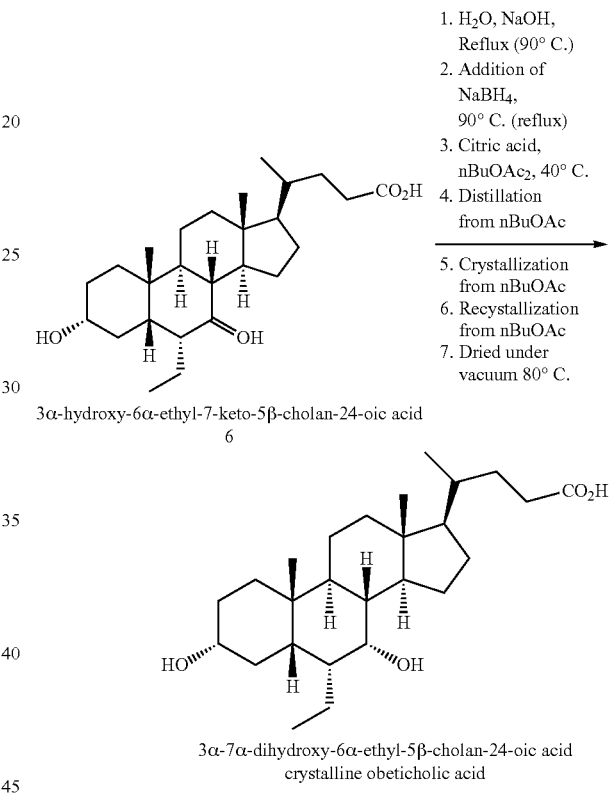

3α-hydroxy-6α-ethyl-7-keto-5β-cholan-24-oic acid
6

1. H₂O, NaOH, Reflux (90° C.)
2. Addition of NaBH₄, 90° C. (reflux)
3. Citric acid, nBuOAc₂, 40° C.
4. Distillation from nBuOAc
5. Crystallization from nBuOAc
6. Recystallization from nBuOAc
7. Dried under vacuum 80° C.

3α-7α-dihydroxy-6α-ethyl-5β-cholan-24-oic acid
crystalline obeticholic acid

A mixture of compound 6 (86 g, 205.4 mmol), water (688 mL) and 50% sodium hydroxide solution (56.4 mL) was reacted with sodium borohydride (7.77 g, 205.4 mmol) in a mixture of 50% wt. sodium hydroxide solution (1.5 mL) and water (20 mL) at 90° C. to 105° C. The reaction mixture was heated to reflux and stirred for at least 3 hours. For the workup, after the reaction was complete, the reaction mixture was cooled to approximately 80° C. and transferred to a cooled reactor. At 30° C. to 50° C., n-butyl acetate (860 mL) and citric acid (320.2 g, anhydrous) in water (491 mL) were added. The aqueous phase was separated and discarded after checking the pH-value to make sure that it was acidic. The organic phase was transferred and distilled. The residue is diluted with n-butyl acetate and was slowly cooled to 15° C. to 20° C. and the crude obeticholic acid was filtered using a centrifuge. The wet product was crystallized from n-butyl acetate. The product obeticholic acid was isolated and washed with n-butyl acetate (43 mL, 4 times) in an inert pressure filter. Drying was done in the pressure filter under vacuum at approximately 80° C. This led to 67.34 g (77.9%)

of crystalline obeticholic acid characterized by an X-ray diffraction pattern including characteristic peaks at about 5.0 and 5.3 degrees 2-Theta. The crystalline obeticholic acid Form A is characterized by an X-ray diffraction pattern substantially similar to that set forth in FIG. 41. See example 3 for full details regarding the identification and characterization of crystalline obeticholic acid.

Step 7—Preparation of Obeticholic Acid Form 1

Reaction 7: Preparation of obeticholic acid Form 1 from crystalline obeticholic acid Form

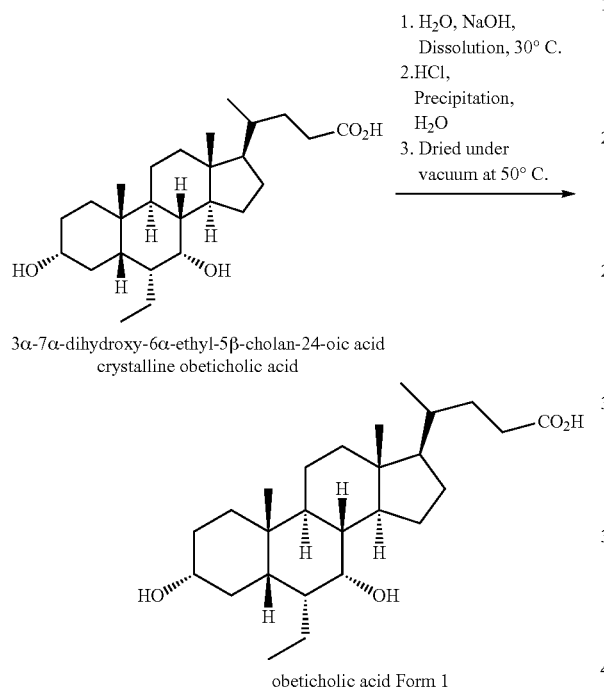

3α-7α-dihydroxy-6α-ethyl-5β-cholan-24-oic acid
crystalline obeticholic acid obeticholic acid Form 1

Crystalline obeticholic acid Form A characterized by an X-ray diffraction pattern including characteristic peaks at about 5.0 and 5.3 degrees 2-Theta (58 g) was dissolved in water (870 mL) and caustic soda solution (50%, 8.7 mL, 166 mmol) at 30° C. to 40° C. The mixture was stirred until all solid has dissolved. The product was precipitated using the following workup. The obeticholic acid solution was slowly added via a filter to diluted hydrochloric acid (37%, 16.05 mL, 193 mmol) in water (870 mL) at 30° C. to 40° C. The suspension was stirred for approximately 30 minutes at 30° C. to 40° C. and then cooled to not more than (NMT) 20° C. The product was isolated and washed with water (465 mL, 6 times) in the inert pressure filter. Drying was done in the pressure filter under vacuum at a temperature of NMT 50° C. This led to 53.2 g (91.7%) of obeticholic acid Form 1.

Example 2

Characterization of E-3α-hydroxy-6-ethylidene-7-keto-5β-cholan-24-oic acid (5)

Compound 5 is the key intermediate for the process of the application. The compound was isolated from ethyl acetate and was then crystallized from ethanol. The highly pure compound 5 allows for efficient and high yielding production of compound 6 and subsequently crystalline obeticholic acid Form A characterized by an X-ray diffraction pattern including characteristic peaks at about 5.0 and 5.3 degrees 2-Theta and obeticholic acid Form 1, including substantially pure obeticholic acid.

The structure of compound 5 from step 4 in example 1 was confirmed using $^1$H NMR, $^{13}$C NMR, and mass spec. Crude product from step 4 resulted in a major product at retention time (RT) 27.457 min and a minor product at RT 28.078 min in the UV chromatogram generated by quality control method 1 by means of LC/MS-coupling. The two products are the E/Z isomers of compound 5:

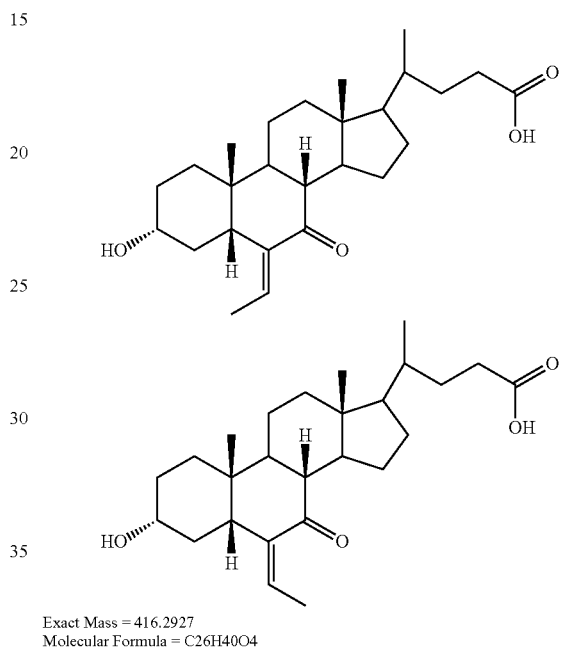

Exact Mass = 416.2927
Molecular Formula = C26H40O4

These two isomers show the same accurate mass and the same fragmentation in the MS/MS spectrum. They cannot be distinguished by the mass spectrometric data.

Using a semi-preparative method to isolate the E/Z isomer peaks, the structures of the E/Z isomers were confirmed using a two stage approach. The HPLC quality control method 1 used a non-volatile phosphoric acid buffer and thus, direct LC/MS coupling with the non-volatile buffer was not possible. Preliminary tests for adjustment of the method showed that only a UPLC method allowed for very high plate numbers for adequate separation of the E/Z isomers. The two stage approach was the following: Step A was identification of the E/Z isomers in two samples with the new developed UPLC/MS method and Step B was isolation of the fraction of the E/Z isomer peaks with the HPLC method 2 and subsequent identification with the UPLC/MS method 1. The experimental details of the methods were as follows:

TABLE C

| 1. MS compatible UPLC method (method 1) | |
|---|---|
| Instrument: | Accela UPL Ccoupling with LTQ FTSpectrometer (ThermoScientific) |
| Column: | 200 × 2 mm Hypersil Gold 1.9 μm |

TABLE C-continued

| | |
|---|---|
| Eluent: | A: Water + 10 mM Ammoniumformiat + 0.1% Formic acid |
| | B: Acetonitrile |
| Gradient: | 45% B in 20 minutes to 60% B (10 min isocratic) |
| Flow: | 0.4 ml/min, 40° C. column temperature |
| Detection: | MS: ESI positive and negative ions; |
| | UV: PDA 200.600 nm |
| Mass resolution: | R = 100000 ICR |
| Sample: | 1 mg/ml in water/acetonitrile (1:1), 3 µl/20 µl injected |

2. HPLC (method 2)

| | |
|---|---|
| Instrument: | Agilent1100 HPLC (Agilent Technologies) |
| Column: | 125 × 4 mm Purospher STAR C18 5 Lm |
| Eluent: | A: Water pH 2.6 with phosphoric acid |
| | B: Acetonitrile |
| Gradient: | 30% B in 10 minutes to 35% B in 30 minutes to 60% B |
| | In 1 minutes to 90% B (9 min isocratic) |
| Flow: | 1 ml/min, 35° C. column temperature |
| Detection: | UV: DAD 200-400 nm (UVA 200 nm) |
| Sample: | 10 mg/ml in water/acetonitrile (9:1), 25 µl injected |

Figure 2:
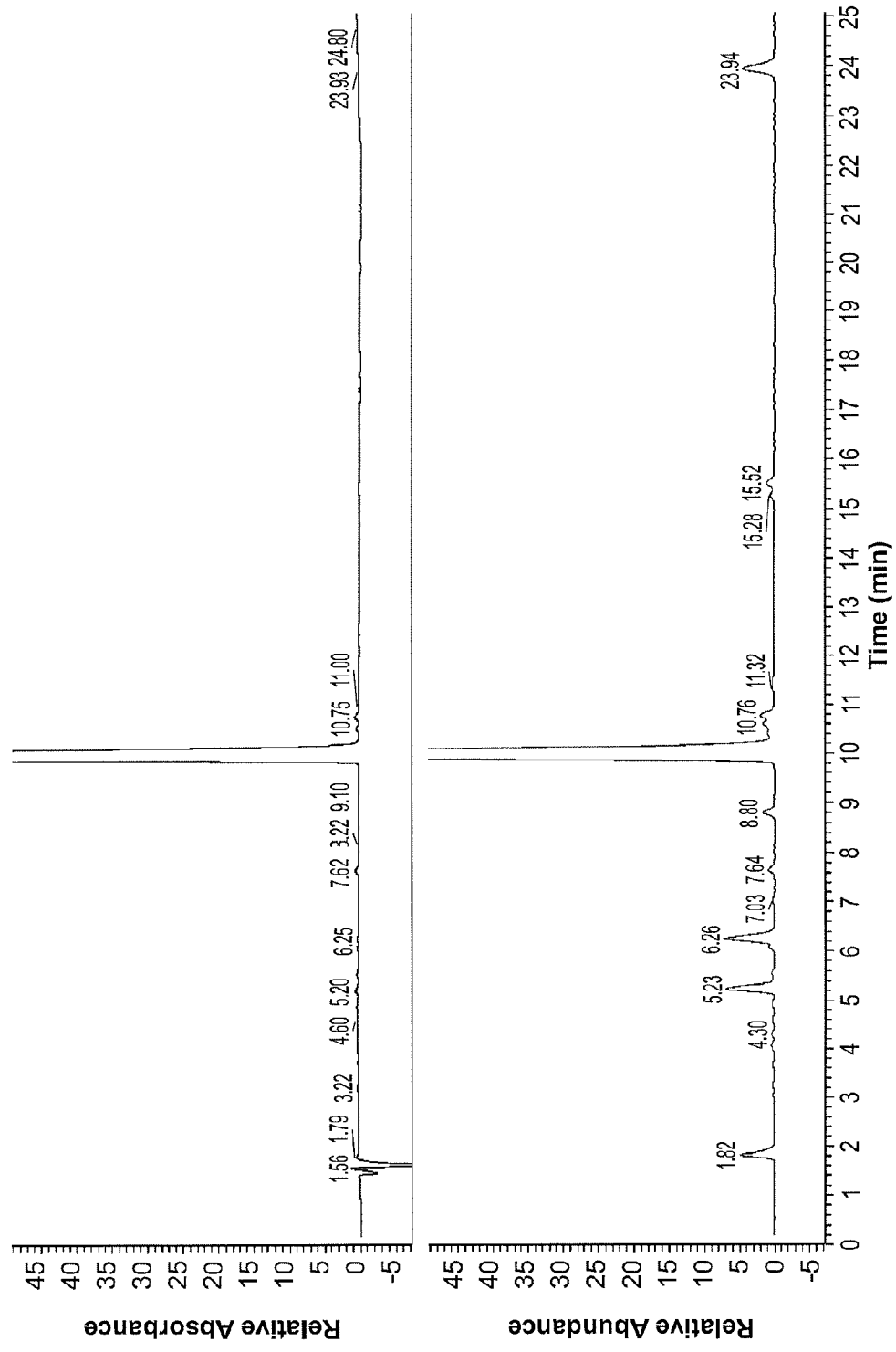
FIG. 2 is a HPLC-UV/MS chromatogram of compound 5 of Step 4 of Example 1, purified reference injected at 1 mg/mL, injection volume 20 µL. The chromatogram is obtained according to the method described in Example 2.

The results are shown in FIGS. 1 and 2. FIGS. 1 and 2 are UPLC UV/MS chromatograms for "crude compound 5" (FIG. 1) and compound 5 "purified reference" (FIG. 2) obtained on a high performance UPLC column. For FIG. 1, the sample was dissolved at 1 mg/mL in ACN/H$_2$O 1:1; 200×2 mm Hypersil GOLD R122; LMA:H$_2$O+10 mM AF+0.1% HFo; LMB:ACN; 45%-20-60%(10); 0.4 mL/min; 40° C.; UVA=200 nm; 3 µL injection volume. For FIG. 2, the sample was dissolved at 1 mg/ml in ACN/H$_2$O; 200×2 mm Hypersil GOLD R122; A: 10 mM AF+0.1% HFo; B:ACN; 45%-20-60% B(10); 0.4 mL/min; 20 µL injection volume. In both samples, the molecular weight of the main component (RT 9.92 min) and of the minor component (RT 10.77 min) was the same as expected and the accurate masses of the two compounds were consistent with the structures provided as shown in Tables D and E of data of the positive and negative ion measurement show below:

TABLE D

Data of the positive ion measurement

| RT(min) | Ion m/z | Formula | Structure proposal |
|---|---|---|---|
| 9.98 | 417.30008 | C$_{26}$ H$_{41}$ O$_4$ ΔM 0.35 ppm | M + H E Isomer |
| | 833.59381 | C$_{52}$ H$_{81}$ O$_8$ ΔM 1.45 ppm | 2M + H E Isomer |
| | 850.61938 | C$_{52}$ H$_{84}$ O$_8$ N ΔM 0.28 ppm | 2M + NH4 E Isomer |
| 10.77 | 417.30023 | C$_{26}$ H$_{41}$ O$_4$ | M + H Z Isomer |
| | 833.59409 | C$_{52}$ H$_{81}$ O$_8$ | 2M + H Z Isomer |
| | 850.61984 | C$_{52}$ H$_{84}$ O$_8$ N | 2M + NH4 Z Isomer |

TABLE E

Data of the negative ion measurement

| RT(min) | Ion m/z | Formula | Structure proposal |
|---|---|---|---|
| 9.98 | 415.28520 | C$_{26}$ H$_{39}$ O$_4$ ΔM −0.44 ppm | M − H Z Isomer |
| | 461.29051 | C$_{27}$ H$_{41}$ O$_6$ ΔM −0.76 ppm | M + Formiat Z Isomer |
| | 831.57683 | C$_{52}$ H$_{79}$ O$_8$ ΔM −1.46 ppm | 2M − H Z Isomer |
| 10.77 | 415.28545 | C$_{26}$ H$_{39}$ O$_4$ | M − H E Isomer |
| | 461.29069 | C$_{27}$ H$_{41}$ O$_6$ | M + Formiat E Isomer |
| | 831.57739 | C$_{52}$ H$_{79}$ O$_8$ | 2M − H E Isomer |

Figure 3:
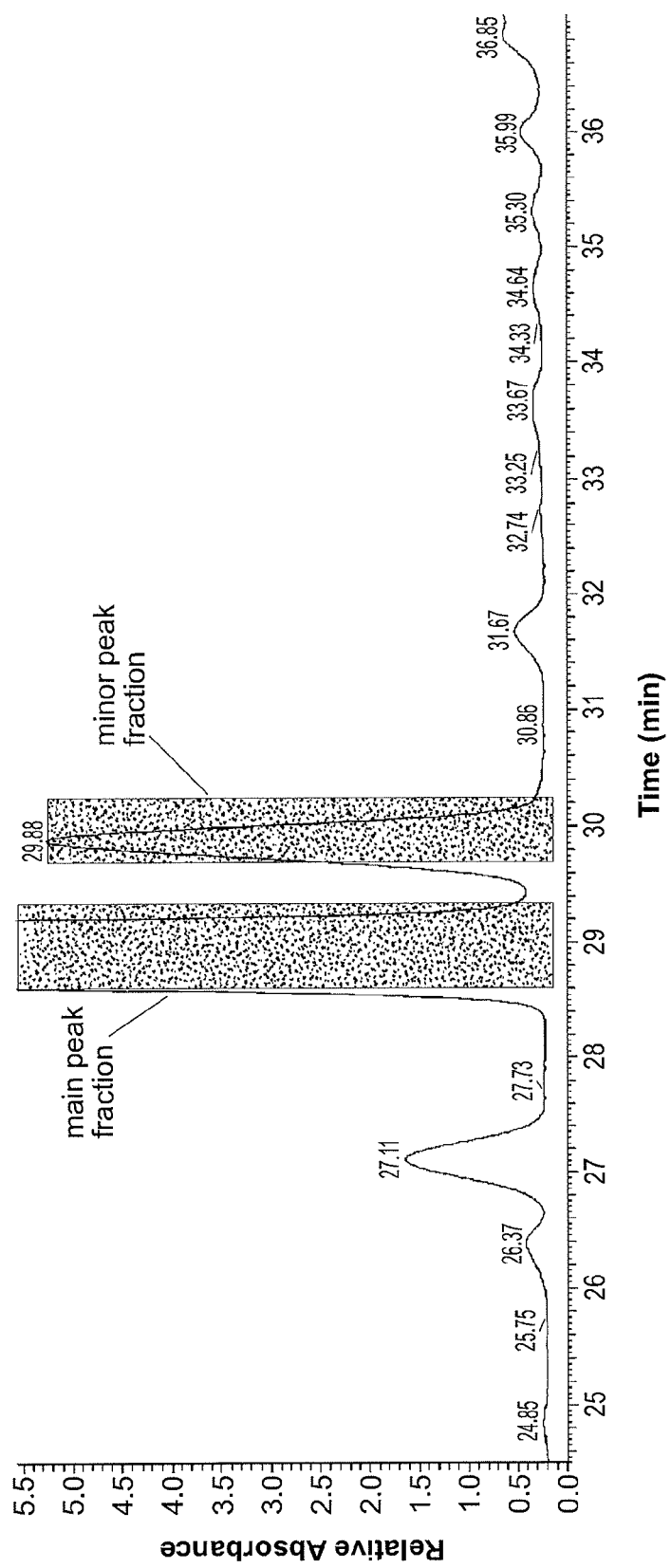
FIG. 3 is a UV chromatogram of crude compound 5 of step 4 of Example 1 using HPLC method. The chromatogram is obtained according to the method described in Example 2.

To ensure the portability of the quality control HPLC method 2, the original separation was repeated exactly under the prescribed conditions. The main peak and the minor peak were isolated as semipreparative. The resulting UV chromatogram with the marked positions of the trapped fractions is shown in FIG. 3. FIG. 3 is a UV chromatogram of crude compound 5 using HPLC method 2; 125×4 mm Purospher STAR C18 5 µm AG; LMA:H$_2$O pH 2.6 with H$_3$PO$_4$; LMB:ACN; 30% B-10-35%-30-60%-1-90%(9); 1 mL/min; 35° C.; UVA=200 nm; ohne MS; 25 mL. Subsequently, the isolated fractions were separately analyzed with the newly developed UPLC/MS method. For the evaluation of the accurate ion trace of the quasimolecular ion [2M+NH$_4$] at 850.61914±3 ppm was used. The resulting chromatograms of the main peak fraction, the minor peak fraction and of the two samples are shown in FIG. 4 (A-D). The MS studies showed that the two peaks generated by quality control method 2 at RT 27.457 min and at RT 28.078 min are two isomers with the formula C$_{26}$H$_{40}$O$_4$. This formula is consistent with the structure proposed for the E/Z isomers. Thus, the development of the UPLC-MS method has shown that the E/Z isomers of 3α-hydroxy-ethyliden-7-keto-5β-cholic-24 acid are chromatographically separable with high resolution. The accurate MS data from the FR-ICR mass spectrometer are consistent with the structure proposed for the E/Z isomers. For both isomers, the same formula C$_{26}$H$_{40}$O$_4$ was derived.

Due to the semi-preparative isolation of the E/Z-isomer peaks with HPLC method 2 and subsequent identification with the UPLC-MS method we can show that the two peaks generated by the quality control method 2 (RT 27.457 minutes and RT 28.078 minutes, see FIG. 1) are the two isomers with the formula C$_{26}$H$_{40}$O$_4$. This formula is consistent with the structure proposal of the E/Z-isomers. In conjunction with the NMR results described below the following assignments were obtained: RT 27.457 minutes belongs to the E-isomer and RT 28.078 minutes to the Z-isomer.

The assignment of the $^1$H and $^{13}$C shifts for the E isomer of 3α-hydroxy-ethyliden-7-keto-5β-cholic-24 acid are shown below. Shifts were estimated according to "L. Bettarello et al., II Farmaco 55 (2000), 51-55 (substance 3α-hydroxy-7-keto-5β-cholan-24-oic acid).

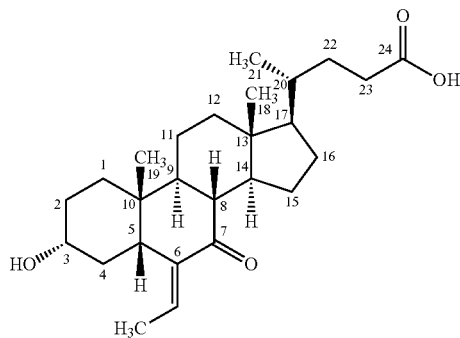

TABLE F

$^1$H Shift Assignment ($^1$H-NMR, 500 MHz, 303K, CD$_3$OD)

| Chemical shift [ppm] | Intensity [H] | Multiplicity | Assignment |
|---|---|---|---|
| 6.10 | 1 | Q | 25 |
| 3.61 | 1 | M | 3 |

TABLE F-continued

¹H Shift Assignment (¹H-NMR, 500 MHz, 303K, CD₃OD)

| Chemical shift [ppm] | Intensity [H] | Multiplicity | Assignment |
|---|---|---|---|
| 2.69 | 1 | DD | 5 |
| 2.28 | 2 | DT | 23 |
| 1.72 | 3 | D | 26 |
| 1.05 | 3 | S | 19 |
| 0.99 | 3 | D | 21 |
| 0.70 | 3 | S | 18 |

TABLE G

¹³C Shift Assignment (¹³C-NMR, 125 MHz, 303K, CD₃OD)

| Chemical shift [ppm] | Multiplicity | Assignment |
|---|---|---|
| 207.5 | S | 7 |
| 178.1 | S | 24 |
| 145.3 | S | 6 |
| 130.4 | D | 25 |
| 71.0 | D | 3 |
| 56.0 | S | 17 |
| 52.0 and 50.1 | D each | 8 and 14 |
| 46.9 | D | 5 |
| 44.7 | S | 13 |
| 40.7 | D | 9 |
| 40.3 | T | 12* |
| 38.3 | T | 4* |
| 36.5 | D | 20 |
| 35.8 | S | 10 |
| 35.4 | T | 1 |
| 32.3 and 32.0 | T each | 22 and 23 |
| 30.5 | T | 2* |
| 29.4 | T | 16* |
| 27.0 | T | 15* |
| 23.2 | Q | 19 |
| 22.4 | T | 11 |
| 18.9 | Q | 21 |
| 12.7 | Q | 26 |
| 12.5 | Q | 18 |

S = singlet
D = doublet
T = triplet
Q = quartet
M = multiplet
DD = doublet of doublets
DT = doublet of triplets

Example 3

Characterization of Crystalline Obeticholic Acid

I. Solid-state characterization of the product from step 6 of Scheme 1 and Example 1 showed that the obeticholic acid is crystalline. This crystalline form is labeled Form A and is substantially similar to the X-ray Diffractogram in FIG. 41 and is characterized by peaks at about 5.0 and 5.3 degrees 2-Theta. The corresponding data for the X-ray Diffractogram of Form A are presented in Table 4 below.

TABLE 4

X-ray Diffractogram Data of Crystalline Obeticholic Acid Form A

| Angle 2-Theta ° | Intensity % |
|---|---|
| 5.0 | 53.8 |
| 5.3 | 34.6 |
| 6.3 | 54.0 |
| 7.3 | 15.6 |
| 7.7 | 23.3 |
| 8.2 | 10.5 |
| 8.3 | 11.8 |
| 8.4 | 11.8 |
| 8.9 | 35.9 |
| 9.4 | 20.4 |
| 10.0 | 63.0 |
| 10.5 | 11.7 |
| 11.0 | 50.8 |
| 12.4 | 83.2 |
| 14.5 | 19.7 |
| 14.9 | 39.9 |
| 15.3 | 36.9 |
| 16.0 | 75.7 |
| 16.5 | 69.1 |
| 16.8 | 100.0 |
| 17.9 | 39.2 |
| 18.7 | 35.6 |
| 19.0 | 34.4 |
| 19.6 | 12.1 |
| 20.6 | 16.2 |
| 21.3 | 22.8 |

Small Scale Synthesis of Crystalline Obeticholic Acid Form A

Amorphous obeticholic acid (approximately 30 mg) was weighed into a glass vial and warmed to 50° C. n-Butyl acetate (60 uL) was added and observations were made. The sample was stirred at 50° C. for 1 hour and was cooled to 5° C. using a linear cooling rate of 0.1° C./min. The sample was stirred at 5° C. for 2 days. Solids were filtered, air dried and analyzed by XRPD. The solution was stored in the freezer for ~48 hours, and then left to evaporate at ambient conditions to afford Form A. Additional methods of preparing Form A are provided in Example 9.

Scale-up Synthesis of Crystalline Obeticholic Acid Form A

Figure 42:
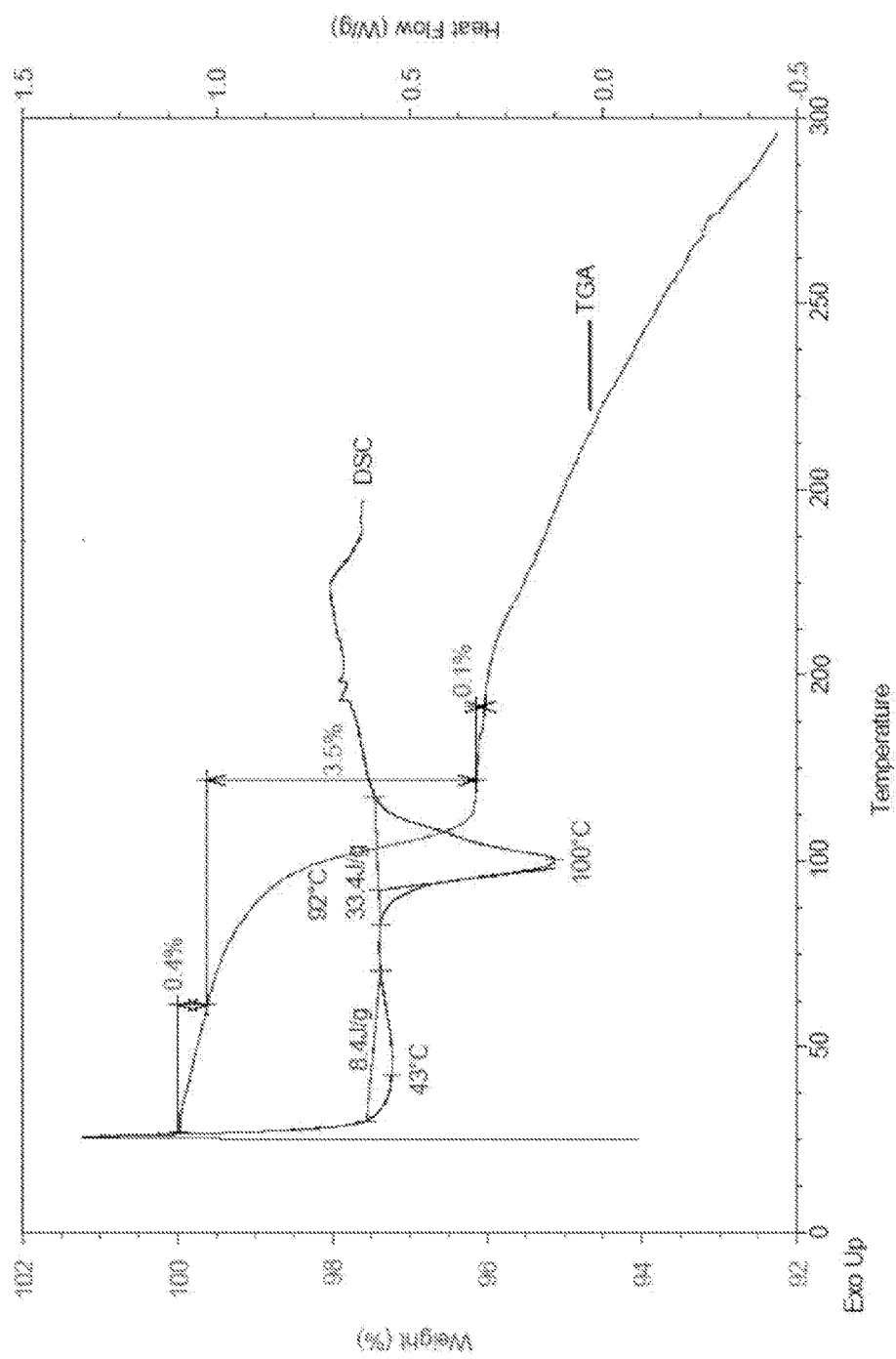
FIG. 42 is an overlay of TGA and DSC thermograms of crystalline obeticholic acid Form A (see example 3).
Figure 43:
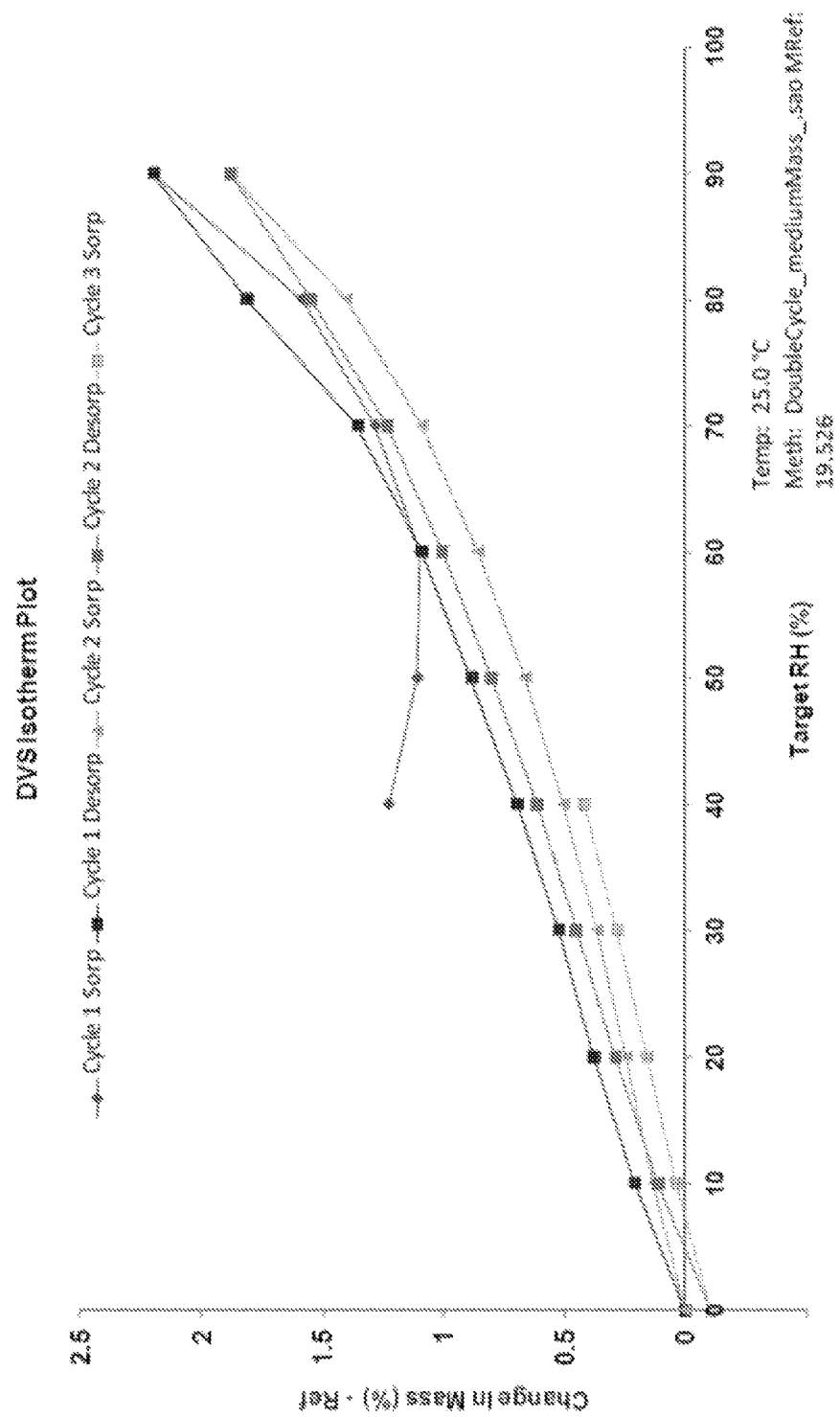
FIG. 43 is an isotherm plot for the GVS experiment with Form A (see example 3).
Figure 44:
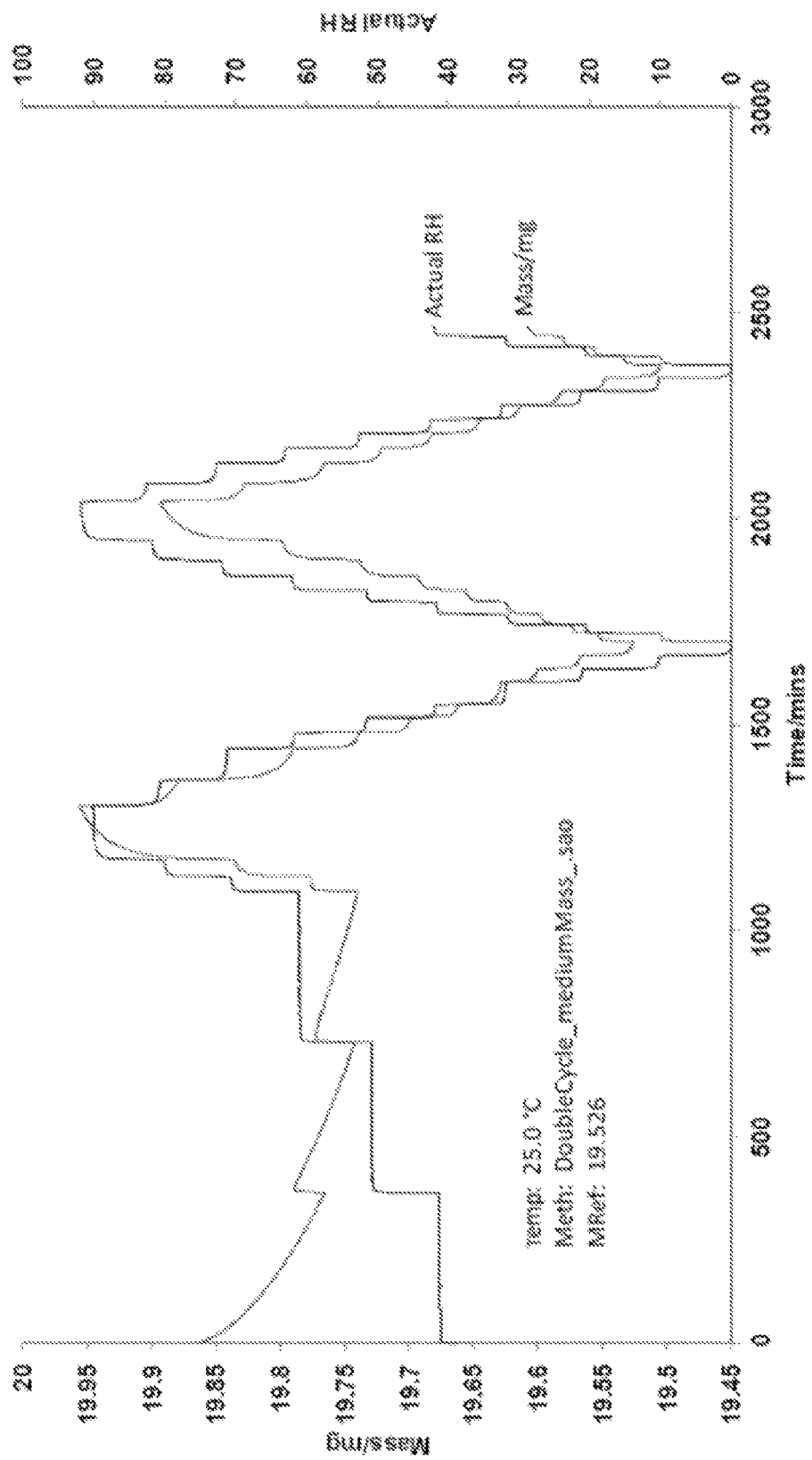
FIG. 44 is a kinetics plot for the GVS experiment with Form A (see example 3).

Amorphous obeticholic acid (approximately 1 g) was weighed into a large glass vial and warmed to 50° C. Ethyl acetate (1.5 ml, 1.5 volumes) was added at 50° C., forming a clear solution. Anti-solvent (heptane, 2.0 ml, 2 volumes) was added, initially forming a cloudy precipitate, which converted to an oil on stirring. After stirring at 50° C. for 1 hour the oil remained so an additional 0.5 ml (0.5 volumes) ethyl acetate was added, which dissolved the oil, forming a cloudy liquid. The sample was seeded with approximately 1 mg of sample from the small scale experiment directly above. The sample was stirred at 50° C. for another hour then was cooled to −20° C. using a linear cooling rate of 0.1° C./min. The sample was stirred at −20° C. overnight, after which a small amount of the solid was filtered, air dried and analyzed by XRPD. The remainder of the sample was filtered through a 0.45 μm PTFE filter and was washed with 2×2 ml portions of heptane. The sample was air dried for approximately 30 minutes then was dried in a vacuum oven overnight at RT. The resulting white solid (898.9 mg) was characterized as Form A having an X-ray Diffractogram substantially similar to that of FIG. 41. FIG. 42 is an overlay of the TGA and DSC thermograms of crystalline obeticholic acid Form A. FIG. 43 is an isotherm plot for the GVS experiment with Form A. FIG. 44 is a kinetics plot for the GVS experiment with Form A.

II. Below is a table that summarizes the characterization of crystalline obeticholic acid Form C:

TABLE G

Summary of Crystalline Obeticholic Acid Form C Characteristics

| Technique | Crystalline Obeticholic Acid Form C |
|---|---|
| appearance | White powder |
| NMR | Consistent with supplied structure ca. 3.5% w/w heptane |
| XRPD | Crystalline |
| TGA | Weight losses between r.t. to 85° C. (0.4%) and 85-115° C. (4.1%) |
| DSC | Endotherm with onset of 97.9° C. |
| GVS | Slightly hygroscopic, 1.2% water uptake at 90% RH |
| Karl Fisher Water Determination | 1.5% w/w |
| Stability at 40° C./75% RH | No change in form or crystallinity |

Thermal Analysis

DSC (Differential Scanning calorimetry) data were collected on a Mettler DSC 823e equipped with a 34 position auto-sampler. The instrument was calibrated for energy and temperature using certified indium. Typically 0.5-1 mg of each sample, in a pin-holed aluminium pan, was heated at 10° C.·min$^{-1}$ from 25° C. to 350° C. A nitrogen purge at 50 ml·min$^{-1}$ was maintained over the sample. The instrument control and data analysis software was STARe v 9.20.

TGA (Thermo-Gravimetric Analysis) data were collected on a Mettler TGA/SDTA 851e equipped with a 34 position auto-sampler. The instrument was temperature calibrated using certified indium. Typically 5-10 mg of each sample was loaded onto a pre-weighed aluminium crucible and was heated at 10° C.·min$^{-1}$ from ambient temperature to 300° C. A nitrogen purge at 50 ml·min$^{-1}$ was maintained over the sample. The instrument control and data analysis software was STARe v 9.20.

Figure 6:
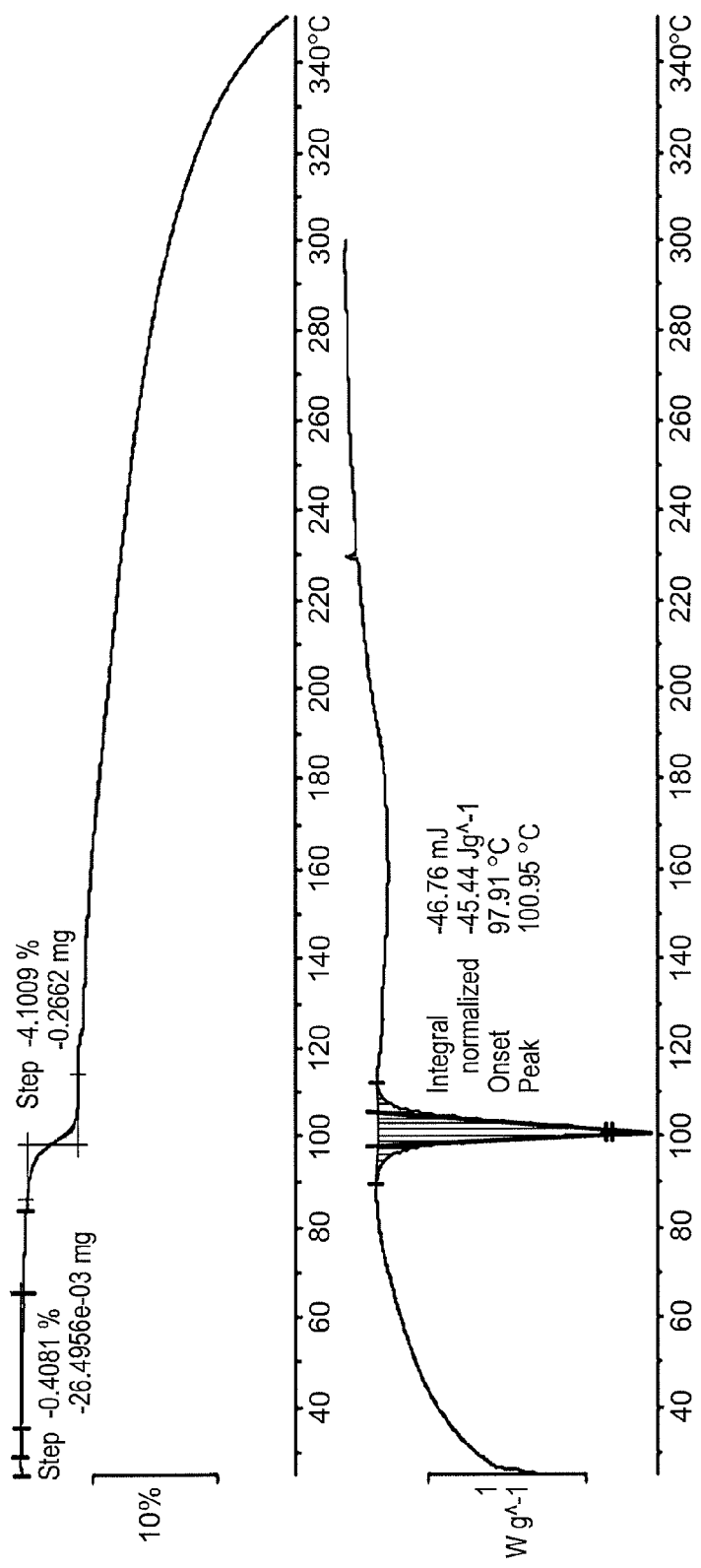
FIG. 6 shows TGA and DSC Thermograms of crystalline obeticholic acid Form C (see Example 3).

Two weight loss steps were observed by TGA of crystalline obeticholic acid Form C. The first took place between room temperature (r.t.) and 85° C. (0.41%) and the second occurred between 85° C.-115° C. (4.10%). The first weight loss step can be attributed to water loss with the second step being attributed to the loss of the remaining water (water responsible for around 1.2% weight loss) and the loss of bound heptane (ca. 3.4% weight loss). Crystalline obeticholic acid Form C contained between 0.15 and 0.2 moles solvent (heptane) and ca. 1.5% w/w (0.3 moles). The DSC thermogram of crystalline obeticholic acid Form C contained one endotherm. This was fairly sharp and had an onset of around 98° C. See FIG. 6. Different solvents would have different boiling points and therefore would evaporate at different temperatures within the DSC and TGA experiments.

X-Ray Powder Diffraction (XRPD) Analysis

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto sample positioning and a HiStar 2-dimensional area detector. X-ray optics consisted of a single Göbel multilayer mirror coupled with a pinhole collimator of 0.3 mm. A weekly performance check was carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample was exposed to the X-ray beam for 120 seconds. The software used for data collection was GADDS for WNT 4.1.16 and the data were analyzed and presented using Diffrac Plus EVA v 9.0.0.2 or v 13.0.0.2.

Ambient conditions: Samples run under ambient conditions were prepared as flat plate specimens using powder as received without grinding. Approximately 1-2 mg of the sample was lightly pressed on a glass slide to obtain a flat surface.

Non-ambient conditions: Samples run under non-ambient conditions were mounted on a silicon wafer with heat-conducting compound. The sample was then heated to the appropriate temperature at ca. 10° C.·min$^{-1}$ and subsequently held isothermally for ca. 1 minute before data collection was initiated.

Bruker AXS/Siemens D5000

X-Ray Powder Diffraction patterns were collected on a Siemens D5000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976). The software used for data collection was Diffrac Plus XRD Commander v2.3.1 and the data were analyzed and presented using Diffrac Plus EVA v 11,0.0.2 or v 13.0.0.2.

Samples were run under ambient conditions as flat plate specimens using powder as received. Approximately 20 mg of the sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 4 s·step$^{-1}$

Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v 2.5.0 and the data were analyzed and presented using Diffrac Plus EVA v 11.0.0.2 or v 13.0.0.2.

Samples were run under ambient conditions as flat plate specimens using powder as received. Approximately 5 mg of the sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 0.5 s·step$^{-1}$

The corresponding data for the X-ray diffractogram is presented in the table below. The software used for data collection was Diffrac Plus XRD Commander v2.6.1 and the data were analyzed and presented using Diffrac Plus EVA v13.0.0.2 or v15.0.0.0. Samples were run under ambient conditions as flat plate specimens using powder as received.

The sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 0.5 s·step$^{-1}$

TABLE H

X-ray Diffractogram Data of Crystalline ObeticholicAcid Form C

| peak | Angle 2-Theta (deg) | d value (Angstrom) |
|---|---|---|
| 1 | 4.2 | 21.0203 |
| 2 | 6.35 | 13.90839 |
| 3 | 8.298 | 10.64718 |
| 4 | 9.5 | 9.30229 |
| 5 | 11.05 | 8.00042 |
| 6 | 12.246 | 7.22192 |
| 7 | 12.498 | 7.07692 |
| 8 | 12.647 | 6.99367 |
| 9 | 15.497 | 5.71337 |
| 10 | 15.843 | 5.5895 |
| 11 | 15.998 | 5.53561 |
| 12 | 16.346 | 5.41836 |
| 13 | 16.695 | 5.30601 |
| 14 | 16.996 | 5.21251 |
| 15 | 17.849 | 4.96547 |
| 16 | 18.593 | 4.76844 |
| 17 | 18.798 | 4.71689 |
| 18 | 19.047 | 4.65579 |
| 19 | 20.493 | 4.33041 |
| 20 | 20.894 | 4.24808 |

VT-XRPD (Variable Temperature-X-ray Diffraction) revealed that the endotherm seen in the DSC thermogram corresponded to the desolvation of the sample as no form changes were observed on heating. A temperature difference exists between the DSC and the VT-XRPD data as the VT-XRPD experiment was carried out in a large space with the sample exposed whereas the DSC experiment was carried out in a confined, closed space. This difference is around 20° C. and explains why the sample melted at a much lower temperature in the DSC experiment and the sample still appears crystalline at 110° C. in the VT-XRPD experiment. VT-XRPD shows that drying of the solvent from the material resulted in loss of crystallinity which is consistent with the material being in a solvated form. See FIG. 7.

Gravimetric Vapor Sorption (GVS)

Sorption isotherms were obtained using a SMS DVS Intrinsic moisture sorption analyzer, controlled by DVS Intrinsic Control software v 1.0.0.30. The sample temperature was maintained at 25° C. by the instrument controls. The humidity was controlled by mixing streams of dry and wet nitrogen, with a total flow rate of 200 ml·min$^{-1}$. The relative humidity was measured by a calibrated Rotronic probe (dynamic range of 1.0-100% RH), located near the sample. The weight change, (mass relaxation) of the sample as a function of % RH (relative humidity) was constantly monitored by the microbalance (accuracy±0.005 mg).

5 to 20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range. Data analysis was undertaken in Microsoft Excel using DVS Analysis Suite v6.0.0.7. Method Parameters for SMS DVS Intrinsic Experiments are as follows:

| Parameters | Values |
|---|---|
| Adsorption - Scan 1 | 40-90% |
| Desorption/Adsorption - Scan 2 | 90-0, 0-40% |
| Intervals (% RH) | 10 |
| Number of Scans | 2 |
| Flow rate (ml · min$^{-1}$) | 200 |
| Temperature (° C.) | 25 |
| Stability (° C. · min$^{-1}$) | 0.2 |
| Sorption Time (hours) | 6 hour time out |

The sample was recovered after completion of the isotherm and re-analyzed by XRPD.

Figure 8A:
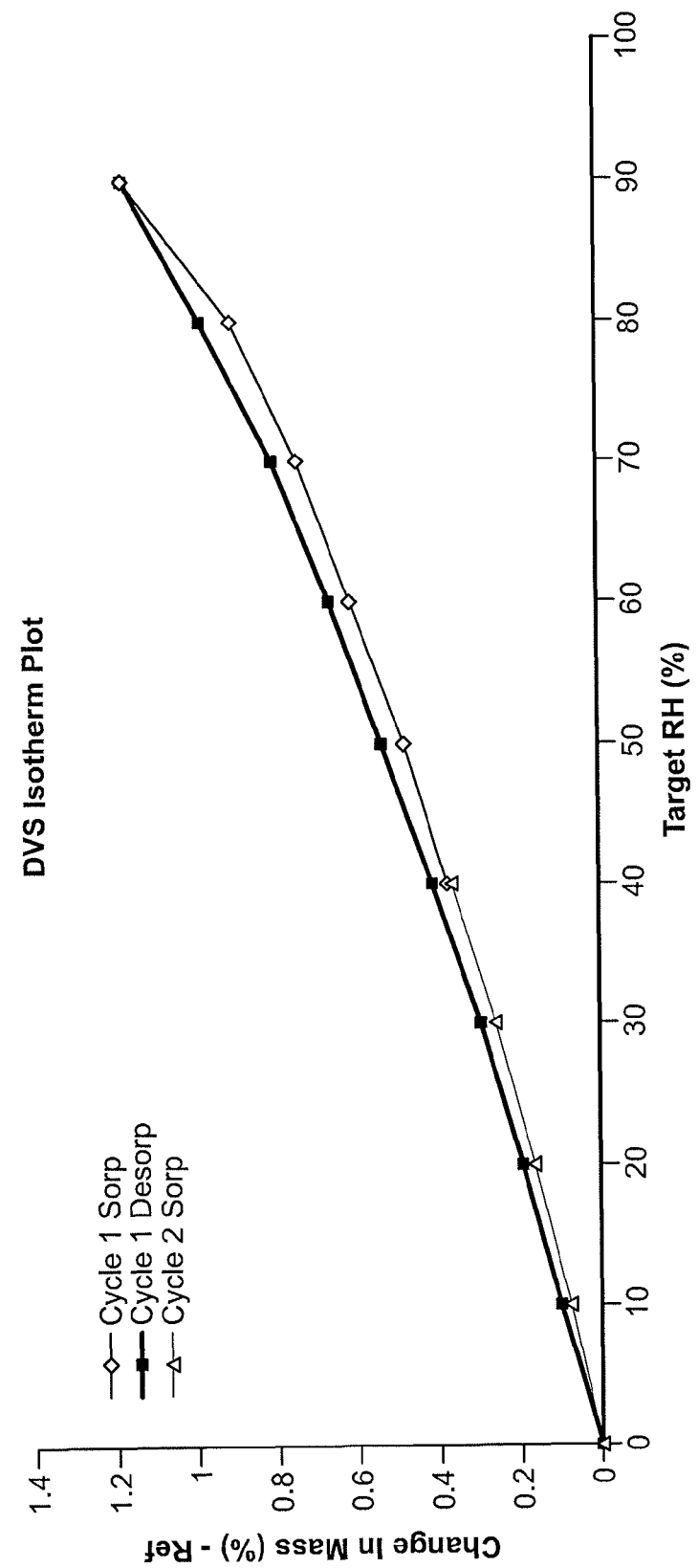
FIG. 8A is a GVS isotherm plot of crystalline obeticholic acid Form C (see Example 3).
Figure 8B:
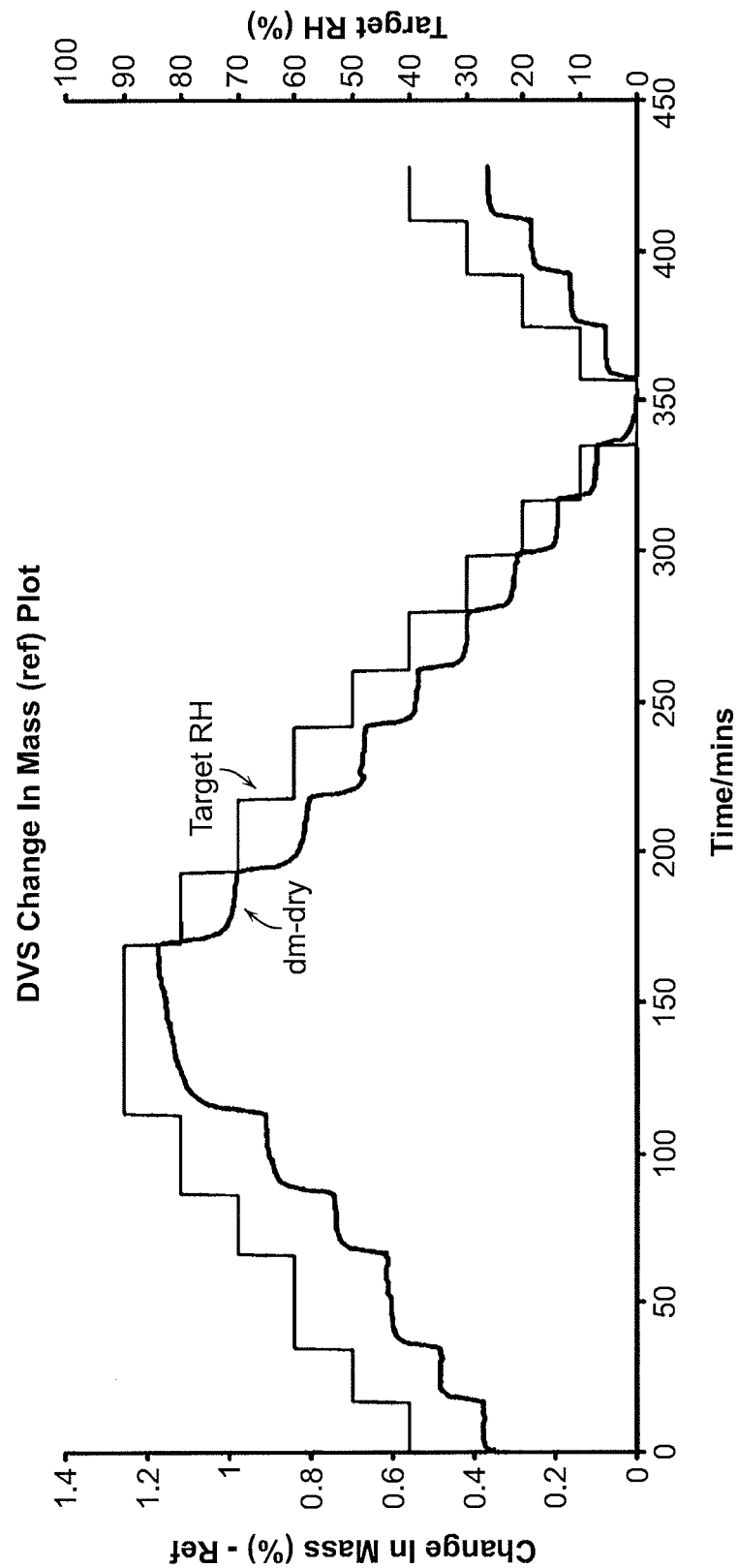
FIG. 8B is a GVS kinetic plot of crystalline obeticholic acid Form C (see Example 3).
Figure 8C:
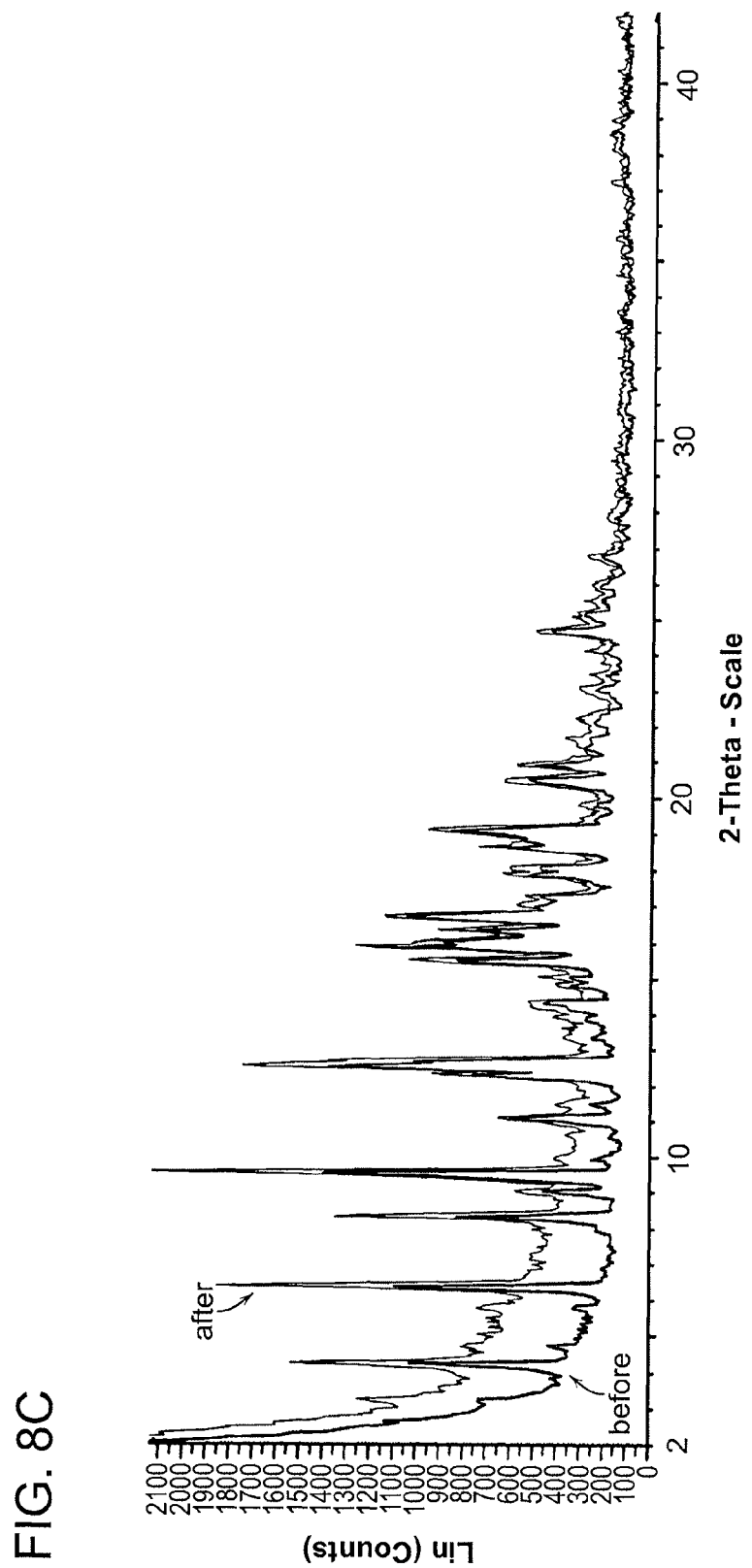
FIG. 8C shows XRPD diffractograms of crystalline obeticholic acid Form C before and after GVS analysis (see Example 3).
Figure 9:
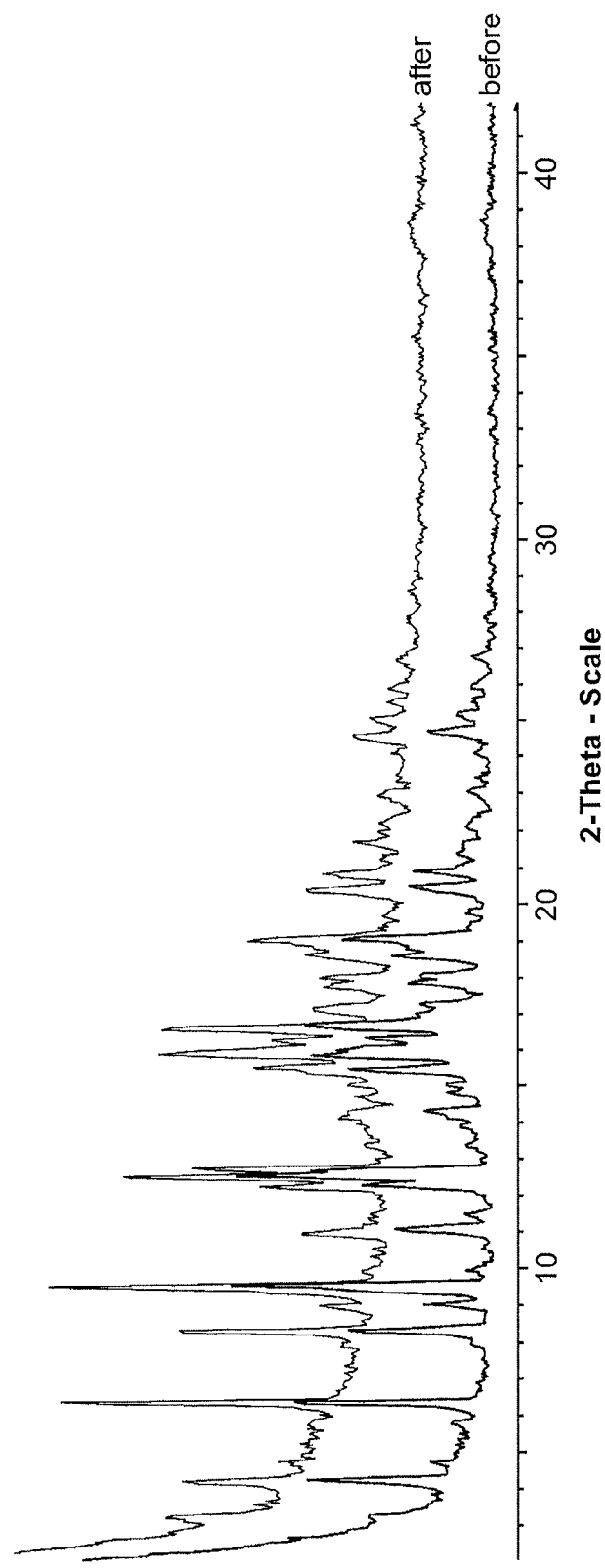
FIG. 9 shows XRPD diffractograms of crystalline obeticholic acid Form C before and after storage at 40° C./75% RH (see Example 3).

Analysis of crystalline obeticholic acid Form C showed that the sample was slightly hygroscopic as a mass increase of 1.18% was noted between 0-90% RH. This uptake of water was steady throughout the analysis and equilibrium was reached for all steps. The hysteresis of the curve was small indicating that the sample readily lost the water it had taken up. XRPD analysis after the GVS analysis showed that the sample was unchanged. See FIGS. 8A, 8B, and 8C.

Water Determination by Karl Fischer Titration (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approximately 10 mg of sample was used per titration and duplicate determinations were made.

Karl Fischer analysis showed that crystalline obeticholic acid Form C contained 1.5% water which corresponds to about 0.3 moles water.

One Week Stability at 40° C. And 75% RH

The stability of obeticholic acid at 40° C. and 75% RH (relative humidity) was determined as follows. A sample of obeticholic acid was stored in a humidity chamber for one week at 40° C./75% RH. The sample was re-analyzed by XRPD and was found to have been unchanged.

The solid state study has shown that the presence of a relatively large amount of organic solvent is required to crystallize obeticholic acid Form C. It is highly unlikely that a sample of obeticholic acid Form 1 will spontaneously crystallize to form crystalline obeticholic acid Form C on storage.

Example 4

Obeticholic Acid Tablet Formulation

The table below shows the quantitative composition of obeticholic acid tablets. The 5 mg, 10 mg, and 25 mg formulations have been used as phase 3 clinical trial material.

TABLE I

| | Film Coated Tablet Film Coated Tablet | | |
|---|---|---|---|
| Component | Quantity per Tablet | Function | Reference to Standard |
| | 1 mg Tablet | | |
| Obeticholic acid | 1.0 mg* | API | HSE |
| Microcrystalline cellulose | 185.0 mg* | Filler/Binder | USP-NF/EP/JP |
| Sodium starch glycolate | 12.0 mg | Disintegrant | USP-NF/EP/JP |

TABLE I-continued

| Component | Film Coated Tablet Quantity per Tablet | Function | Film Coated Tablet Reference to Standard |
|---|---|---|---|
| Magnesium stearate | 2.0 mg | Lubricant | USP-NF/EP/JP |
| Opadry ® II green or white | 8.0 mg | Coating Material | HSE |
| Total weight | 208.0 mg 5 mg Tablet | | |
| Obeticholic acid | 5.0 mg* | API | HSE |
| Microcrystalline cellulose | 181.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Opadry ® II green or white | 8.0 mg | Coating Material | HSE |
| Total weight | 208.0 mg 10 mg Tablet | | |
| Obeticholic acid | 10.0 mg* | API | HSE |
| Microcrystalline cellulose | 176.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Opadry ® II green or white | 8.0 mg | Coating Material | HSE |
| Total weight | 208.0 mg 25 mg Tablet | | |
| Obeticholic acid | 25.0 mg* | API | HSE |
| Microcrystalline cellulose | 157.0 mg* | Filler/Binder | USP-NF/EP/JP |
| Sodium starch glycolate | 12.0 mg | Disintegrant | USP-NF/EP/JP |
| Magnesium stearate | 2.0 mg | Lubricant | USP-NF/EP/JP |
| Collodial silicon dioxide | 4.0 mg | Glidant | USP-NF/EP/JP |
| Opadry ® II green or white | 8.0 mg | Coating Material | HSE |
| Total weight | 208.0 mg | | |

API: Active pharmaceutical ingredient
HSE = In house specification
USP-NF = US Pharmacopeia National Formulary
Ph Eur = European Pharmacopeia
JP = Japanese Pharmacopeia
*obeticholic acid quantity presented assumes API is anhydrous and 100% pure; actual amount is adjusted based on the potency of the drug substance Lot used, and amount of microcrystalline cellulose is correspondingly decreased.

Example 5

Characterization of Obeticholic Acid Form 1

Obeticholic acid Form 1 refers to the non-crystalline form of obeticholic acid. This form of obeticholic acid can be produced via a crystalline obeticholic acid as a synthetic intermediate. Obeticholic acid Form 1 can be used as the pharmaceutically active ingredient. Obeticholic acid Form 1 was characterized and analyzed as follows.

Batch 1 of obeticholic acid form 1 was characterized using the following techniques: assessment by X-ray powder diffraction (XPRD) for crystallinity, $^1$H and $^{13}$C nuclear magnetic resonance (NMR), Fourier transform infrared spectroscopy (FT-IR), optical assessment (e.g., particle shape/size), thermal properties (e.g., differential scanning calorimetry (DSC) and thermo-gravimetric analysis (TGA)), water determination by Karl Fischer (KF), storage at 40° C. and 75% RH and reanalysis after 2 weeks by XRPD, pKa by potentiometric method, Log P/D (octanol/water) by potentiometry, and stability to moisture using gravimetric vapor sorption (GVS; e.g., complete sorption-desorption cycle with analysis of solid collected by XRPD). Five other batches (e.g., batch 2, 3, 4, 5, and 6) of obeticholic acid Form 1 were also characterized and compared using the following techniques: assessment by XRPD and comparison to main batch 1 pattern, $^1$H and $^{13}$C NMR, FT-IR, optical assessment (e.g., particle shape/size), thermal properties (e.g., DSC, TGA, and hot-stage microscopy), and water determination by KF.

X-Ray Powder Diffraction (XRPD) Analysis

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample was exposed to the X-ray beam for 120 seconds. The software used for data collection was GADDS for WNT 4.1.16 and the data were analyzed and presented using Diffrac Plus EVA v 9.0.0.2 or v 13.0.0.2.

Figure 10:
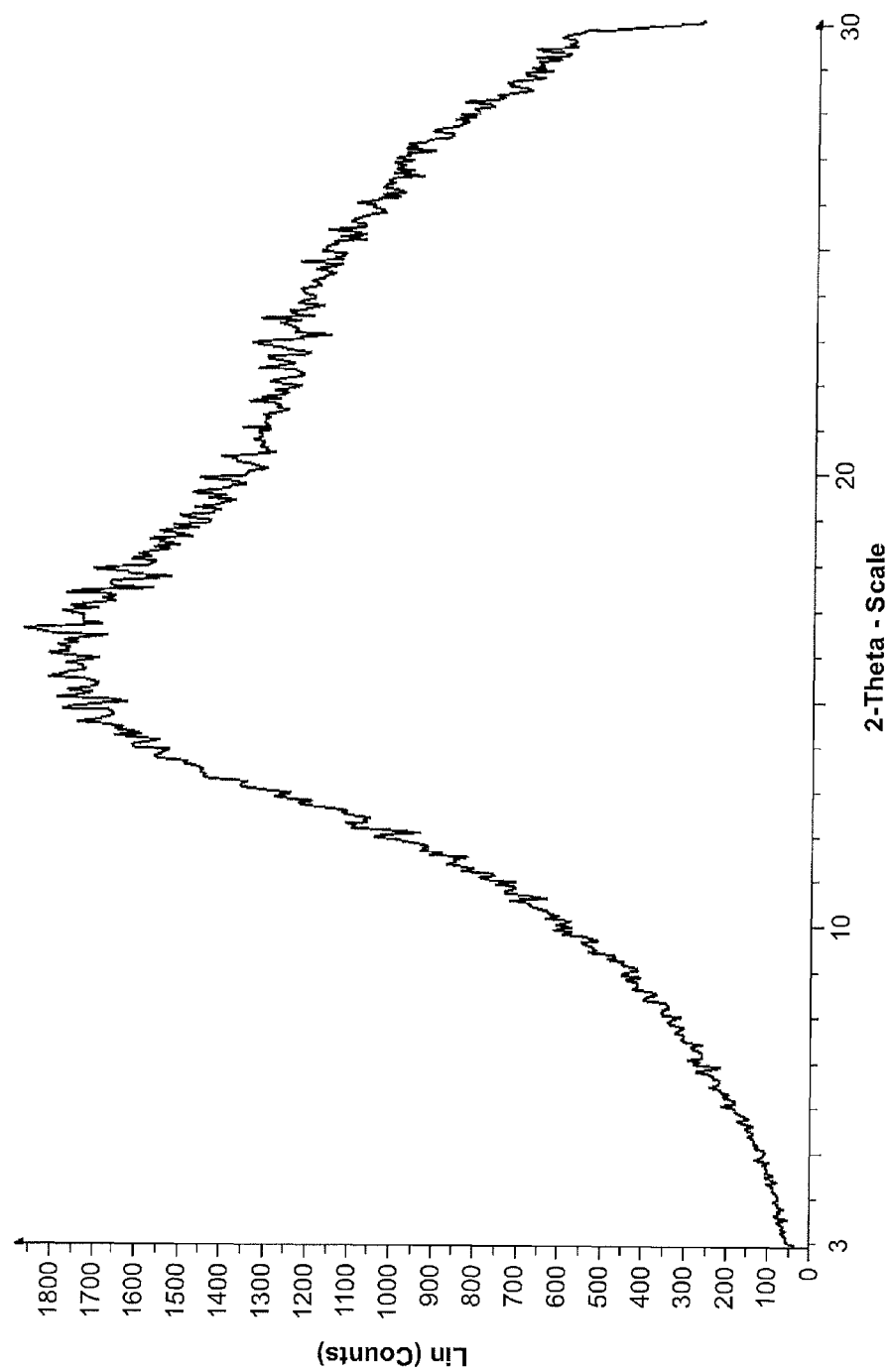
FIG. 10 is an XRPD diffractogram of batch 1 of obeticholic acid Form 1 (see Example 5).
Figure 11:
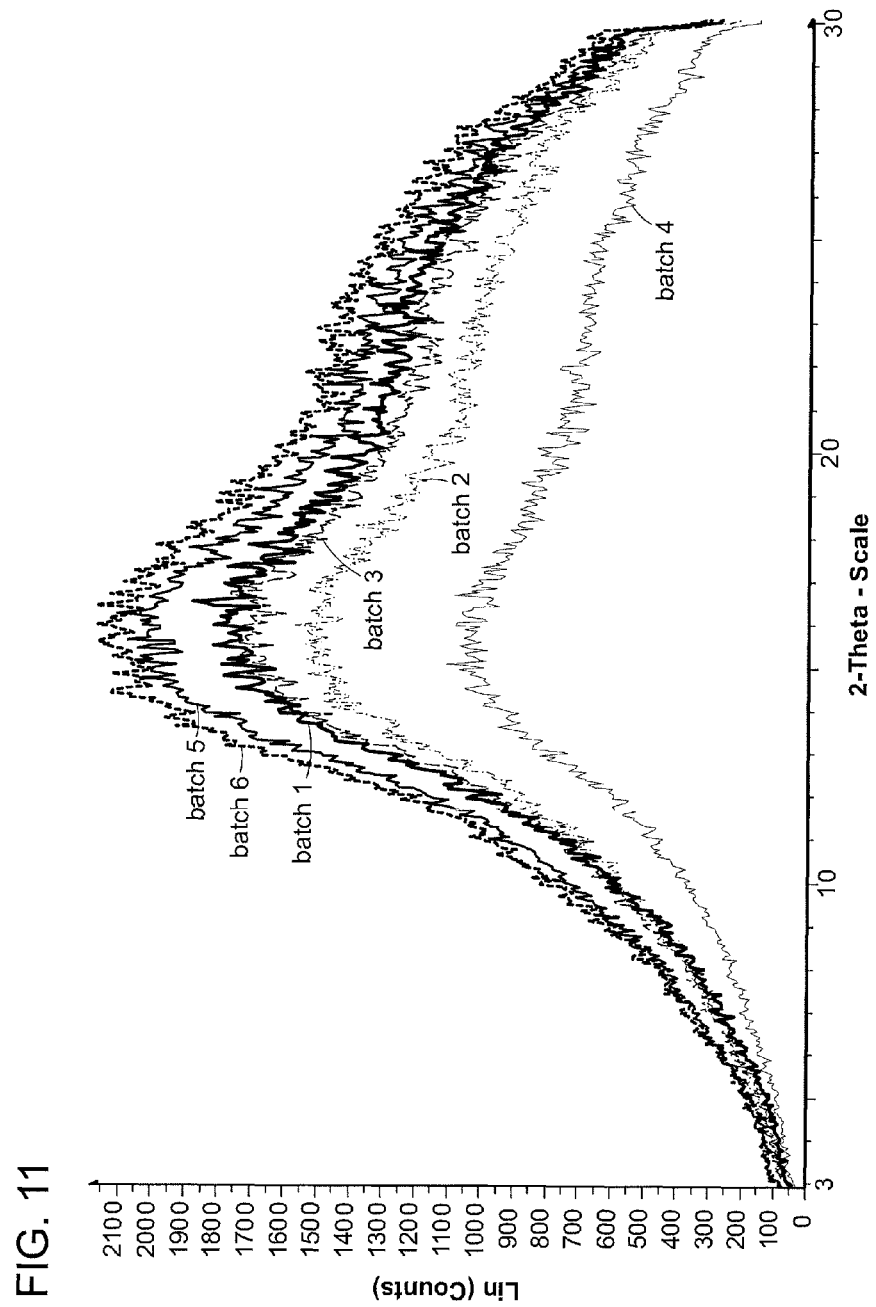
FIG. 11 shows the XRPD diffractorgraphs for batches 1, 2, 3, 4, 5 and 6 of obeticholic acid Form 1 (see Example 5).

Samples run under ambient conditions were prepared as flat plate specimens using powder as received without grinding. Approximately 1-2 mg of the sample was lightly pressed on a silicon wafer to obtain a flat surface. The diffractograms show that obeticholic acid Form 1 is non-crystalline (See, FIG. 10 and FIG. 11).

NMR Characterization

NMR spectra were collected on a Bruker 400 MHz instrument equipped with an auto-sampler and controlled by a DRX400 console. Automated experiments were acquired using ICONNMR v4.0.4 (build 1) running with Topspin v 1.3 (patch level 8) using the standard Bruker loaded experiments. For non-routine spectroscopy, data were acquired through the use of Topspin alone. Samples were prepared in d6-DMSO, unless otherwise stated. Off-line analysis was carried out using ACD SpecManager v 9.09 (build 7703).

Figure 12:
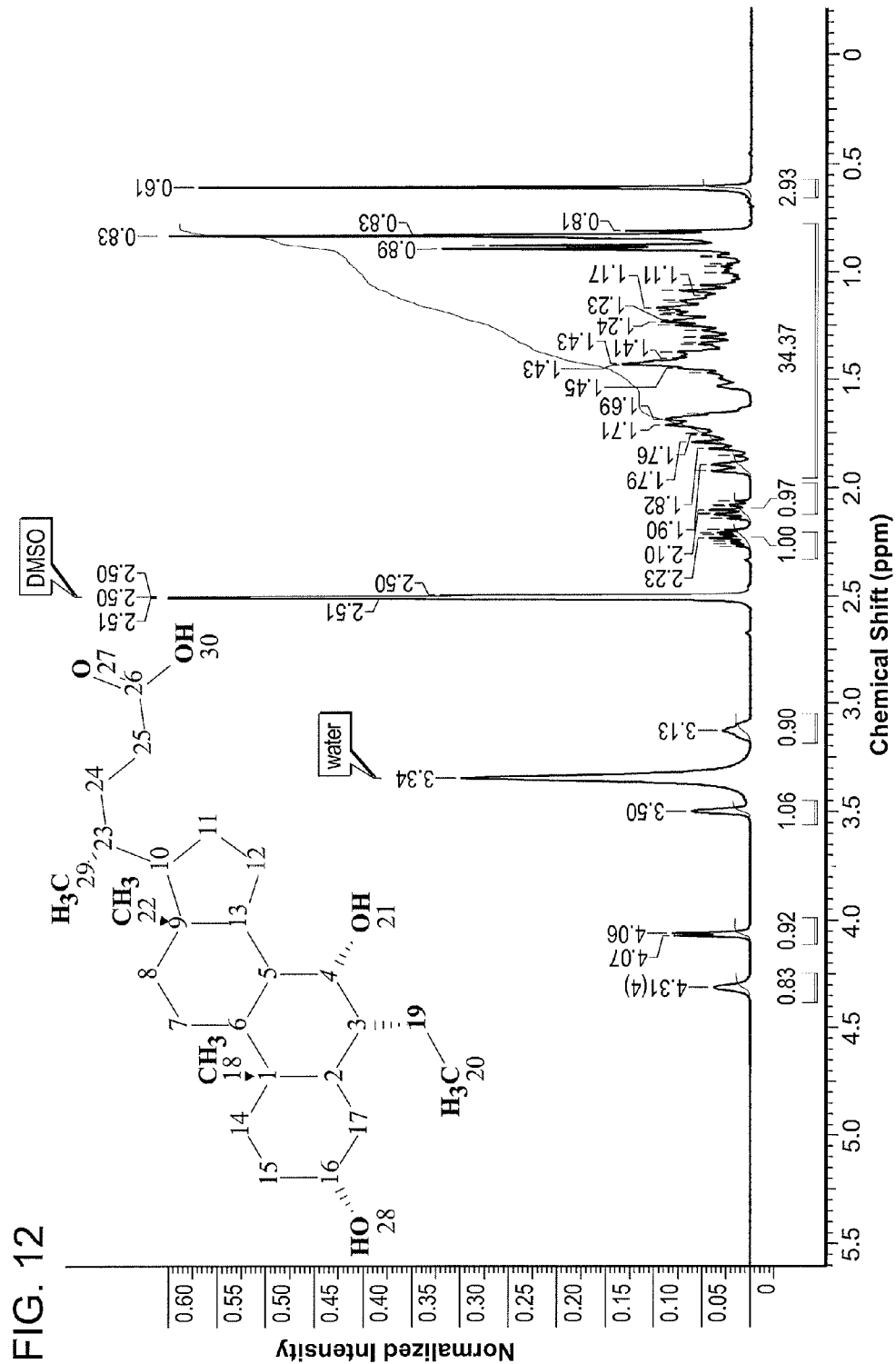
FIG. 12 is a NMR spectrum of batch 1 of obeticholic acid Form 1 in $d_6$-DMSO (see Example 5).
Figure 13:
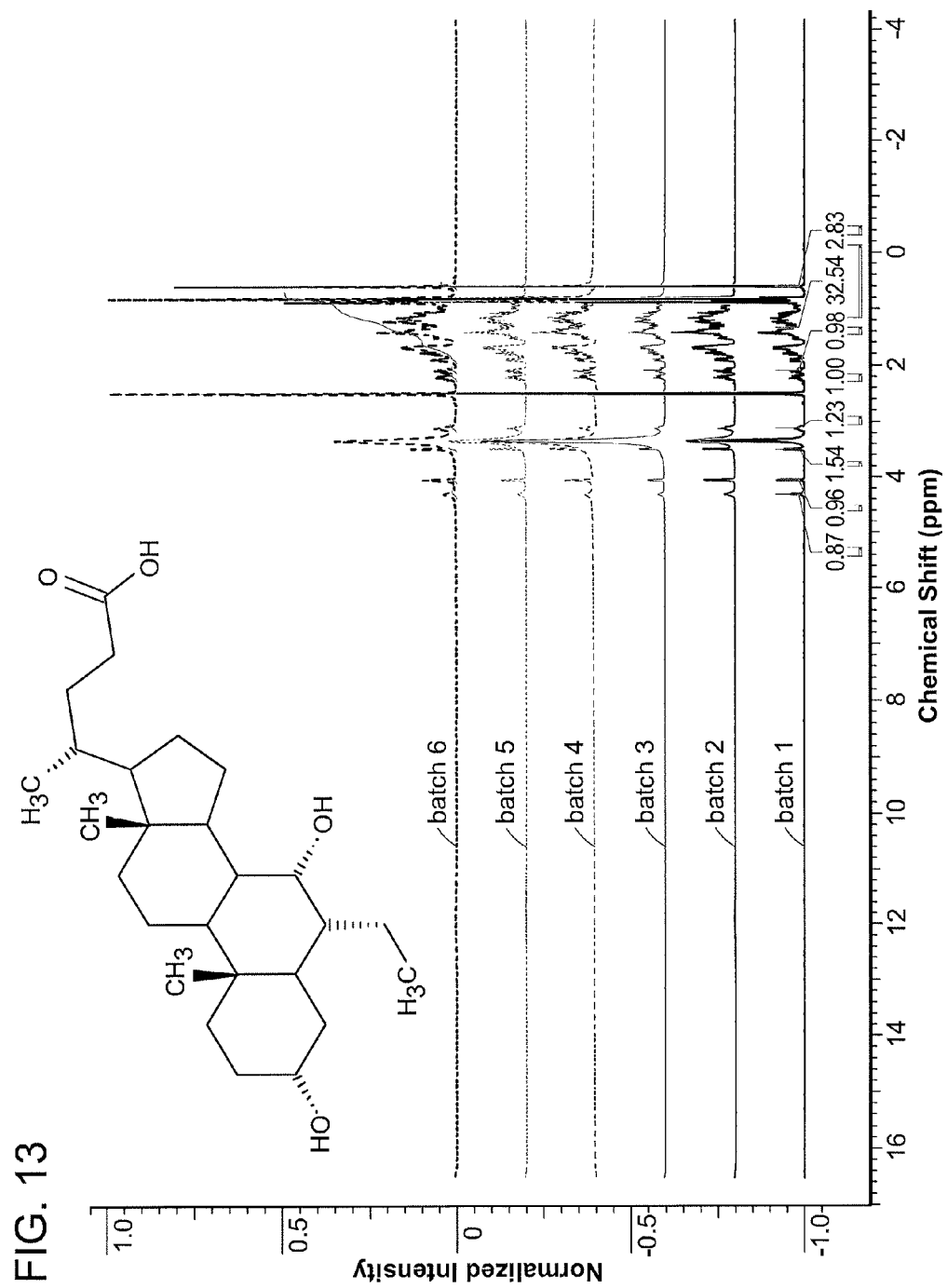
FIG. 13 shows the $^1$H NMR spectra for batches 1, 2, 3, 4, 5 and 6 of obeticholic acid Form 1 (see Example 5).

FIG. 12 shows the $^1$H NMR spectrum for batch 1. $^1$H NMR spectra of batches 2-6 were also recorded and compared with the spectrum of batch 1. See FIG. 13. The spectra are all similar, but with varying amounts of water. Some differences are noted in the integration of the large group of protons between 0.75 ppm and 2 ppm, where peaks overlap and cannot be integrated separately. Table J shows the total number of protons integrated in the spectra of batches 1-6, taking into account the variation in the 0.75-2 ppm region.

TABLE J

| Batch number | Number of H by integration (excluding COOH) |
|---|---|
| 1 | 43 |
| 2 | 42 |
| 3 | 40 |
| 4 | 41 |
| 5 | 42 |
| 6 | 41-42 |

The carboxylic acid proton has been excluded, so the number of protons should be 43, but it actually varies from 40 to 43 between the 6 spectra. However, the area where the variation comes from (0.75-2 ppm) is quite wide, and due to the quality of the baseline, this integration cannot be relied upon.

Figure 14:
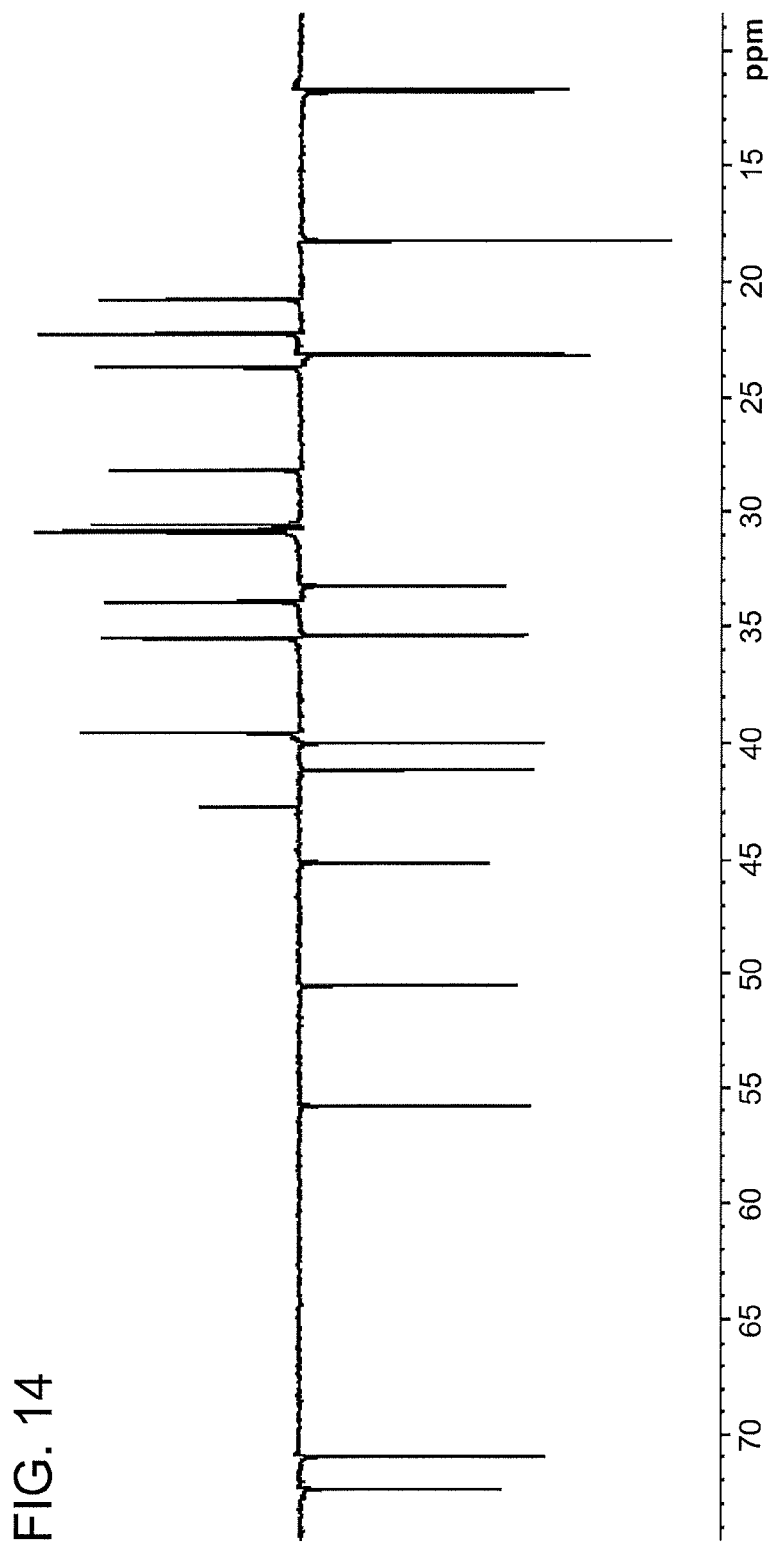
FIG. 14 is an expansion of $^{13}$C DEPTQ NMR spectrum of obeticholic acid Form 1 from region 10-75 ppm (see Example 5).
Figure 15:
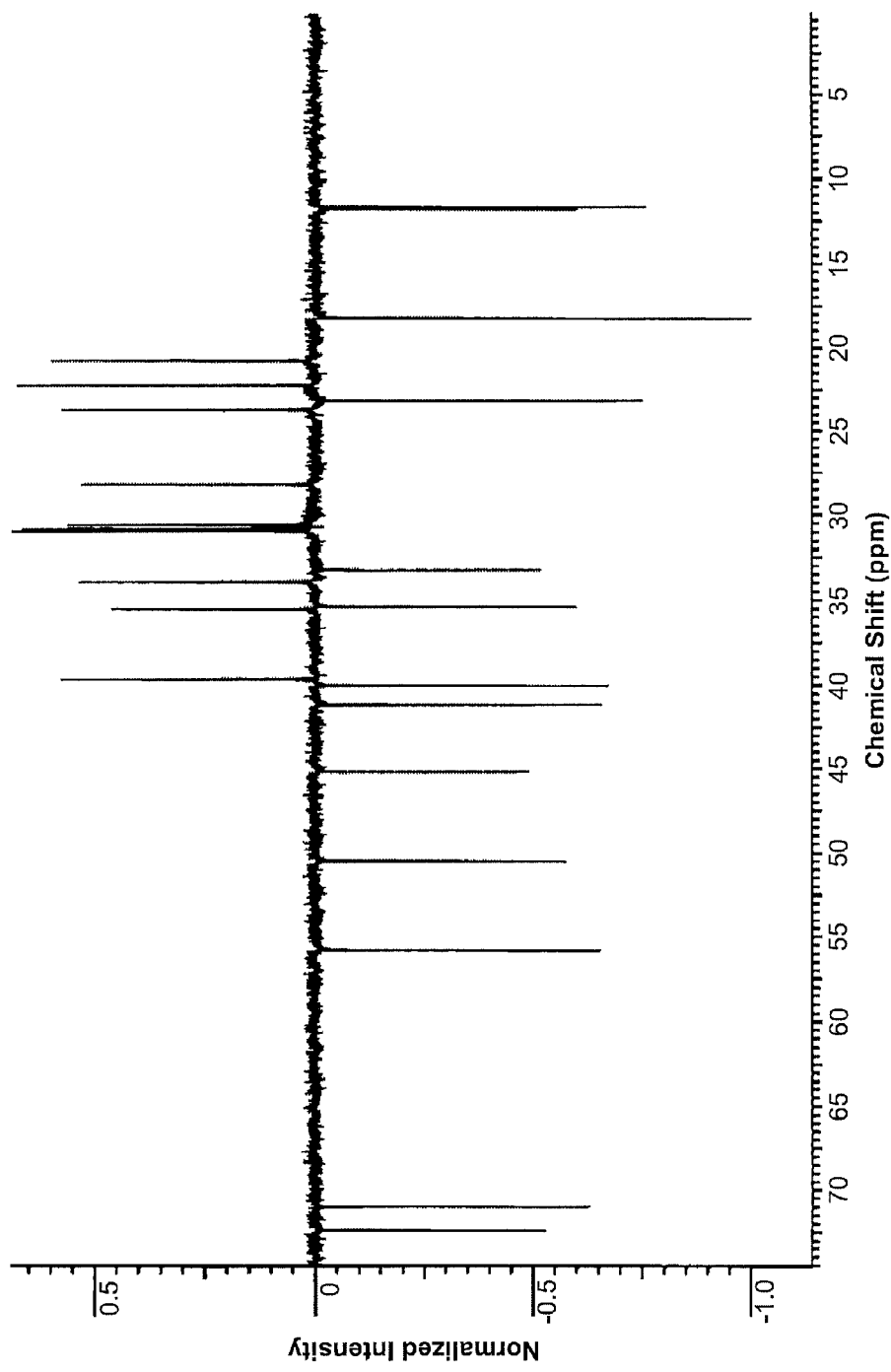
FIG. 15 is an expansion of $^{13}$C DEPT135 NMR spectrum of obeticholic acid Form 1 supressing quaternary carbons from region 0-75 ppm (see Example 5).

As the spectrum could not be fully assigned and the integration varied, a $^{13}$C NMR spectrum of batch 2 was recorded. FIG. 14 shows the DEPTQ spectrum, where $CH_2$ and quaternary carbons peaks point up, while $CH_3$ and CH groups point down. There are thirteen peaks pointing down, which correspond to nine CHs and four $CH_3$ groups. This is consistent with the structure. The peak of the carbon of the carboxylic acid was seen at 175 ppm. It has been excluded from this expanded view for clarity of the area of interest. However, there are only eleven peaks pointing up, whereas there should be twelve, as there are ten $CH_2$ groups and two quaternary carbons in the molecule (excluding the carbonyl). One carbon appears to be overlapping with another signal. Therefore, a DEPT135 spectrum was collected, suppressing the quaternary carbon signals, which could show whether the overlapping signal is quaternary. See FIG. 15. A comparison of the DEPT135 spectrum with the DEPTQ spectrum shows that one peak (at 42.5 ppm) disappears. There are two quaternary carbons in the molecule, which should correspond to two peaks disappearing. Therefore the overlapping carbon signal is a quaternary one.

Figure 16:
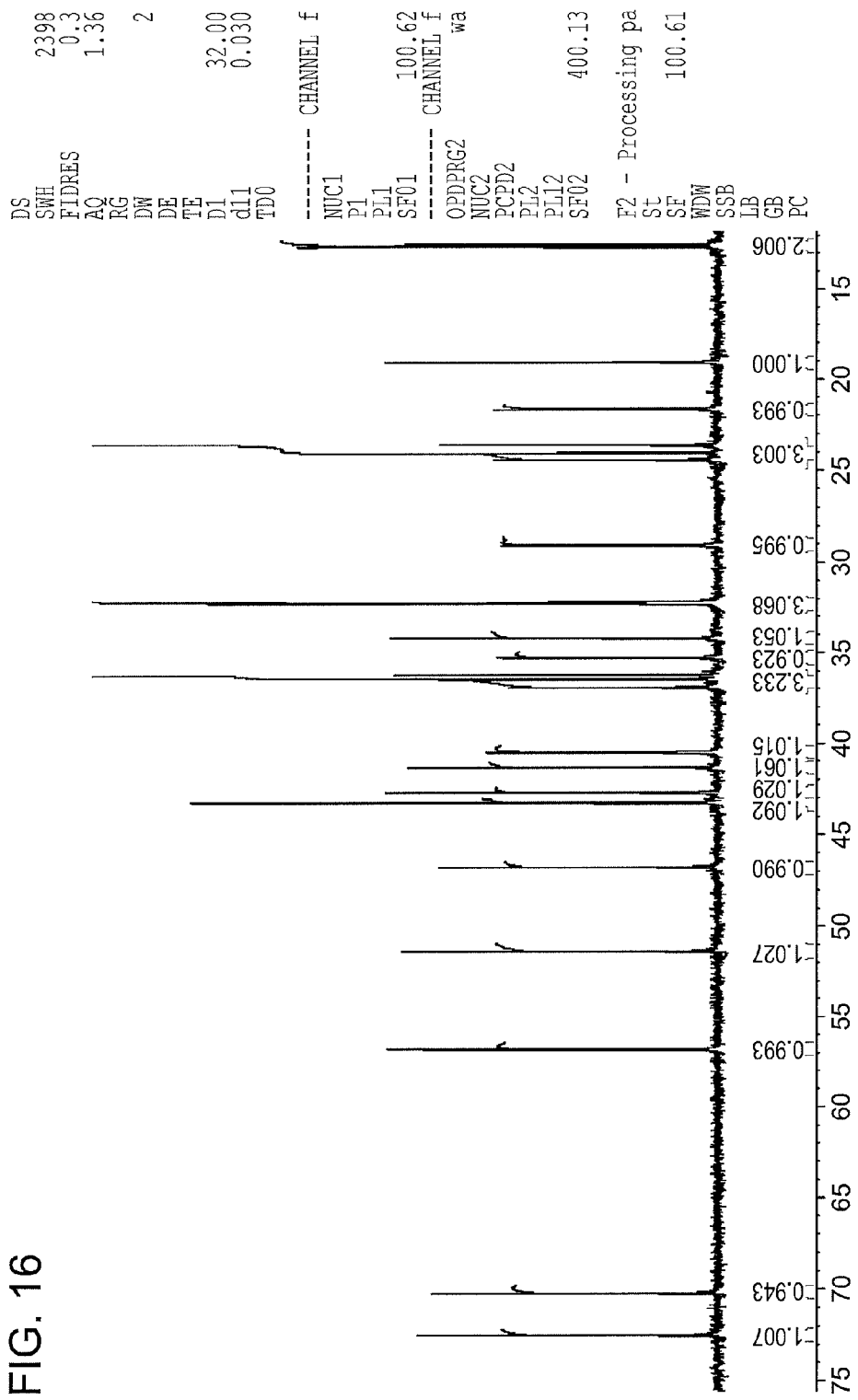
FIG. 16 is a quantitative $^{13}$C NMR of obeticholic acid Form 1 (see Example 5).
Figure 17:
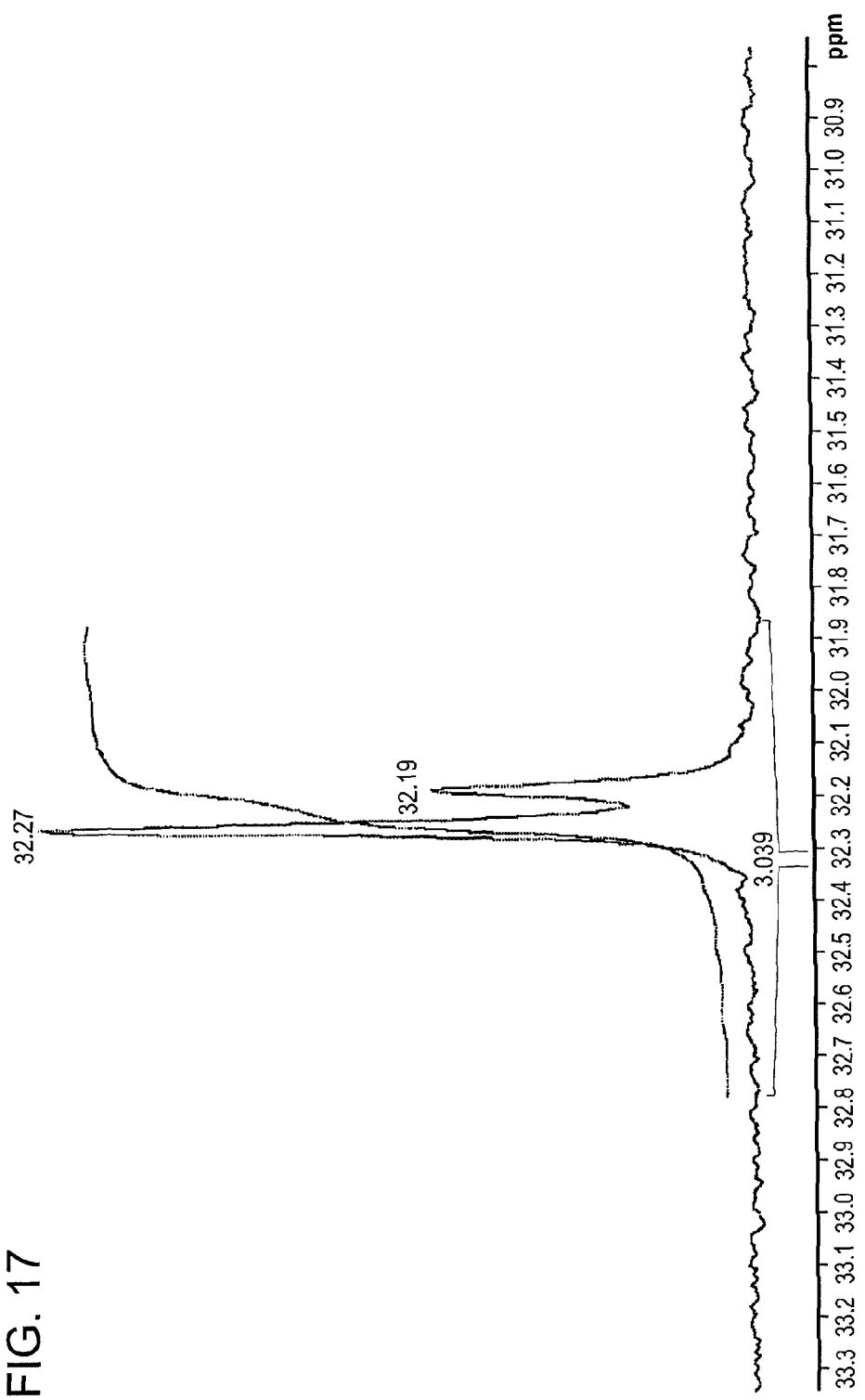
FIG. 17 is an expanded view of peaks at 32.3 ppm of FIG. 16 (see Example 5).

Further, an experiment to determine the relaxation time of the carbons was carried out to determine where the missing quaternary carbon signal is overlapping with another carbon signal. See FIG. 16. This $^{13}C$ spectrum contains peaks that were integrated. This showed that peak at 32.3 ppm accounts for two carbons. See FIG. 17 for an expanded view of the peak at 32.3 ppm. Thus, twenty-six carbons are now accounted for by integrations (including the carboxylic acid), which is consistent with the structure.

FT-IR by ATR

Figure 18:
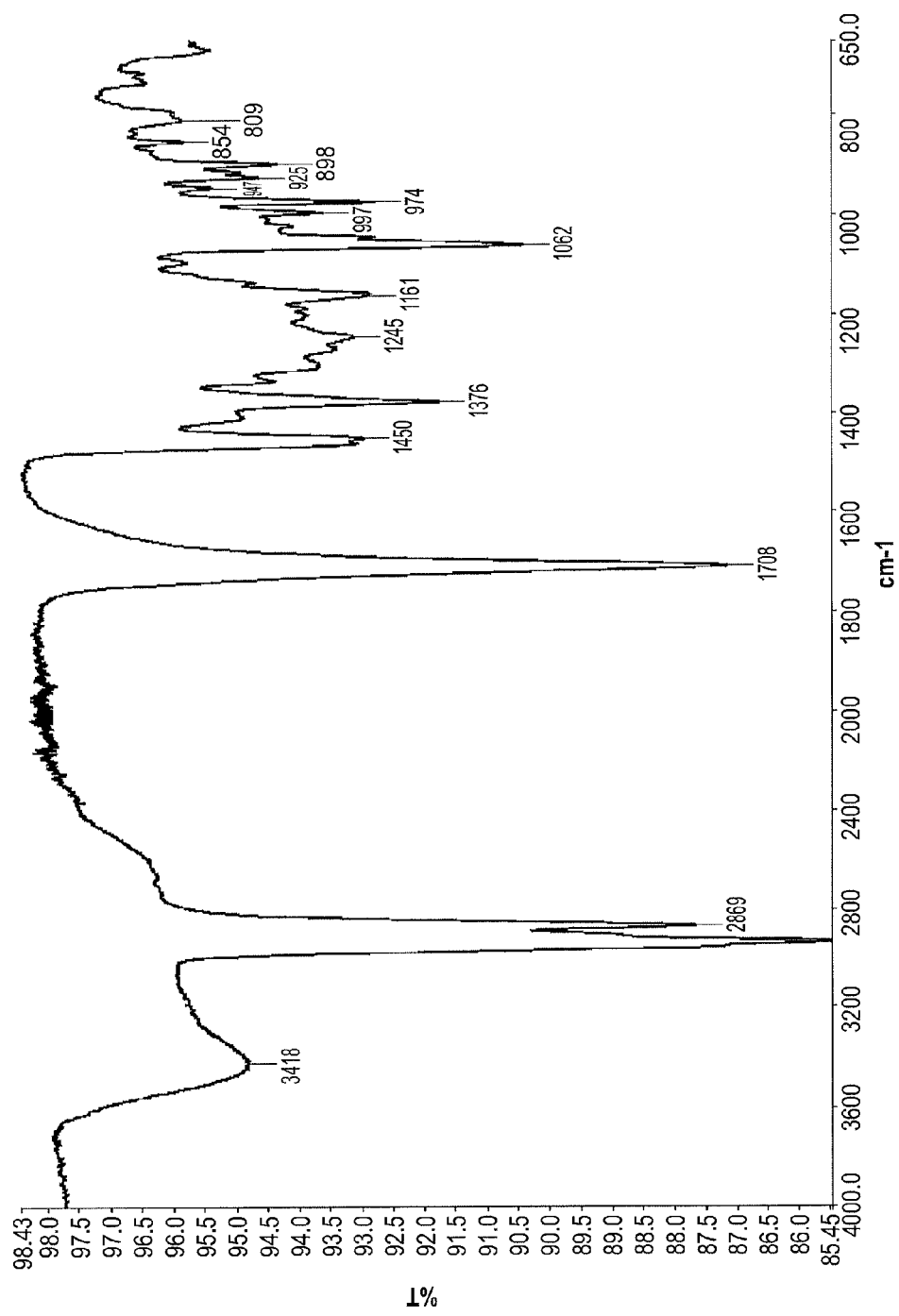
FIG. 18 is a FT-IR spectrum of batch 1 of obeticholic acid Form 1 (see Example 5).

Data were collected on a Perkin-Elmer Spectrum One fitted with a Universal ATR sampling accessory. The data were collected and analyzed using Spectrum v5.0.1 software. See FIG. 18.

Thermal Analysis by Differential Scanning Calorimetry (DSC) and Thermo-Gravimetric Analysis (TGA)

DSC data were collected on a TA Instruments Q2000 equipped with a 50 position autosampler. The instrument was calibrated for energy and temperature calibration using certified indium. Typically 0.5-3 mg of each sample, in a pin-holed aluminum pan, was heated at 10° $C.min^{-1}$ from 25° C. to 300° C. A nitrogen purge at 50 ml·$min^{-1}$ was maintained over the sample. The instrument control software was Advantage for Q Series v2.8.0.392 and Thermal Advantage v4.8.3 and the data were analyzed using Universal Analysis v4.3A. For modulated DSC, the sample was prepared as before, and the pan was heated at 2° $C.min^{-1}$ from 25° C. to 200° C. Modulator conditions were an amplitude of 0.20° C. and a periodicity of 40 s. The sampling interval was 1 sec/pt.

TGA data were collected on a TA Instruments Q500 TGA, equipped with a 16 position autosampler. The instrument was temperature calibrated using certified Alumel. Typically 5-10 mg of each sample was loaded onto a pre-tared platinum crucible and aluminum DSC pan, and was heated at 10° $C.min^{-1}$ from ambient temperature to 350° C. A nitrogen purge at 60 ml·$min^{-1}$ was maintained over the sample. The instrument control software was Advantage for Q Series v2.8.0.392 and Thermal Advantage v4.8.3.

Figure 19:
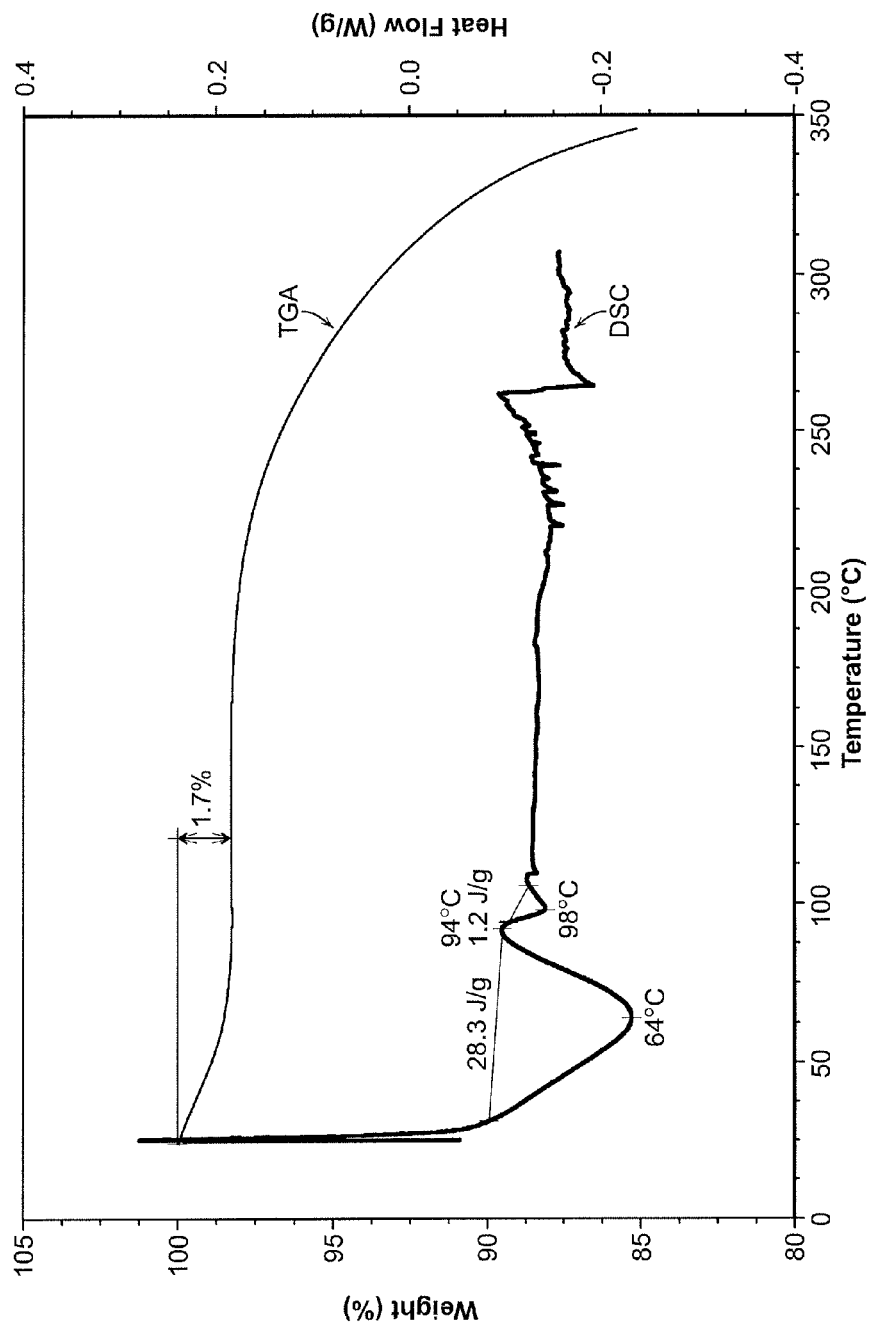
FIG. 19 shows TGA and DSC thermograms of batch 1 of obeticholic acid Form 1 (see Example 5).

Thermal analysis of batch 1 was performed by DSC and TGA. The TGA trace (see FIG. 19) shows a weight loss of 1.7% between ambient temperature and 121° C., which is likely to be loss of water. The DSC trace (see FIG. 19) shows a broad low temperature endotherm, probably corresponding to the loss of water, followed by a small endotherm with onset at 94° C.

Figure 20:
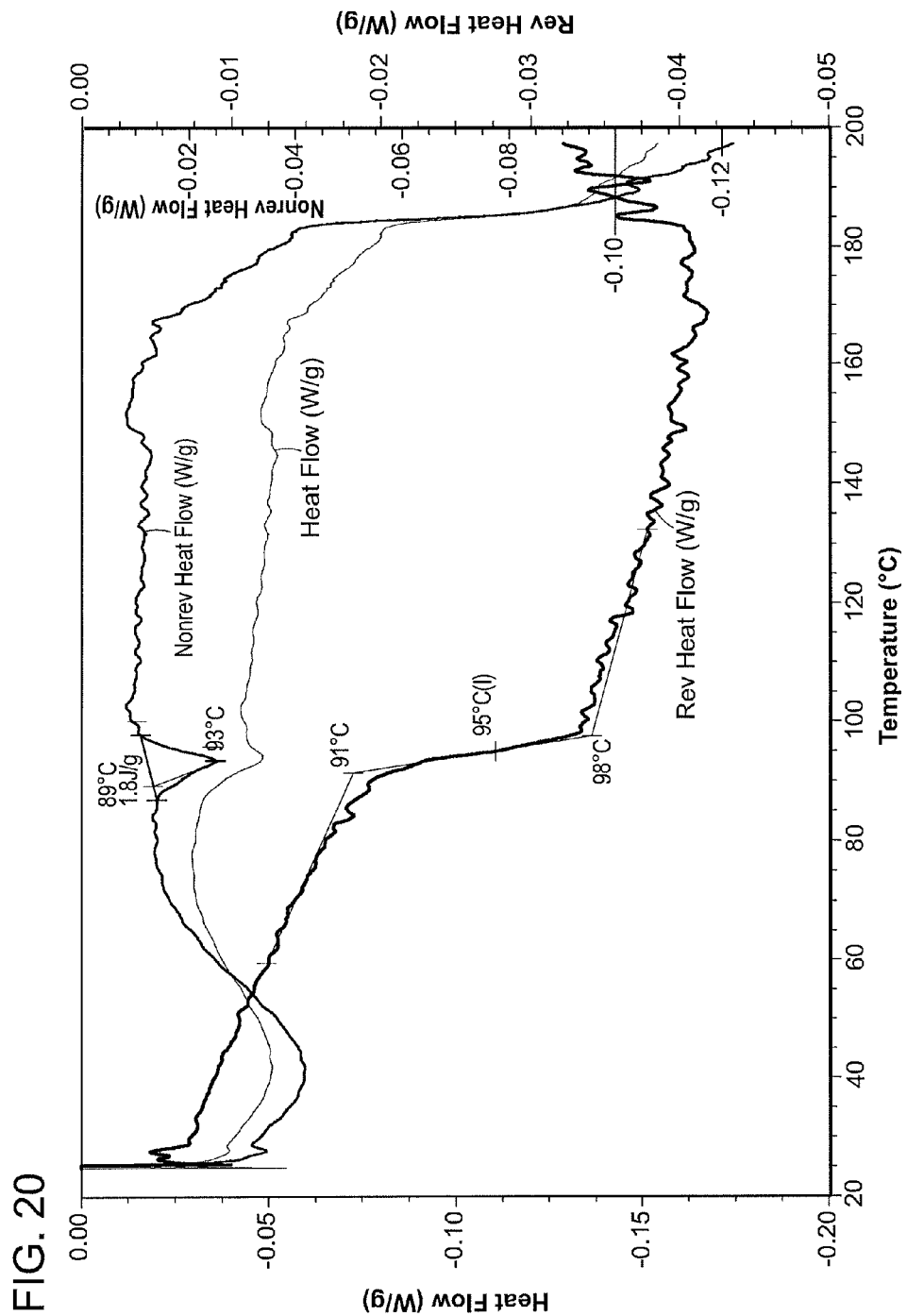
FIG. 20 shows modulated DSC thermograms of batch 1 of obeticholic acid Form 1 (see Example 5).

This second endotherm might indicate a glass transition and was further investigated by modulated DSC (see FIG. 20). This technique enables reversible events, such as a glass transition, to be separated from irreversible ones, such as loss of solvent or a melt of a crystalline form. The reversible heat flow trace in modulated DSC shows the glass transition as a step with an inflexion point (Tg) at 95° C. This is high for a glass transition and suggests that Form 1 is stable. The small endotherm with onset at 89° C. on the non-reversible heat flow trace corresponds to molecular relaxation of the bulk material at the glass transition temperature.

The DSC trace (see FIG. 19) shows decomposition starting around 220° C., which also corresponds to the TGA trace curving down.

Figure 21:
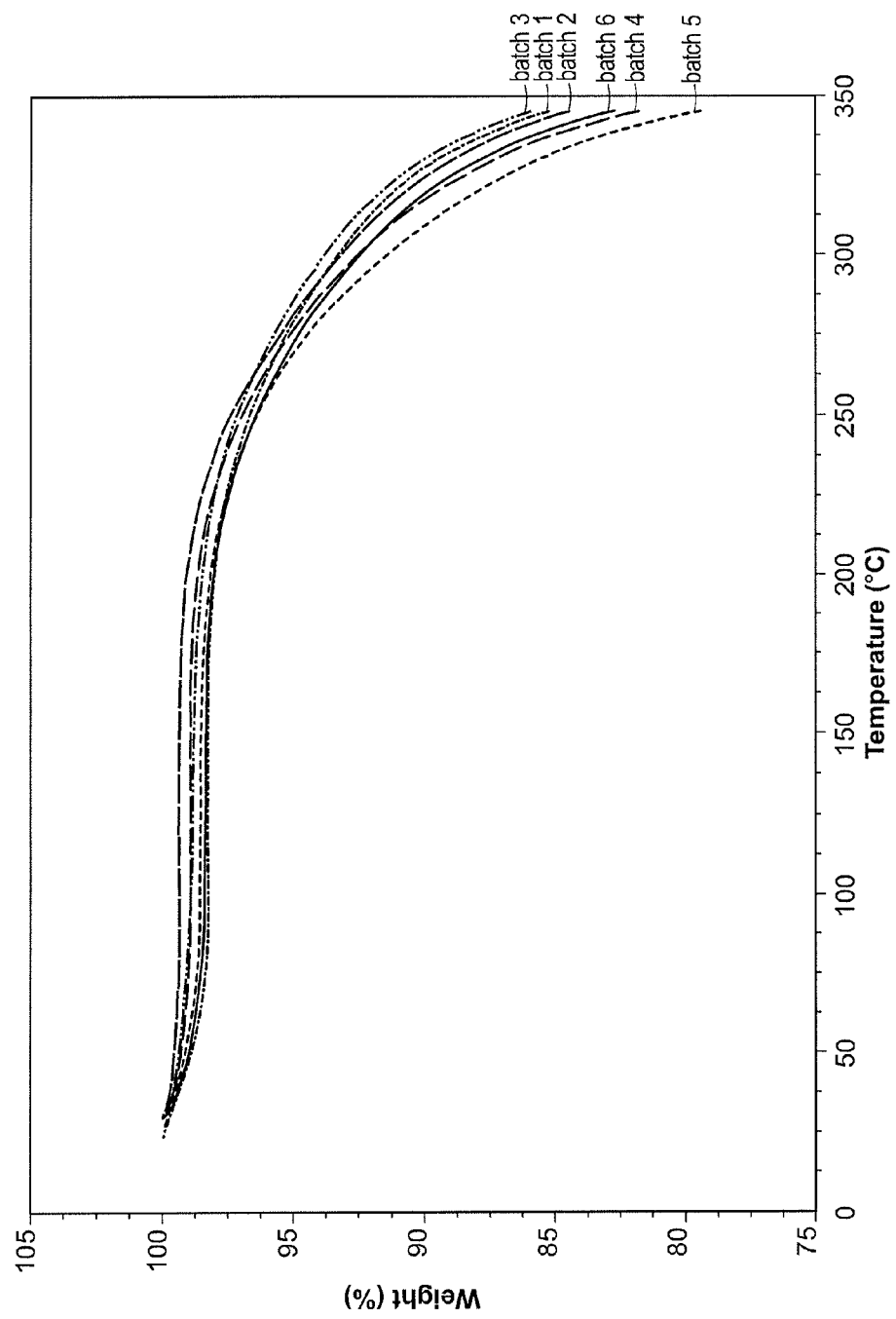
FIG. 21 shows the TGA traces of batches 1, 2, 3, 4, 5, and 6 of obeticholic acid Form 1 (see Example 5).

The TGA traces of batches 1, 2, 3, 4, 5, and 6 are of similar shape (FIG. 21). The weight losses measured between ambient and 120° C. are shown in Table K. They are consistent with the varying amounts of water observed by NMR. These amounts were further quantified by Karl Fischer (KF) water titration. See water determination by KF.

TABLE K

Summary of TGA weight losses of received samples

| Batch number | Weight loss by TGA |
|---|---|
| 1 | 1.7% |
| 2 | 0.6% |
| 3 | 1.2% |
| 4 | 0.9% |
| 5 | 1.5% |
| 6 | 1.6% |

Figure 22:
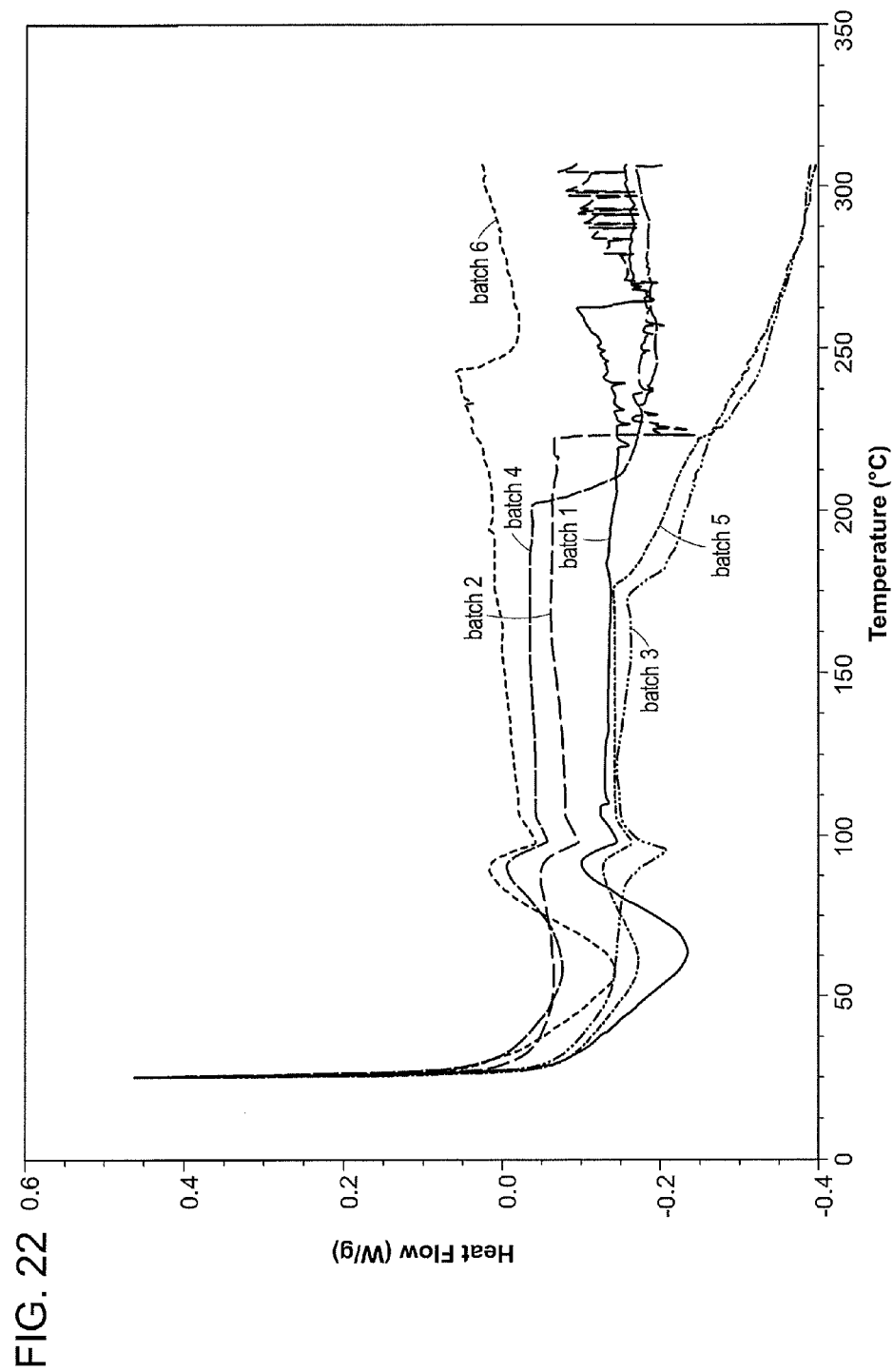
FIG. 22 shows the DSC traces of batches 1, 2, 3, 4, 5, and 6 of obeticholic acid Form 1 (see Example 5).
Figure 23A:
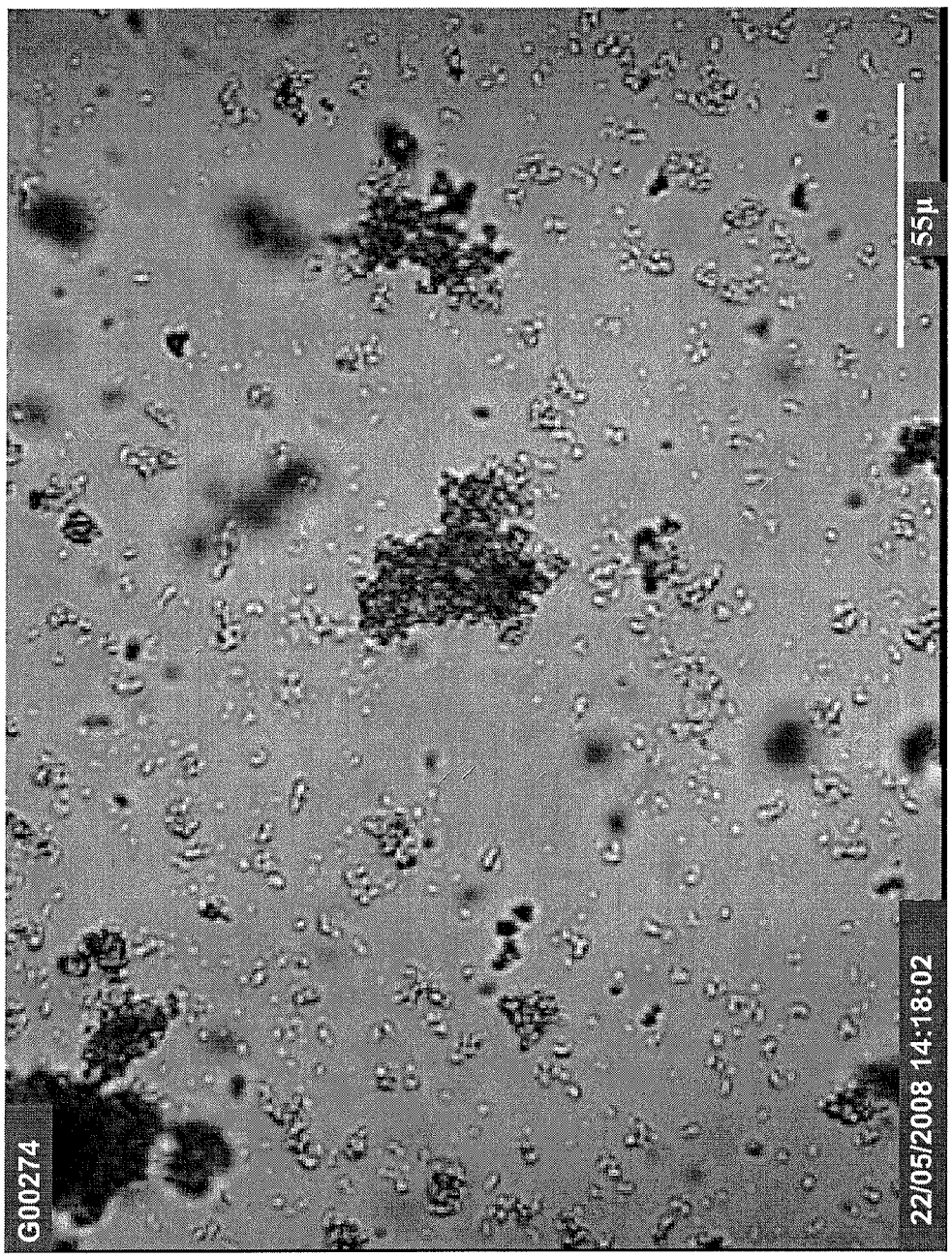
FIG. 23A is a picture of batch 1 of obeticholic acid Form 1 under polarized light microscopy.
Figure 23B:
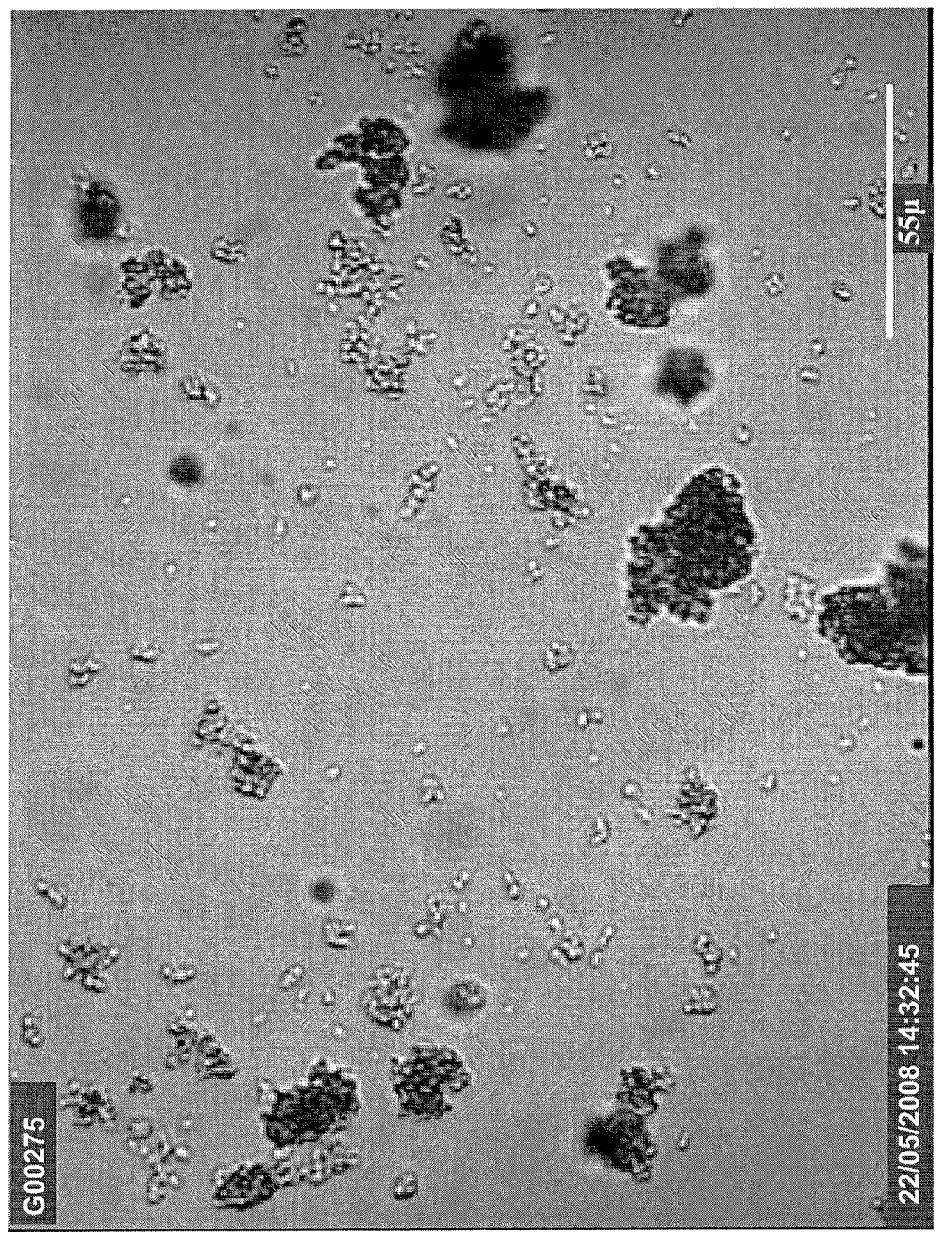
FIG. 23B is a picture of batch 2 of obeticholic acid Form 1 under polarized light microscopy.
Figure 23C:
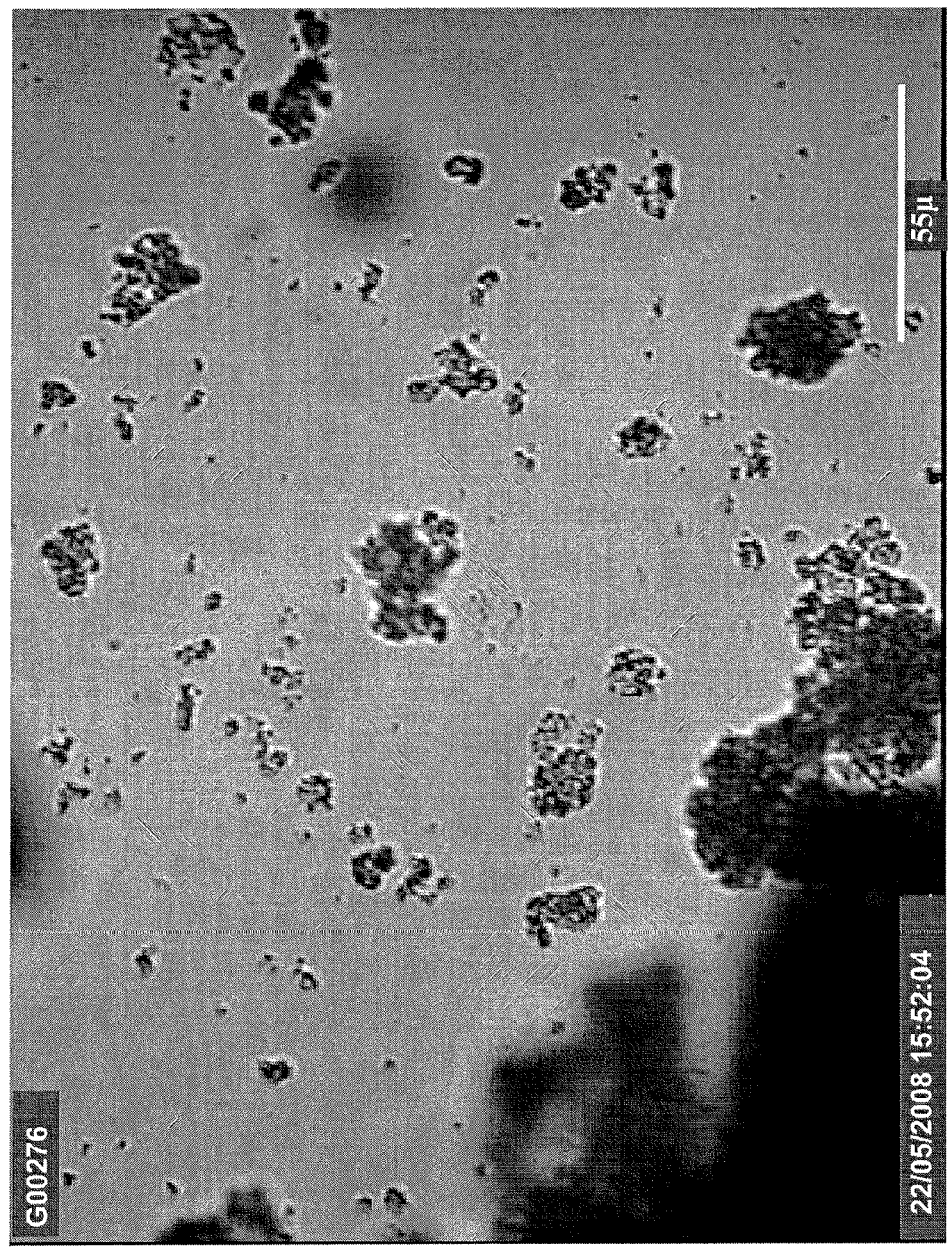
FIG. 23C is a picture of batch 3 of obeticholic acid Form 1 under polarized light microscopy.
Figure 23D:
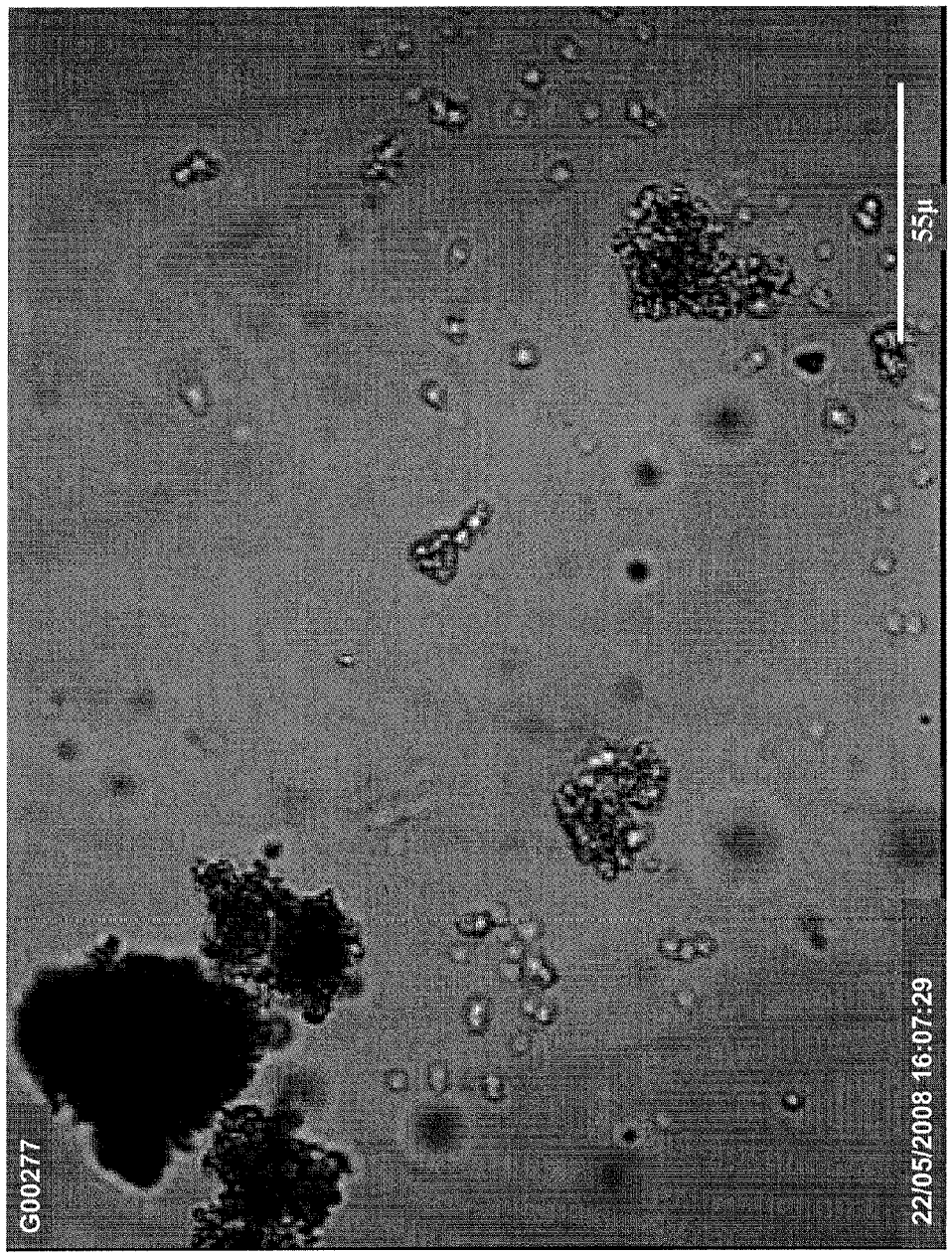
FIG. 23D is a picture of batch 4 of obeticholic acid Form 1 under polarized light microscopy.
Figure 23E:
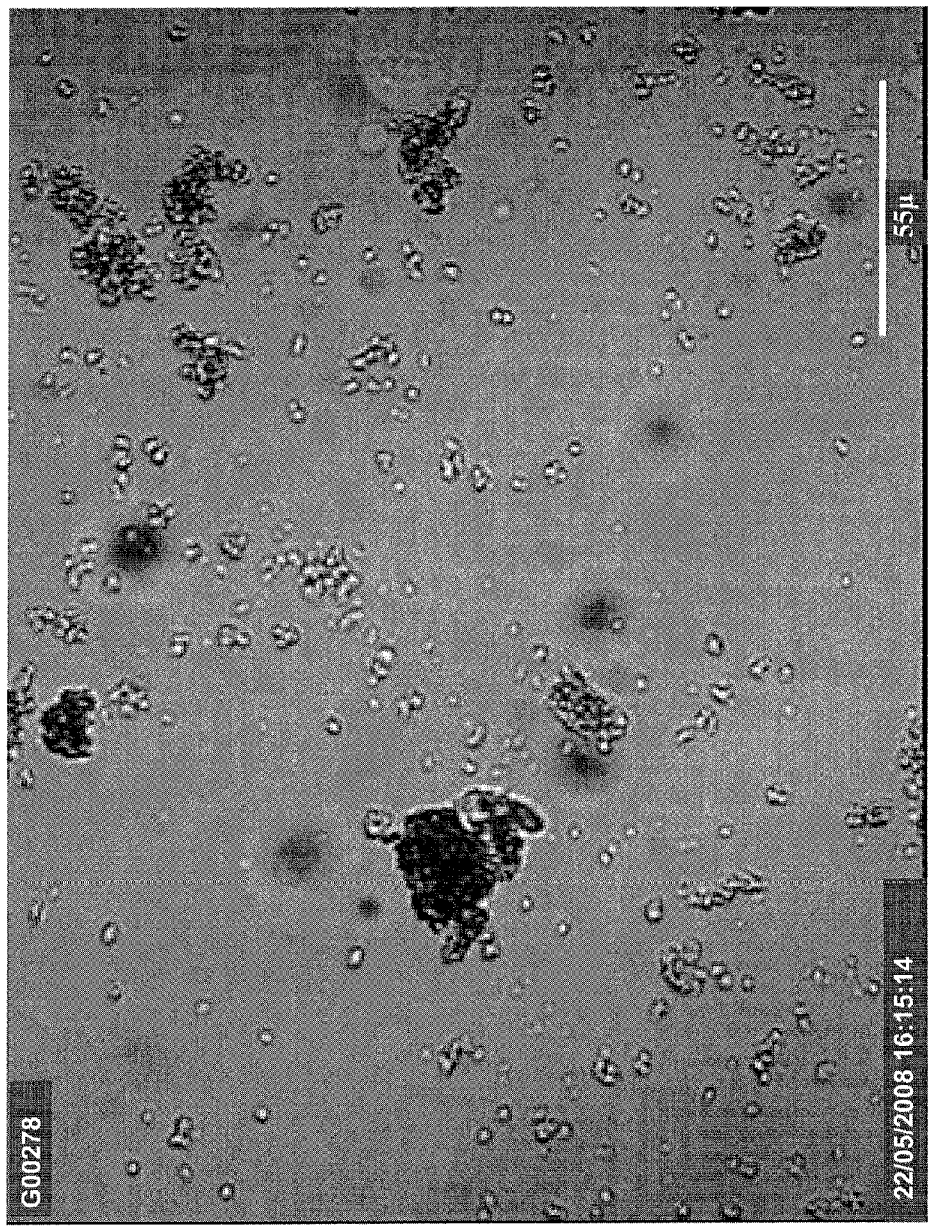
FIG. 23E is a picture of batch 5 of obeticholic acid Form 1 under polarized light microscopy.
Figure 23F:
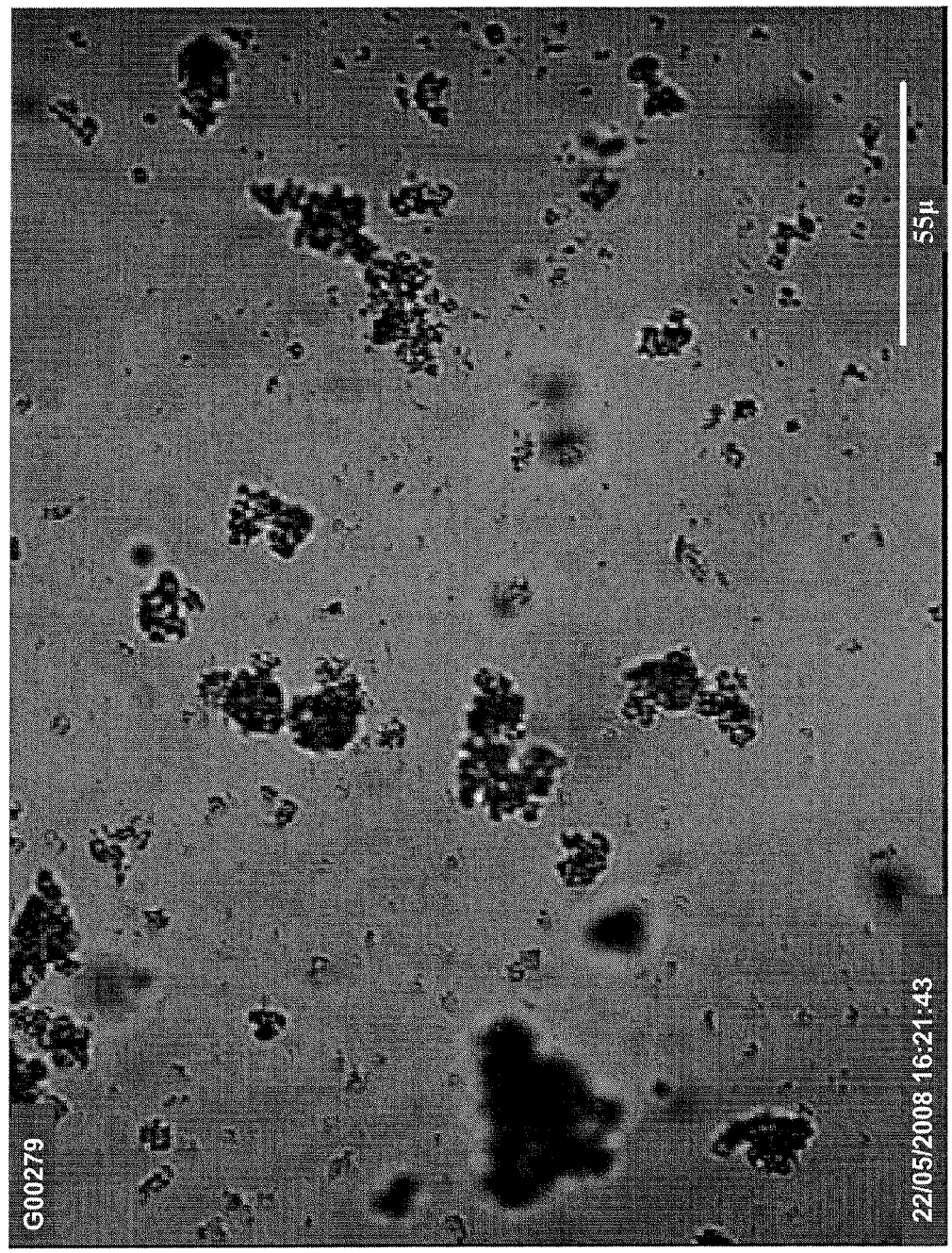
FIG. 23F is a picture of batch 6 of obeticholic acid Form 1 under polarized light microscopy.

FIG. 22 shows the DSC traces of the six batches for comparison. The traces are similar, with a broad low temperature endotherm of varying size, consistent with varying amounts of water, followed by a small endotherm around the glass transition temperature as seen in section DSC and TGA. The results are summarized in Table L.

TABLE L

Summary of DSC results of received samples

| Batch number | 1$^{st}$ endotherm, broad | 2$^{nd}$ endotherm, small | Start of decomposition |
|---|---|---|---|
| 1 | 28.3 J/g, Tmax = 64° C. | 1.2 J/g, Tonset = 94° C. | 220° C. |
| 2 | 7.4 J/g, Tmax = 48° C. | 1.4 J/g, Tonset = 94° C. | 220° C. |
| 3 | none | 2.0 J/g, Tonset = 89° C. | 175° C. |
| 4 | 14.5 J/g, Tmax = 58° C. | 1.3 J/g, Tonset = 94° C. | 200° C. |
| 5 | 12.2 J/g, Tmax = 59° C. | 1.2 J/g, Tonset = 94° C. | 175° C. |
| 6 | 28.7 J/g, Tmax = 59° C. | 1.5 J/g, Tonset = 94° C. | 200° C. |

Polarized Light Microscopy (PLM)

Samples were studied on a Leica LM/DM polarized light microscope with a digital video camera for image capture. A small amount of each sample was placed on a glass slide, mounted in silicone oil and covered with a glass slip, the individual particles being separated as well as possible. The sample was viewed with appropriate magnification and partially polarized light, coupled to a λ false-color filter.

FIGS. 23A-23F show that batches 1, 2, 3, 4, 5, and 6 are material made up of large hard agglomerates of small irregular particles. Batches 1, 2, 3, 4, 5, and 6 all look similar. No birefringence was observed under plane polarized light, which is consistent with the material being non-crystalline. Particle size ranges from less than 1 μm to 3 μm. The small size of these particles suggests that they have been precipitated out very quickly.

Gravimetric Vapor Sorption (GVS)

Sorption isotherms were obtained using a SMS DVS Intrinsic moisture sorption analyzer, controlled by SMS Analysis Suite software. The sample temperature was maintained at 25° C. by the instrument controls. The humidity was controlled by mixing streams of dry and wet nitrogen, with a total flow rate of 200 ml·min$^{-1}$. The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range.

TABLE M

| Parameters | Values |
| --- | --- |
| Adsorption-Scan 1 | 40-90 |
| Desorption/Adsorption-Scan 2 | 85-Dry, Dry-40 |
| Intervals (% RH) | 10 |
| Number of Scans | 2 |
| Flow rate (ml · min$^{-1}$) | 200 |
| Temperature (° C.) | 25 |
| Stability (° C. min$^{-1}$) | 0.2 |
| Sorption Time (hours) | 6 hour time out |

Figure 24:
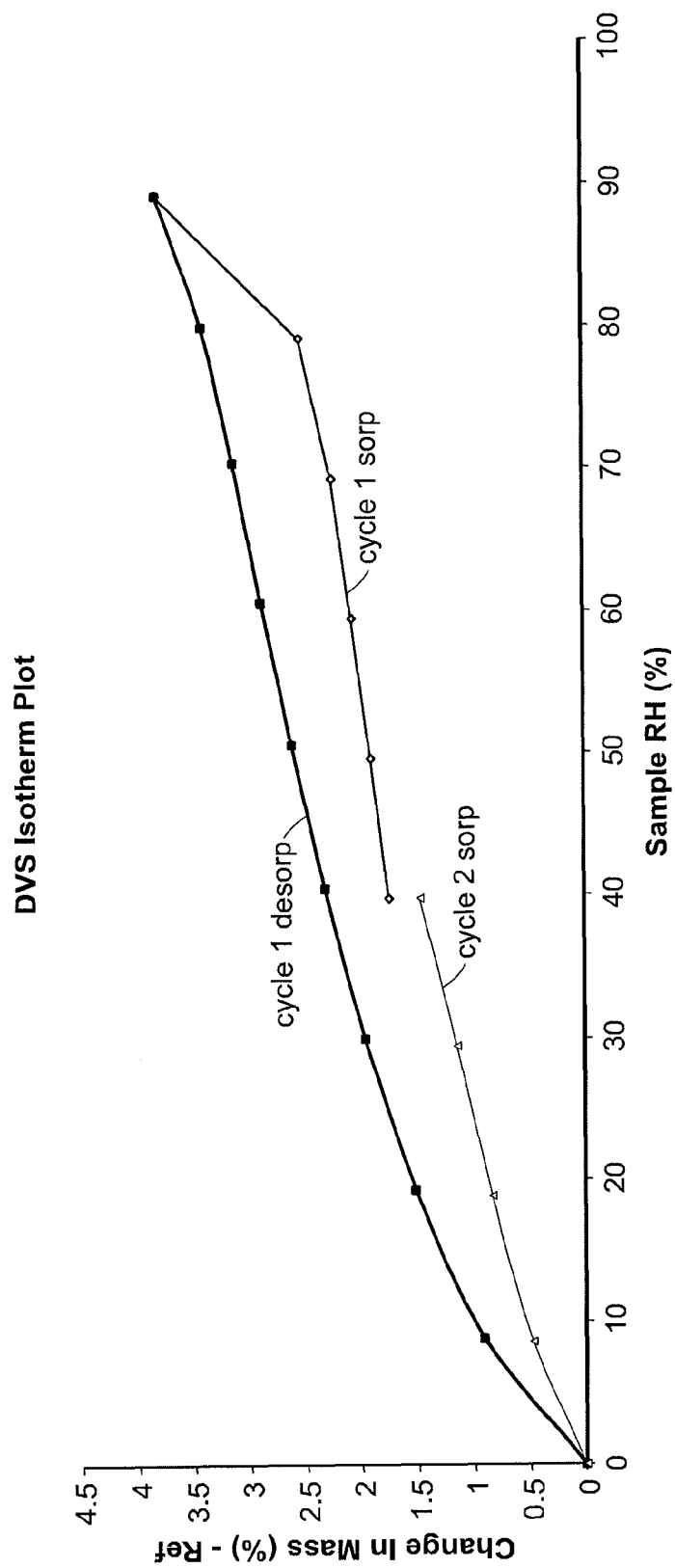
FIG. 24 shows GVS isotherm plot of batch 1 of obeticholic acid Form 1 (see Example 5).

The Gravimetric Vapor Sorption (GVS) isotherm was obtained for batch 1 at 25° C. and is shown in FIG. 24. The sample appears to be moderately hygroscopic, with a total weight change of 3.8% from 0 to 90% relative humidity (RH). The hysteresis (area between adsorption and desorption curves) is small, indicating that the solid releases quite readily the water adsorbed. No formation of hydrate is observed. There was no significant weight change after the whole experiment (0.3%).

Figure 25:
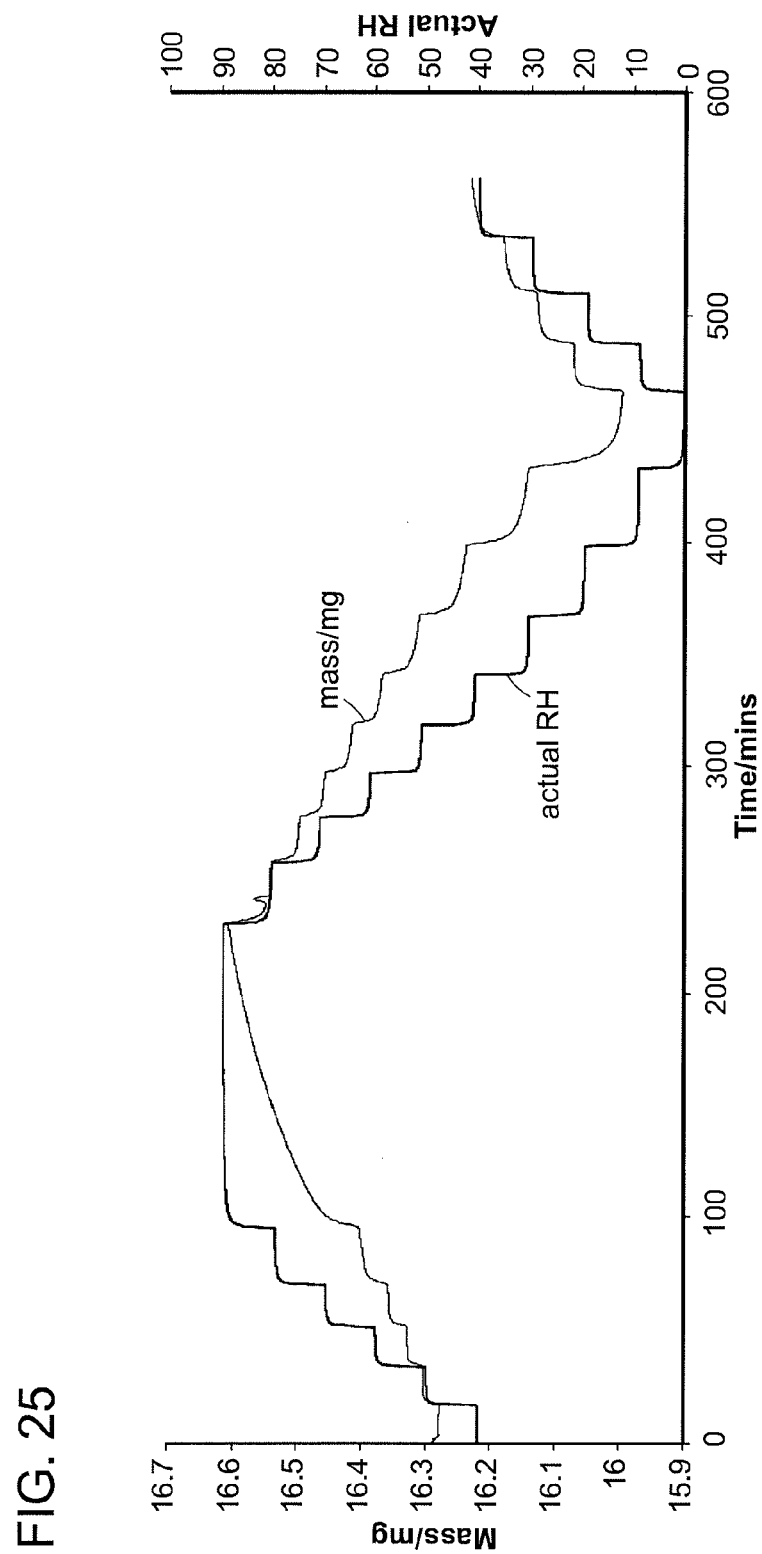
FIG. 25 shows GVS kinetics plot of batch 1 of obeticholic acid Form 1 (see Example 5).

The kinetics plot of the GVS (FIG. 25) shows that the adsorption of the water occurred mostly at very high humidities and the desorption at very low humidities. On the adsorption phase, the sample reached equilibrium quite quickly up to 80% RH and took longer to equilibrate at 90% RH. On desorption, the mass stabilized at all steps.

Figure 26:
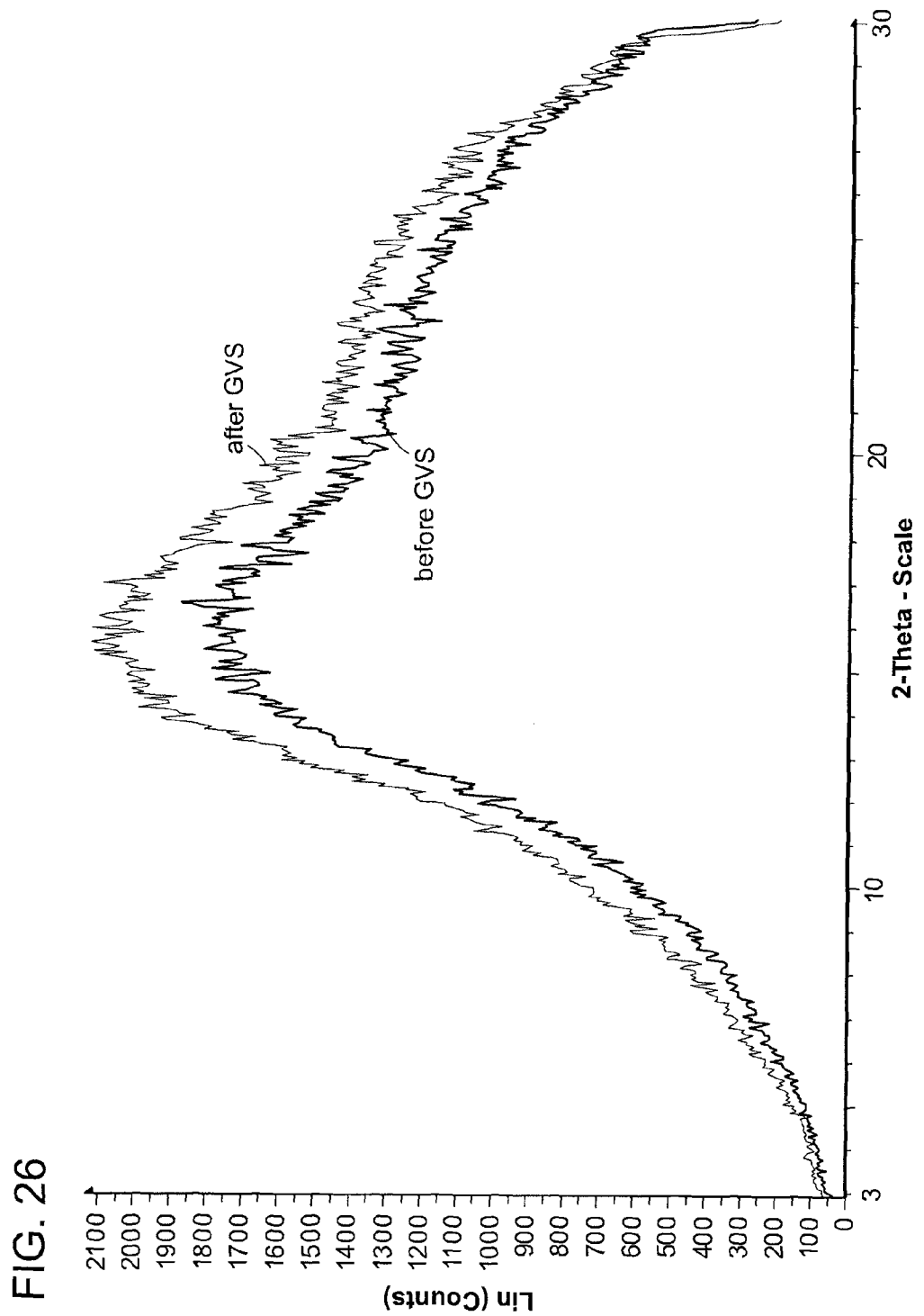
FIG. 26 shows XRPD diffractograms of batch 1 of obeticholic acid Form 1 before and after GVS (see Example 5).

After completion of the GVS, the sample was recovered and reanalyzed by XRPD, which showed that the material was still non-crystalline (FIG. 26).

Water Determination by Karl Fischer (KF)

The water content of each sample was measured on a Mettler Toledo DL39 Coulometer using Hydranal Coulomat AG reagent and an argon purge. Weighed solid samples were introduced into the vessel on a platinum TGA pan, which was connected to a subaseal to avoid water ingress. Approximately 10 mg of sample was used per titration and duplicate determinations were made.

Titration of water by coulometric Karl Fischer gave a result of 2.4 wt % water. This is slightly higher than the weight loss observed by TGA. It could mean that some of the water is not released from the material on heating, but it is likely to be due to the different experimental procedures for these two techniques.

The water content of each batch was determined by coulometric Karl Fischer. Table N shows these results and compares them with earlier Karl Fischer results obtained and with the weight losses observed by TGA. Data are consistent as the trend is the same in all three analyses. The Karl Fischer data obtained earlier show lower amounts of water than the results obtained here. This is consistent with the material being hygroscopic, although some samples have taken up more water than others. TGA weight loss is consistently lower than the results obtained by Karl Fischer titration, which might mean that some water stays trapped in the material and is not released on heating but might also be due to the experimental procedure.

TABLE N

Karl Fischer (KF) results and summary of water content data

| Batch number | KF water content | Earlier KF results | TGA weight loss |
| --- | --- | --- | --- |
| 1 | 2.4% | 2.1% | 1.7% |
| 2 | 1.9% | 0.4% | 0.6% |
| 3 | 2.5% | 1.4% | 1.2% |
| 4 | 2.2% | 0.92% | 0.9% |
| 5 | 2.3% | 0.53% | 1.5% |
| 6 | 2.8% | 2.1% | 1.6% | pKa Determination and Prediction pKa determination data were collected on a Sirius GlpKa instrument with a D-PAS attachment. Measurements were made at 25° C. in aqueous solution by UV and in methanol water mixtures by potentiometry. The titration media was ionic-strength adjusted (ISA) with 0.15 M KCl (aq). The values found in the methanol water mixtures were corrected to 0% co-solvent via a Yasuda-Shedlovsky extrapolation. The data were refined using Refinement Pro software v1.0. Prediction of pKa values was made using ACD pKa prediction software v9.

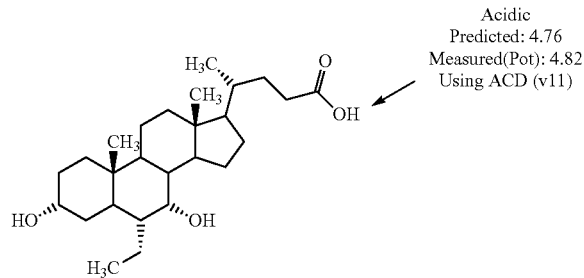

Acidic
Predicted: 4.76
Measured(Pot): 4.82
Using ACD (v11)

Figure 27:
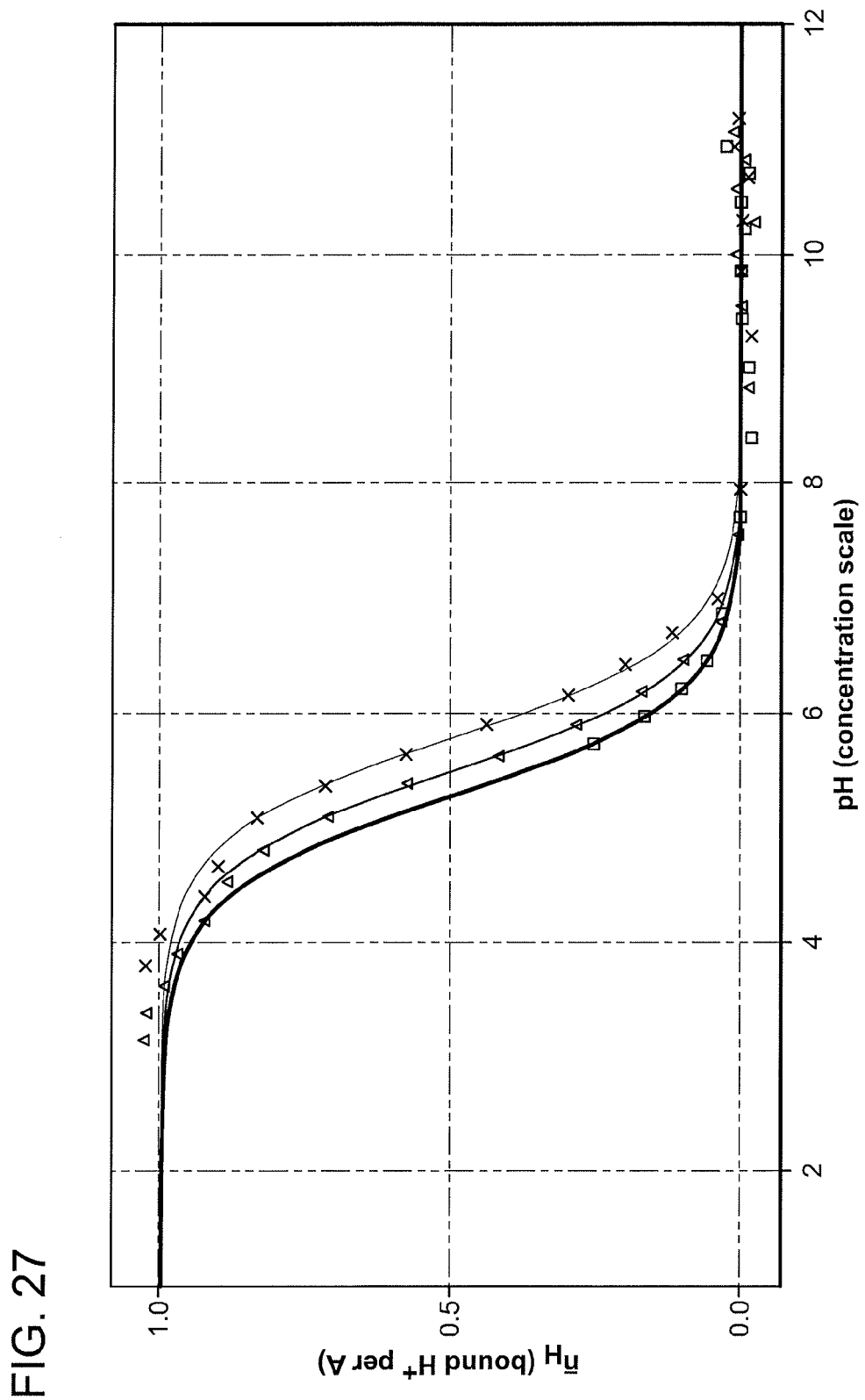
FIG. 27 is a graph of the measurement of pKa at three different methanol/water ratios for obeticholic acid Form 1 (see Example 5).
Figure 28:
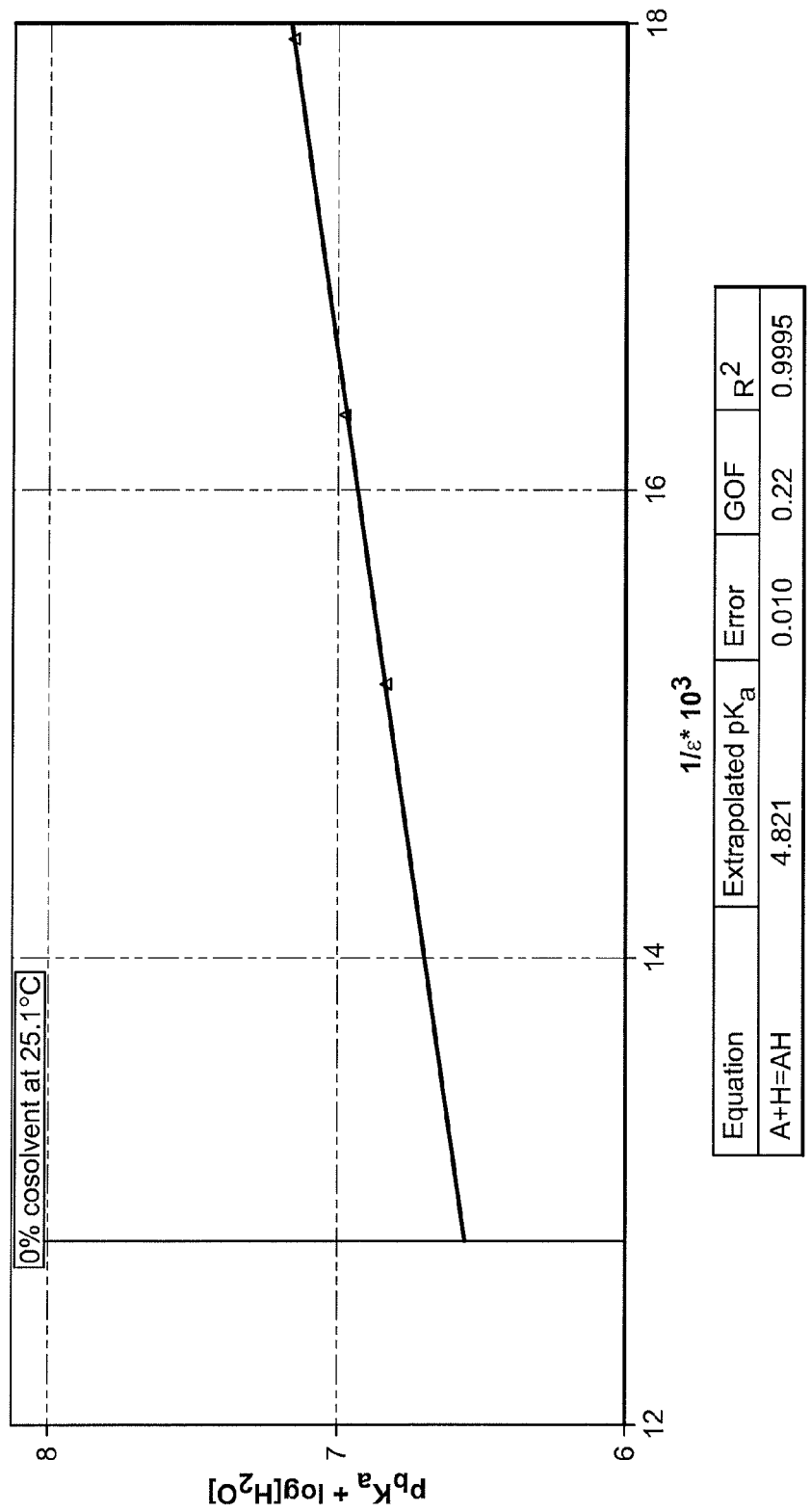
FIG. 28 is a Yasuda-Shedlovsky plot for obeticholic acid Form 1 (see Example 5).
Figure 29:
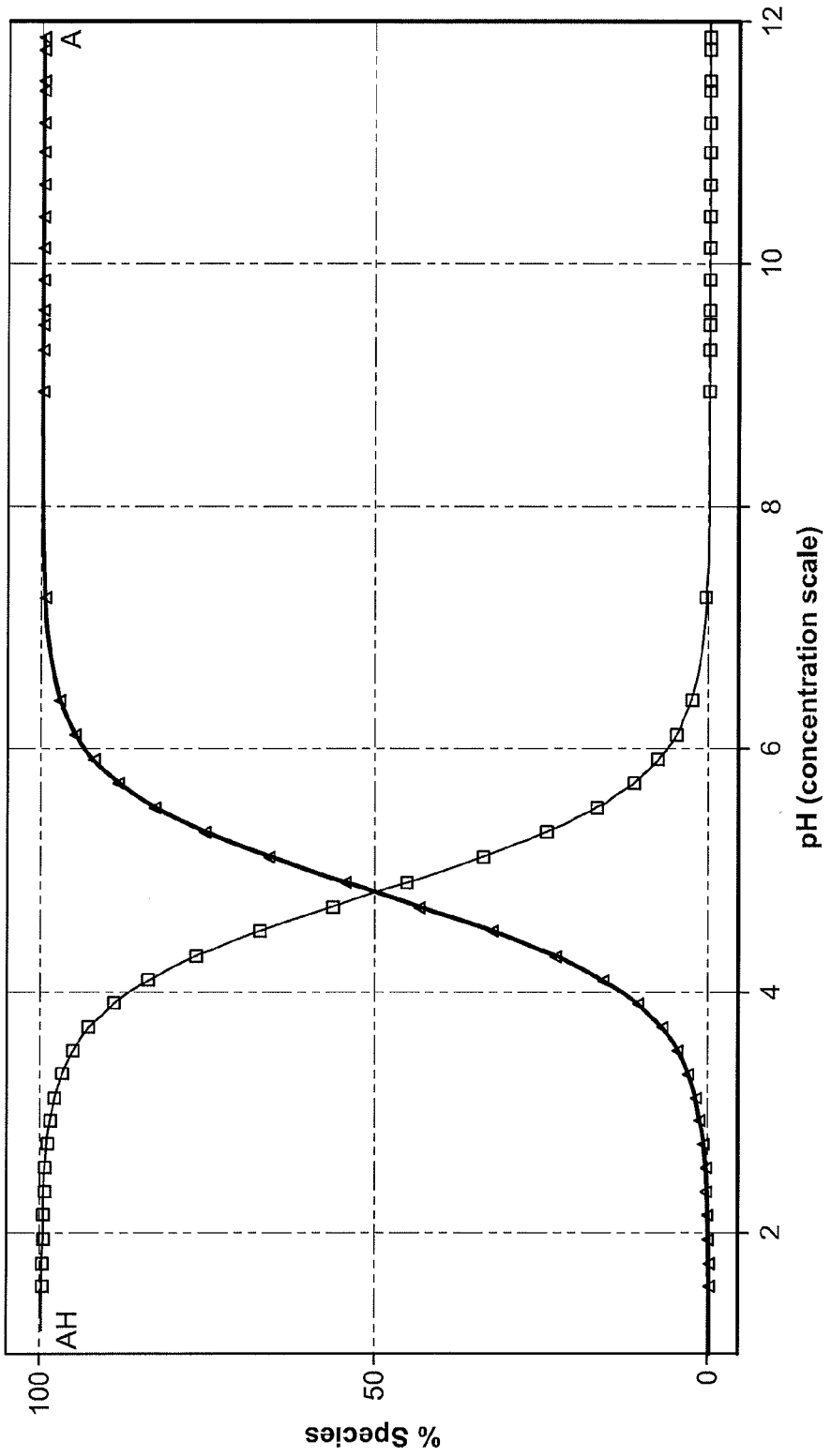
FIG. 29 is a graph showing the distribution of the species depending on pH for obeticholic acid Form 1 (see Example 5).

The pKa of obeticholic acid was measured by potentiometry using methanol as a cosolvent (FIG. 27) and extrapolated to 0% co-solvent using a Yasuda-Shedlovsky extrapolation (FIG. 28). The pKa enables determination of the proportion of the neutral and the ionized form of the compound at a given pH. FIG. 29 shows the distribution of the species depending on pH.

Log P Determination

Data were collected by potentiometric titration on a Sirius GlpKa instrument using three ratios of octanol: ionic-strength adjusted (ISA) water to generate Log P, Log P$_{ion}$, and Log D values. The data were refined using Refinement Pro software v1.0. Prediction of Log P values was made using ACD v9 and Syracuse KOWWIN v1.67 software.

TABLE O

Predicted and measured LogP

| | |
|---|---|
| ACD (V9) Predicted LogP | 5.81 |
| Measured LogP | 5.54 |
| Measured LogPion | 1.58 |
| Measured LogD7.4 | 2.98 |

Figure 30:
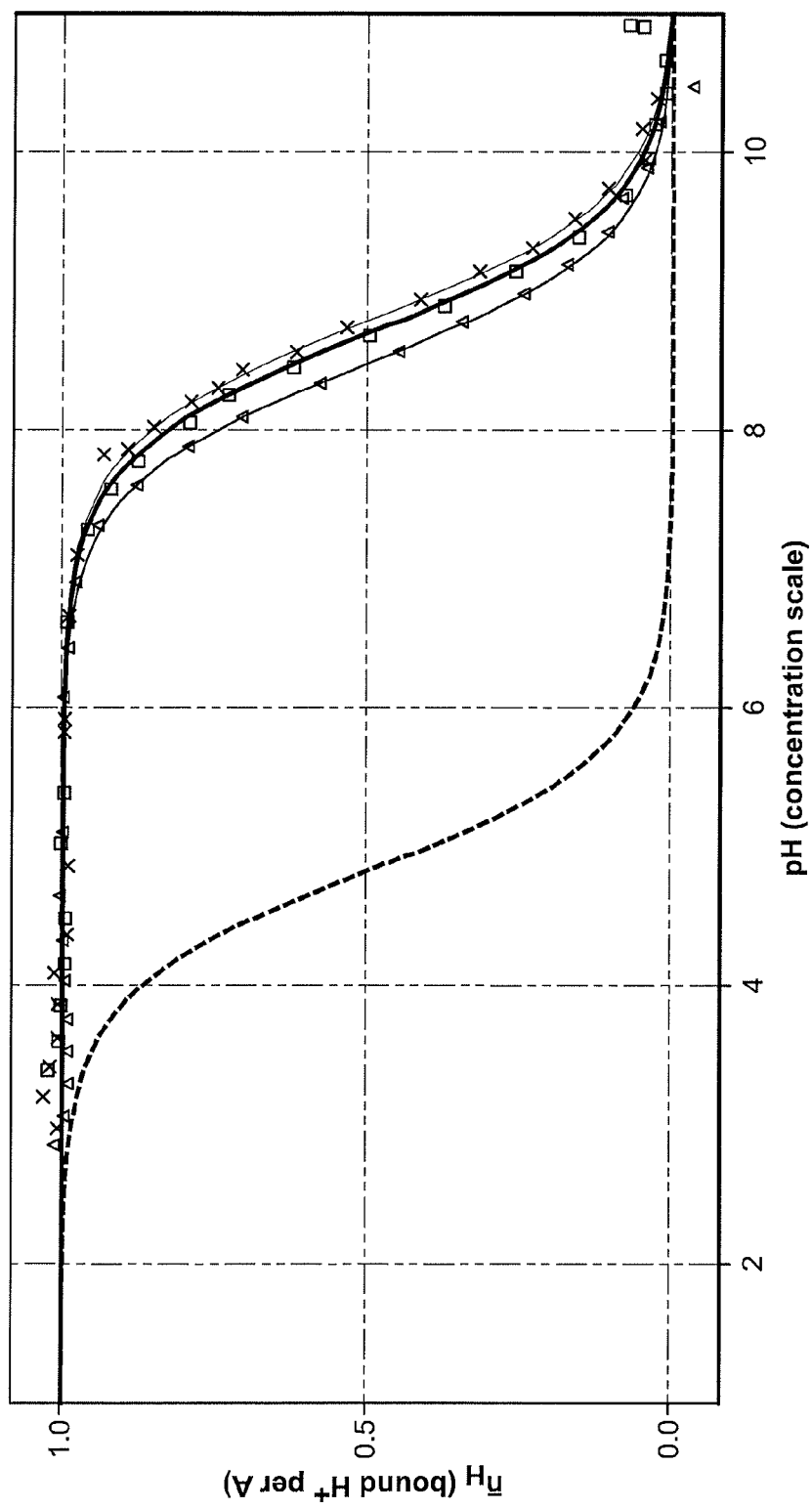
FIG. 30 is a graph showing the difference curve obtained by potentiometry for obeticholic acid Form 1 (see Example 5).

Log P was predicted using ACD software then measured by potentiometry. Three titrations were performed at three different octanol/ISA water ratios, giving the difference curve plotted in FIG. 30. The black curve is the pure aqueous pKa titration and the 3 colored curves correspond to the three octanol/ISA water ratios. The shifts in pKa enable determination of Log P.

Figure 31:
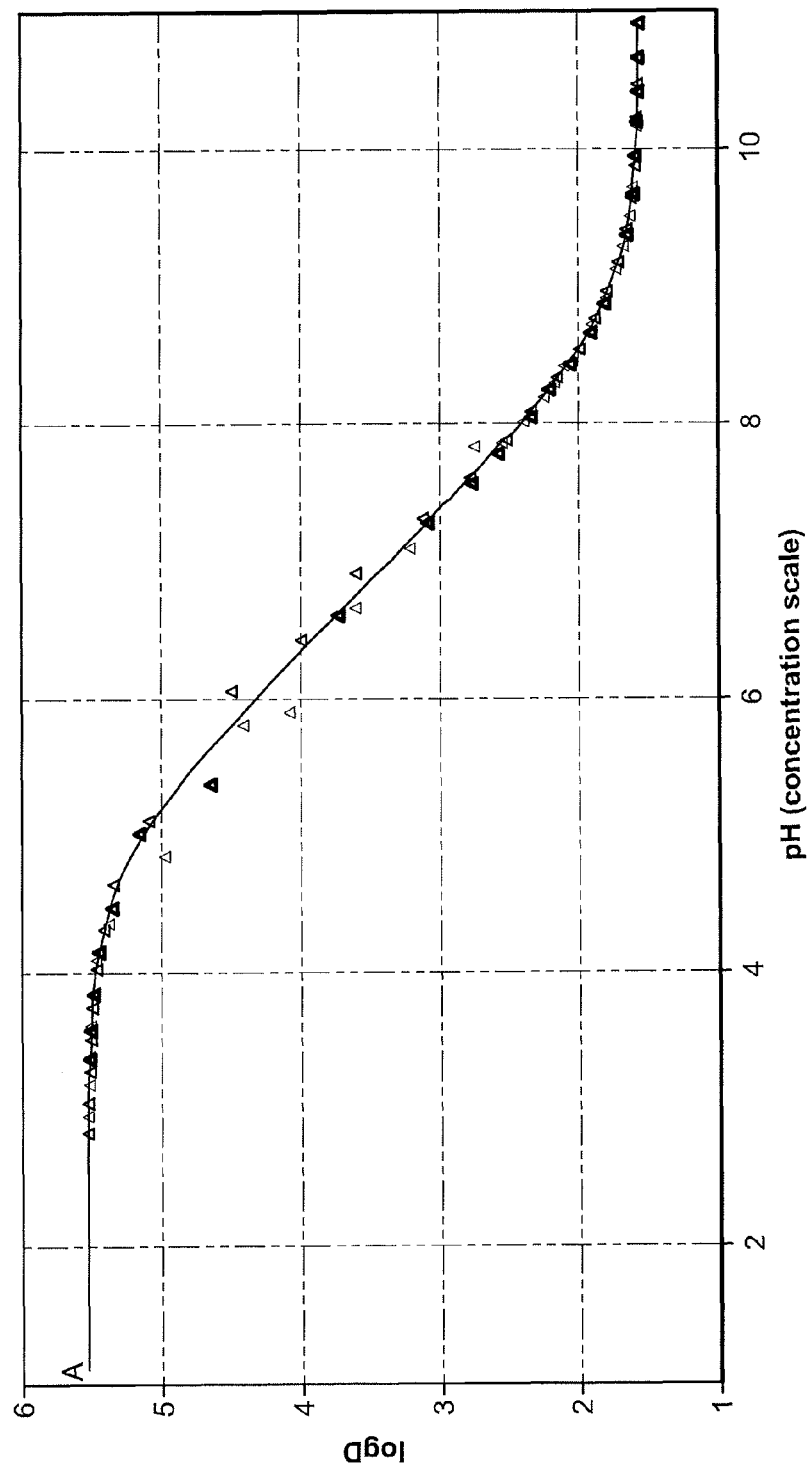
FIG. 31 shows the lipophilicity profile of obeticholic acid Form 1 (see Example 5).

The lipophilicity curve (log D as a function of pH) is shown in FIG. 31. Log D is the distribution coefficient, representing the combined lipophilicity of all species present at a specific pH. Log P is a compound constant, which corresponds to the partition coefficient of the pure neutral species, while Log Pion is that of the pure ionized species. Log P and Log Pion can be determined from the lipophilicity curve, as the intersection of the Y axis with respectively the tangent at the start of the pH scale (when the molecule is purely in its neutral form) and the tangent at the end of the pH scale (when the molecule is completely ionized).

Two Weeks Stability at 40° C. & 75% RH and 25° C. & 97% RH

Figure 32:
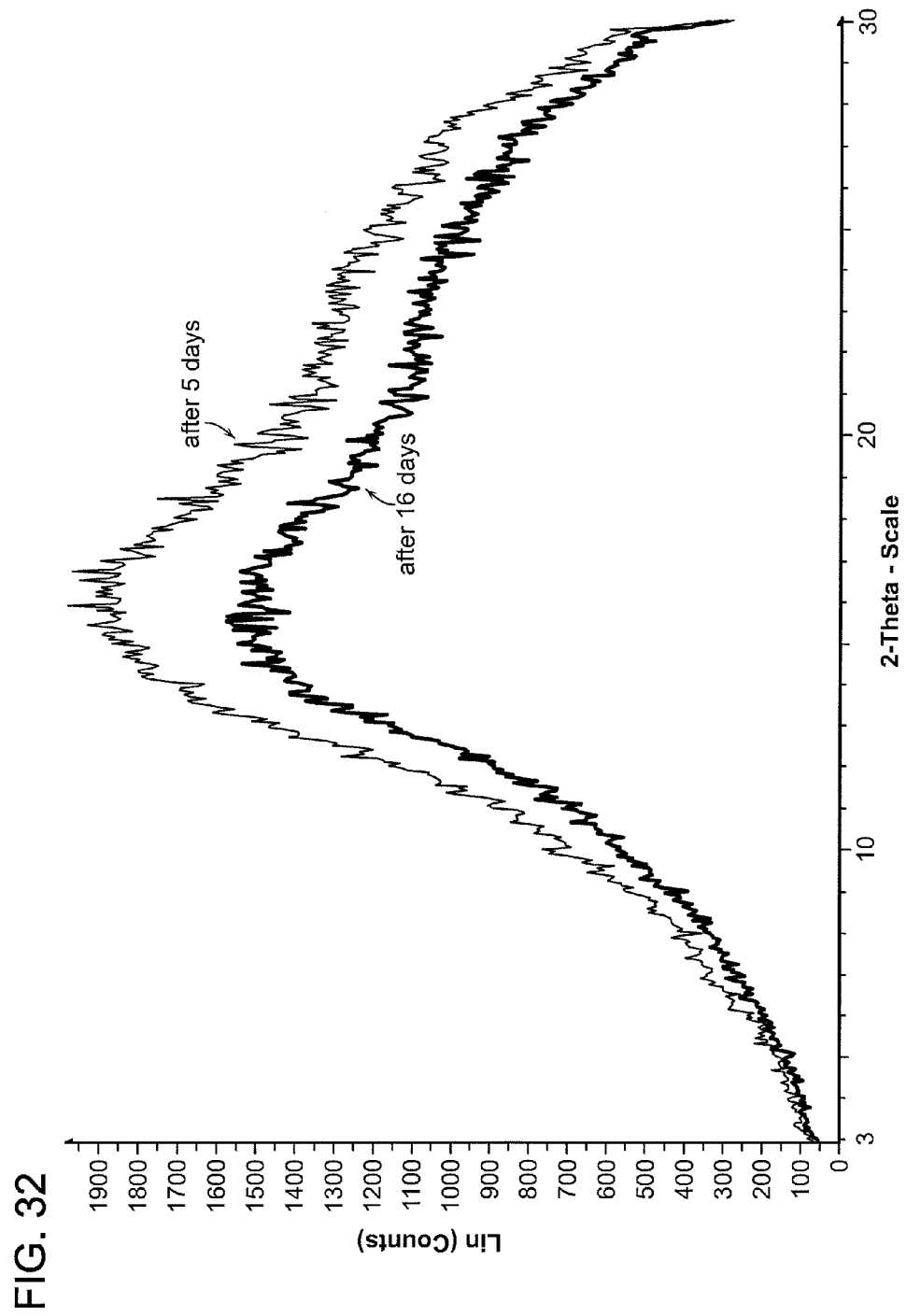
FIG. 32 shows the XRPD diffractograms of batch 1 of obeticholic acid Form 1 after storage at 40° C./75% RH (see Example 5).
Figure 33:
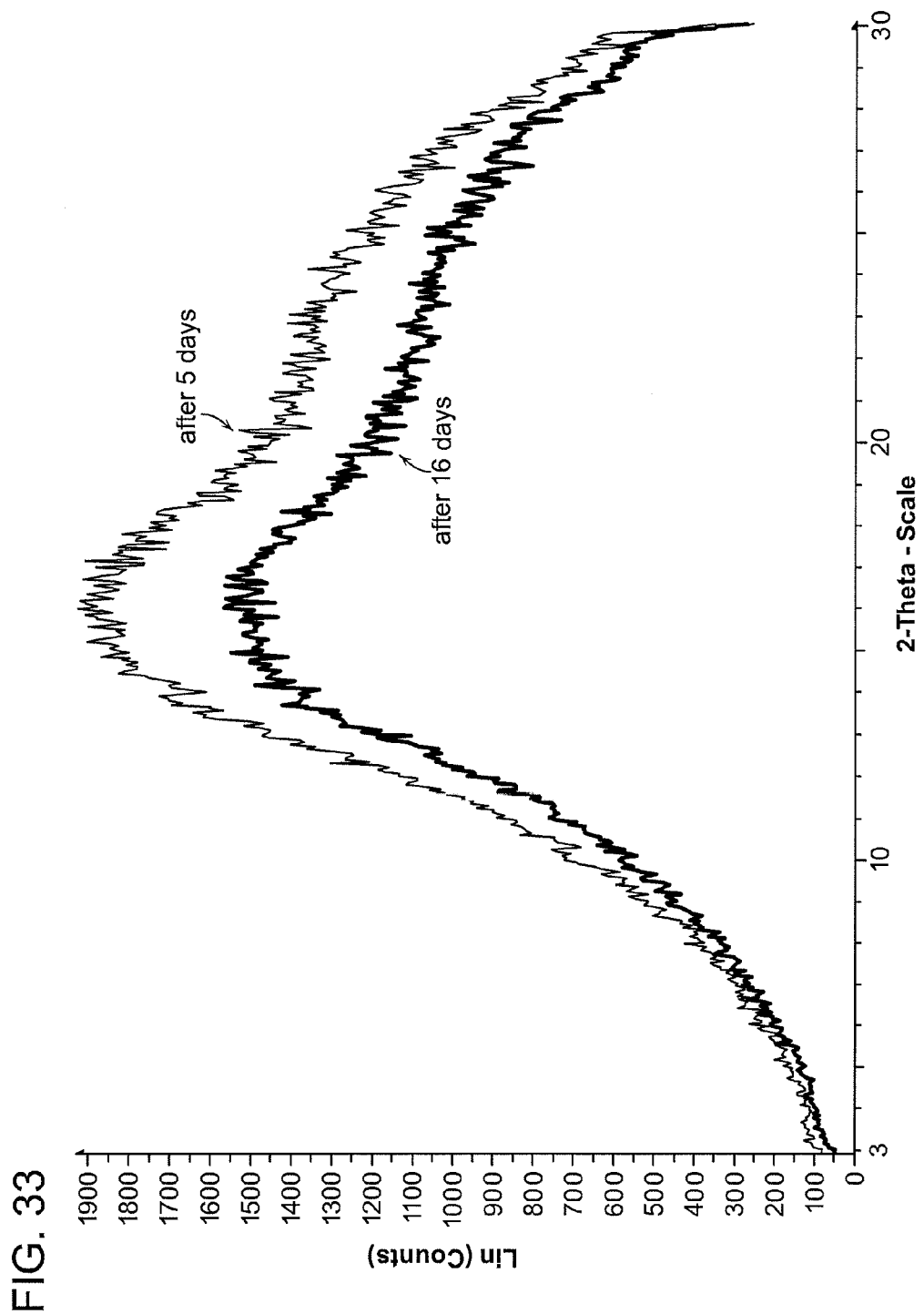
FIG. 33 shows the XRPD diffractograms of batch 1 of obeticholic acid Form 1 after storage at 25° C./97% RH (see Example 5).

A sample of batch 1 was stored at 40° C. and 75% relative humidity (RH) in an accelerated stability testing of the solid form. Another sample was stored at 25° C. and 97% relative humidity to check the effect of very high humidity. Both samples were re-analyzed by XRPD after five days and after two weeks. Both samples remained non-crystalline under the two storage conditions for up to two weeks, showing that Form 1 is stable to these conditions. See FIG. 32 and FIG. 33.

The six batches analyzed were all non-crystalline. The glass transition temperature was measured at 95° C. with a modulated DSC experiment. The six batches appeared very similar with all analytical techniques used, the only difference between them being their water content, which varied from 1.9% to 2.8% by Karl Fischer titration. Thermal analysis showed the varying amount of water and indicated decomposition starting around 175-220° C. Measured pKa was 4.82 and Log P is 5.54. Microscopic evaluation showed large hard agglomerates of very small irregular particles.

Stability testing showed that the material was still non-crystalline after two weeks under accelerated conditions (40° C./75% RH) or under high humidity (25° C./97% RH). Gravimetric Vapor Sorption (GVS) analysis showed the material is only moderately hygroscopic, with a total weight gain of 3.8% from 0 to 90% relative humidity (RH). No hydrate formation was observed under GVS. The sample re-analyzed by XRPD after GVS was still non-crystalline. The high glass transition temperature and the stability testing results suggest that the non-crystalline form is stable.

Example 6

Single Crystal X-Ray Structure and Absolute Stereochemistry

Figure 34:
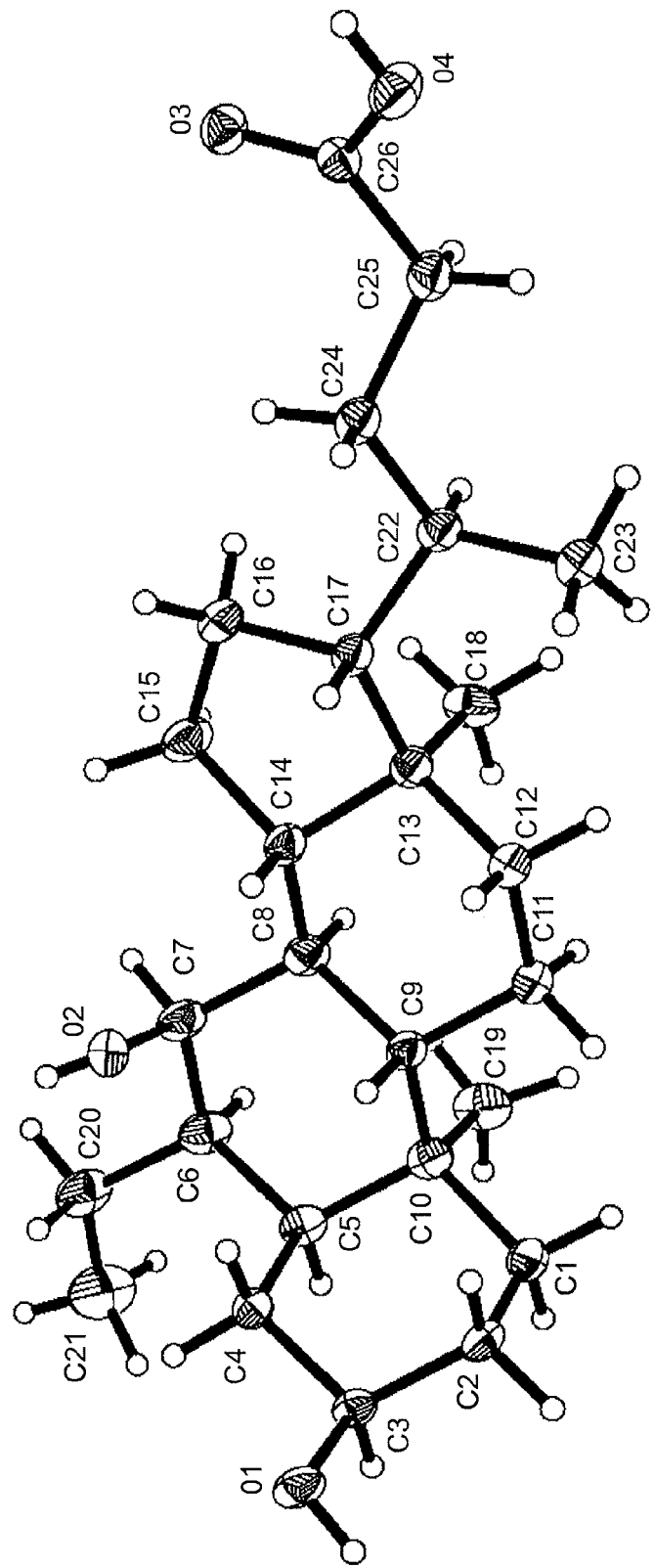
FIG. 34 shows a view of the molecule of obeticholic acid Form G from the crystal structure showing anisotropic atomic displacement ellipsoids for the non-hydrogen atoms at the 50% probability level (see Example 6).

The single crystal X-ray structure of obeticholic acid was determined from a crystal obtained from the recrystallization of obeticholic acid from an acetonitrile solution after cooling to 5° C. at 0.1° C./min followed by maturation at RT/50° C. 8 h cycles for 1 week (see FIG. 34). The structure is consistent with Form G and a simulated XRPD pattern has been generated as a reference pattern for this material. Form G can be prepared by cooling a solution of obeticholic acid in e.g., acetonitrile.

The structure is orthorhombic, space group $P2_12_12_1$, and contains one molecule of obeticholic acid in the asymmetric unit. Final R1 [I>2σ(I)]=3.22%. The crystal exhibited prism morphology of approximate dimensions 0.4×0.4×0.3 mm. The absolute stereochemistry of the molecule was determined as Sat chiral centers C5, C9, C10 and C14 and R at chiral centers C3, C6, C7, C8, C13, C17 and C22 with a Flack parameter=−0.01 (13). For the inverted structure with chiral centers C5, C9, C10 and C14 in the R configuration and chiral centers C3, C6, C7, C8, C13, C17 and C22 in the S configuration, the Flack parameter=1.01(13), confirming the assignation mentioned above.

Overall, the structure had a strong data set and no disorder.

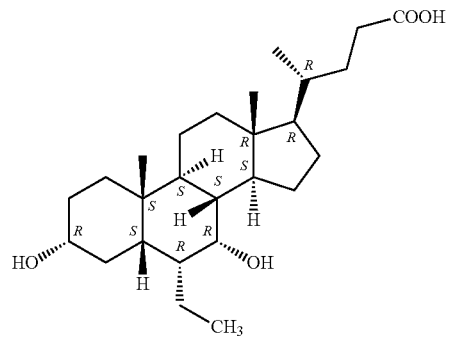

The software used to assign the stereochemistry (PLATON) determines the chiral center (C8) as an R stereocenter, whereas ACD software (and the Cahn-Ingold-Prelog) assignment for (C8) is S. However, the assignment of the trans ring junction for B/C ring system is absolutely defined from the crystal structure.

Determination of the absolute structure using Bayesian statistics on Bijvoet differences, (Hooft et al., *J. Appl. Cryst.*, (2008), 41, 96-103), reveals that the probability of the absolute structure as presented being correct is 1.000, while the probabilities of the absolute structure being a racemic twin or false are 0.000 and 0.000 respectively. The Flack equivalent and its uncertainty are calculated through this program to be −0.019(17).

The structure of obeticholic acid contains one 5 membered ring and 3 six membered rings which are fused together. Conformational analysis on the 5 membered ring (C13, C14, C15, C16 and C17)) reveals that the closest puckering descriptor for this ring is a half-chair. Conformational analysis on the three 6 membered rings (C1, C2, C3, C4, C5 and C10); (C5, C6, C7, C8, C9 and C10) and (C 8, C9, C11, C12 C13 and C14) reveals that the closest puckering descriptor for these rings is a chair.

Figure 35:
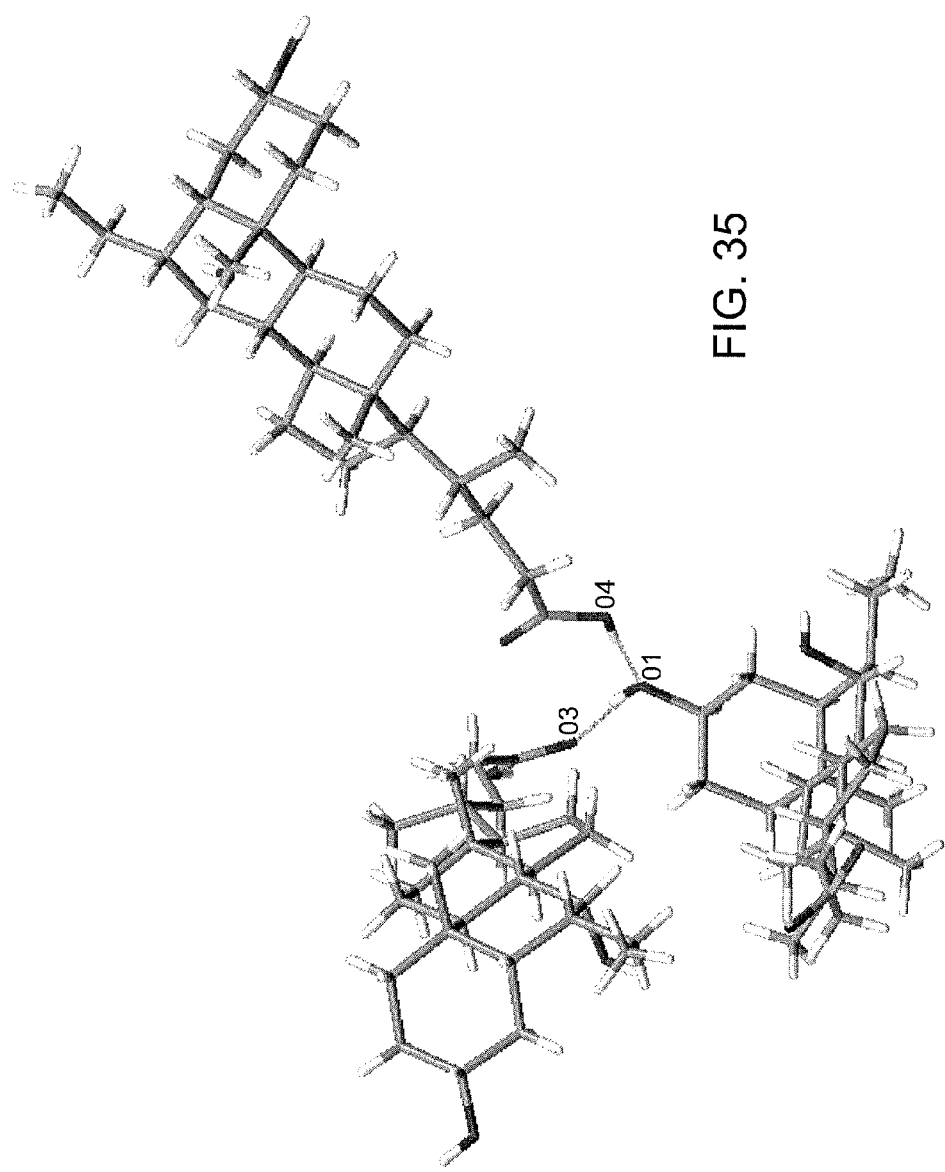
FIG. 35 shows a view of the intermolecular hydrogen bonds of the crystal structure of obeticholic acid Form G where hydrogen bondings are shown in dashed lines (See Example 6).

Two unique intermolecular hydrogen bonds are observed in the crystal structure. Each molecule of obeticholic acid forms a hydrogen bond to two different symmetry related molecules of obeticholic acid, with the oxygens, O1 and O4, acting as donors to the oxygens, O3 and O1 respectively, acting as acceptors, O1-H1C-O3 [D•••A=2.7419(12)Å] and O4-H4C-O1 [D•••A=2.6053(13)Å] (see FIG. 35). These interactions result in a complex 3 dimensional hydrogen bonded network. The final Fourier difference map shows maximal and minimal electron densities of 0.402 and −0.176 eÅ$^{-3}$, respectively.

Figure 36:
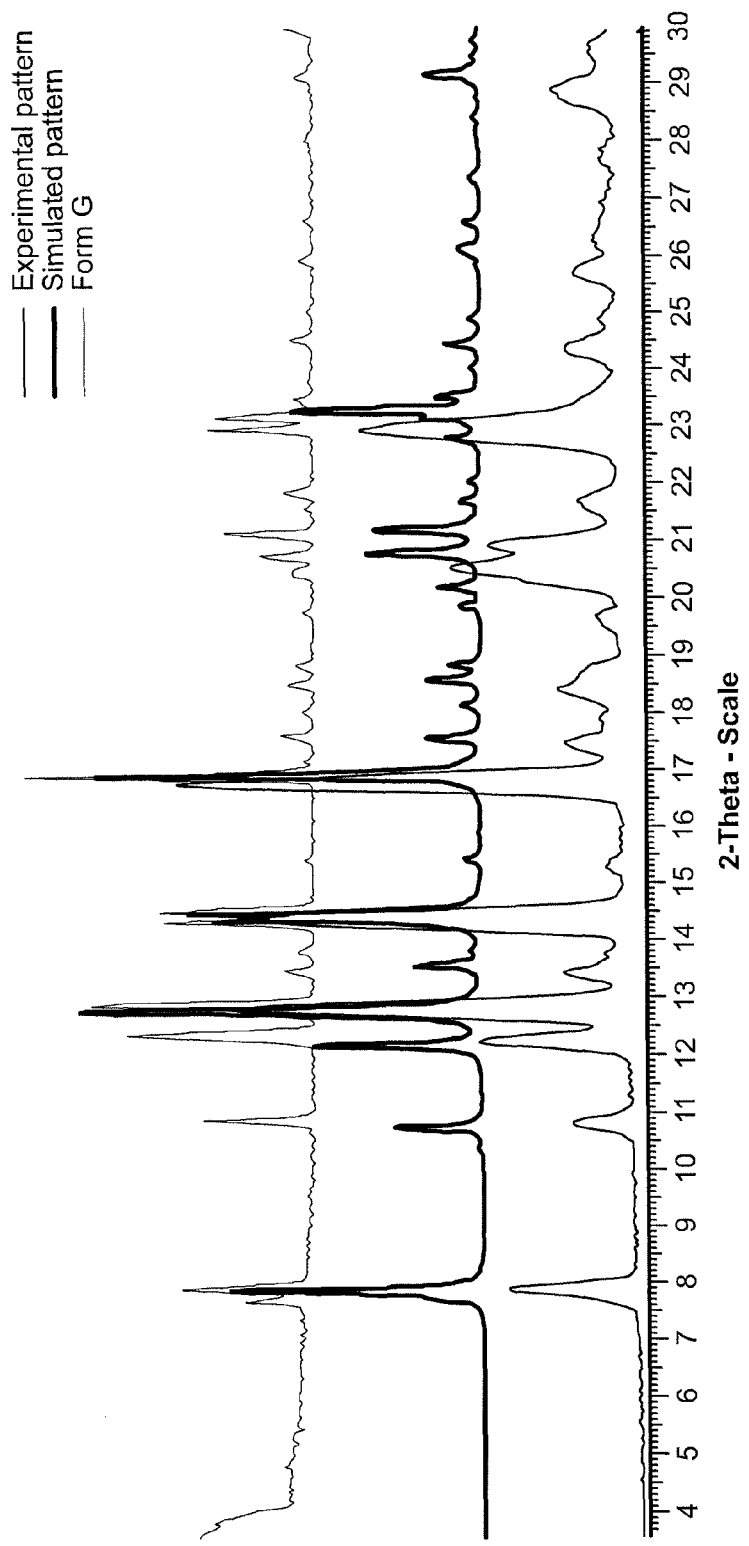
FIG. 36 shows an XRPD overlay of the simulated powder pattern, experimental patterns of the collected crystal, and obeticholic acid Form G (see Example 6).

An overlay of the calculated XRPD pattern for the structure with the experimental batches shows that the crystal is consistent with the bulk and is obeticholic acid Form G (see FIG. 36).

TABLE 1

Crystal data for obeticholic acid Form G

| | |
|---|---|
| Crystallization solvents | Acetonitrile |
| Crystallization method | Maturation at RT/50° C. |
| Empirical formula | $C_{26} H_{44} O_4$ |
| Formula weight | 420.63 |
| Temperature | 100(2) K |
| Wavelength | 1.54178 Å |
| Crystal size | 0.40 × 0.40 × 0.30 mm |
| Crystal habit | Colourless Prism |
| Crystal system | Orthorhombic |
| Space group | $P2_1 2_1 2_1$ |
| Unit cell dimensions | a = 8.72510(10) Å    α = 90° |
| | b = 12.69860(10) Å   β = 90° |
| | c = 22.5408(2) Å     γ = 90° |
| Volume | 2497.44(4) Å$^3$ |
| Z | 4 |
| Density (calculated) | 1.119 Mg/m$^3$ |
| Absorption coefficient | 0.574 mm$^{-1}$ |
| F(000) | 928 |

TABLE 2

Data collection and structure refinement for obeticholic acid Form G

| | |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 9.15 to 74.49° |
| Index ranges | −10 ≤ h ≤ 10, −15 ≤ k ≤ 15, −28 ≤ l ≤ 26 |
| Reflections collected | 50001 |
| Independent reflections | 5073 [R(int) = 0.0220] |
| Coverage of independent reflections | 99.4% |
| Variation in check reflections | N/A |
| Absorption correction | Semi-empirical from equivalents |
| Max. and min. transmission | 1.00000 and 0.78605 |
| Structure solution technique | direct |
| Structure solution program | SHELXTL (Sheldrick, 2001) |
| Refinement technique | Full-matrix least-squares on F$^2$ |
| Refinement program | SHELXTL (Sheldrick, 2001) |
| Function minimized | $\Sigma w(F_o^2 - F_c^2)^2$ |
| Data/restraints/parameters | 5073/0/286 |
| Goodness-of-fit on F$^2$ | 1.060 |
| Δ/σmax | 0.001 |
| Final R indices | |
| 5039 data; I > 2σ(I) | R1 = 0.0320, wR2 = 0.0859 |
| all data | R1 = 0.0322, wR2 = 0.0861 |
| Weighting scheme | calc w = 1/[σ$^2$ (F$_o^2$) + (0.0503P)$^2$ + 0.5520 P] where P = (F$_o^2$ + 2 F$_c^2$)/3 |
| Absolute structure parameter | −0.01(13) |
| Largest diff. peak and hole | 0.402 and −0.176 eÅ$^{-3}$ |

Refinement summary of the structure is as follows:

| | |
|---|---|
| Ordered Non-H atoms, XYZ | Freely refining |
| Ordered Non-H atoms, U | Anisotropic |
| H atoms (on carbon), XYZ | Idealized positions riding on attached atoms |
| H atoms (on carbon), U | Appropriate multiple of U(eq) for bonded atom |
| H atoms (on heteroatoms), XYZ | Freely refining |
| H atoms (on heteroatoms), U | Isotropic |
| Disordered atoms, OCC | No disorder |
| Disordered atoms, XYZ | No disorder |
| Disordered atoms, U | No disorder |

Example 7

Bioavailability Difference Between Obeticholic Acid Form 1 (Non-Crystalline) and Crystalline (Form F) Forms The physical state of a solid obeticholic acid can play a role in the bioavailability of the molecule when administered orally to a subject (e.g., rats). The study described below was carried out to evaluate the plasma kinetics after a single oral administration and the efficiency of the intestinal absorption and the pharmacokinetics of solid non-crystalline and crystalline forms of obeticholic acid. The profiles of obeticholic acid plasma concentration vs time, the $t_{max}$, $C_{max}$ and AUC after administration of obeticholic acid Form 1 (non-crystalline) or Form F were compared (see FIGS. 37-38)

Obeticholic acid Form 1 (non-crystalline) and Form F were administered to rats and in each animal blood was collected at different period of times for at least 3 hours. Six animals were studied for each form of obeticholic acid.

Experimental Protocol:

The test substance used was obeticholic acid Form 1 (non-crystalline) and crystalline Form F. Form F can be prepared by maturation from acetonitrile or nitromethane. The formulation was prepared as a suspension in water at pH 4. The study model is adult male Sprague Dawley rats about 225 to about 250 g (Harlan Laboratories). Six animals were used per dosage route. The dosage is PO 20 mg/kg/5 mL. The animals were fasted overnight before treatment with the formulation of obeticholic acid. Oral administration was performed by gastric gavage.

On day one animals were be fitted with a cannula implanted in the left jugular vein (SOP VIVO/SAF6), anaesthesia was obtained by Isoflurane. The experiment was started after one day of recovery from surgery. About 500 µL of blood (250 µL of plasma) was taken via cannula in a heparinised syringe (Na Heparin) and collected immediately in microtubes in an ice/water bath. Within 1 hour, samples were centrifuged at 10000×g for 5 minutes at 4° C. Plasma was immediately transferred in microtubes and stored at −20° C. Samples of blood were collected 30 minutes, 1 hour, 1.3 hour, 2 hours, and 3 hour post-dose. Plasma samples were analyzed using the HPLC-ES/MS/MS quantitative method. Pharmacokinetics study was preformed using non-compartmental methods.

Figure 37:
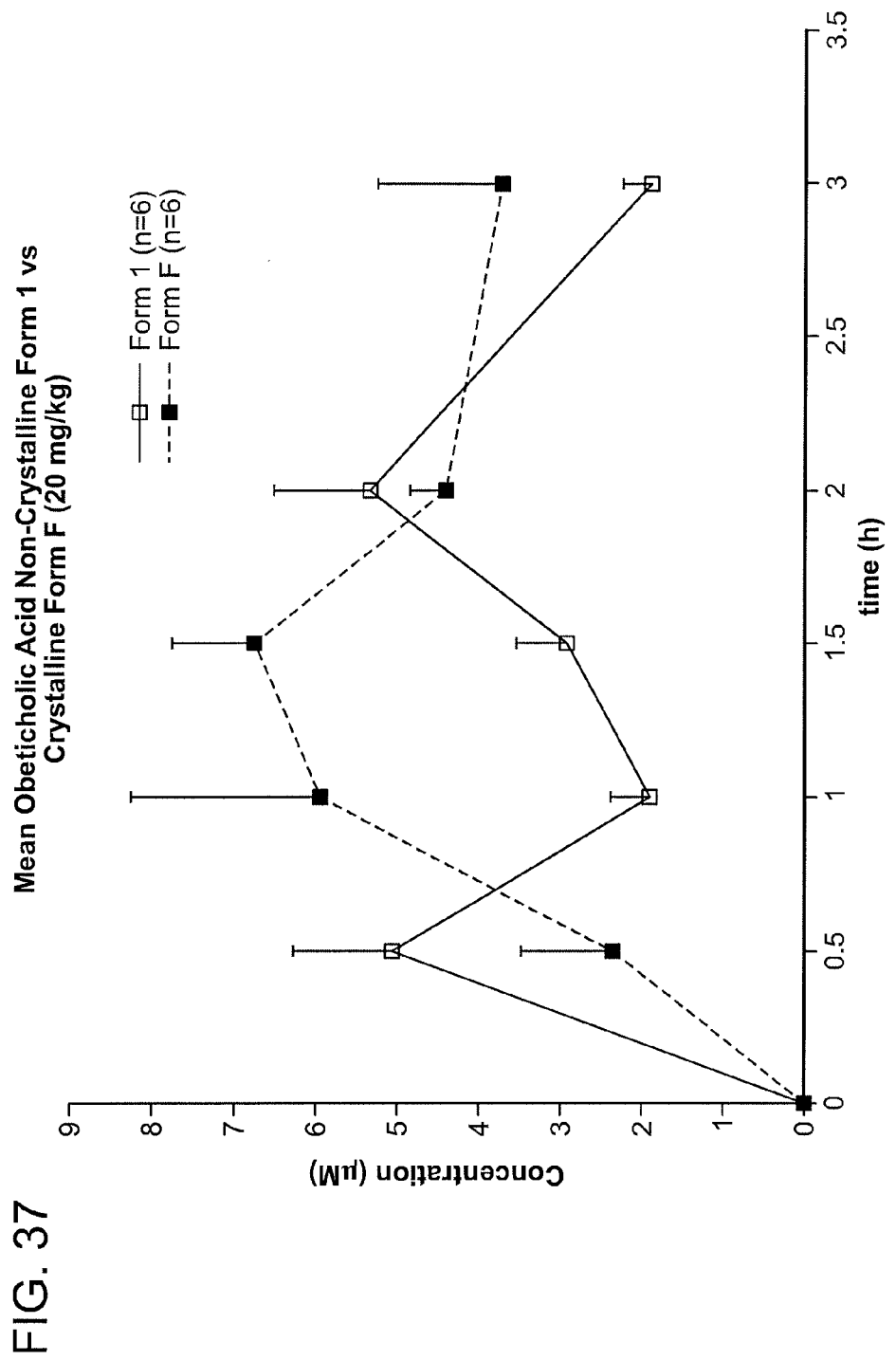
FIG. 37 shows a graph of the plasma obeticholic acid profile vs. time after oral administration of 20 mg/kg of obeticholic acid Form 1 and crystalline Form F (see Example 7).
Figure 38:
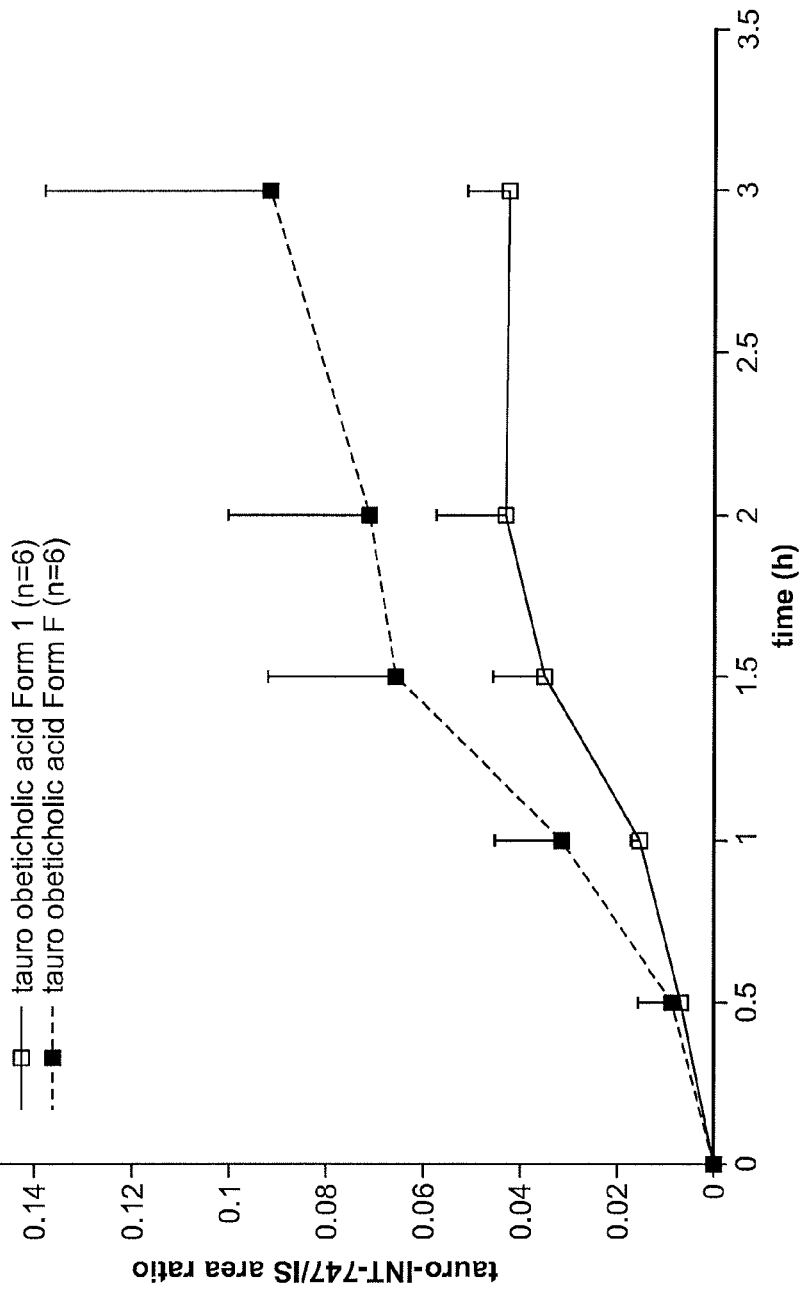
FIG. 38 shows a graph of the plasma concentration of tauro conjugate of obeticholic acid Form 1 and crystalline Form F at different time interval after the administration (see Example 7).

Results:

The mean plasma concentrations of obeticholic after 20 mg/Kg b.w oral single dose administration of the two solid forms are reported in FIG. 37. Values are the mean of six set of experiments for each formulation. The standard deviations are reported in the graph.

After administration of the crystalline form the Cmax is achieved after 1.5 hours and the plasma obeticholic acid concentration follows a regular kinetics with one maximum value and after 3 hours the dose is almost half of the Cmax.

The kinetics profile after the administration of obeticholic acid Form 1 (non-crystalline) Form 1 is different from that of the crystalline Form F. An early plasma concentration peak is obtained after 30 minutes and a second one after 2 hours. The variability of the data in the 6 rats is very low and this behaviour is statistically different from that of the crystalline form. The AUC for the three hours studied is higher for the crystalline form. The kinetics suggest that the obeticholic acid is still present in plasma after 3 hours. It has previously been demonstrated that the passage of obeticholic acid through the liver produce the hepatic metabolite tauro conjugate, which is secreted into bile and accumulate in the enterohepatic circulation. Thus, the measurement of the tauro conjugate can be used to determine the passage of the amount of obeticholic acid through the liver. The rate of tauro conjugate formation is reported in FIG. 38, which shows that the tauro conjugate formation is faster and a higher concentration is achieved after administration of the crystalline form.

Melting Point and Glass Transition

The melting point of obeticholic acid Form 1 (non-crystalline) Form 1 and crystalline Form F were measured using a conventional method. The melting point of Cheno-deoxycholic acid and Ursodeoxycholic acid were measured as reference compounds. Measurements have been performed in triplicate. For the crystalline form the transition from the solid to liquid state is defined as melting temperature ($T_m$) while for the non-crystalline form is defined as glass temperature transition ($T_g$), In the table are reported the measured values expressed in both Celsius ° C. and Kelvin ° K.

TABLE 3

Melting points of obeticholic acid (Form 1 and Form F) and CDCA and UDCA

| | Experimental data | | Literature data | |
|---|---|---|---|---|
| Compound | $T_m$ (° C.) | $T_g$ (° C.) | $T_m$ (° C.) | $T_g$ (° C.) |
| CDCA | 136-140 | — | 119 | 98 |
| | | | 143 | |
| | | | 163 | |
| UDCA | 203-207 | — | 203 | 105 |
| Obeticholic acid | 120-124 235-237 | 108-112 | — | — |

| | Experimental data | | | Literature data | | |
|---|---|---|---|---|---|---|
| Compound | $T_m$ (° K) | $T_g$ (° K) | $T_g/T_m$ (° K) | $T_m$ (° K) | $T_g$ (° K) | $T_g/T_m$ (° K) |
| CDCA | 409-413 | — | — | 392 | 371 | 0.85 |
| | | | | 416 | | |
| | | | | 436 | | |
| UDCA | 476-480 | — | — | 477 | 378 | 0.79 |
| Obeticholic acid | 393-397 508-510 | 381-385 | 0.75 | — | — | 0.75 |

Results:

The values obtained for CDCA and UDCA agree with those previously reported, where the melting point of UDCA is higher than that of CDCA. The transition glass temperature Tg of Form 1 (102-112° C.) is lower than the melting point temperature Tm of Form F (120-124° C.). This observed pattern agrees with previous reported data when the two solid state forms are compared. Form F has an additional transition at a higher temperature (235-237° C.).

The ratio between the highest melting point temperature and the glass transition temperature expressed in Kelvin degree is quite similar to other drugs and other bile acids. (J. Kerc et al. Thermochim. Acta, 1995 (248) 81-95).

Differential Scanning Calorimetry Analysis

Differential scanning calorimetry (DSC) analysis was carried out to better define the melting points and the physical state of obeticholic acid crystalline and non-crystalline forms. The instrument used was a Mettler Toledo DSC model 821e. Approximately 4-5 mg of each Form 1 and Form F were submitted to analysis. The compounds were exposed to the temperature range of 30-300° C. at 10° C./min heating rate.

Figure 39:
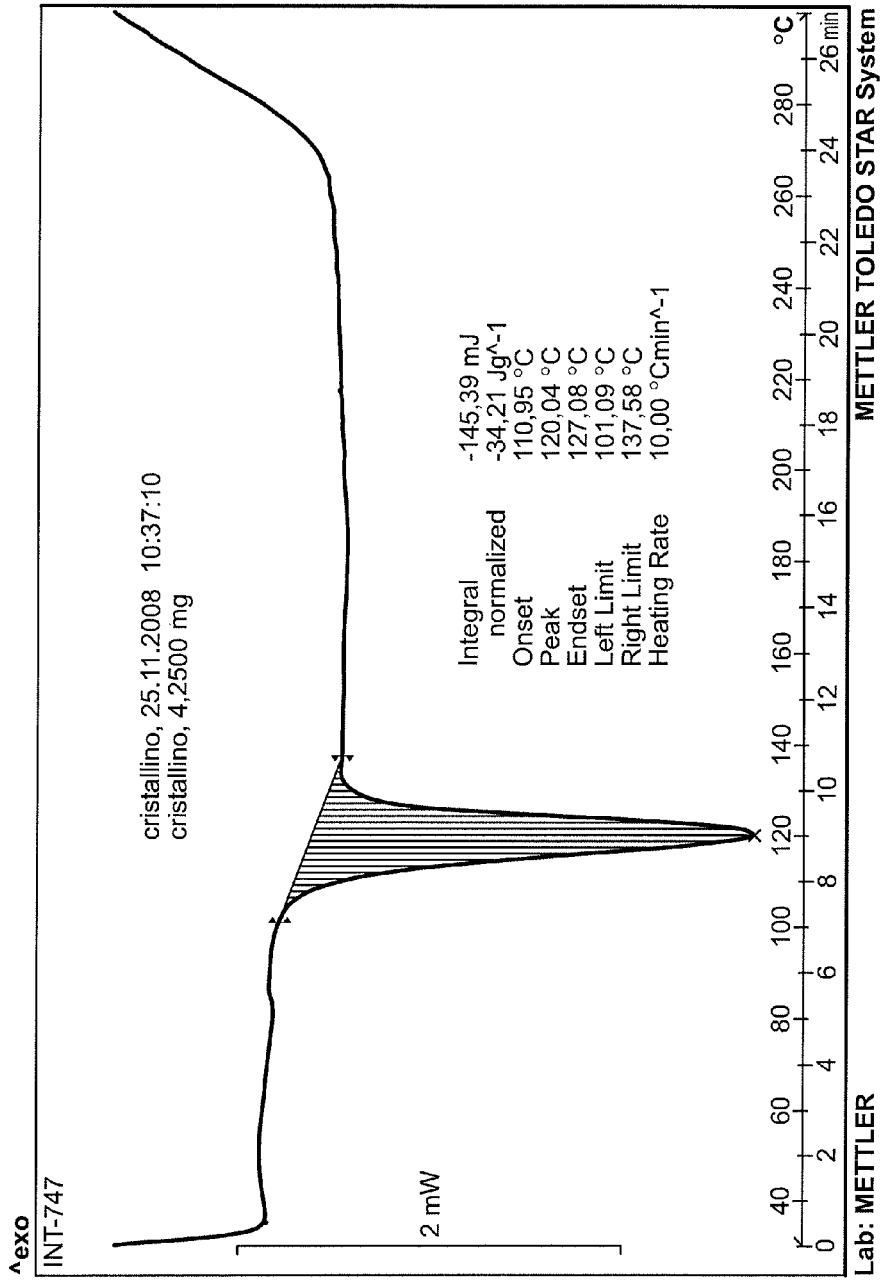
FIG. 39 shows the DSC curve of Form 1 (see Example 7).

FIG. 39 shows the DSC curve obtained for obeticholic acid crystalline Form F. One endothermic transition at 120.04° C. was detected corresponding to the melting point of the compound. This result was confirmed also by hot stage microscopy (HSM); in the range 30°-240° C. the solid-liquid transition observed was at 122-124° C. In the DSC trace, the peak shape and intensity obtained for Form F are in agreement with typical behaviour showed by crystalline forms. However, the peak width is rather broad; this can be due to not homogeneous crystals. Thermo gravimetric analysis (TGA) did not show any weight loss in the 30-300° C. temperature range.

Figure 40:
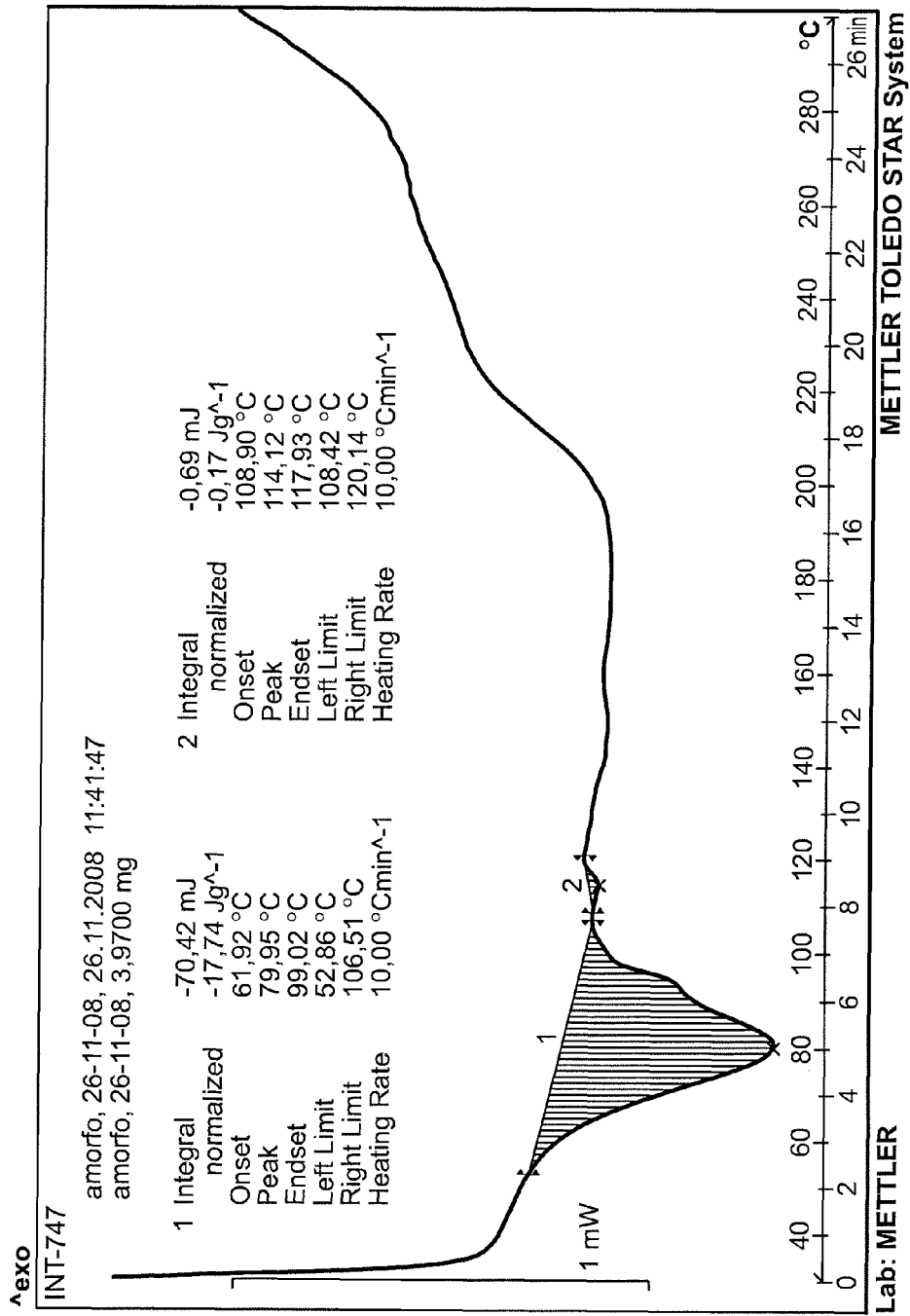
FIG. 40 shows the DSC curve of Form F (see Example 7).

FIG. 40 shows the DSC curve obtained for obeticholic acid non-crystalline Form 1. One endothermic transition at 79.95° C. was observed. Peak shape and intensity are in agreement with behaviour expected for non-crystalline compounds. For these substances energy required for solid-liquid transition (glass transition) is less than for crystalline compounds. The thermogram did not show any weight loss in the 30-300° C. temperature range.

Water Solubility

The water solubility of obeticholic acid Form 1 (non-crystalline) and crystalline Form F was measured following procedures known in the art. Briefly, the solid was suspended in water at a low pH (HCl 0.1 mol/L) and left to equilibrate at 25° C. for one week under slightly mixing. The saturate solution was filtered and the concentration of the compound in solution measured by HPLC-ES-MS/MS.
Results:

| | Water solubility (μmol/L) |
|---|---|
| Form 1 | 17.9 |
| Form F | 9.1 |

Form 1 present a higher solubility 17.9 μmol/L vs. 9.1 μmol/L for Form F.

According to the bioavailability data of the obeticholic acid, crystalline Form F is higher than the obeticholic acid Form 1 (non-crystalline). Despite an earlier plasma concentration peak after administration of the Form 1, the plasma profiles show that the Form F is absorbed more efficiently (higher AUC) and even the kinetics is more regular, reflecting an optimal distribution of the drug in the intestinal content. Form 1 shows this early peak then a later second one with a Cmax lower that than of Form F.

The water solubility of the Form 1 is higher than that of Form F. Form F appears to be stable as the thermo gravimetric analysis (TGA) did not show any weight loss in the temperature range studied.

According to these results, Form F when administered orally appears more efficiently absorbed by the intestine and taken up by the liver. The rate of formation of the main hepatic metabolite tauro conjugate is almost twice for Form F compared to Form 1, suggesting a more efficient transport and accumulation in the enterohepatic circulation and the plasma concentration after 3 hours.

Example 8

Preparation of Radiolabeled Obeticholic Acid

Radiolabeled obeticholic acid was prepared according to the scheme below.

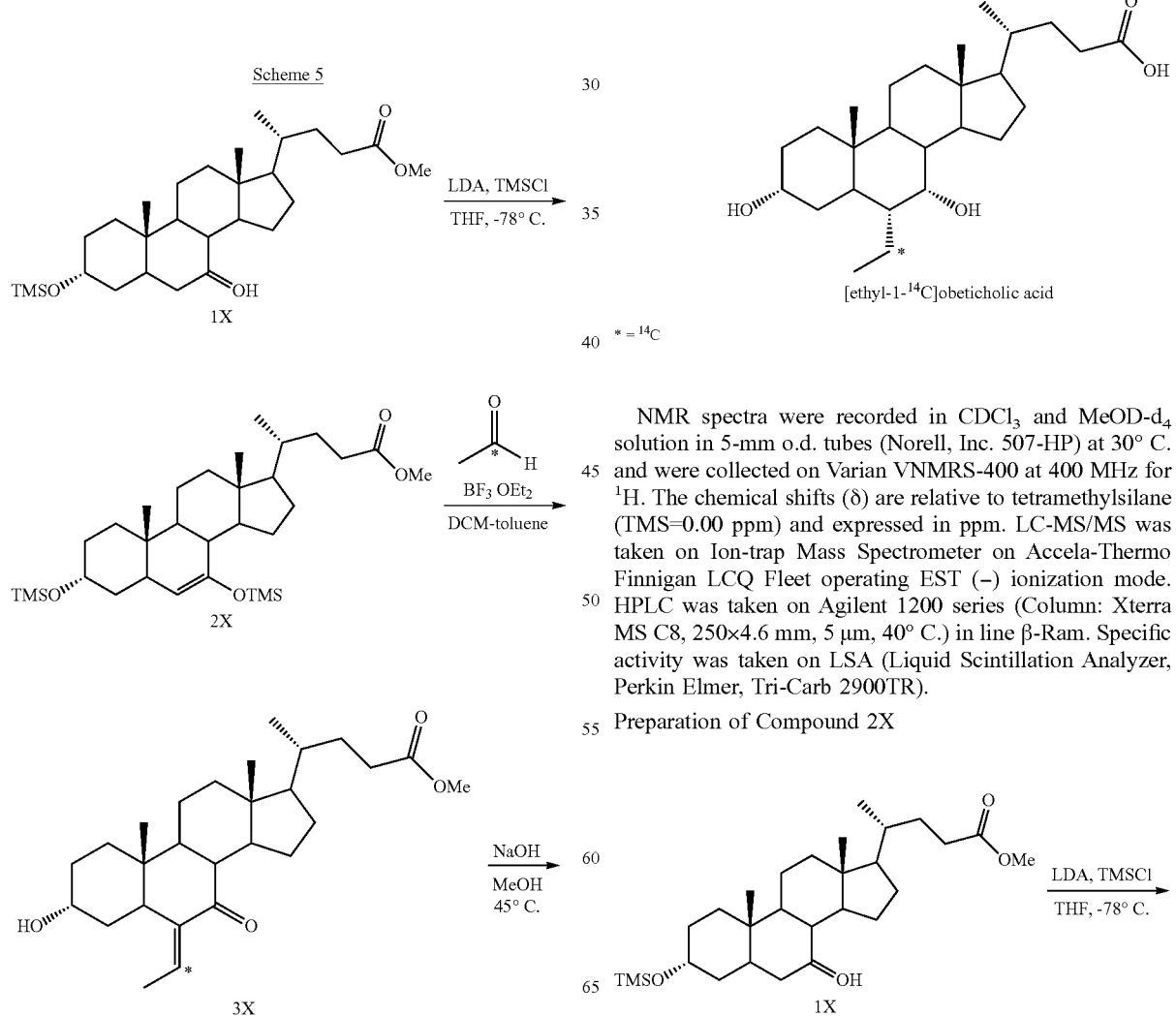

$* = {}^{14}C$

NMR spectra were recorded in $CDCl_3$ and MeOD-$d_4$ solution in 5-mm o.d. tubes (Norell, Inc. 507-HP) at 30° C. and were collected on Varian VNMRS-400 at 400 MHz for $^1H$. The chemical shifts (δ) are relative to tetramethylsilane (TMS=0.00 ppm) and expressed in ppm. LC-MS/MS was taken on Ion-trap Mass Spectrometer on Accela-Thermo Finnigan LCQ Fleet operating EST (−) ionization mode. HPLC was taken on Agilent 1200 series (Column: Xterra MS C8, 250×4.6 mm, 5 μm, 40° C.) in line β-Ram. Specific activity was taken on LSA (Liquid Scintillation Analyzer, Perkin Elmer, Tri-Carb 2900TR).

Preparation of Compound 2X

-continued

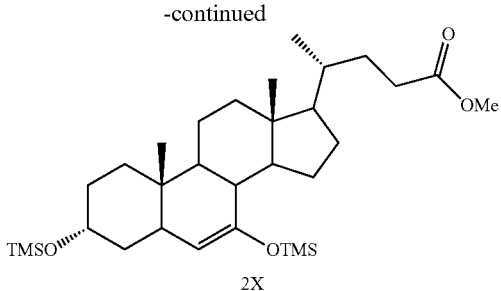

2X

To a solution of diisopropylamine (1.59 g, 15.8 mmol) in dry THF (6.0 mL) was added n-BuLi (6.30 mL, 2.5 M, 15.8 mmol) at −20° C. After stirring the reaction mixture for 1 h at −20° C., cooled to −78° C. and TMSCl (1.72 g, 15.8 mmol) was added followed by compound 1X (3.00 g, 6.29 mmol) in dry THF (6.0 mL). The reaction mixture was stirred for 1 h at −78° C., quenched by addition of NaHCO$_3$ and stirred for 30 min at room temperature. The organic layer was separated and concentrated in vacuo to give the compound 2X (3.29 g, 95%) and used for next step without further purification.

Preparation of Compound 3X

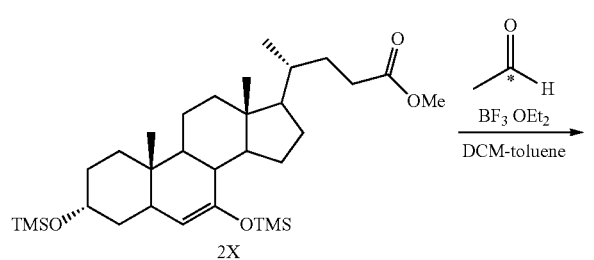

2X

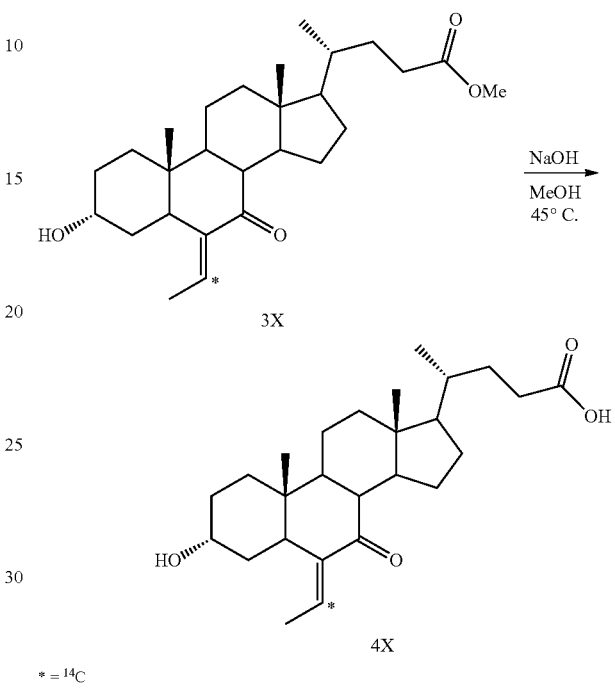

* = $^{14}$C

The [1-$^{14}$C]acetaldehyde (330 mCi, 5.63 mmol) (prepared from [$^{14}$C]BaCO$_3$, SA=58.6 mCi/mmol) in toluene (1.0 mL) and acetaldehyde (130 mg, 2.95 mmol) in DCM (2.0 mL) were mixed at −78° C. and then transferred to a solution of compound 2X (3.29 g, 6.00 mmol) in DCM (13.0 mL) followed by addition of BF$_3$.OEt$_2$ (1.05 g, 7.40 mmol) at −78° C. After stirring for 1 h at −78° C., the reaction mixture was allowed to warm up to 35° C. and stirred for 1 h at the above temperature. The reaction was quenched by addition of water (10 mL), the aqueous layer was extracted with DCM, the combined organic layer was dried over anhydrous Na$_2$SO$_4$, filtered and concentrated in vacuo The residue was purified by column chromatography on SiO$_2$ (Hexane: EtOAc=5:1 to 3:1) to give the compound 3X (102 mCi, 31%, SAW 37.0 mCi/mmol) as a white solid.

$^1$H—NMR (CDCl$_3$, Varian, 400 MHz): δ 0.65 (3H, s); 0.93 (3H, d, J=6.0 Hz), 1.01 (3H, s), 1.06-1.49 (12H, m), 1.62-2.04 (7H, m), 1.69 (3H, d, J=6.8 Hz), 2.18-2.28 (2H, m), 2.32-2.43 (2H, m), 2.58 (1H, dd, J=12.8, 4.0 Hz), 3.62-3.70 (1H, m), 3.67 (3H, s), 6.18 (1H, q, J=6.8 Hz).

Preparation of Compound 4X

To a solution of compound 3X (102 mCi, 2.75 mmol) in MeOH (6.0 mL) was added NaOH (220 mg, 5.50 mmol) in H$_2$O (3.0 mL) at room temperature. After stirring the reaction mixture for 1 h at 45° C., cooled to room temperature, MeOH was removed under reduced pressure and diluted with H$_2$O (12 mL). The aqueous layer was acidified with H$_3$PO$_4$, extracted with DCM and the organic layer was concentrated in vacuo. The residue was suspended in Et$_2$O and the precipitate was collected by filtration to give the compound 4X (86.3 mCi, 85%) as a white solid.

$^1$H—NMR (CDCl$_3$, Varian, 400 MHz); δ 0.63 (3H, s), 0.92 (3H, d, J=6.0 Hz), 0.99 (3H, s), 1.04-1.50 (13H, m), 1.61-2.01 (7H, m), 1.67 (3H, d, J=7.2 Hz), 2.21-2.28 (2H, m), 2.35-2.41 (2H, m), 2.56 (1H, dd, J=12.8, 4.0 Hz), 3.58-3.69 (1H, m), 6.16 (1H, q, J=7.2 Hz).

Preparation of Compound 5X

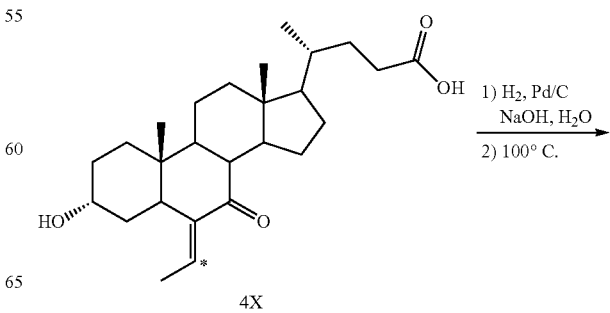

4X

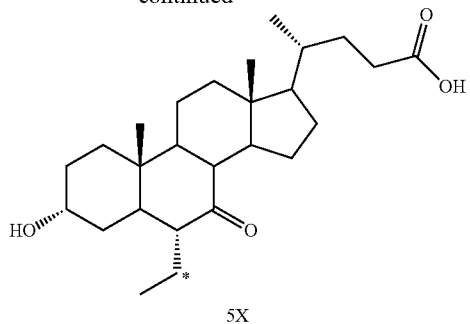

The mixture of compound 4X (86.3 mCi, 2.35 mmol) and 5%-Pd/C (100 mg) in aq. 0.5 M NaOH (10 mL, 5.0 mmol) was stirred for 10 h at room temperature under $H_2$ atmosphere (balloon) and then stirred for 14 h at 100° C. The catalyst was removed by filtration, washed with water and the filtrate was acidified with $H_3PO_4$. The precipitates was collected by filtration, the solid was dissolved in EtOAc, washed with brine, filtered through a short pad of $SiO_2$ and concentrated in vacuo. The residual solid was recrystallization with EtOAc to give the compound 5X (67.7 mCi, 78%) as a white solid.

$^1H$—NMR (MeOD-$d_4$, Varian, 400 MHz): δ 0.71 (3H, s), 0.75-0.84 (1H, m), 0.81 (3H, t, J=7.4 Hz), 0.92-1.01 (1H, m), 0.96 (3H, d, J=6.4 Hz), 1.06-1.38 (7H, m), 1.25 (3H, s), 1.41-1.96 (12H, m), 2.01-2.05 (1H, m), 2.11-2.24 (2H, m), 2.30-2.37 (1H, m), 2.50 (1H, t, J=11.4 Hz), 2.80-2.85 (1H, m), 3.42-3.49 (1H, m).

Preparation of [ethyl-1-$^{14}$C]obeticholic acid

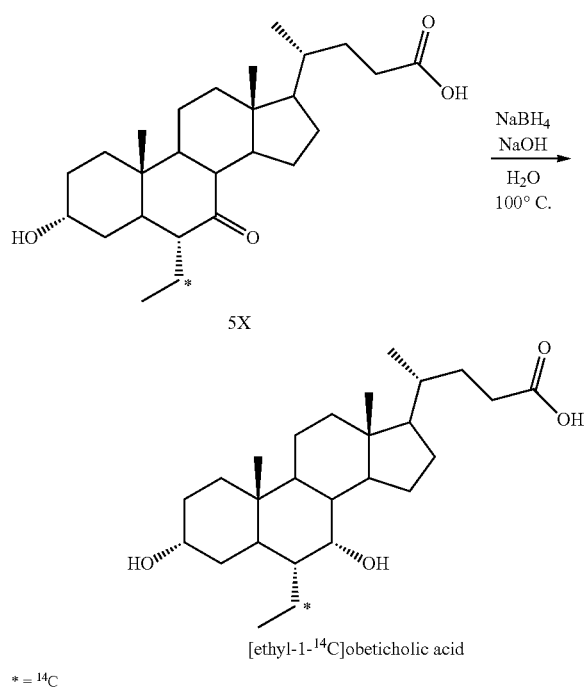

To a solution of compound 5X (67.7 mCi, 1.83 mmol) in aq. 2 M NaOH (4.50 mL, 9.00 mmol) was added a solution of $NaBH_4$ (416 mg, 11.0 mmol) in H2O (2.0 ml) at 80° C. After stirring the reaction mixture for 2 h at 100° C., water (6.0 mL) was added at room temperature and acidified with $H_3PO_4$. The aqueous layer was extracted with DCM, dried over anhydrous $Na_2SO_4$, filtered through a short pad of $SiO_2$ and concentrated in vacuo, The residue was purified by column chromatography on $SiO_2$ (Hexane:EtOAc=1:1 to 1:3) to give the product (44.0 mCi, 65%) as a white solid. The product (44.0 mCi, 1.19 mmol) and obeticholic acid (120 mg, 0.285 mmol) were dissolved in EtOAc (4 mL), the solution was stirred for 2 h at 50° C. and then concentrated in vacuo. The residual oil suspended in $Et_2O$, the precipitate was collected by filtration to give the [ethyl-1-$^{14}$C]obeticholic acid (560 mg, 38.5 mCi, SA=29 mCi/mmol) as a white solid.

$^1H$—NMR (CDCl$_3$, Varian, 400 MHz): δ 0.66 (3H, s), 0.88 (3H, s), 0.93 (3H, t, J=7.2 Hz), 0.93 (3H, d, J=6.4 Hz), 0.96-1.04 (1H, m), 1.08-1.52 (14H, m), 1.51-1.60 (10H, m), 2.22-2.30 (1H, m), 2.36-2.44 (1H, m), 3.38-3.45 (1H, m), 3.71 (1H, s).

LC-MS/MS (MS: LCQ Fleet): MS Calcd.: 421.56; MS Found: 421.07 [M-H]$^-$.

Radio TLC: TLC plate of silica 60 F$_{254}$, and mobile phase is EtOAc. Radiochemical purity is 98.90%, Rf=0.675

HPLC (Agilent 1200 series): Mobile phase; acetonitrile: 5 mM Phosphate buffer (pH=3):MeOH=450:450:100. Radiochemical purity is 98.19% (β-ram), Rt=20.00 min. [Ethyl-1-$^{14}$C]obeticholic acid has a molecular formula of $^{14}C_1C_{25}H_{44}O_4$ and a molecular weight of 421.46 at the specific activity of 29 mCi/mmol by LSC.

Example 9

Synthesis of Crystalline Obeticholic Acid

The procedures for the selective synthesis of Forms A, C, D, F, G, and I were identified and listed below. The results of these experiments are provided in Table 5.

Procedure 1: Cooling then Maturation

Amorphous obeticholic acid (approximately 30 mg) was weighed into a glass vial and warmed to 50° C. 2 volume (60 μl) portions of acetonitrile were added at 50° C. Initially the sample formed a gum, which dissolved after the addition of 14 volumes of solvent. On stirring flakes of solid precipitate were observed. The sample was cooled to 5° C. using a linear cooling rate of 0.25° C./min. The resulting suspension was analyzed by XRPD and was then matured (shaken in 8 hour cycles at 50° C./RT). After 5 days of maturation the sample was equilibrated to room temperature and was re-analyzed by XRPD.

Procedure 2: Cooling

Amorphous obeticholic acid (approximately 30 mg) was weighed into glass vials and warmed to 50° C. Solvent was added (as per Table 5 and observations were made. Samples were stirred at 50° C. for 1 hour then were cooled to 5° C. using a linear cooling rate of 0.1° C./min. Samples were stirred at 5° C. for 2 days. Any solids were filtered, air dried and analyzed by XRPD. Solutions were stored in the freezer for ~48 hours, and then were left to evaporate at ambient conditions. Solids were analyzed by XRPD.

Procedure 3: Anti-Solvent Addition then Cooling

Amorphous obeticholic acid (approximately 30 mg) was weighed into glass vials and warmed to 50° C. Solvent was added (as per Table 5) to dissolve the amorphous material and then anti-solvent (heptane, volumes as per Table 5) was added and observations were made. Samples were stirred at 50° C. for 1 hour then were cooled to 5° C. using a linear cooling rate of 0.1° C./min. Samples were stirred at 5° C. for 2 days. Solids were filtered, air dried and analyzed by XRPD.

Procedure 4: Maturation

Amorphous obeticholic acid (approximately 30 mg) was weighed into glass vials and warmed to 50° C. Solvent was added (as per Table 5) to dissolve the amorphous material. Samples were stirred at 50° C. for 1 hour then were matured (shaken in 8 hour cycles at 50° C./RT). After 3 days samples containing solids were filtered, air dried and analyzed by XRPD. Samples that were solutions were matured with a cooler upper temperature (stirred in 4 hour cycles at 40° C./RT, Procedure 4b) and any that formed solids were analyzed by XRPD after 1 and 2 days.

Procedure 5: Anti-Solvent then Cooling

Amorphous obeticholic acid (approximately 30 mg) was weighed into a glass vial and warmed to 50° C. MTBE (90 µl, 3 volumes) was added to dissolve the amorphous material and then anti-solvent (heptane, 90 µl, 3 volumes) was added and observations were made. The sample was stirred at 50° C. for 1 hour then was cooled to 25° C. using a linear cooling rate of 0.2° C./min. After ~30 minutes at 25° C. the resulting solid was filtered, air dried and analyzed by XRPD.

Procedure 6: Maturation

Amorphous obeticholic acid (approximately 30 mg) was weighed into a glass vial and warmed to 50° C. Anisole (90 µl, 3 volumes) was added to dissolve the amorphous material. The sample was matured (shaken in 4 hour cycles at 40° C./RT) for a total of 17 days.

Procedure 7: Cold Slurry

Amorphous obeticholic acid (approximately 30 mg) was weighed into a glass vial and cooled to 5° C. Acetonitrile/water mixtures (as per, pre-cooled to 5° C.) were added and samples were stirred at 5° C. overnight. Observations were made and solids were filtered, air dried and analyzed by XRPD. Some solids were large lumps which were crushed prior to XRPD analysis. One sample was a sticky solid so was left to stir at 5° C. for a total of 17 days, forming a hard lump of solid, which was crushed and analyzed by XRPD.

Procedure 8: Cooling

Amorphous obeticholic acid (approximately 30 mg) was weighed into glass vials and warmed to 50° C. Solvent (see Table 5) was added to dissolve the amorphous material the samples were stirred at 50° C. for 1 hour. The samples were cooled to −20° C. using a linear cooling rate of 0.1° C./min. After stirring at −20° C. overnight the samples were equilibrated to room temperature and resulting solids were filtered, air dried and analyzed by XRPD.

TABLE 5

Summary of Methods to Synthesize Crystalline obeticholic acid and Results

| Procedure | Solvent | Volume (µL) | Anti-Solvent | Volume (µL) | Crystalline Form |
|---|---|---|---|---|---|
| 1 | Acetonitrile | 60 | n/a | n/a | G |
| 2 | n-Butyl acetate | 60 | n/a | n/a | A |
| 2 | Diisopropyl ether | 60 | n/a | n/a | C* |
| 2 | Methyl isobutyl ketone | 90 | n/a | n/a | D* |
| 2 | Nitromethane | 1800 | n/a | n/a | F |
| 2 | Acetonitrile | 300 | n/a | n/a | G |
| 3 | Methyl isobutyl ketone | 90 | Heptane | 90 | A |
| 3 | n-Butyl acetate | 90 | Heptane | 60 | A |
| 3 | Ethyl acetate | 60 | Heptane | 60 | A |
| 3 | Isopropyl acetate | 60 | Heptane | 60 | A |
| 3 | Methyl t-butyl ether | 90 | Heptane | 90 | A |
| 4 | Acetonitrile | 150 | n/a | n/a | G |
| 4 | Nitromethane | 450 | n/a | n/a | F |
| 4b | Diisopropyl ether | 60 | n/a | n/a | C* |
| 5 | Methyl t-butyl ether | 90 | Heptane | 90 | C |
| 6 | Anisole | 90 | n/a | n/a | oil |
| 7 | Acetonitrile/Water 90/10 | 60 | n/a | n/a | I |
| 7 | Acetonitrile/Water 80/20 | 60 | n/a | n/a | I |
| 7 | Acetonitrile/Water 50/50 | 60 | n/a | n/a | I |
| 7 | Acetonitrile/Water 25/75 | 90 | n/a | n/a | I |
| 8 | Dichloromethane | 60 | n/a | n/a | C* |
| 8 | Isopropylacetate | 90 | n/a | n/a | C* |

*Partially Crystalline

A. Small Scale Synthesis of Crystalline Obeticholic Acid Form D In one method, amorphous obeticholic acid (approximately 30 mg) was weighed into a glass vial and warmed to 50° C. Methyl isobutyl ketone (90 µL) was added and observations were made. The sample was stirred at 50° C. for 1 hour then was cooled to 5° C. using a linear cooling rate of 0.1° C./min. The ample was stirred at 5° C. for 2 days. Any solids were filtered, air dried and analyzed by XRPD. Solutions were stored in the freezer for ~48 hours, and then were left to evaporate at ambient conditions. Solids were analyzed by XRPD and the peaks are provided in Table 6.

TABLE 6

Peak listings for Form D

| Angle 2-Theta ° | Intensity % % |
|---|---|
| 4.4 | 16.9 |
| 5.2 | 18.8 |
| 6.3 | 34.7 |
| 7.5 | 22.4 |
| 7.8 | 9.0 |
| 8.4 | 10.8 |
| 9.0 | 19.6 |
| 9.5 | 70.1 |
| 10.1 | 47.5 |
| 10.4 | 24.4 |
| 11.0 | 24.6 |
| 11.3 | 27.5 |
| 11.5 | 28.4 |
| 11.8 | 11.4 |
| 12.3 | 87.2 |
| 12.7 | 42.8 |
| 13.4 | 8.4 |
| 13.7 | 10.1 |
| 14.5 | 63.7 |
| 14.9 | 39.3 |
| 15.4 | 19.7 |
| 15.9 | 63.9 |
| 16.5 | 80.0 |
| 16.8 | 100.0 |
| 17.5 | 20.4 |
| 17.8 | 26.1 |
| 18.7 | 32.1 |
| 19.1 | 32.5 |
| 19.8 | 13.9 |
| 20.2 | 13.9 |
| 20.8 | 18.2 |
| 21.2 | 25.0 |

B. Scale-Up Synthesis of Crystalline Obeticholic Acid Form D

Figure 45:
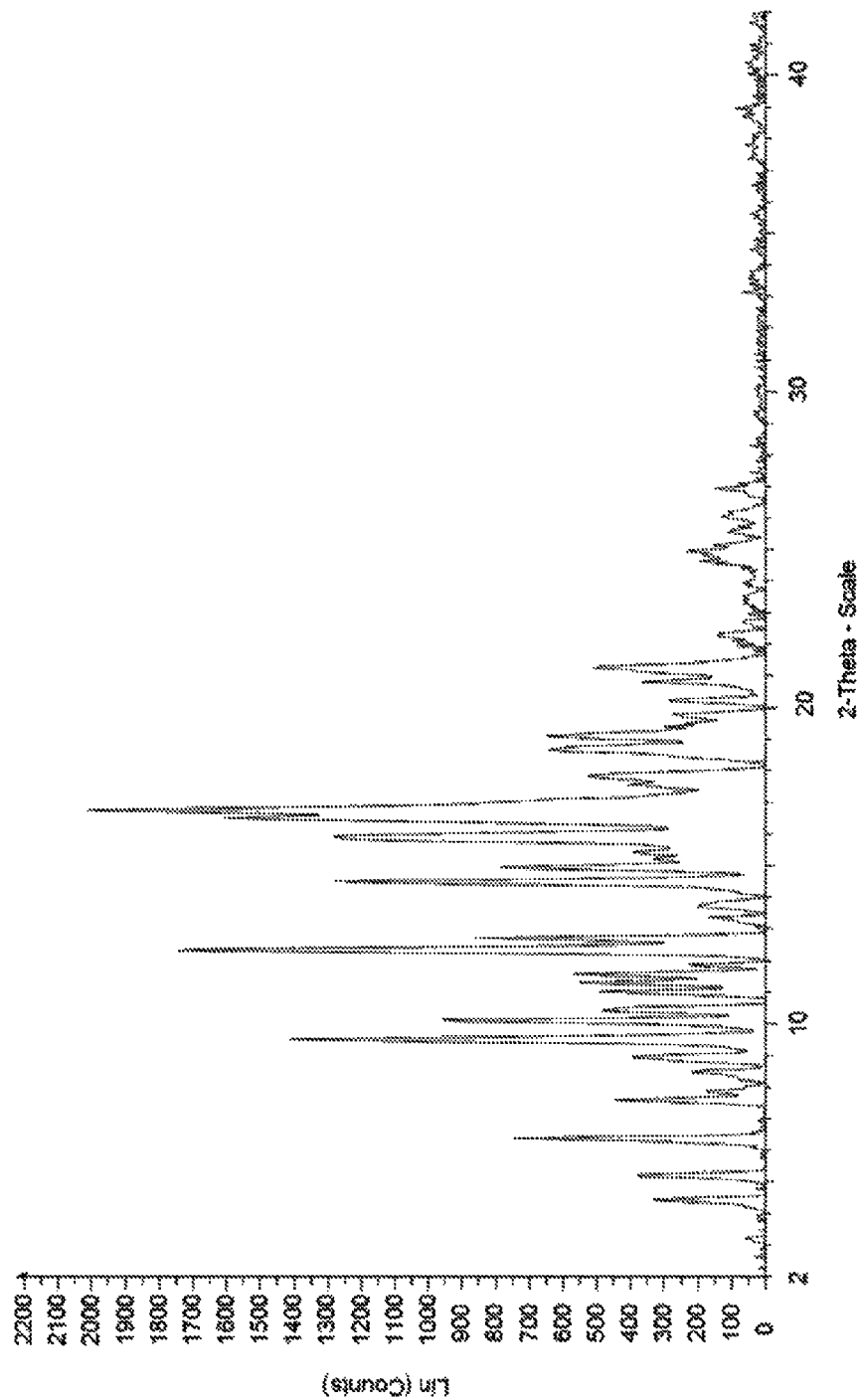
FIG. 45 is an XRPD diffractogram of crystalline obeticholic acid Form D (see example 9).
Figure 46:
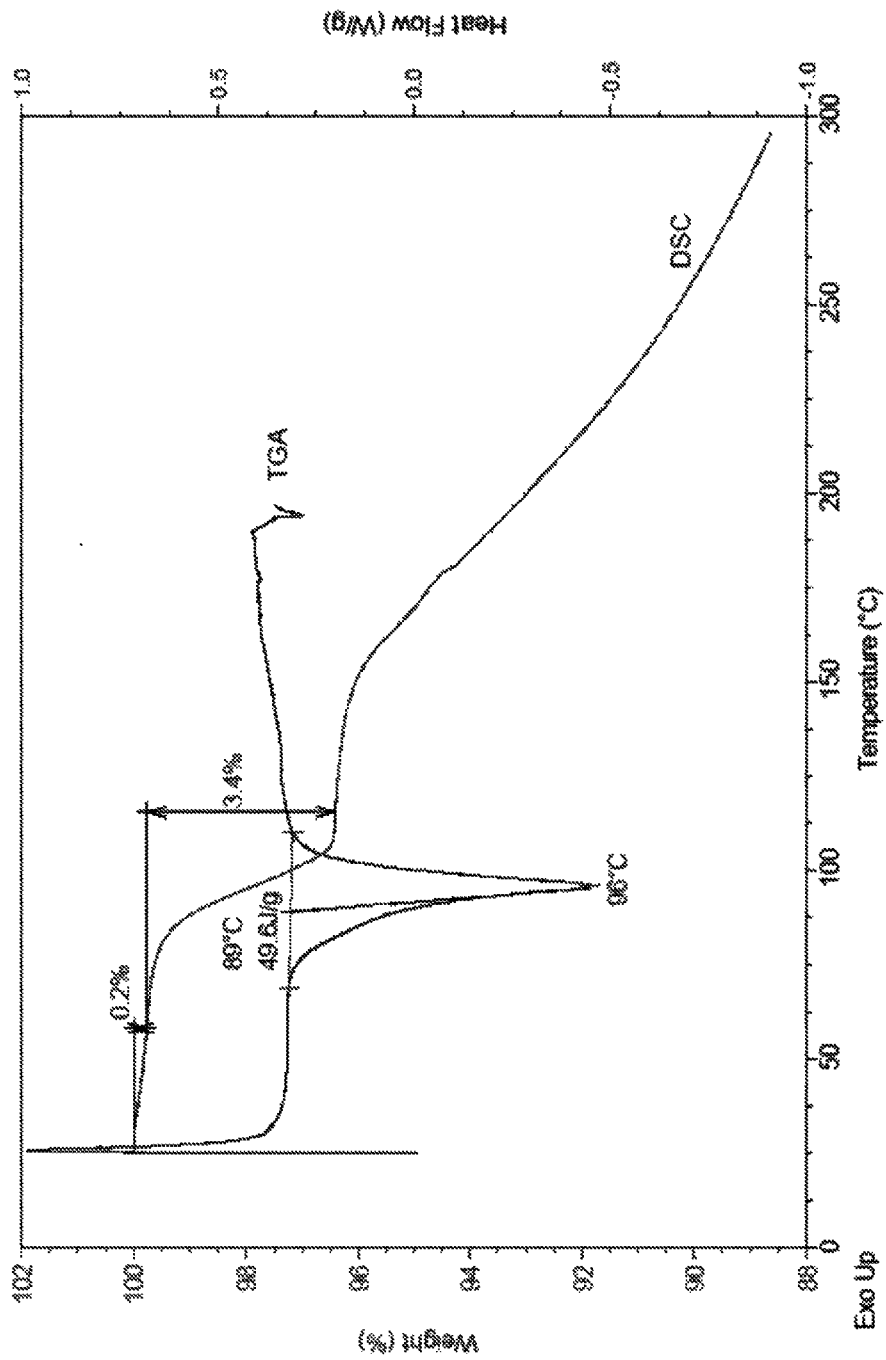
FIG. 46 is an overlay of TGA and DSC thermograms of crystalline obeticholic acid Form D (see example 9).
Figure 47:
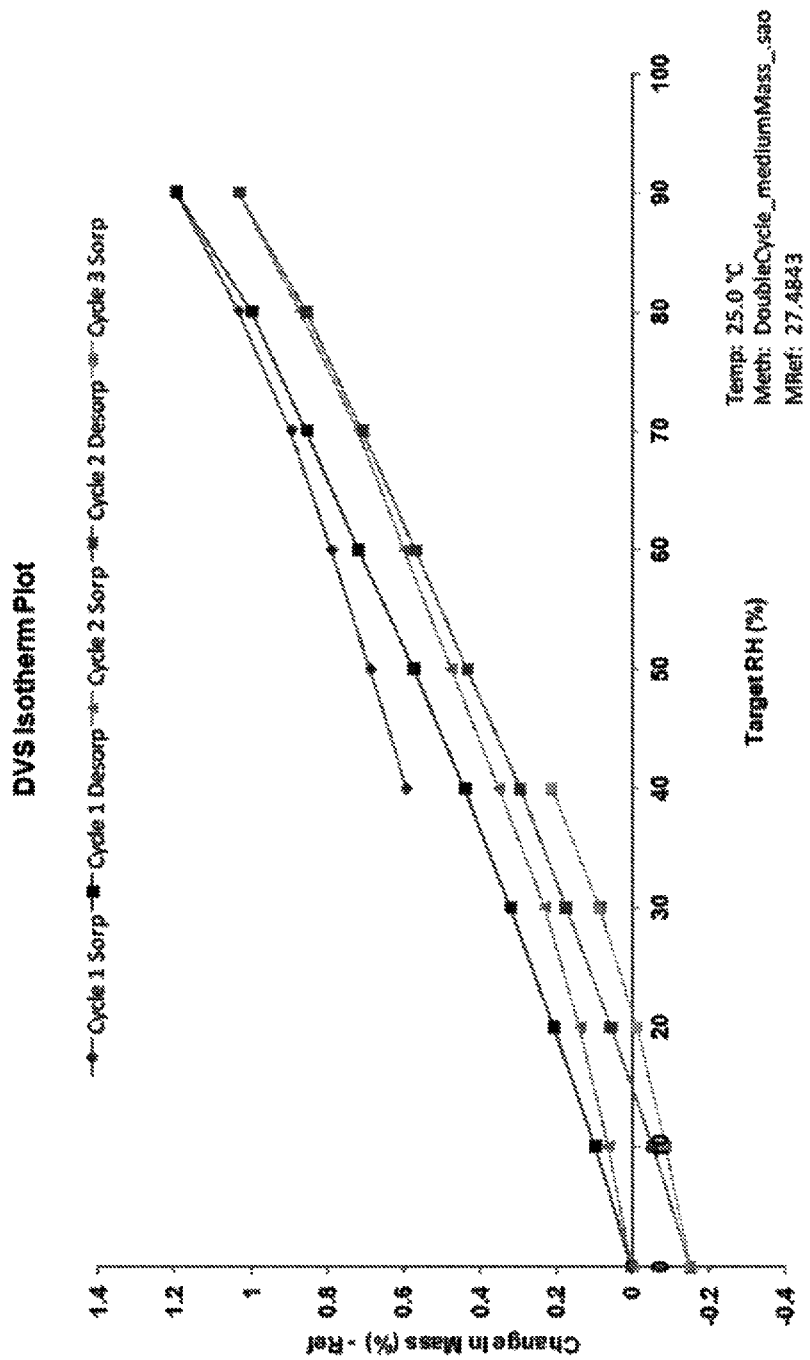
FIG. 47 is an isotherm plot for the GVS experiment with Form D (see example 9).
Figure 48:
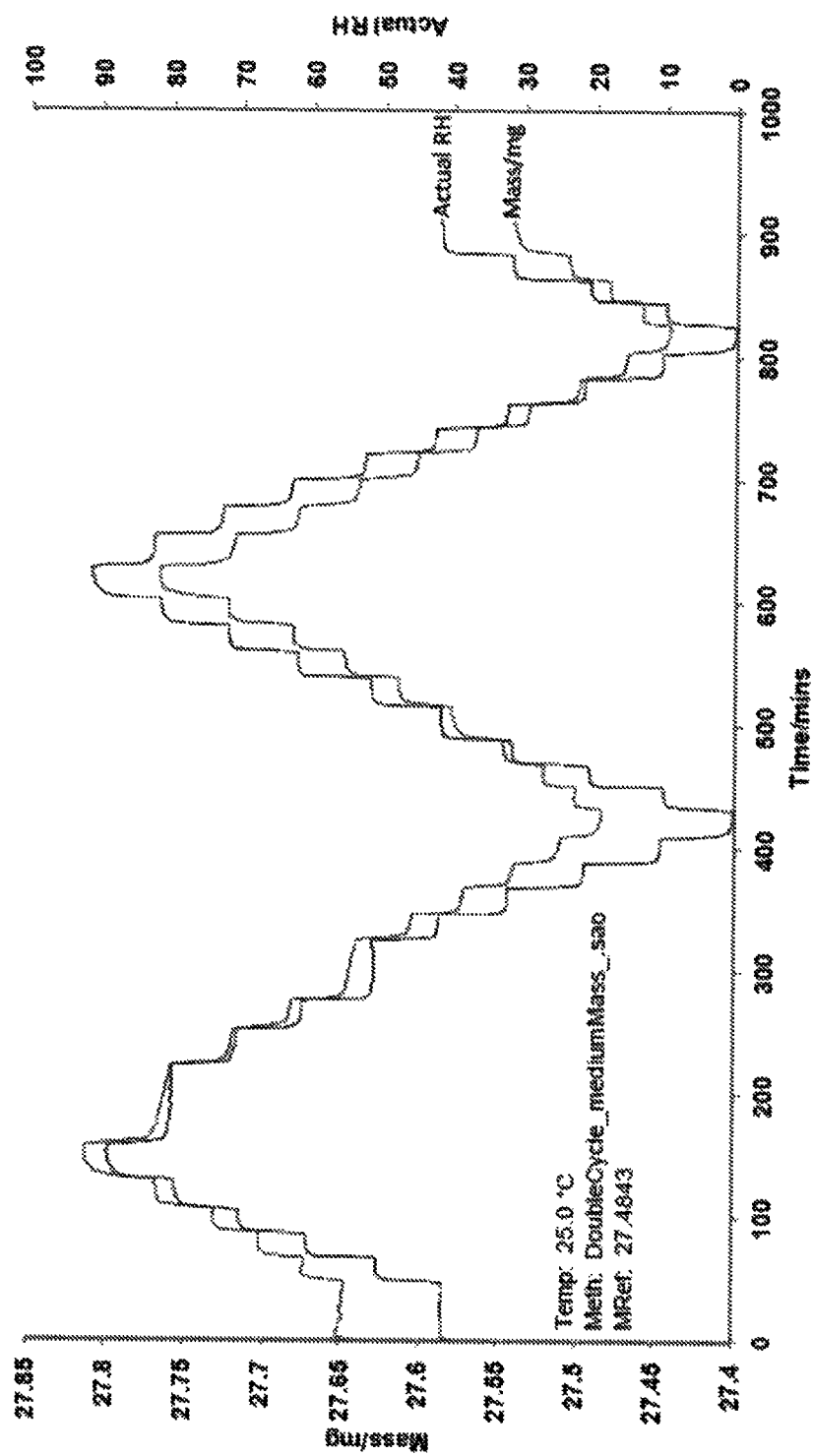
FIG. 48 is a kinetics plot for the GVS experiment with Form D (see example 9).

In one method, amorphous obeticholic acid (approximately 1 g) was weighed into a large glass vial and warmed to 50° C. MIBK (2.0 ml, 2 volumes) was added at 50° C., forming a clear solution on stirring. The sample was stirred at 50° C. for 2 hours then was cooled to −20° C. using a linear cooling rate of 0.1° C./min. The sample was stirred at −20° C. overnight, after which a small amount of the solid was filtered, air dried and analyzed by XRPD. The remainder of the sample was filtered through a 0.45 µm PTFE filter. The sample was air dried for approximately 30 minutes then was dried in a vacuum oven overnight at RT. The resulting white solid was characterized as Form D. FIG. 45 is an XRPD diffractogram of crystalline obeticholic acid Form D. FIG. 46 is an overlay of TGA and DSC thermograms of crystalline obeticholic acid Form D. FIG. 47 is an isotherm plot for the GVS experiment with crystalline obeticholic acid Form D. FIG. 48 is a kinetics plot for the GVS experiment with crystalline obeticholic acid Form D.

C. Small Scale Synthesis of Crystalline Obeticholic Acid Form F

In one method, amorphous obeticholic acid (approximately 30 mg) was weighed into glass vials and warmed to 50° C. Nitromethane was added to dissolve the amorphous material. Samples were stirred at 50° C. for 1 hour then were matured (shaken in 8 hour cycles at 50° C./RT). After 3 days samples containing solids were filtered, air dried and analyzed by XRPD. Solids were analyzed by XRPD and the peaks are provided in Table 7.

TABLE 7

Peak listings for Form F

| Angle 2-Theta ° | Intensity % % |
|---|---|
| 7.9 | 78.2 |
| 8.0 | 78.9 |
| 8.4 | 4.7 |
| 9.4 | 6.1 |
| 9.9 | 82.8 |
| 10.5 | 100.0 |
| 11.4 | 19.5 |
| 12.0 | 11.2 |
| 12.5 | 7.0 |
| 13.2 | 56.2 |
| 13.8 | 26.9 |
| 14.1 | 32.4 |
| 15.0 | 37.9 |
| 15.6 | 44.1 |
| 15.7 | 44.2 |
| 16.0 | 53.8 |
| 16.5 | 23.8 |
| 16.8 | 20.4 |
| 17.5 | 47.5 |
| 18.1 | 18.0 |
| 19.2 | 17.8 |
| 19.6 | 19.2 |
| 20.3 | 3.4 |
| 21.1 | 23.7 |
| 21.6 | 9.5 |
| 22.7 | 7.1 |
| 23.3 | 5.9 |
| 24.5 | 14.9 |

D. Scale-Up Synthesis of Crystalline Obeticholic Acid Form F

Figure 49:
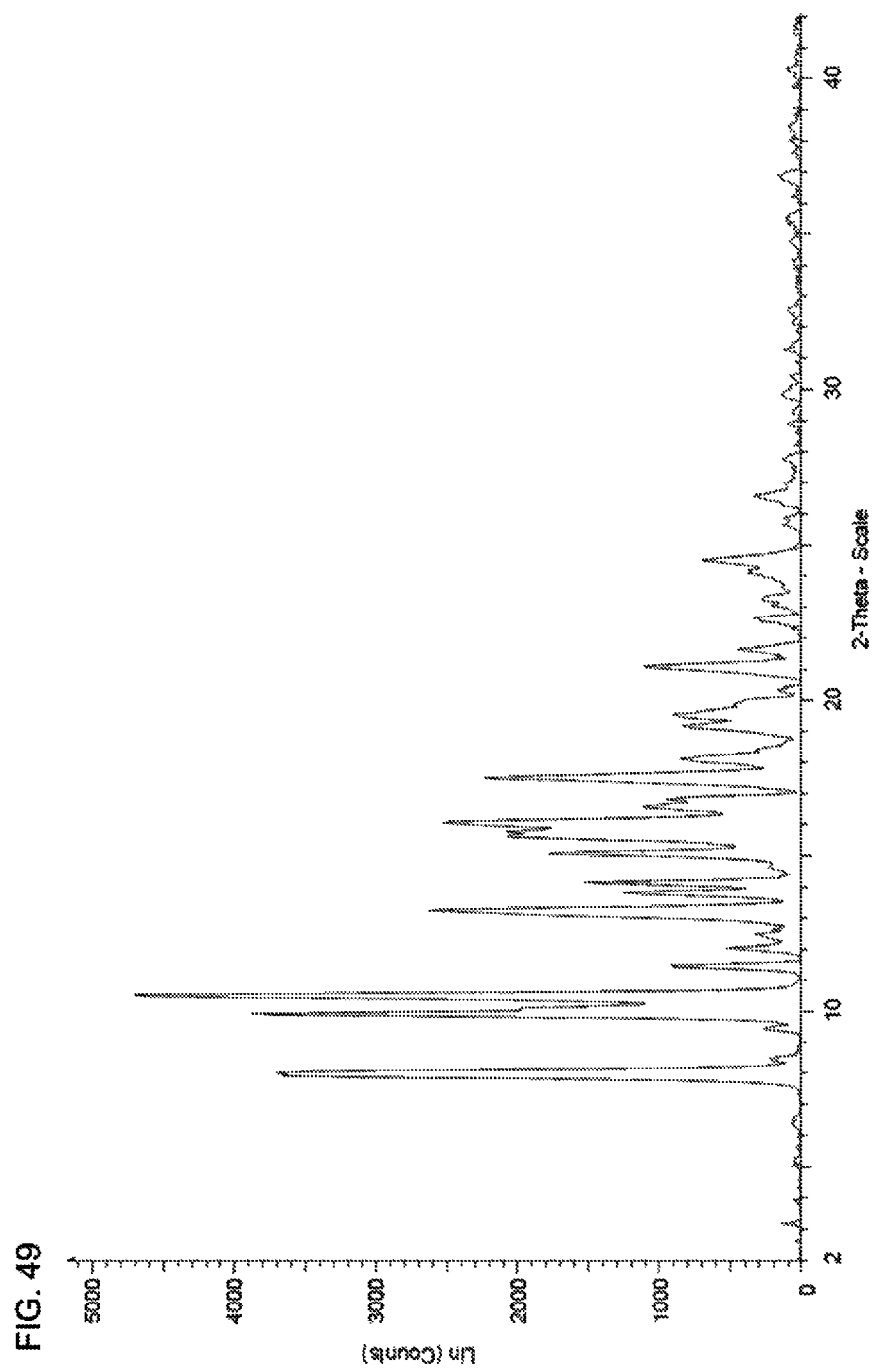
FIG. 49 is an XRPD diffractogram of crystalline obeticholic acid Form F (see example 9).
Figure 50:
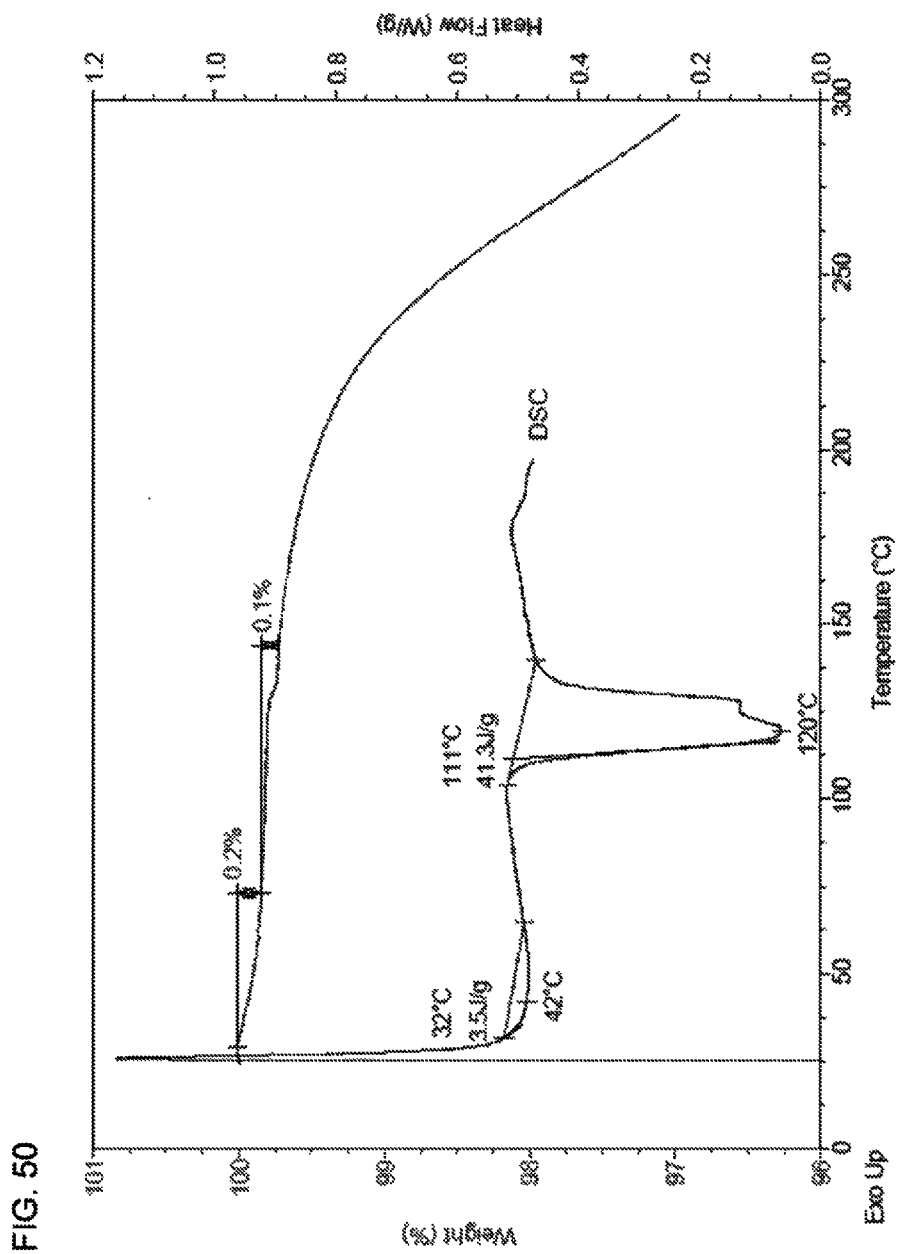
FIG. 50 is an overlay of TGA and DSC thermograms of crystalline obeticholic acid Form F (see example 9).
Figure 51:
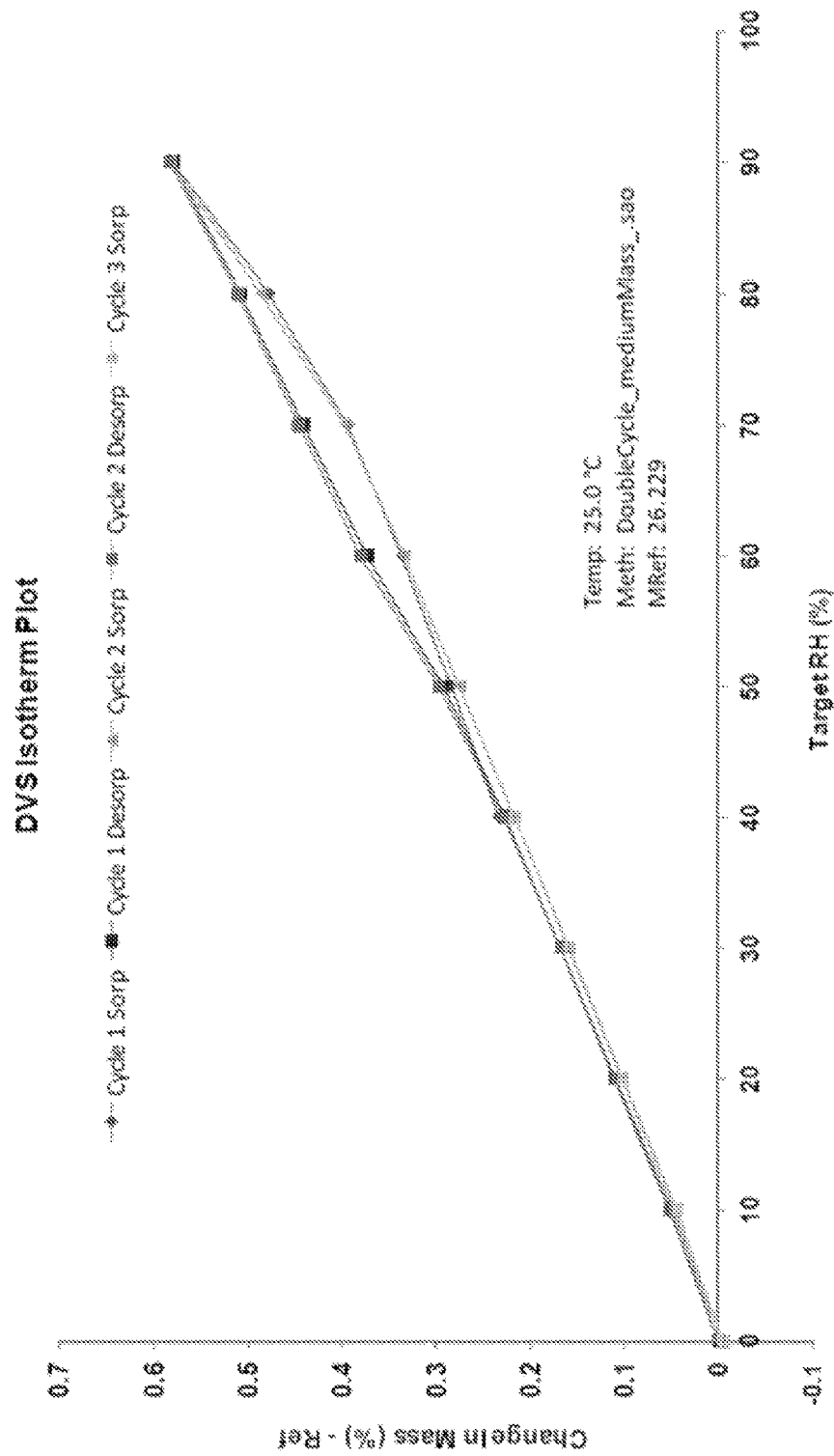
FIG. 51 is an isotherm plot for the GVS experiment with Form F (see example 9).
Figure 52:
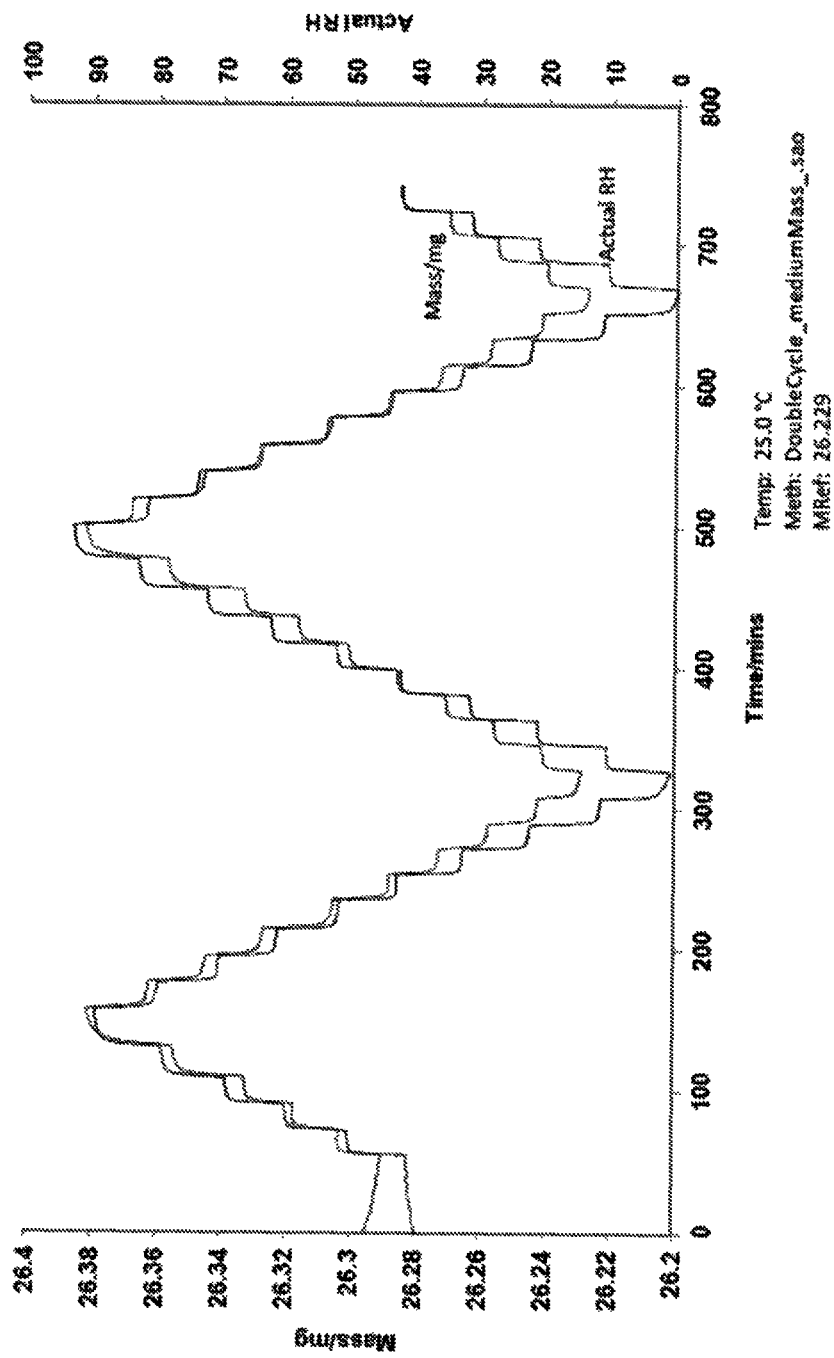
FIG. 52 is a kinetics plot for the GVS experiment with Form F (see example 9).

In one method, obeticholic acid (approximately 1 g) was weighed into a large glass vial and warmed to 50° C. Nitromethane (15.0 ml, 15 volumes) was added at 50° C., resulting in the sample forming balls of gummy solid. The sample was matured (shaken in 8 hour cycles at 50° C./RT) overnight after which the sample was a suspension of large hard lumps of solid and needle shaped particles. Some of the solid was crushed into a white powder and was analyzed by XRPD. The lumps of solid were broken up manually and the sample was matured for a further 24 hours. A small amount of the resulting suspension was filtered, air dried and analyzed by XRPD. The remainder of the sample was filtered through a 0.45 µm PTFE filter. The sample was air dried for approximately 40 minutes then was dried in a vacuum oven overnight at 40° C. The resulting white solid was characterized as Form F. FIG. 49 is an XRPD diffractogram of crystalline obeticholic acid Form F. FIG. 50 is an overlay of TGA and DSC thermograms of crystalline obeticholic acid Form F. FIG. 51 is an isotherm plot for the GVS experiment with Form F. FIG. 52 is a kinetics plot for the GVS experiment with Form F.

E. Small Scale Synthesis of Crystalline Obeticholic Acid Form G

In one method, amorphous obeticholic acid (approximately 30 mg) was weighed into a glass vial and warmed to 50° C. 2 volume (60 µl) portions of acetonitrile were added at 50° C. Initially the sample formed a gum, which dissolved after the addition of 14 volumes of solvent. On stirring flakes of solid precipitate were observed. The sample was cooled to 5° C. using a linear cooling rate of 0.25° C./min. The resulting suspension was analyzed by XRPD and was then matured (shaken in 8 hour cycles at 50° C./RT). After 5 days of maturation the sample was equilibrated to room temperature and was re-analyzed by XRPD and the peaks are provided in Table 8.

TABLE 8

Peak listings for Form G

| Angle 2-Theta ° | Intensity % % |
|---|---|
| 7.9 | 40.7 |
| 10.9 | 20.8 |
| 12.3 | 39.4 |
| 12.8 | 80.2 |
| 12.9 | 91.4 |
| 13.4 | 12.5 |
| 13.8 | 4.5 |
| 14.3 | 48.6 |
| 14.5 | 65.9 |
| 15.4 | 4.5 |
| 16.9 | 100.0 |
| 17.2 | 2.0 |
| 17.6 | 10.5 |
| 18.1 | 4.5 |
| 18.5 | 15.2 |
| 18.8 | 7.4 |
| 19.8 | 4.4 |
| 20.4 | 20.3 |
| 20.7 | 24.1 |
| 21.1 | 21.4 |
| 21.6 | 1.9 |
| 21.8 | 8.5 |
| 23.0 | 14.6 |
| 23.1 | 30.5 |
| 23.5 | 4.5 |
| 23.8 | 2.3 |
| 24.5 | 7.8 |
| 24.6 | 7.5 |

F. Scale-Up Synthesis of Crystalline Obeticholic Acid Form G

Figure 53:
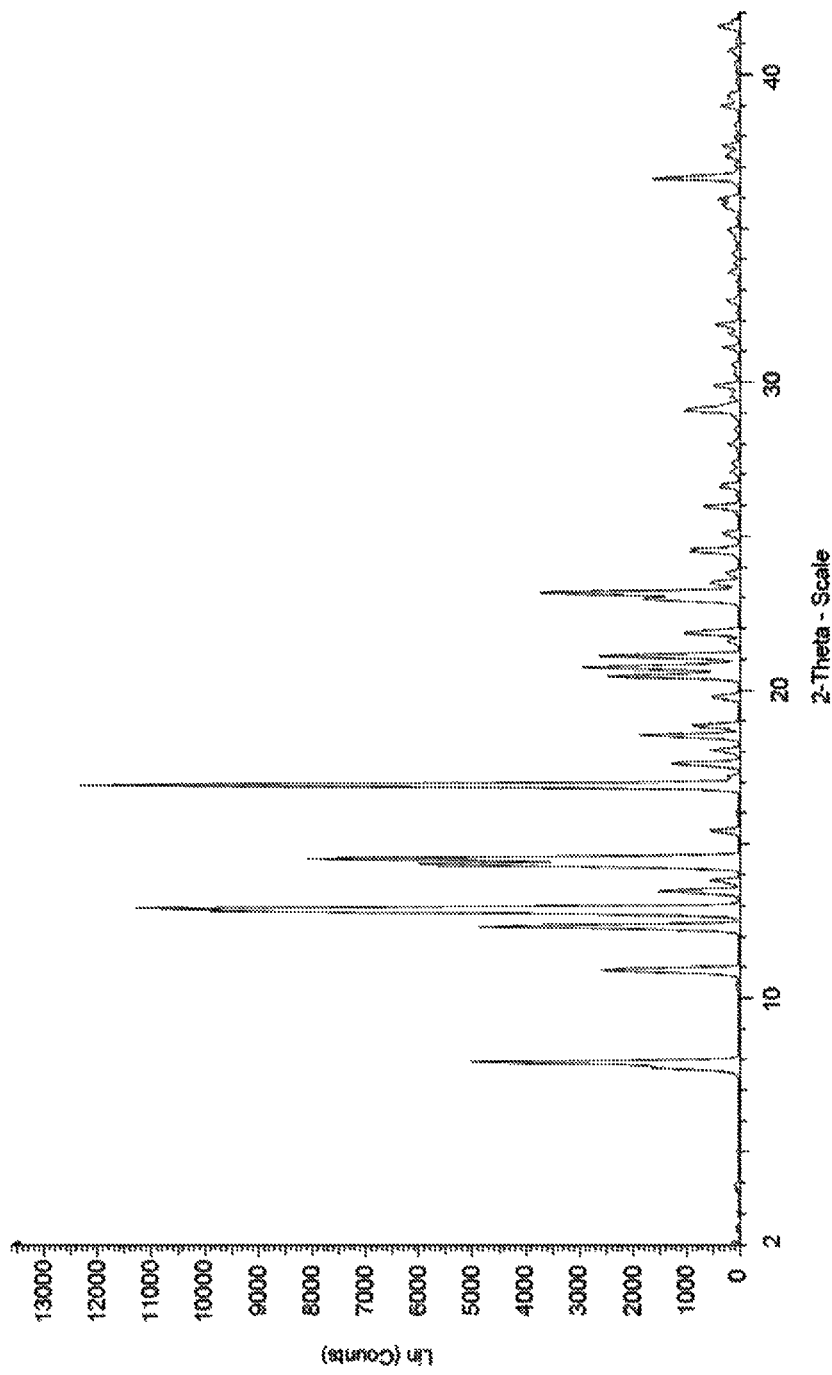
FIG. 53 is an XRPD diffractogram of crystalline obeticholic acid Form G (see example 9).
Figure 54:
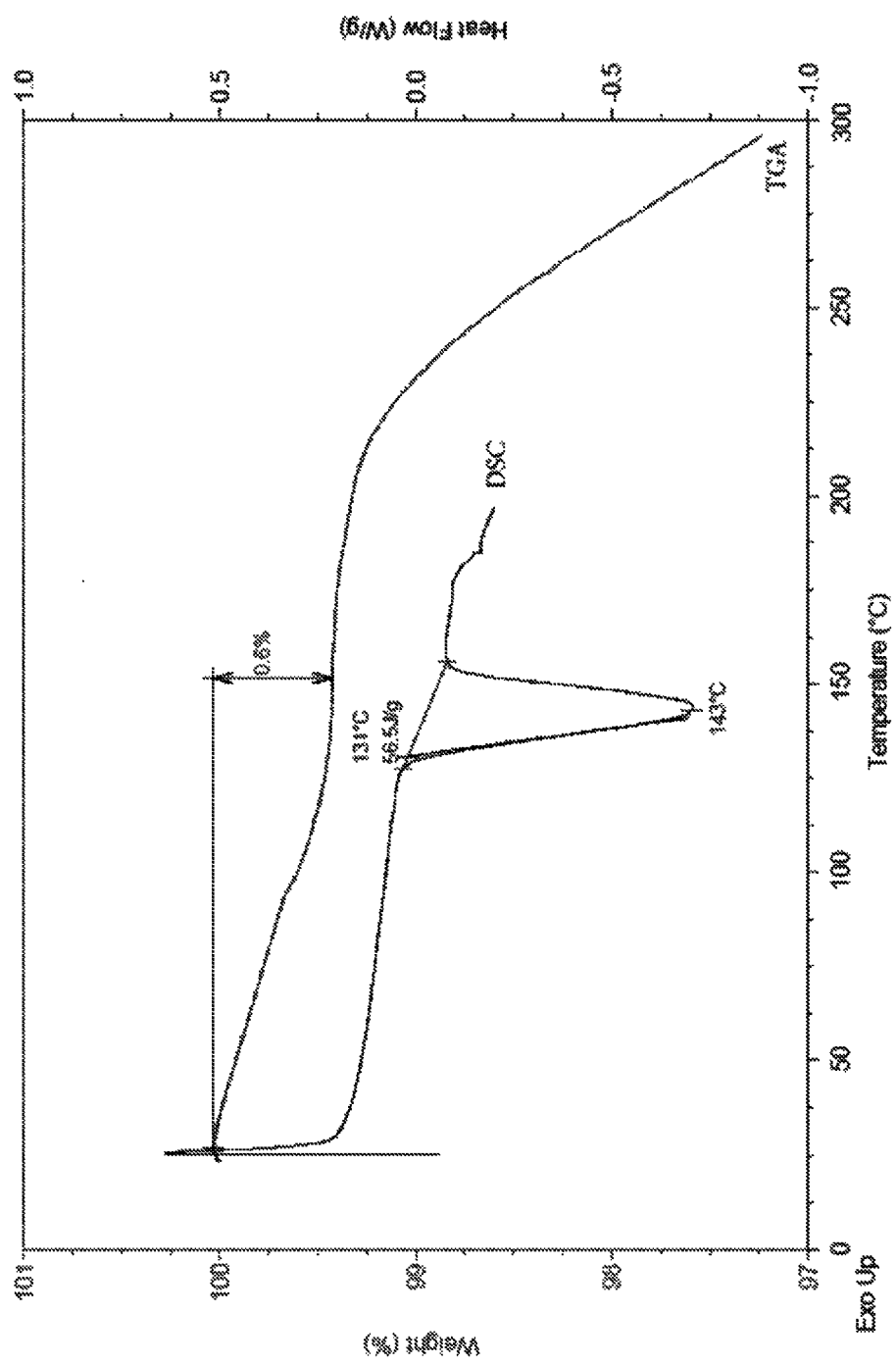
FIG. 54 is an overlay of TGA and DSC thermograms of crystalline obeticholic acid Form G (see example 9).
Figure 55:
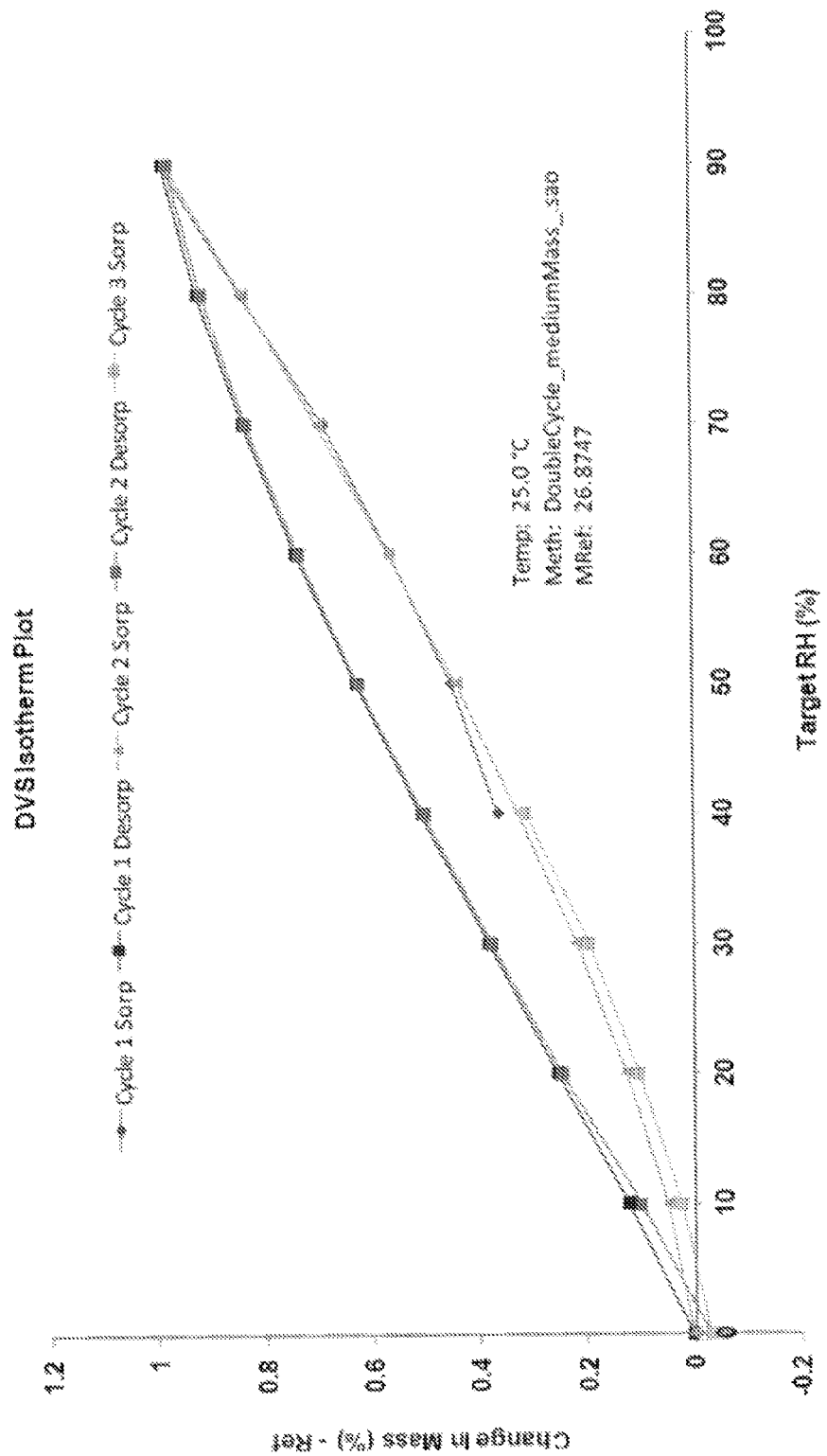
FIG. 55 is an isotherm plot for the GVS experiment with Form G (see example 9).
Figure 56:
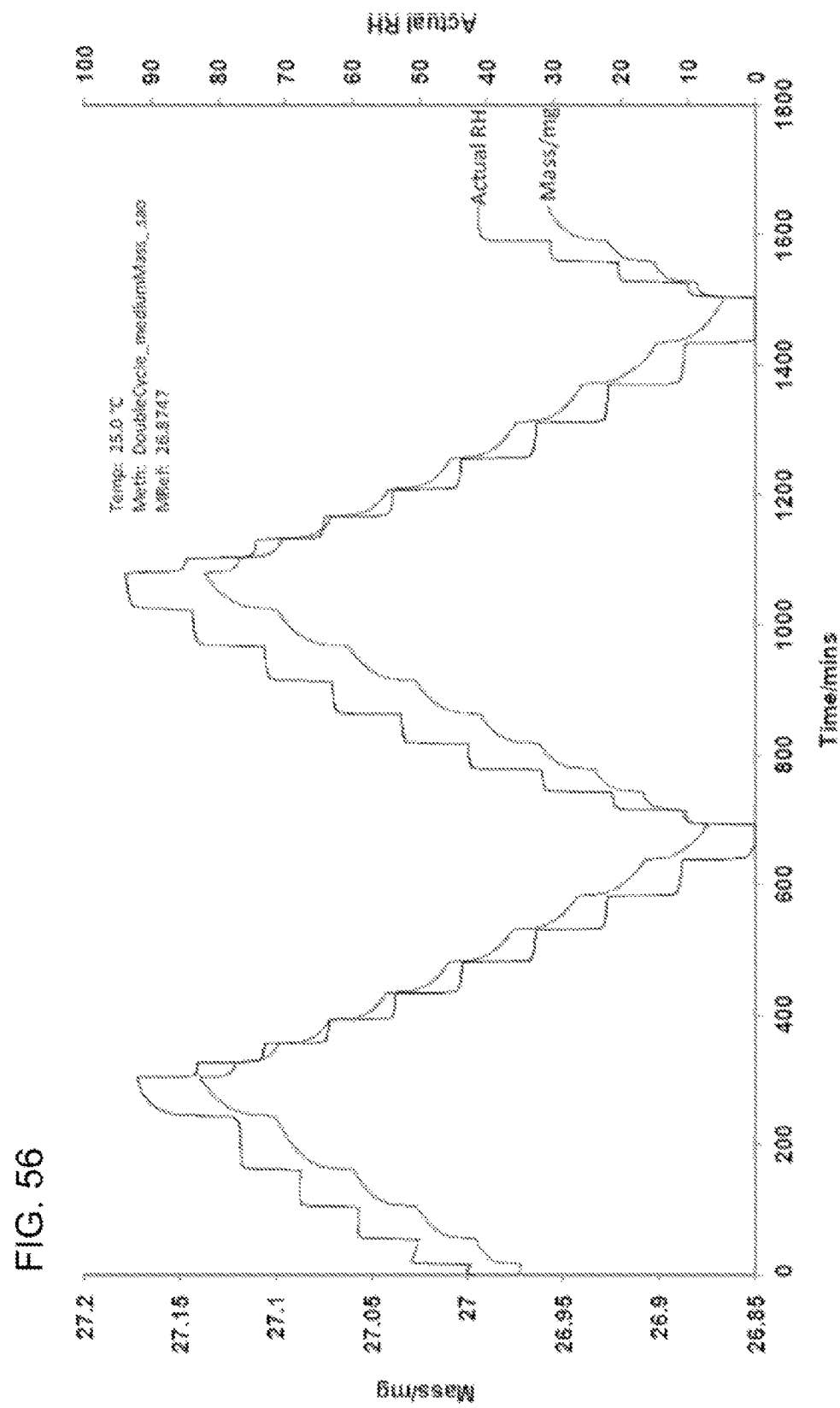
FIG. 56 is a kinetics plot for the GVS experiment with Form G (see example 9).

Amorphous obeticholic acid (approximately 100 mg) was weighed into glass vials and warmed to 50° C. Ten 100 mg scale experiments were carried out in parallel. Acetonitrile (0.5 ml, 5 volumes, pre-warmed to 50° C.) was added to each sample forming a colorless gum which mostly dissolved on standing at 50° C. Each sample was seeded with ~1 mg of the product in the small scale experiment and the samples were matured (shaken in 8 hour cycles at 50° C./RT) for 3 days. After maturation the samples contained crystals on the walls of the vial and a hard solid on the base of the vial which formed a white powder on scratching. Each sample was analyzed by XRPD and the samples were combined by filtering them all through a 0.45 µm PTFE filter. The sample was air dried for approximately 30 minutes then was dried in a vacuum oven overnight at RT. The resulting white solid (795.8 mg) was characterized and identified as Form G. FIG. 53 is an XRPD diffractogram of crystalline obeticholic acid Form G. FIG. 54 is an overlay of TGA and DSC thermograms of crystalline obeticholic acid Form G. FIG. 55 is an isotherm plot for the GVS experiment with Form G. FIG. 56 is a kinetics plot for the GVS experiment with Form G.

G. Small Scale Synthesis of Crystalline Obeticholic Acid Form I

In one method, amorphous obeticholic acid (approximately 30 mg) was weighed into a glass vial and cooled to 5° C. Acetonitrile/water mixtures (50/50, 60 uL) were added and samples were stirred at 5° C. overnight. Observations were made and solids were filtered, air dried and analyzed by XRPD. Some solids were large lumps which were crushed prior to XRPD analysis. One sample was a sticky solid so was left to stir at 5° C. for a total of 17 days, forming a hard lump of solid, which was crushed and analyzed by XRPD and the peaks are provided in Table 9.

TABLE 9

Peak listings for Form I

| Angle 2-Theta ° | Intensity % % |
| --- | --- |
| 7.2 | 79.8 |
| 10.5 | 8.9 |
| 12.2 | 6.1 |
| 12.7 | 38.7 |
| 13.9 | 92.6 |
| 14.5 | 100.0 |
| 15.7 | 16.9 |
| 15.7 | 16.6 |
| 16.5 | 14.1 |
| 17.4 | 38.5 |
| 17.9 | 10.2 |
| 18.5 | 19.6 |
| 18.8 | 13.4 |
| 19.0 | 13.0 |
| 19.2 | 28.4 |
| 19.5 | 20.6 |
| 22.8 | 28.4 |
| 23.8 | 2.6 |
| 24.2 | 8.4 |
| 25.3 | 4.3 |

H. Scale-Up Synthesis of Crystalline Obeticholic Acid Form I

Figure 57:
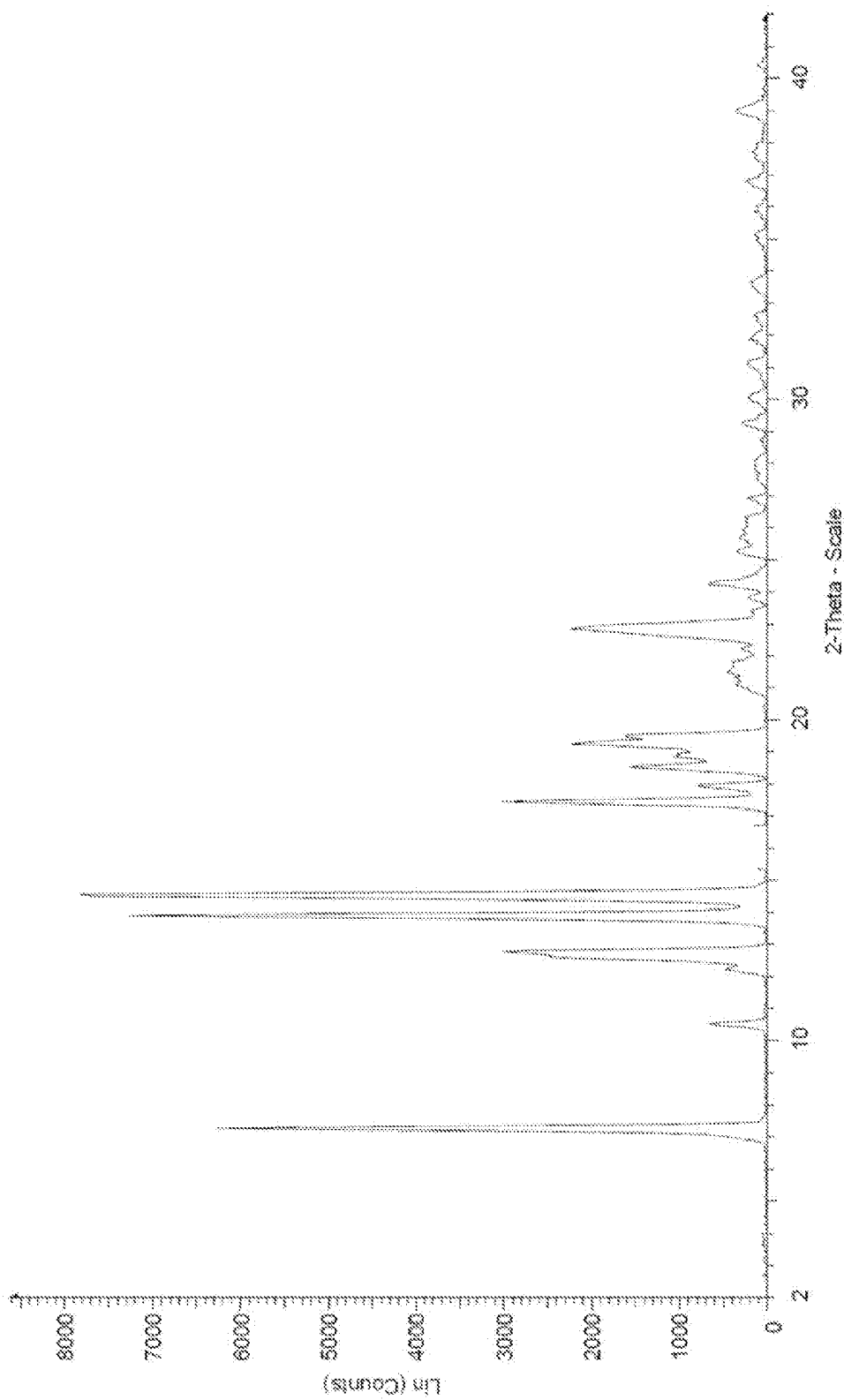
FIG. 57 is an XRPD diffractogram of crystalline obeticholic acid Form I (see example 9).
Figure 58:
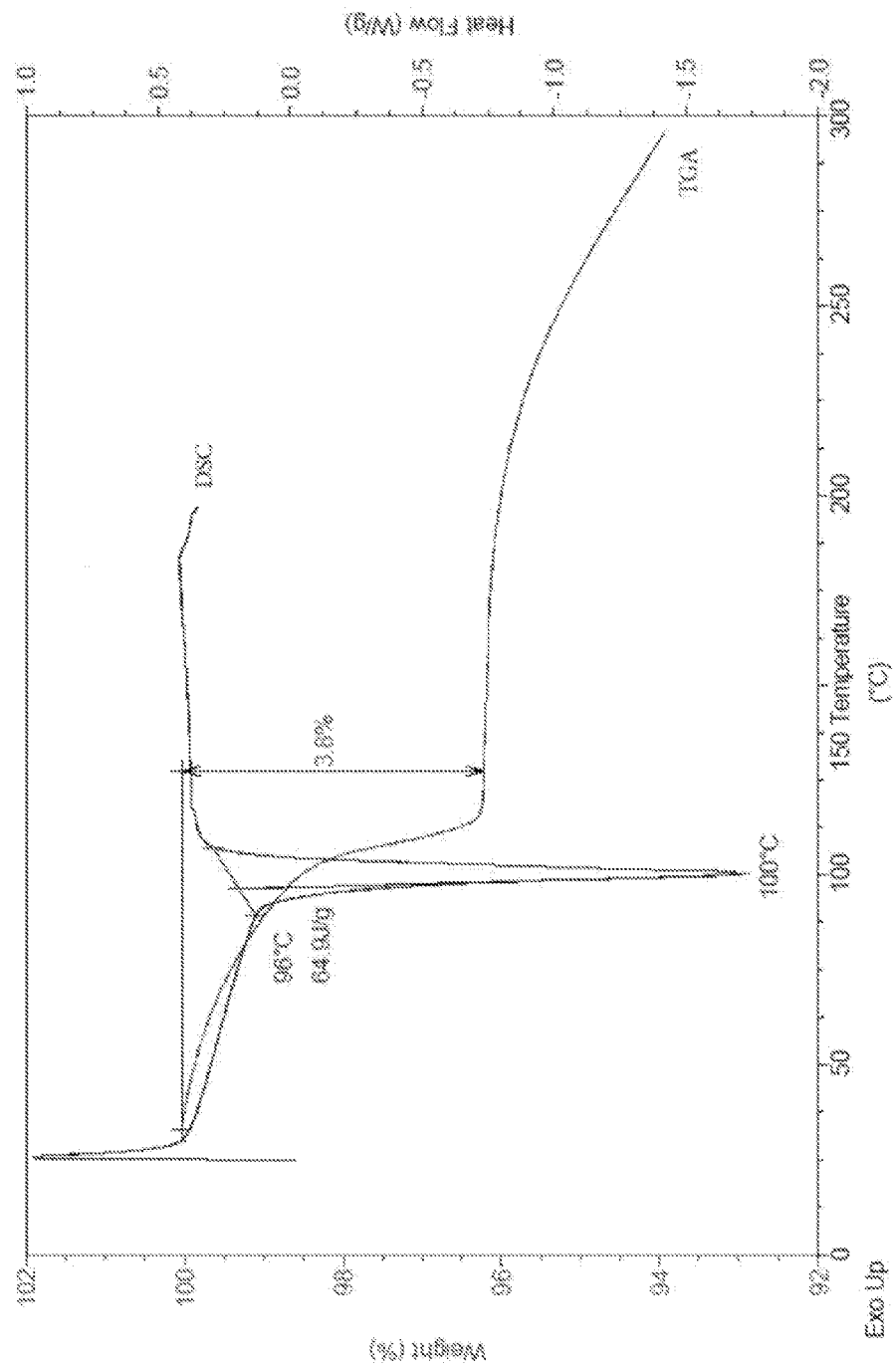
FIG. 58 is an overlay of TGA and DSC thermograms of crystalline obeticholic acid Form I (see example 9).
Figure 59:
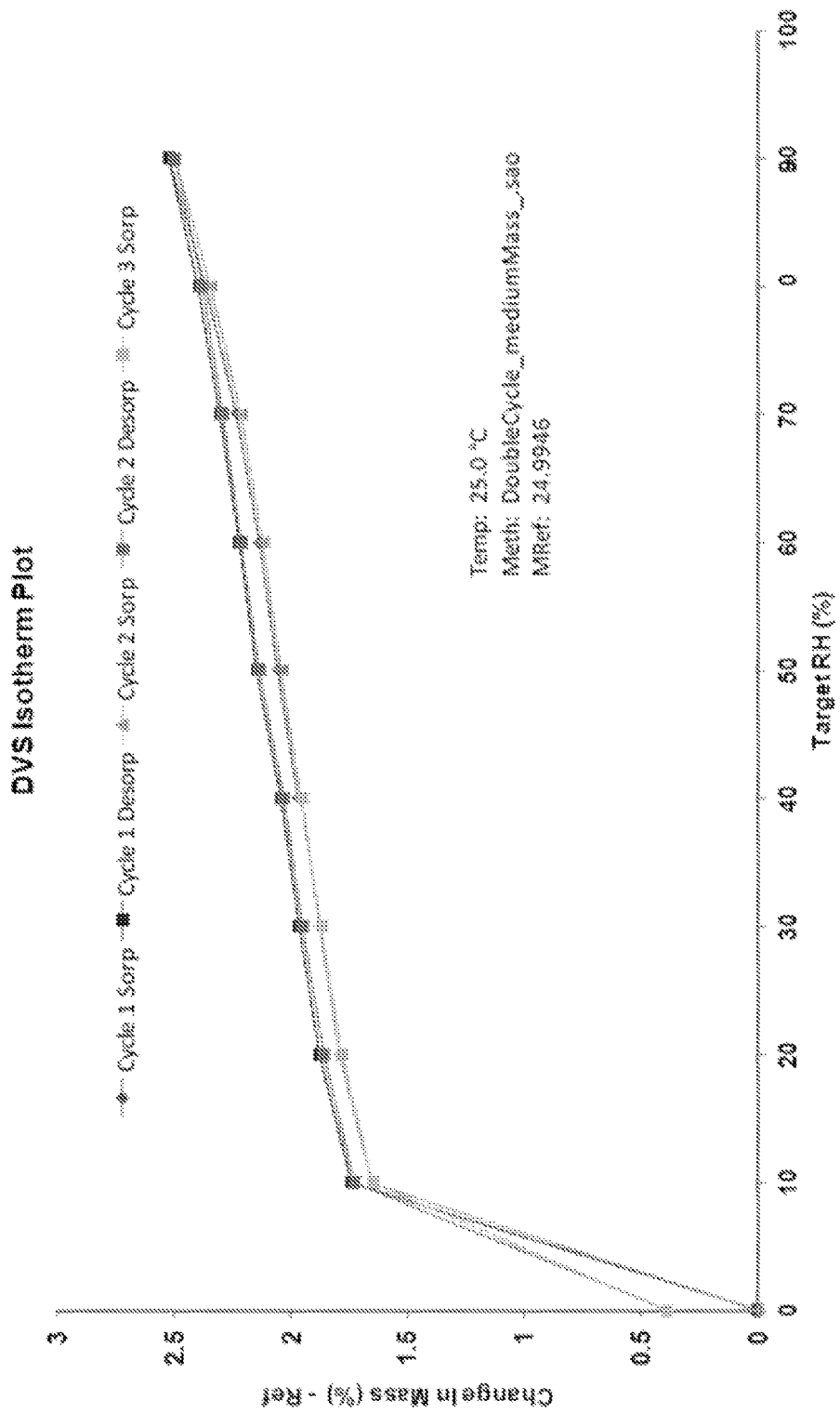
FIG. 59 is an isotherm plot for the GVS experiment with crystalline obeticholic acid Form I (see example 9).
Figure 60:
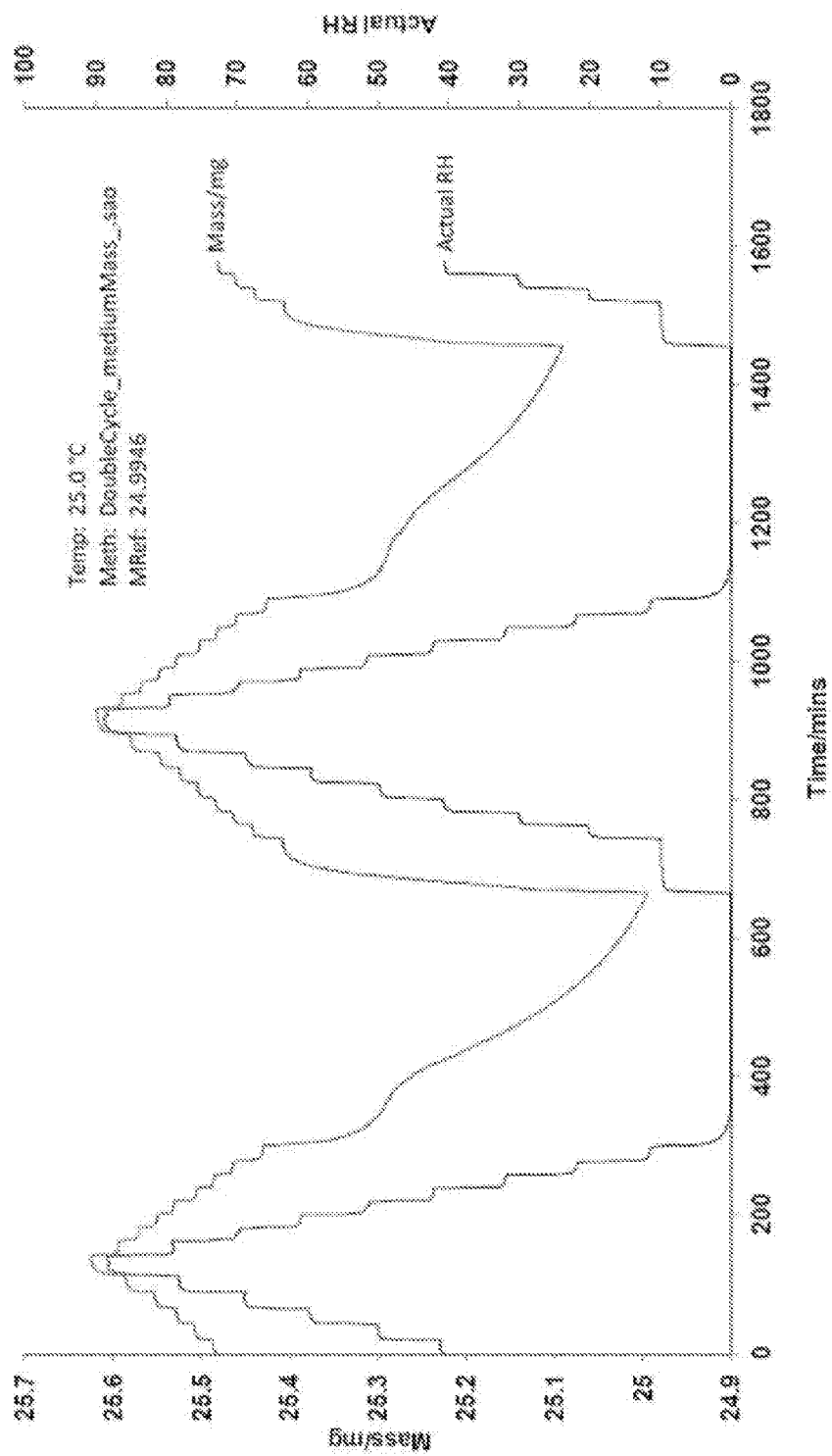
FIG. 60 is a kinetics plot for the GVS experiment with crystalline obeticholic acid Form I (see example 9).

Amorphous obeticholic acid (approximately 1 g) was weighed into a large glass vial and cooled to 5° C. Acetonitrile/water mixture (2 ml, 2 volumes of a 50/50 v/v premixed mixture, pre-cooled to 5° C.) was added and the sample formed a large lump of gummy off-white solid. The sample was stirred at 5° C. overnight after which it consisted of a large lump of hard white solid. The solid lump was broken up into a white powder and a small amount was filtered, air dried and analyzed by XRPD. The sample was stirred at 5° C. for a further 4 days then a small amount of the resulting suspension was filtered, air dried and analyzed by XRPD. The remainder of the sample was filtered through a 0.45 PTFE filter. The sample was air dried for approximately 40 minutes then was dried in a vacuum oven overnight at RT. The resulting white solid (955.4 mg) was characterized. FIG. 57 is an XRPD diffractogram of crystalline obeticholic acid Form I. FIG. 58 is an overlay of TGA and DSC thermograms of crystalline obeticholic acid Form I. FIG. 59 is an isotherm plot for the GVS experiment with Form I. FIG. 60 is a kinetics plot for the GVS experiment with Form I.

The invention claimed is:

1. A crystalline form of obeticholic acid characterized by an X-ray powder diffraction pattern comprising characteristic peaks at 5.0±0.2 degrees 2-theta, 5.3±0.2 degrees 2-theta, and 16.8±0.2 degrees 2-theta, wherein the crystalline form of obeticholic acid is obtainable by a process comprising crystallizing crude obeticholic acid in n-butyl acetate.

2. The crystalline form of obeticholic acid of claim 1, characterized by an X-ray powder diffraction pattern further comprising a peak at 6.3±0.2 degrees 2-theta.

3. The crystalline form of claim 1 characterized by an X-ray powder diffraction pattern further comprising a peak at 10.0±0.2 degrees 2-theta.

4. The crystalline form of claim 1 characterized by an X-ray powder diffraction pattern further comprising a peak at 11.0±0.2 degrees 2-theta.

5. The crystalline form of claim 1 characterized by an X-ray powder diffraction pattern further comprising a peak at 12.4±0.2 degrees 2-theta.

6. The crystalline form of claim 1 having a purity of greater than about 96%.

7. The crystalline form of claim 6 having a purity of greater than about 98%.

8. The crystalline form of claim 1 having a total of less than about 4% of one or more impurities selected from the group consisting of 6-ethylursodeoxycholic acid, 3 α-hydroxy-6α-ethyl-7-cheto-5β-cholan-24-oic acid, 6β-ethyl-chenodeoxycholic acid, 3α,7α-dihydroxy-6-ethyliden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid.

9. The crystalline form of claim 8, wherein the total percentage of impurities is less than about 3.8%.

10. The crystalline form of claim 8, wherein the total percentage of impurities is less than about 3.6%.

11. A crystalline form of obeticholic acid characterized by an X-ray powder diffraction pattern comprising a peak at 5.0±0.2 degrees 2-theta, 6.3±0.2 degrees 2-theta, 10.0±0.2 degrees 2-theta, 11.0±0.2 degrees 2-theta, 12.4±0.2 degrees 2-theta, 16.0±0.2 degrees 2-theta, 16.5±0.2 degrees 2-theta, and 16.8±0.2 degrees 2-theta.

12. The crystalline form of claim 1 characterized by an X-ray powder diffraction pattern further comprising a peak at 7.7±0.2 degrees 2-theta.

13. The crystalline form of claim 1 characterized by an X-ray powder diffraction pattern further comprising a peak at 14.9±0.2 degrees 2-theta.

14. A crystalline form of obeticholic acid characterized by an X-ray powder diffraction pattern comprising a peak at 5.0±0.2 degrees 2-theta, 5.3±0.2 degrees 2-theta, 7.7±0.2 degrees 2-theta, 10.0±0.2 degrees 2-theta, 11.0±0.2 degrees 2-theta, 12.4±0.2 degrees 2-theta, and 14.9±0.2 degrees 2-theta.

* * * * *